(12) United States Patent
Pasternak et al.

(10) Patent No.: US 11,207,312 B2
(45) Date of Patent: Dec. 28, 2021

(54) METALLO-BETA-LACTAMASE INHIBITORS AND METHODS OF USE THEREOF

(71) Applicant: Merck Sharp & Dohme Corp., Rahway, NJ (US)

(72) Inventors: Alexander Pasternak, Princeton, NJ (US); Shuzhi Dong, Plainsboro, NJ (US); Jack D. Scott, Scotch Plains, NJ (US); Haiqun Tang, Belle Mead, NJ (US); Zhiqiang Zhao, Scotch Plains, NJ (US); Dexi Yang, Livingston, NJ (US); Xin Gu, Scotch Plains, NJ (US); Jinlong Jiang, Scotch Plains, NJ (US); Li Xiao, Cranbury, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 30 days.

(21) Appl. No.: 16/631,673

(22) PCT Filed: Jul. 12, 2018

(86) PCT No.: PCT/US2018/041721
§ 371 (c)(1),
(2) Date: Jan. 16, 2020

(87) PCT Pub. No.: WO2019/018186
PCT Pub. Date: Jan. 24, 2019

(65) Prior Publication Data
US 2020/0281913 A1 Sep. 10, 2020

Related U.S. Application Data
(60) Provisional application No. 62/533,171, filed on Jul. 17, 2017.

(51) Int. Cl.
| | | |
|---|---|---|
| *A61K 31/454* | (2006.01) |
| *A61P 31/04* | (2006.01) |
| *A61K 31/198* | (2006.01) |
| *A61K 31/407* | (2006.01) |
| *A61K 31/41* | (2006.01) |
| *A61K 31/438* | (2006.01) |
| *A61K 31/439* | (2006.01) |
| *A61K 31/496* | (2006.01) |
| *A61K 31/5377* | (2006.01) |
| *A61K 31/5386* | (2006.01) |
| *A61K 31/55* | (2006.01) |
| *A61K 31/551* | (2006.01) |
| *C07D 401/10* | (2006.01) |
| *C07D 401/14* | (2006.01) |
| *C07D 403/10* | (2006.01) |
| *C07D 403/14* | (2006.01) |

(Continued)

(52) U.S. Cl.
CPC .......... *A61K 31/454* (2013.01); *A61K 31/198* (2013.01); *A61K 31/407* (2013.01);
(Continued)

(58) Field of Classification Search
CPC .. A61K 31/454; A61K 31/198; A61K 31/407; A61K 31/41; A61K 31/438; A61K 31/439; A61K 31/496; A61K 31/5377; A61K 31/5386; A61K 31/55; A61K 31/551; A61P 31/04; C07D 401/10; C07D 401/14; C07D 403/10; C07D 403/14; C07D 405/14; C07D 413/10; C07D 471/08; C07D 471/10; C07D 498/10
See application file for complete search history.

(56) References Cited

U.S. PATENT DOCUMENTS

| | | |
|---|---|---|
| 4,746,353 A | 5/1988 | Levitt |
| 4,786,311 A | 11/1988 | Levitt |

(Continued)

FOREIGN PATENT DOCUMENTS

| | | |
|---|---|---|
| CN | 1095549 A | 11/1994 |
| CN | 103130686 A | 6/2013 |

(Continued)

OTHER PUBLICATIONS

Drawz; Antimicrobial Agents and Chemotherapy 2014, 58, 1835-1846. (Year: 2014).*

(Continued)

*Primary Examiner* — Daniel R Carcanague
(74) *Attorney, Agent, or Firm* — Eric A. Meade; John C. Todaro

(57) ABSTRACT

The present invention relates to metallo-β-lactamase inhibitor compounds of Formula (I) and pharmaceutically acceptable salts thereof, wherein Z, $R^4$, $X_1$, $X_2$ and $R^1$ are as defined herein. The present invention also relates to compositions which comprise a metallo-β-lactamase inhibitor compound of the invention or a pharmaceutically acceptable salt thereof, and a pharmaceutically acceptable carrier, optionally in combination with a beta lactam antibiotic and/or a beta-lactamase inhibitor. The invention further relates to methods for treating a bacterial infection comprising administering to a patient a therapeutically effective amount of a compound of the invention, in combination with a therapeutically effective amount of one or more β-lactam antibiotics and optionally in combination with one or more beta-lactamase inhibitor compounds. The compounds of the invention are useful in the methods described herein for overcoming antibiotic resistance.

(I)

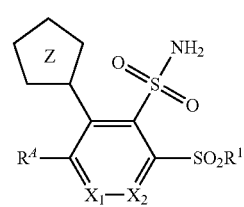

14 Claims, No Drawings

(51) Int. Cl.
| | |
|---|---|
| *C07D 405/14* | (2006.01) |
| *C07D 413/10* | (2006.01) |
| *C07D 471/08* | (2006.01) |
| *C07D 471/10* | (2006.01) |
| *C07D 498/10* | (2006.01) |

(52) U.S. Cl.
CPC ............ *A61K 31/41* (2013.01); *A61K 31/438* (2013.01); *A61K 31/439* (2013.01); *A61K 31/496* (2013.01); *A61K 31/5377* (2013.01); *A61K 31/5386* (2013.01); *A61K 31/55* (2013.01); *A61K 31/551* (2013.01); *A61P 31/04* (2018.01); *C07D 401/10* (2013.01); *C07D 401/14* (2013.01); *C07D 403/10* (2013.01); *C07D 403/14* (2013.01); *C07D 405/14* (2013.01); *C07D 413/10* (2013.01); *C07D 471/08* (2013.01); *C07D 471/10* (2013.01); *C07D 498/10* (2013.01)

(56) References Cited

U.S. PATENT DOCUMENTS

| | | | |
|---|---|---|---|
| 4,838,925 | A | 6/1989 | Tseng |
| 5,510,343 | A | 4/1996 | Charnas et al. |
| 5,698,577 | A | 12/1997 | Hubschwerlen et al. |
| 5,854,179 | A | 12/1998 | Schnabel et al. |
| 6,472,406 | B1 | 10/2002 | Besterman et al. |
| 9,708,336 | B2 | 7/2017 | Mandal et al. |
| 9,839,642 | B2 | 12/2017 | Tang et al. |
| 10,221,163 | B2 | 3/2019 | Bennett et al. |
| 10,227,331 | B2 | 3/2019 | Bennett et al. |
| 10,239,863 | B2 | 3/2019 | Shao |
| 10,544,130 | B2 * | 1/2020 | Bennett ................ A61K 31/546 |
| 2003/0199541 | A1 | 10/2003 | Lampilas et al. |
| 2004/0157826 | A1 | 8/2004 | Lampilas et al. |
| 2009/0176891 | A1 | 7/2009 | Chogle et al. |
| 2014/0315861 | A1 * | 10/2014 | Shoichet ................ A61K 45/06 514/64 |
| 2016/0333021 | A1 * | 11/2016 | Mandal ................ A61K 31/407 |
| 2018/0179190 | A1 * | 6/2018 | Bennett ................ C07D 407/14 |
| 2018/0244656 | A1 * | 8/2018 | Bennett ............. A61K 31/4184 |
| 2019/0144432 | A1 | 5/2019 | Bennett et al. |
| 2020/0375987 | A1 * | 12/2020 | Pasternak .......... A61K 31/4985 |

FOREIGN PATENT DOCUMENTS

| | | |
|---|---|---|
| CN | 103191091 A | 7/2013 |
| EP | 204513 A2 | 12/1986 |
| EP | 244166 A2 | 11/1987 |
| WO | 2008039420 A2 | 4/2008 |
| WO | 2015112441 A1 | 7/2015 |
| WO | 2016210234 A1 | 6/2016 |
| WO | 2016210215 A1 | 12/2016 |
| WO | WO-2016206101 A1 * | 12/2016 ........... C07D 417/14 |
| WO | 2019135920 A1 | 7/2019 |

OTHER PUBLICATIONS

Eidam; Proc. Natl. Acad. Sci. U. S. A., 2012, 109, 17448-17453. (Year: 2012).*
Rotondo; Current Opinion in Microbiology 2017, 39, 96-105. (Year: 2017).*
Wong; Drugs, 2017, 77, 615-628. (Year: 2017).*
Anderson, The pandemic of antibiotic resistance, Nature Medicine, 1999, 147-149, 5(2).
Bush et al., Tackling antibiotic resistance, Nature Reviews in Microbiology, 2011, 894-896, 9.
Cohen, Epidemiology of Drug Resistance: Implications for a Post-Antimicrobial Era, Science, 1992, 1050-1055, 257.
Coulton et al., 6 Beta-Lactamases: Targets for Drug Design, Progress in Medicinal Chemistry, 1994, 297-349, 31.
Dudley, Bacterial Resistance Mechanisms to Beta-Lactam Antibiotics: Assessment of Management Strategies, Pharmacotherapy, 1995, 9S-14S, 15.
English language abstract for CN103130686.
English language abstract for CN1095549, published Nov. 30, 1994.
English Language abstract of CN103191091.
Fast et al., Metallo-β-lactamase: inhibitors and reporter substiates, Biochimica et Biophysica Acta—Proteins and Proteomics, 2013, 1648-1659, 1834(8).
Heinze-Krauss et al., Structure-Based Design of β-Lactamase Inhibitors. 1. Synthesis and Evaluation of Bridged Monobactams, J. Med. Chem., 1998, 3961-3971, 41.
Levy et al., Antibacterial resistance worldwide: causes, challenges and responses, Nature Medicine, 2004, S122-S129, 10.
Livermore, Bacterial resistance: origins, epidemiology, and impact, Clinical Infectious Diseases, 2003, S11-S23, 36.
Livermore, Potentiation of beta-lactams against Pseudomonas aeruginosa strains by Ro 48-1256, a bridged monobactam inhibitor of AmpC beta-lactamases, J. Med. Chem., 1997, 335-343, 40.
Neu, The Crisis in Antibiotic Resistance, Science, 1992, 1064-1073, 257.
Poole, Resistance to beta-lactam antibiotics, Cell. Mol. Life Sci., 2004, 2200-2223, 61.
PubChem-CID-91378958, Create Date: Mar. 17, 2015, p. 4, Fig.
Roberts et al., Hospital and societal costs of antimicrobial-resistant infections in a Chicago teaching hospital implications for antibiotic stewardship, Clinical Infectious Diseases, 2009, 1175-1184, 49.
Shen et al., Inhibitor Discovery of Full-Length New Delhi Metallo-Beta-Lactamase-1 (NDM-1), PLOS One, May 2013, pp. 1-7, vol. 8, Issue 5.

* cited by examiner

METALLO-BETA-LACTAMASE INHIBITORS AND METHODS OF USE THEREOF

CROSS REFERENCE TO RELATED APPLICATIONS

This application is the National Stage of International Application No. PCT/US2018/041721, filed Jul. 12, 2018 which claims priority to U.S. provisional Application No. 62/533,171 filed Jul. 17, 2017.

FIELD OF THE INVENTION

This invention relates to novel metallo-β-lactamase inhibitors and their uses. A preferred use of the metallo-β-lactamase inhibitors is for reducing bacterial beta-lactam antibiotic resistance.

BACKGROUND OF THE INVENTION

Bacterial antibiotic resistance has become one of the most serious threats to modern health care. Infections caused by resistant bacteria frequently result in longer hospital stays, higher mortality and increased cost of treatment. See, e.g., Cohen, *Science* 1992, 257:1051-1055. The need for new antibiotics will continue to escalate because bacteria have a remarkable ability to develop resistance to new agents, rendering them quickly ineffective. See, e.g., Neu, *Science* 1992, 257: 1064-1073. The spread of antibiotic resistance has been referred to as a pandemic. A solution to the growing public health threat will require an interdisciplinary approach. See, e.g., Anderson, *Nature America* 1999, 5: 147-149. See also Bush et al., *Nature Reviews in Microbiology* 2011, 9: 894-896; Levy and Marshall, *Nature Medicine* 2004, 10: S122S129; Livermore, *Clinical Infectious Diseases* 2003, 36: S11-S23; and Roberts et al., *Clinical infectious Diseases* 2009, 49: 1175-1184.

The present crisis has prompted various efforts to elucidate the mechanisms responsible for bacterial resistance. The widespread use of penicillins and cephalosporins has resulted in the emergence of β-lactamases, a family of bacterial enzymes that catalyze the hydrolysis of the β-lactam ring common to numerous presently used antibiotics. See, Coulton et al., *Progress in Medicinal Chemistry* 1994, 31: 297-349. This family of bacterial β-lactamases is further divided into four sub-families: A, C, and D families, which comprise β-lactamases that have a serine at the active site that catalyzes the hydrolysis of β-lactam antibiotics, and B family, which comprises β-lactamases that are zinc metalloenzymes. Resistance mediated by β-lactamases is a critical aspect at the core of the development of bacterial antibiotic resistance. See, Dudley, *Pharmacotherapy* 1995, 15: 9S-14S. Clavulanic acid, which is a metabolite of *Streptomyces clavuligerus*, and two semi-synthetic inhibitors, sulbactam and tazobactam, are currently available semi-synthetic or natural product β-lactamase inhibitors. Synthetic β-lactamase inhibitors have also been described. See, U.S. Pat. Nos. 5,698,577; 5,510,343; 6,472,406; Hubschwerlen et al., *J. Med. Chem.* 1998, 41: 3961; and Livermore et al., *J. Med. Chem.* 1997, 40: 335-343. Poole (*Cell. Mol. Life Sci.* 2004, 61: 2200-2223) provides a review of the resistance of bacterial pathogens to β-lactam antibiotics and approaches for overcoming resistance. For a review of inhibitors of metallo β-lactamases, see Fast and Sutton, *Biochimica et Biophysica Acta—Proteins and Proteomics* 2013, 1834(8): 1648-1659.

U.S. Patent Application Publication No. US 2003/0199541 discloses certain azabicyclic compounds including certain 7-oxo-6-diazabicyclic[3.2.1]octane-2-carboxamides and their use as anti-bacterial agents. U.S. Patent Application Publication No. US 2004/0157826 discloses heterobicyclic compounds including certain diazepine carboxamide and diazepine carboxylate derivatives and their use as antibacterials and β-lactamase inhibitors. International Patent Application Publication No. WO 2008/039420 discloses 7-oxo-2,6-diazabicyclo[3.2.0]heptane-6-sulfooxy-2-carboxamides and their use as β-lactamase inhibitors.

Zheng et at (*PLOS One* 2013, 8(5), e62955) disclose substituted 2,5-bis-tetrazolylmethyl-thiophenes and their use as β-lactamase inhibitors, Chinese Patent Application Publication No. CN103130686 A discloses N,N'-diarylureas and their use as inhibitors of metallo β-lactamases. Chinese Patent Application Publication No. CN103191091 A discloses substituted arylsulfonamides and their use as inhibitors of metallo β-lactamases.

U.S. Pat. Nos. 4,786,311; 4,746,353; 4,838,925; European Patent Application Publication Nos. EP204513; EP244166; and Chinese Patent Application Publication No. CN1095549A disclose substituted 2-(1H-tetrazol-5-yl)benzenesulfonamides and their use as herbicides.

International Patent Application Publication No, WO 2015/112441 discloses substituted 1H- and 2H-tetrazol-5-yl sulfonamide compounds as metallo β-lactamase inhibitors. WO 2016/210215 discloses 3-tetrazolyl-benzene-1,2-disulfonamide derivatives as metallo-lactamase inhibitors. WO 2016/210234 discloses additional compounds as metallo β-lactamase inhibitors.

SUMMARY OF THE INVENTION

The present invention is directed to substituted 1H- and 2H-tetrazol-5-yl sulfonamide and sulfone compounds and related compounds which are metallo-β-lactamase inhibitors. The compounds, and their pharmaceutically acceptable salts, are useful, for example, in combination with β-lactam antibiotics, and optionally serine β-lactamase inhibitors, for the treatment of bacterial infections, particularly antibiotic-resistant bacterial infections. More particularly, the present invention includes compounds of Formula I:

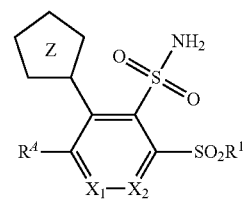

(I)

or a pharmaceutically acceptable salt thereof, wherein:
$X_1$ is N or CH;
$X_2$ is N or CH;
Z is tetrazolyl, wherein Z is linked through a carbon to carbon bond to the six-membered core ring having $X_1$ and $X_2$;
$R^A$ is:
1) HetA1;
2) —$NR^a(C_2)_n$-HetA2;
3) —$NR^a$—$C_1$-$C_6$alkyl optionally substituted with 1, 2, 3, or 4 substituents independently selected from: —F, —$CF_3$, $C_1$-$C_6$alkyl, —$CH(NH_2)C(O)NH_2$, —C(O)

NR$^a$R$^b$, —C(O)OH, —(CH$_2$)$_{1-2}$NH$_2$, —NR$^a$(CH$_2$)$_{2-3}$ NH$_2$, —NR$^a$(CH$_2$)$_{2-3}$OH, —NR$^a$R$^b$, —N$^+$R$^a$R$^b$CH$_3$, —NHCH$_2$CH$_2$OCH$_3$, —OR$^a$, and —O(CH$_2$)$_{2-3}$NH$_2$;

4) —NR$^a$—C$_4$-C$_6$cycloalkyl, or —NR$^a$—C$_4$-C$_6$cycloalkenyl, wherein said —NH—C$_4$-C$_6$cycloalkyl and —NH—C$_4$-C$_6$cycloalkenyl are optionally substituted with 1, 2, or 3 substituents, independently selected from —NH$_2$, —OH, —F, and —NR$^a$C(O)C$_1$-C$_6$alkyl optionally substituted with 1 or 2 substituents independently selected from —F, —CF$_3$, —NR$^a$R$^b$, and —OR$^a$; or 5) —NR$^a$AryA2;

R$^1$ is:
1) —NH$_2$;
2) —NR$^a$—C$_1$-C$_6$alkyl, optionally substituted with 1, 2, or 4 substituents independently selected from: —F, —CF$_3$, —CH(NH$_2$)C(O)NH$_2$, —C(O)NR$^a$R$^b$, —C(O)OH, —(CH$_2$)$_{1-2}$NH$_2$, —NR$^a$(CH$_2$)$_{2-3}$NH$_2$, —NR$^a$R$^b$, —N$^+$R$^a$R$^b$, —NHCH$_2$CH$_2$OCH$_3$, —OR$^a$, and —O(CH$_2$)$_{2-3}$NH$_2$;
3) —C$_1$-C$_6$alkyl, optionally substituted with 1, 2, or 3 substituents independently selected from: —F, —CF$_3$, —C$_1$-C$_6$alkyl, —CH(NH$_2$)C(O)NH$_2$, —C(O)NR$^a$R$^b$, —C(O)OH, —(CH$_2$)$_{1-2}$NH$_2$, —NR$^a$(CH$_2$)$_{2-3}$NH$_2$, —NR$^a$R$^b$, N$^+$R$^a$R$^b$CH$_3$, —NHCH$_2$CH$_2$OCH$_3$, —OR$^a$, and —O(CH$_2$)$_{2-3}$NH$_2$;
4) —NR$^a$C(O)C$_1$-C$_6$alkyl optionally substituted with 1 or 2 substituents independently selected from: —F, —CF$_3$, —C(O)NR$^a$R$^b$—C(O)OH, —NR$^a$R$^b$, —NR$^a$R$^b$, —N$^+$R$^a$R$^b$CH$_3$, —NHCH$_2$CH$_2$OCH$_3$, —OR$^a$ and —O(CH$_2$)$_{2-3}$NH$_2$;
5) —NR$^a$(CH$_2$)$_n$—C$_3$-C$_6$cycloalkyl, wherein the C$_3$-C$_6$cycloalkyl is optionally substituted with —CH$_2$OH, —OH or —NH$_2$;
6) —NR$^a$—(CH$_2$)$_n$-AryB1, wherein the —(CH$_2$)$_n$— is optionally substituted with —NH$_2$;
7) —NR$^a$—(CH$_2$)$_n$-HetB1; and
8) Het1;

HetA1 is:
1) a nitrogen-linked 4-7 membered monocyclic heterocycloalkyl with 0, 1, or 2, additional heteroatom ring atoms independently selected from N, O and S,
2) a nitrogen-linked 4-7 membered monocyclic heterocycloalkenyl with 0, 1, or 2, additional heteroatom ring atoms independently selected from N, O and S,
3) a nitrogen-linked 6- to 12-membered bicyclic heterocycloalkyl with 0, 1, 2, or 3 additional heteroatom ring atoms selected from N, O and S wherein the bicyclic ring may be bridged, fused or spirocyclic, or
4) a nitrogen-linked 6- to 12-membered bicyclic heterocycloalkenyl with 0, 1, 2, or 3 additional heteroatom ring atoms selected from N, O and S wherein the bicyclic ring may be bridged, fused or spirocyclic, wherein the nitrogen-linked 4-7 membered monocyclic, heterocycloalkyl, the nitrogen-linked 4-7 membered monocyclic heterocycloalkenyl, the nitrogen-linked 6- to 12-membered bicyclic heterocycloalkyl and the nitrogen-linked 6- to 12-membered bicyclic heterocycloalkenyl are optionally substituted with one to three substituents, independently selected from:
a) halogen
b) —(CH$_2$)$_n$NR$^a$R$^b$,
c) oxo,
d) =S
e) =N—OH
f) —OR$^a$,
g) —O(CH$_2$)$_{1-3}$OH,
h) —(CH$_2$)$_p$O(CH$_2$)$_p$NH$_1$,
i) —(CH$_2$)$_n$SO$_2$CH$_3$,
j) —SO$_2$NH$_2$,
k) —SO$_2$NH(CH$_2$)$_{1-2}$OH,
l) —SO$_2$NH(CH$_2$)$_{1-2}$NH$_2$,
m) —(CH$_2$)$_n$NH(CH$_2$)$_{1-2}$OH,
n) —NHC(O)C$_1$-C$_6$alkyl,
o) —C(=O)NH(CH$_2$)$_{1-3}$OH,
p) —C(=O)(CH$_2$)$_p$NH$_2$,
q) —C(=O)(CH$_2$)$_{1-3}$OH,
r) —(CH$_2$)$_n$C(=O)NH$_2$,
s) —(CH$_2$)$_n$C(=O)OH,
t) —C(=O)OCH$_3$,
u) —(CH$_2$)$_p$AryA2
v) —O-AryA2,
w) HetA2,
x) —C$_1$-C$_6$ alkyl, and
y) —C$_1$-C$_6$alkenyl;

wherein the C$_1$-C$_6$ alkyl and the —C$_1$-C$_6$ alkenyl are optionally substituted with one to three substituents independently selected from: —OH, —CH$_2$OH, —F, NR$^a$R$^b$, —C$_1$-C$_6$alkyl, oxo, AryA2;

AryA2 is a 5-6-membered aromatic monocyclic ring with 1, 2, or 3 heteroatom ring atoms independently selected from N and S, or 4 N ring atoms, optionally substituted with —CH$_2$OH, —COOH, —CONH$_2$, —C(O)OC$_1$-C$_6$alkyl and —(CH$_2$)$_p$NHR$^a$, wherein the —C(O)OC$_1$-C$_6$alkyl and the —(CH$_2$)$_p$NHR$^a$ are optionally substituted with one or two substituents independently selected from NR$^a$R$^b$ and —OR$^a$;

HetA2 is a 4-6-membered saturated monocyclic ring with 1 or 2 heteroatom ring atoms independently selected from N, O and S, wherein the ring is optionally substituted with 1 or 2 substituents independently selected from C$_1$-C$_6$alkyl, —CN, —OH, —NH$_2$ and —CH$_2$OH and oxo;

AryB1 is a 5-6 membered monocyclic aromatic ring with 0, 1, 2, or 3 N ring atoms, optionally substituted with 1 substituent selected from —CF$_3$, —C$_1$-C$_6$ alkyl, —(CH$_2$)$_n$NH$_2$ and —OCH$_3$;

HetB1 is a saturated ring selected from:
1) a 4-6 membered monocyclic ring with 1 or 2 heteroatom ring atoms independently selected from N, O and S, wherein a N ring atom is optionally in the form of a quaternary amine, and wherein the ring is optionally substituted with 1 or 2 substituents independently selected from —F, —C$_1$-C$_6$ alkyl, —C$_1$-C$_6$ hydroxyalkyl, —C(O)OR$^a$, —(CH$_2$)$_k$NR$^a$R$^b$, —OR$^a$, and oxo; or
2) a 6-10-membered bicyclic ring with 1 or 2 heteroatom ring atoms independently selected from N and O, optionally substituted with —OH or —NH$_2$, wherein the bicyclic ring is bridged or fused;

R$^a$ and R$^b$ are independently H or —C$_1$-C$_6$ alkyl;
k is 0, 1, 2, 3, or 4;
each n is independently 0, 1, or 2; and
each p is independently 0, 1, 2, or 3.

Compounds of Formula I inhibit metallo-β lactamases and can synergize the antibacterial effects of β lactam antibiotics (e.g., imipenem, ceftazidime, ceftolozane, and piperacillin) against microorganisms normally resistant to β lactam antibiotics as a result of the presence of the metallo-β lactamases. Compounds of the present invention are effective against metallo-β lactamases and their combination with a β-lactam antibiotic, such as imipenem, ceftazidime, ceftolozane, or piperacillin, can provide effective treatment of bacterial infections caused by metallo-β lactamase-producing microorganisms. Accordingly, in certain embodiments, the present invention provides compositions comprising a compound of Formula I, IA, IB, IC, ID or IE with a β-lactam antibiotic, and optionally one or more additional β-lactamase inhibitors, suitable for use against metallo-β lactamase producing bacteria such as *Pseudomonas* spp. and *Klebsiella* spp. In some embodiments, the additional one or more β-lactamase inhibitor(s) is a serine (Class A, C and D) β-lactamase inhibitor. The invention also includes compositions comprising a compound of Formula I I, IA, IB, IC, ID or IE or a pharmaceutically acceptable salt thereof, and a pharmaceutically acceptable carrier. The invention further includes methods for treating bacterial infections and inhibiting bacterial growth by administration of a compound of Formula I, IA, IB, IC, ID or IE, or a pharmaceutically acceptable salt thereof, to a patient in need thereof, or by administration of a pharmaceutical composition comprising a compound of Formula I, IA, IB, IC, ID or IE or its salt and a pharmaceutically acceptable carrier.

Embodiments, sub-embodiments, aspects and features of the present invention are either further described in or will be apparent from the ensuing description, examples and appended claims.

DETAILED DESCRIPTION OF THE INVENTION

As noted above, the present invention includes compounds of Formula I, IA, IB, IC, ID or IE, wherein the compounds are metallo-β-lactamase inhibitors suitable for use in combination with β-lactam antibiotics and optionally class A, C, and/or D β-lactamase inhibitors for the treatment of bacterial infections.

The invention is based, in part, on the presence of a sulfur linker at the 6-position of the core ring as a sulfone or sulfonamide. The presence of a sulfur at this position results in improved enzyme potency compared to when the linker is carbon and also provides improved activity on difficult to penetrate *Pseudomonas* bacterial strains. The improved Pseudomonal activity is likely due to a decrease in efflux from the cells as a result of the sulfone or sulfonamide linker.

In each of the various embodiments of the compounds of the invention described herein, each variable including those of Formulas I, IA, IB, IC, ID or IE and the various embodiments thereof, is selected independently of the other variables unless otherwise indicated.

The present invention encompasses for each of the various embodiments of the compounds of the invention described herein, including those of Formulas I, IA, IB, IC, ID or IE, and the various embodiments thereof and the compounds of the examples, all forms of the compounds such as, for example, any solvates, hydrates, stereoisomers, and tautomers of said compounds and of any pharmaceutically acceptable salts thereof, unless otherwise indicated. Additionally, in the examples described herein, the compounds of the invention may be depicted in the salt form. In such cases, it is to be understood that the compounds of the invention include the free acid or free base forms of such salts, and any pharmaceutically acceptable salt of said free acid or free base forms. In addition, in instances where an acidic group such as tetrazole and a basic group such as an amine are present within the same compound, these compounds may be drawn herein for convenience as the free acid and base forms but it should be understood that these can also be alternatively depicted in their zwitterionic forms in which the tetrazole bears a negative charge and the amine bears a positive charge, which are also included as compounds of the invention.

The Compounds of Formula (I):

In one aspect, the present invention includes compounds of Formula I:

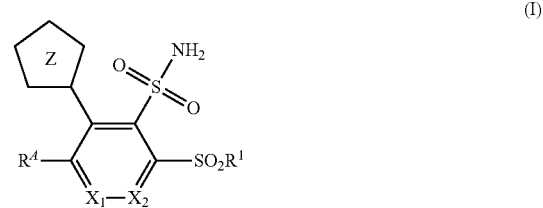

(I)

or a pharmaceutically acceptable salt thereof, wherein $X_1$, $X_2$, $Z$, $R^A$ and $R^1$ are as defined herein for the Compounds of Formula (I) (i.e. as defined in the Summary of the Invention); wherein the compounds may be suitable for use for the treatment of bacterial infections.

A first embodiment of the invention (Embodiment E1) is a compound of Formula I, or a pharmaceutically acceptable salt thereof, wherein $X_1$, $X_2$, $Z$, $R^A$ and $R^1$ are as defined in Formula (I) in the Summary of the Invention.

A second embodiment (Embodiment E2) is a compound of Formula I, or a pharmaceutically acceptable salt thereof, wherein $X_1$ is CH, and all other variables are as defined in Embodiment E1.

A third embodiment (Embodiment E3) is a compound of Formula I, or a pharmaceutically acceptable salt thereof, wherein $X_1$ is N, and all other variables are as defined in Embodiment E1.

A fourth embodiment (Embodiment E4) is a compound of Formula I, or a pharmaceutically acceptable salt thereof, wherein $X_1$ is defined in Embodiment E2 or E3, $X_2$ is CH, and all other variables are as defined in Embodiment E1.

A fifth embodiment (Embodiment E5) is a compound of Formula I, or a pharmaceutically acceptable salt thereof, wherein $X_1$ is defined in Embodiment E2 or E3, $X_2$ is N, and all other variables are as defined in Embodiment E1.

A sixth embodiment (Embodiment E6) is a compound of Formula I, or a pharmaceutically acceptable salt thereof, wherein $X_1$ is defined in Embodiment E2 or E3, $X_2$ is defined in Embodiment E4 or E5, $R^A$ is HetA1 and all other variables are as defined in Embodiment E1.

A seventh embodiment (Embodiment E7) is a compound of Formula I, or a pharmaceutically acceptable salt thereof, wherein $X_1$ is defined in Embodiment E2 or E3, $X_2$ is defined in Embodiment E4 or E5, $R^A$ is —NR$^a$(CH$_2$)$_n$-HetA2, and all other variables are as defined in Embodiment E1.

An eighth embodiment (Embodiment E5) is a compound of Formula I, or a pharmaceutically acceptable salt thereof, wherein $X_1$ is defined in Embodiment E2 or E3, $X_2$ is defined in Embodiment E4 or E5, $R^A$ is —NR$^a$C$_1$-C$_6$alkyl, optionally substituted with 1, 2, 3, or 4 substituents independently selected from: —F, —CF$_3$, —CH(NH$_2$)C(O)NH$_2$, —C(O)NR$^a$R$^b$, —C(O)OH, —(CH$_2$)$_{1-2}$NH$_2$, —NR$^a$(CH$_2$)$_{2-3}$NH$_2$, —NR$^a$(CH$_2$)$_{2-3}$OH, —NR$^a$R$^b$, —N$^+$R$^a$R$^b$CH$_3$, —NHCH$_2$CH$_2$OCH$_3$, —OR$^3$, and —O(CH$_2$)$_{2-3}$NH$_2$, and all other variables are as defined in Embodiment E1.

In one sub-embodiment of Embodiment E8, —NR$^a$C$_1$-C$_6$alkyl is unsubstituted. In another sub-embodiment of Embodiment E8, —NR$^a$C$_1$-C$_6$alkyl is substituted with 1 substituent. In another sub-embodiment of Embodiment E8, —NR$^a$C$_1$-C$_6$alkyl is substituted with 2 substituents. In another sub-embodiment of Embodiment E8, —NR$^a$C$_1$-

$C_6$alkyl is substituted with 3 substituents. In another sub-embodiment of Embodiment E8, —$NR^aC_1$-$C_6$alkyl is substituted with 4 substituents.

A ninth embodiment (Embodiment E9) is a compound of Formula I, or a pharmaceutically acceptable salt thereof, wherein $X_1$ is defined in Embodiment E2 or E3, $X_2$ is defined in Embodiment E4 or E5, $R^A$ is —$NR^a$—$C_4$-$C_6$cycloalkyl, or —$NR^a$—$C_4$-$C_6$cycloalkenyl, wherein said —NH—$C_4$-$C_6$cycloalkyl and NH—$C_4$-$C_6$cycloalkenyl are optionally substituted with 1, 2, or 3 substituents, independently selected from —$NH_2$, —OH, —F, and —$NR^aC(O)$ $C_1$-$C_6$alkyl optionally substituted with 1 or 2 substituents independently selected from —F, —$CF_3$, —$NR^aR^b$, and —$OR^a$ and all other variables are as defined in Embodiment E1.

A tenth embodiment (Embodiment E10) is a compound of Formula I, or a pharmaceutically acceptable salt thereof, wherein $X_1$ is defined in Embodiment E2 or E3, $X_2$ is defined in Embodiment E4 or E5, $R^A$ is —$R^a$AryA2 and all other variables are as defined in Embodiment E1.

An eleventh embodiment (Embodiment E11) is a compound of Formula I, or a pharmaceutically acceptable salt thereof, wherein $X_1$ is defined in Embodiment E2 or E3, $X_2$ is defined in Embodiment E4 or E5, $R^A$ is a nitrogen-linked 4- to 7-membered monocyclic heterocycloalkyl with 0, 1, or 2 additional heteroatom ring atoms independently selected from N, O and S, optionally substituted as set forth in Formula (I) in the Summary of the Invention, and all other variables are as defined in Embodiment E1.

A twelfth embodiment (Embodiment E12) is a compound of Formula I, or a pharmaceutically acceptable salt thereof, wherein $X_1$ is defined in Embodiment E2 or E3, $X_2$ is defined in Embodiment E4 or E5, $R^A$ is a nitrogen-linked 4- to 7-membered monocyclic heterocycloalkenyl with 0, 1, or 2 additional heteroatom ring atoms independently selected from N, O and S, optionally substituted as set forth in Formula (I) in the Summary of the Invention, and all variables are as defined in Embodiment E1.

A thirteenth embodiment (Embodiment E13) is a compound of Formula I, or a pharmaceutically acceptable salt thereof, wherein $X_1$ is defined in Embodiment E2 or E3, $X_2$ is defined in Embodiment E4 or E5, $R^A$ is a nitrogen-linked 6- to 12-membered bicyclic heterocycloalkyl with 0, 1, 2, or 3 additional heteroatom ring atoms independently selected from N, O and S, wherein the bicyclic ring can be bridged, fused or spirocyclic, optionally substituted as set forth in Formula (I) in the Summary of the Invention, and all other variables are as defined in Embodiment E1.

A fourteenth embodiment (Embodiment E14) is a compound of Formula I, or a pharmaceutically acceptable salt thereof, wherein $X_1$ is defined in Embodiment E2 or E3, $X_2$ is defined in Embodiment E4 or E5, $R^A$ is a nitrogen-linked 6- to 12-membered bicyclic heterocycloalkenyl with 0, 1, 2, or 3 additional heteroatom ring atoms independently selected from N, O and S, wherein the bicyclic ring can be bridged, fused or spirocyclic, optionally substituted as set forth in Formula (I) in the Summary of the Invention, and all other variables are as defined in Embodiment E1.

A fifteenth embodiment (Embodiment E15) is a compound of Formula I, or a pharmaceutically acceptable salt thereof, wherein $X_1$ is defined in Embodiment E2 or E3, $X_2$ is defined in Embodiment E4 or E5, $R^A$ is selected from the group consisting of:

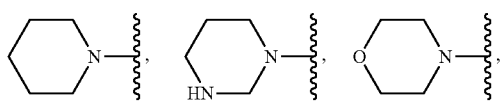

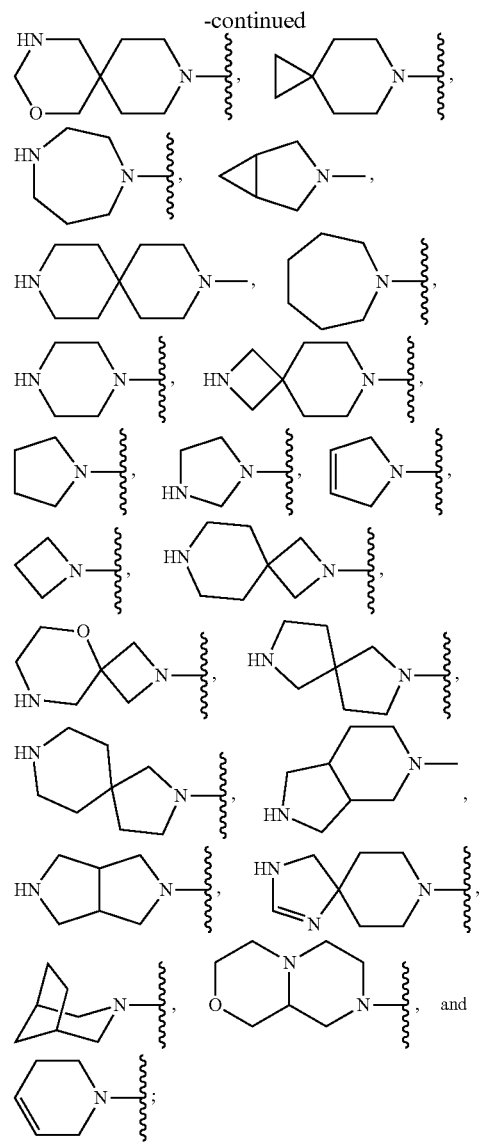

optionally substituted as set forth in Formula (I) in the Summary of the Invention, and all other variables are as defined in Embodiment E1.

In one sub-embodiment of Embodiment E15, $R^A$ is unsubstituted. In another sub-embodiment of Embodiment E15, $R^A$ is substituted with 1 substituent. In another sub-embodiment of Embodiment E15, $R^A$ is substituted with 2 substituents. In another sub-embodiment of Embodiment E15, $R^A$ is substituted with 3 substituents.

In one sub-embodiment of Embodiment E15, $R^A$ is substituted with at least one occurrence of —$NH_2$ and optionally additional substituents as set forth in Formula I in the Summary of the Invention.

In one sub-embodiment of Embodiment E15, $R^A$ is substituted with at least one occurrence of —OH and optionally additional substituents as set forth in Formula I in the Summary of the Invention. In a further sub-embodiment of Embodiment E15, $R^A$ is substituted with one occurrence of —OH and one occurrence of —$CH_3$. In another sub-embodiment of Embodiment E15, $R^A$ is substituted with two occurrences of —OH. In a further sub-embodiment of Embodiment E15, $R^A$ is substituted with one occurrence of —OH and one occurrence of —$N(CH_3)_2$.

In one sub-embodiment of Embodiment E15, $R^A$ is substituted with at least one occurrence of F and optionally additional substituents as set forth in Formula I in the Summary of the invention. In a further sub-embodiment of Embodiment E15, $R^A$ is substituted one occurrence of and one occurrence of —$NH_2$. In another sub-embodiment of Embodiment E15, $R^A$ is substituted one occurrence of and one occurrence of —$CH_2NH_2$.

In one sub-embodiment of Embodiment E15, $R^A$ is substituted with at least one occurrence of —$CH_3$ and optionally additional substituents as set forth in Formula I in the Summary of the Invention.

In one sub-embodiment of Embodiment E15, $R^A$ is substituted with at least one occurrence of —$(CH_2)_{1-3}NH_2$ or —$(CH_2)_{1-3}OH$ and optionally additional substituents as set forth in Formula I in the Summary of the Invention.

In one sub-embodiment of Embodiment E15, $R^A$ is substituted with at least one occurrence of —$OCH_3$ and optionally additional substituents as set forth in Formula I in the Summary of the Invention.

In one sub-embodiment of Embodiment E15, $R^A$ is substituted with at least one occurrence of —$O(CH_2)_{1-3}OH$ and optionally additional substituents as set forth in Formula I in the Summary of the Invention.

In one sub-embodiment of Embodiment E15, $R^A$ is substituted with at least one occurrence of —$O(CH_2)_{1-3}NH_2$ and optionally additional substituents as set forth in Formula I in the Summary of the Invention. In a further sub-embodiment of Embodiment E15, $R^A$ is substituted with at least one occurrence of —$CH_2O(CH_2)_{1-3}NH_2$.

In one sub-embodiment of Embodiment E15, R' is substituted with at least one occurrence of —$(CH_2)_{0-1}C(O)NH_2$ and optionally additional substituents as set forth in Formula I in the Summary of the Invention.

In one sub-embodiment of Embodiment E15, $R^A$ is substituted with at least one occurrence of =N—OH and optionally additional substituents as set forth in Formula I in the Summary of the Invention.

In one sub-embodiment of Embodiment E15, $R^A$ is substituted with at least one occurrence of =S and optionally additional substituents as set forth in Formula I in the Summary of the Invention.

In one sub-embodiment of Embodiment E15, $R^A$ is substituted with one occurrence of oxo and optionally additional substituents as set forth in Formula I in the Summary of the invention. In another sub-embodiment of Embodiment E15, $R^A$ is substituted with two occurrences of oxo. In a further sub-embodiment of Embodiment E15, $R^A$ is substituted with oxo and —$CH_3$. In a further sub-embodiment of Embodiment E15, $R^A$ is substituted with oxo and —OH. In a further sub-embodiment of Embodiment E15, $R^A$ is substituted with oxo and —$NH_2$. In a further sub-embodiment of Embodiment E15, $R^A$ is substituted with oxo and $(CH_2)_{1-2}OH$. In a further sub-embodiment of Embodiment E15, $R^A$ is substituted with oxo and $(CH_2)_{1-2}NH_2$ in a further sub-embodiment of Embodiment E15, $R^A$ is substituted with oxo and —$ONH_2$. In a further sub-embodiment of Embodiment E15, $R^A$ is substituted with oxo and —$CH_3$.

In one sub-embodiment of Embodiment E15, $R^A$ is substituted with at least one occurrence of —$CH(NH_2)CH_3$ and optionally additional substituents as set forth in Formula I in the Summary of the Invention.

In one sub-embodiment of Embodiment E15, $R^A$ is substituted with at least one occurrence of —$(CH_2)_{0-1}N(CH_3)_2$ and optionally additional substituents as set forth in Formula I in the Summary of the Invention.

In one sub-embodiment of Embodiment E15, $R^A$ is substituted with at least one occurrence of —$CH_2NHCH_3$ and optionally additional substituents as set forth in Formula I in the Summary of the Invention. In a further sub-embodiment of Embodiment E15, $R^A$ is substituted with at least one occurrence of —$CH_2NH(CH_2)_{1-2}OH$. In a further sub-embodiment of Embodiment E15, $R^A$ is substituted with at least one occurrence of —$NH(CH_2)_{1-2}OH$.

In one sub-embodiment of Embodiment E15, $R^A$ is substituted with at least one occurrence of —$C(O)NHCH_3$ and optionally additional substituents as set forth in Formula I in the Summary of the Invention. In a further sub-embodiment of Embodiment E15, $R^A$ is substituted with at least one occurrence of —$C(O)NH(CH_2)_{1-3}OH$.

In one sub-embodiment of Embodiment E15, $R^A$ is substituted with at least one occurrence of —$SO_2NH_2$ and optionally additional substituents as set forth in Formula I in the Summary of the Invention. In a further sub-embodiment of Embodiment E15, $R^A$ is substituted with at least one occurrence of —$SO_2NH(CH_2)_{1-2}NH_2$.

In one sub-embodiment of Embodiment E15, $R^A$ is substituted with at least one occurrence of —$NHC(O)CH_3$ and optionally additional substituents as set forth in Formula I in the Summary of the Invention.

In one sub-embodiment of Embodiment E15, $R^A$ is substituted with at least one occurrence of =$CHCH_2NH_2$ and optionally additional substituents as set forth in Formula I in the Summary of the Invention.

In one sub-embodiment of Embodiment E15, $R^A$ is substituted with at least one occurrence of —$(CH_2)_{1-3}F$ and optionally additional substituents as set forth in Formula I in the Summary of the Invention.

In one sub-embodiment of Embodiment E15, $R^A$ is substituted with at least one occurrence of —$CHF_2$ and optionally additional substituents as set forth in Formula I in the Summary of the Invention.

In one sub-embodiment of Embodiment E15, $R^A$ is substituted with —$(CH_2)_p$AryA2 and optionally additional substituents as set forth in Formula I in the Summary of the Invention. In a further sub-embodiment of Embodiment E15, $R^A$ is substituted with —O-AryA2.

In one sub-embodiment of Embodiment E15, $R^A$ is substituted with a 3-6-membered saturated monocyclic ring with 1 or 2 heteroatom ring atoms independently selected from N, O and S, wherein the ring is optionally substituted with 1 or 2 substituents independently selected from —$C_1$-$C_6$alkyl, —CN, —OH, —$NH_2$ and —$CH_2OH$ and oxo, and optionally additional substituents as set forth in Formula I in the Summary of the Invention.

A sixteenth embodiment (Embodiment E16) is a compound of Formula I, or a pharmaceutically acceptable salt thereof, wherein $X_1$ is defined in Embodiment E2 or E3, $X_2$ is defined in Embodiment E4 or E5, $R^A$ is:

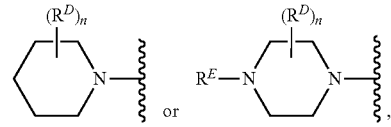

wherein:
$R^D$ is —$NR^aR^b$, —F, —$C_1$-$C_6$alkyl-$NH_2$, —$C_1$-$C_6$alkyl-OH, wherein the —$C_1$-$C_6$alkyl-$NH_2$, and the —$C_1$-$C_6$alkyl-OH are optionally substituted with one or two substituents, independently selected from: —OH, —$CH_2OH$, —F, —NH₂, or C₁-C₃ alkyl; R^E is H, or C₁-C₆alkyl-OH, or C₁-C₆alkyl-NH₂; and each n is independently 0, 1, or 2; and all other variables are as defined in Embodiment E1.

A seventeenth embodiment (Embodiment E17) is a compound of Formula I, or a pharmaceutically acceptable salt thereof, wherein X₁ is defined in Embodiment E2 or E3, X₂ is defined in Embodiment E4 or E5, R^A is:

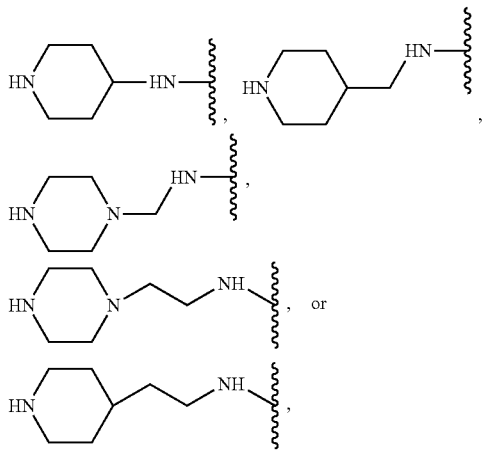

and all other variables are as defined in Embodiment E1.

An eighteenth embodiment (Embodiment E18) is a compound of Formula I, or a pharmaceutically acceptable salt thereof, wherein X₁ is defined in Embodiment E2 or E3, X₂ is defined in Embodiment E4 or E5. R^A is:

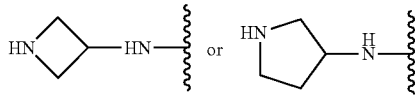

and all other variables are as defined in Embodiment E1.

A nineteenth embodiment (Embodiment E19) is a compound of Formula I, or a pharmaceutically acceptable salt thereof, wherein X₁ is defined in Embodiment E2 or E3, X₂ is defined in Embodiment E4 or E5, R^A is:

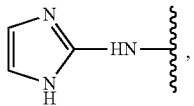

and all other variables are as defined in Embodiment E1.

A twentieth embodiment (Embodiment E20) is a compound of Formula I, or a pharmaceutically acceptable salt thereof, wherein X₁ is defined in Embodiment E2 or E3, X₂ is defined in Embodiment E4 or E5, R^A is:

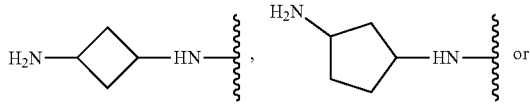

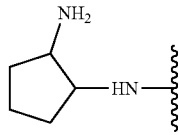

and all other variables are as defined in Embodiment E1.

A twenty-first embodiment (Embodiment E21) is a compound of Formula I, or a pharmaceutically acceptable salt thereof, wherein X₁ is defined in Embodiment E2 or E3, X₂ is defined in Embodiment E4 or E5, R^A is:

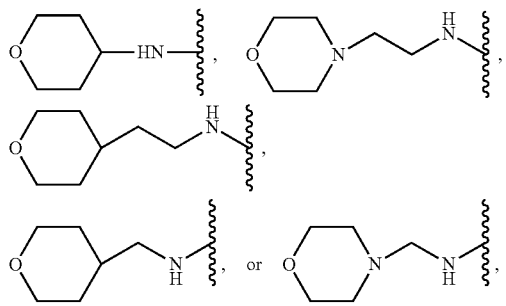

and all other variables are as defined in Embodiment E1.

A twenty-second embodiment (Embodiment E22) is a compound of Formula I, or a pharmaceutically acceptable salt thereof, wherein X₁ is defined in Embodiment E2 or E3, X₂ is defined in Embodiment E4 or E5, R^A is —NH(CH₂)₁₋₄N⁺(CH₃)₃, and all other variables are as defined in Embodiment E1.

A twenty-third embodiment (Embodiment E23) is a compound of Formula I, or a pharmaceutically acceptable salt thereof, wherein X₁ is defined in Embodiment E2 or E3, X₂ is defined in Embodiment E4 or E5, R^A is —N(CH₃)(CH₂)₂N(CH₃)(CH₂)₂OH; and all other variables are as defined in Embodiment E1.

A twenty-fourth embodiment (Embodiment E24) is a compound of Formula I, or a pharmaceutically acceptable salt thereof, wherein X₁ is defined in Embodiment E2 or E3, X₂ is defined in Embodiment E4 or E5, R^A is defined in any of Embodiments E6-E23, R¹ is NH₂ and all other variables are as defined in Embodiment E1.

A twenty-fifth embodiment (Embodiment E25) is a compound of Formula I, or a pharmaceutically acceptable salt thereof, wherein X₁ is defined in Embodiment E2 or E3, X₂ is defined in Embodiment E4 or E5, R^A is defined in any of Embodiments E6-E23, R¹ is —NR^a—C₁-C₆alkyl, optionally substituted with 1, 2, 3, or 4 substituents independently selected from: —F, —CF₃, —C₁-C₆-alkyl, —CH(NH₂)C(O)NH₂, —C(O)NR^aR^b, —C(O)OH, —(CH₂)₁₋₂NH₂, —NR^a(CH₂)₂₋₃NH₂, —NR^aR^b, —N⁺R^aR^bCH₃, —NHCH₂CH₂OCH₃, —OR^a, and —O(CH₂)₂₋₃NH₂, and all other variables are as defined in Embodiment E1.

A twenty-sixth embodiment (Embodiment E26) is a compound of Formula I, or a pharmaceutically acceptable salt thereof, wherein X₁ is defined in Embodiment E2 or E3, X₂ is defined in Embodiment E4 or E5, R^A is defined in any of Embodiments E6-E23, R¹ is —C₁-C₆alkyl, optionally substituted with 1, 2, or 3 substituents independently selected from: —F, —CF₃, —C₁-C₆alkyl, —CH(NH₂)C(O)NH₂, —C(O)NR^aR^b, —C(O)OH, —(CH₂)₁₋₂NH₂, —NR^a(CH₂)₂₋₃NH₂, —NR^aR^b, —N⁺R^aR^bCH₃, —NHCH$_2$CH$_2$OCH$_3$, —OR$^a$, and —O(CH$_2$)$_{2-3}$NH$_2$, and all other variables are as defined in Embodiment E1.

A twenty-seventh embodiment (Embodiment E27) is a compound of Formula I, or a pharmaceutically acceptable salt thereof, wherein X$_1$ is defined in Embodiment E2 or E3, X$_2$ is defined in Embodiment E4 or E5, R$^A$ is defined in any of Embodiments E6-E23, R$^1$ is —NR$^a$C(O)C$_1$-C$_6$alkyl optionally substituted with 1 or 2 substituents independently selected from: —F, —CF$_3$, —C(O)NR$^a$R$^b$, —C(O)OH, —NR$^a$R$^b$, —N$^+$R$^a$R$^b$CH$_3$, —NHCH$_2$CH$_2$CH$_3$, —OR$^a$, and —O(CH$_2$)$_{2-3}$NH$_2$, and all other variables are as defined in Embodiment E1.

A twenty-eighth embodiment (Embodiment E28) is a compound of Formula I, or a pharmaceutically acceptable salt thereof, wherein X$_1$ is defined in Embodiment E2 or E3, X$_2$ is defined in Embodiment E4 or E5, R$^A$ is defined in any of Embodiments E6-E23, R$^1$ is —NR$^a$(CH$_a$)$_n$—C$_3$-C$_6$cycloalkyl, wherein the C$_3$-C$_6$cycloalkyl is optionally substituted with —CH$_2$OH, —OH or —NH$_2$, and all other variables are as defined in Embodiment E1.

A twenty-ninth embodiment (Embodiment E29) is a compound of Formula I, or a pharmaceutically acceptable salt thereof, wherein X$_1$ is defined in Embodiment E2 or E3, X$_2$ is defined in Embodiment E4 or E5, R$^A$ is defined in any of Embodiments E6-E23, R$^1$ is —NR$^a$—(CH$_2$)$_n$-AryB1, wherein the —(CH$_2$)$_n$— is optionally substituted with —NH$_2$, and all other variables are as defined in Embodiment E1.

A thirtieth embodiment (Embodiment E30) is a compound of Formula I, or a pharmaceutically acceptable salt thereof, wherein X$_1$ is defined in Embodiment E2 or E3, X$_2$ is defined in Embodiment E4 or E5, R$^A$ is defined in any of Embodiments E6-E23, R$^1$ is —NR$^a$—(CH$_2$)$_n$-HetB1, and all other variables are as defined in Embodiment E1.

A thirty-first embodiment (Embodiment E31) is a compound of Formula I, or a pharmaceutically acceptable salt thereof, wherein X$_1$ is defined in Embodiment E2 or E3, X$_2$ is defined in Embodiment E4 or E5, R$^A$ is defined in any of Embodiments E6-E23, R$^1$ is HetB1, and all other variables are as defined in Embodiment E1.

A thirty-second embodiment (Embodiment E32) is a compound of Formula I, or a pharmaceutically acceptable salt thereof, wherein X$_1$ is defined in Embodiment E2 or E3, X$_2$ is defined in Embodiment E4 or E5, R$^A$ is defined in any of Embodiments E6-E23, R$^1$ is:

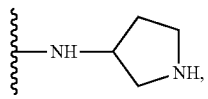 [SMILES: *NC1CCNC1]

and all other variables are as defined in Embodiment E1.

A thirty-third embodiment (Embodiment E33) is a compound of Formula I, or a pharmaceutically acceptable salt thereof, wherein X$_1$ is defined in Embodiment E2 or E3, X$_2$ is defined in Embodiment E4 or E5, R$^A$ is defined in any of Embodiments E6-E23, R$^1$ is:

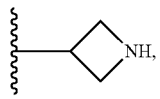 [SMILES: *C1CNC1]

and all other variables are as defined in Embodiment E1.

A thirty-fourth embodiment (Embodiment E34) is a compound of Formula I, or a pharmaceutically acceptable salt thereof, wherein X$_1$ is defined in Embodiment E2 or E3, X$_2$ is defined in Embodiment E4 or E5, R$^A$ is defined in any of Embodiments E6-E23, R$^1$ is —NH-A-NH$_2$, wherein A is —C$_1$-C$_4$alkyl, optionally substituted with —OR$^a$, —NR$^a$R$^b$, —CH$_2$NH$_2$, —CH$_2$OH, or C$_1$-C$_3$ alkyl, and all other variables are as defined in Embodiment E1.

A thirty-fifth embodiment (Embodiment E35) is a compound of Formula I, or a pharmaceutically acceptable salt thereof, wherein X$_1$ is defined in Embodiment E2 or E3, X$_2$ is defined in Embodiment E4 or E5, R$^A$ is defined in any of Embodiments E6-E23, R$^1$ is -A-NH$_2$, wherein A is —C$_1$-C$_4$alkyl-, optionally substituted with —OR$^a$, —NR$^a$R$^b$, —CH$_2$NH$_2$, —CH$_2$OH, or C$_1$-C$_3$ alkyl, and all other variables are as defined in Embodiment E1.

A thirty-sixth embodiment (Embodiment E36) is a compound of Formula I, or a pharmaceutically acceptable salt thereof, wherein X$_1$ is defined in Embodiment E2 or E3, X$_2$ is defined in Embodiment E4 or E5, R$^A$ is defined in any of Embodiments E6-E23, R$^1$ is —NH(C$_1$-C$_4$alkyl)NH$_2$, optionally substituted with —OH, —CH$_3$ or —CH$_2$OH, all other variables are as defined in Embodiment E1.

A thirty-seventh embodiment (Embodiment E37) is a compound of Formula I, or a pharmaceutically acceptable salt thereof, having the Formula:

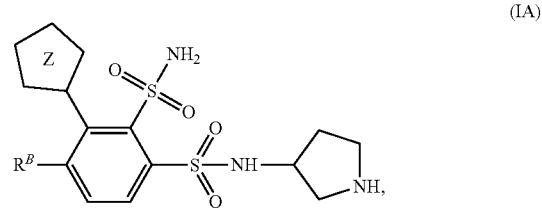
(IA)

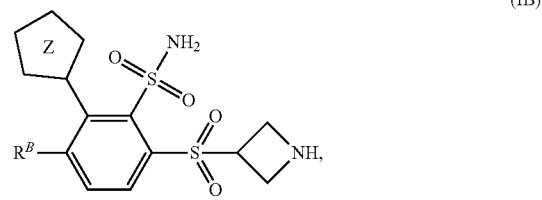
(IB)

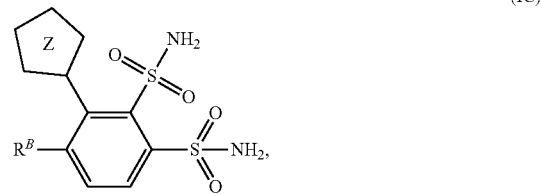
(IC)

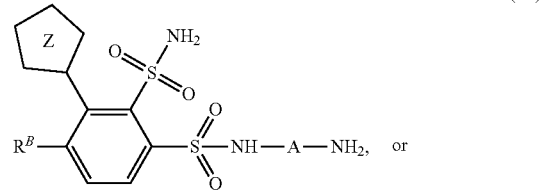
(ID)

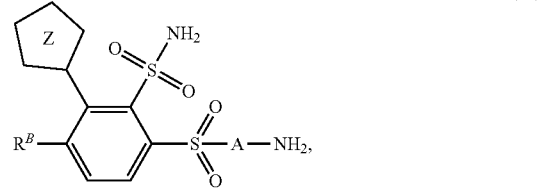
(IE)

wherein: A is —$C_1$-$C_4$alkyl, optionally substituted with —$OR^a$, —$NR^aR^b$, —$CH_2NH_2$, —$CH_2OH$, or $C_1$-$C_3$ alkyl; and $R^b$ is HetA1, optionally substituted as set forth in Formula I of the Summary of the Invention and all other variables are as defined in Embodiment E1.

A thirty-eighth embodiment of the invention (Embodiment E38) is: (1) a compound having a structure of any of the compounds numbered 1-209 in the Examples herein, (2) the free acid or free base base form (when a basic amine group is present) of any compound numbered 1-209 herein that is depicted as a salt, (3) the zwitterionic form of any of compounds 1-209 which contains a basic amine group, wherein the tetrazole bears a negative charge and the amine group bears a positive charge, or (4) a pharmaceutically acceptable salt of the compounds described in (1), (2), and/or (3).

A thirty-ninth embodiment of the invention (Embodiment E39) is a compound having the structure:

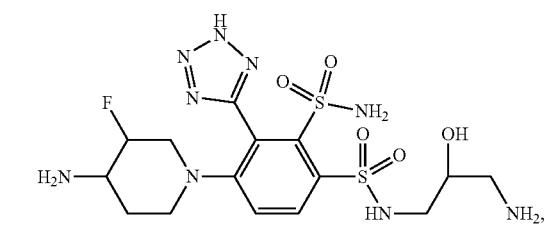

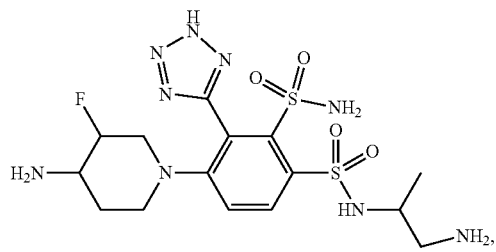

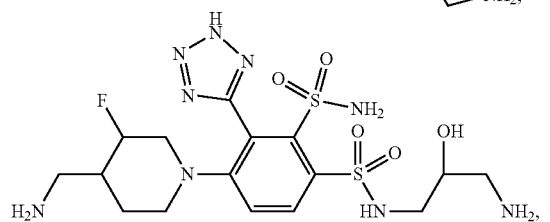


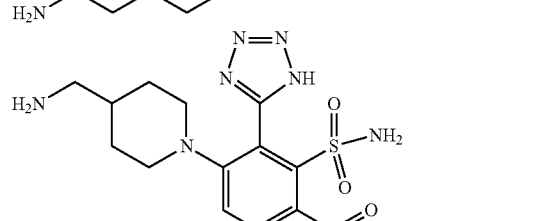

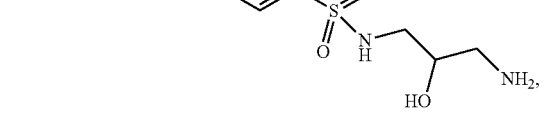

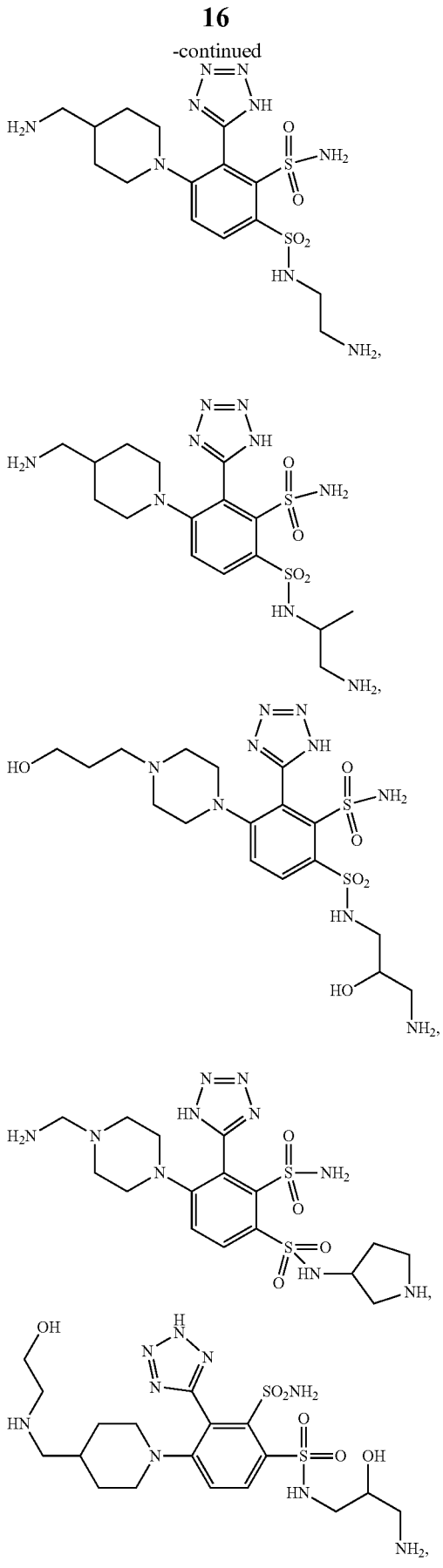

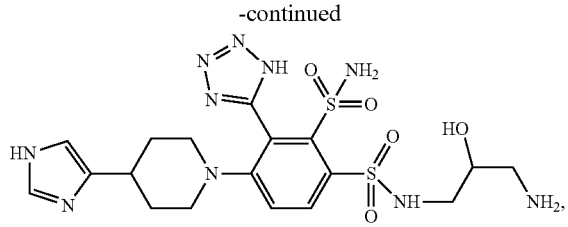
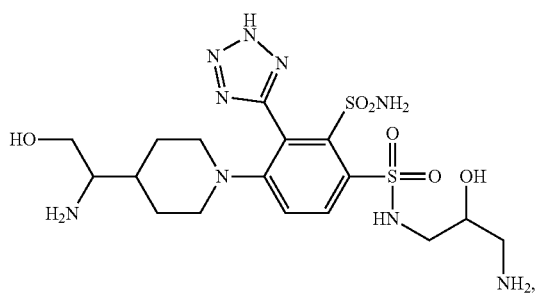
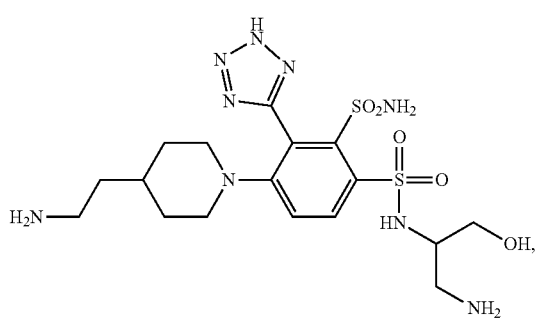
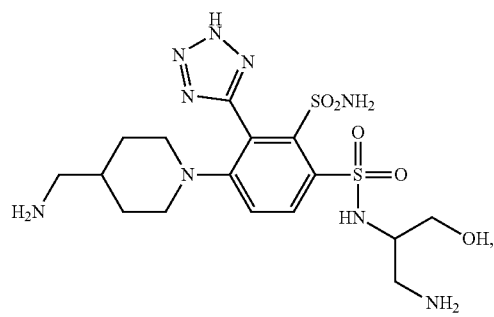
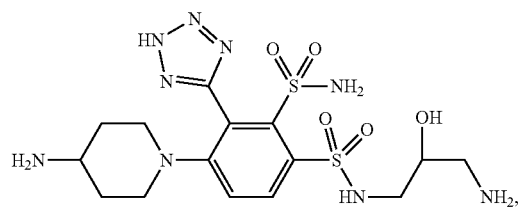
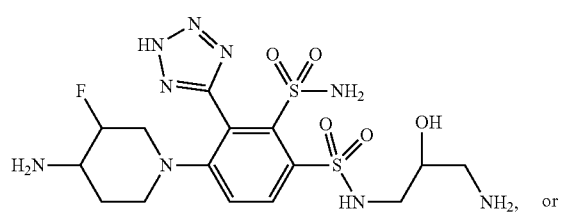
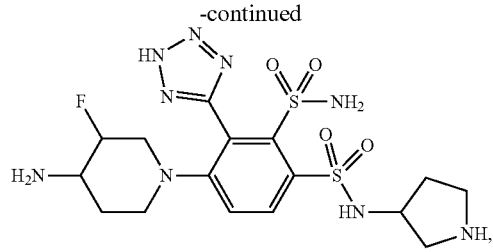
or a pharmaceutically acceptable salt thereof.
A fortieth embodiment of the invention (Embodiment E40) is a compound having the structure:
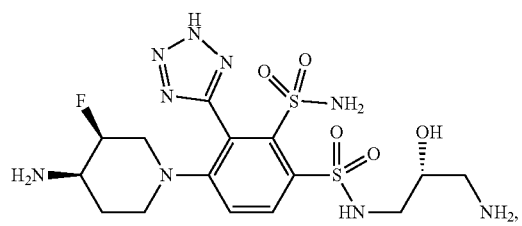
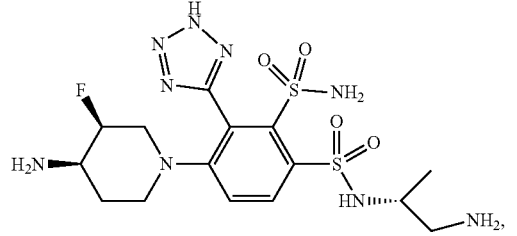
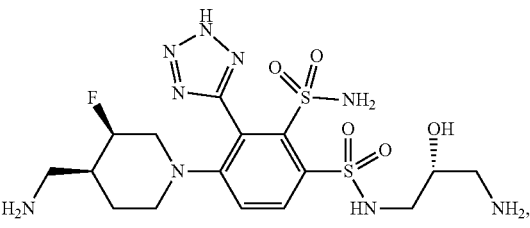
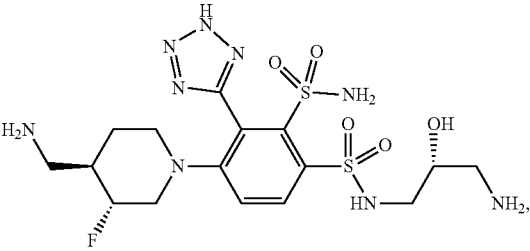
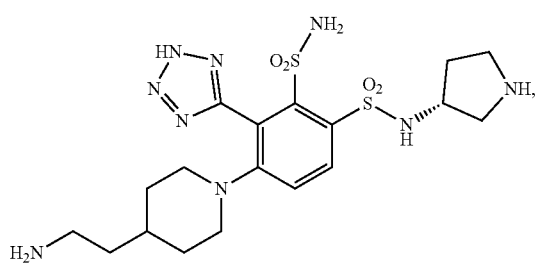

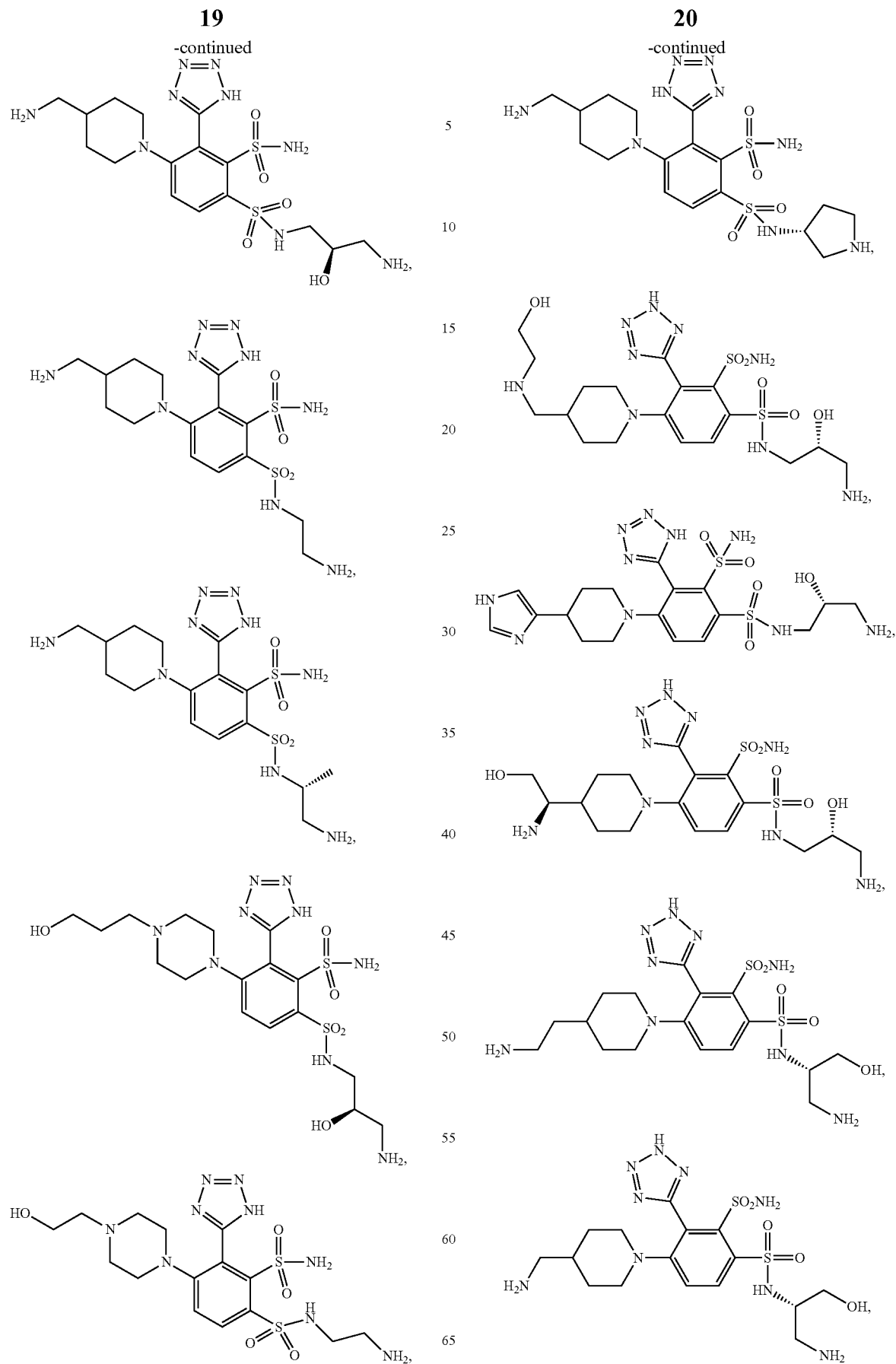

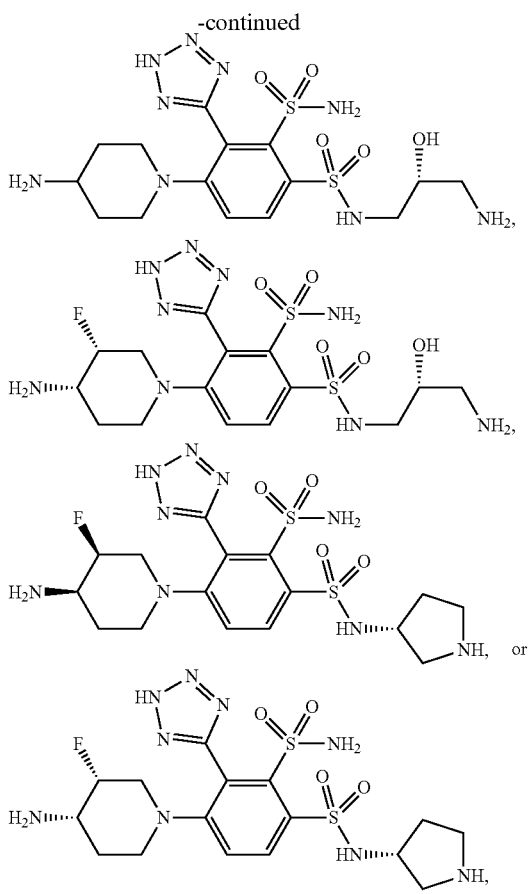

or a pharmaceutically acceptable salt thereof.

Other embodiments of the present invention include the following:

(a) A pharmaceutical composition comprising an effective amount of a compound of Formula I, IA, IB, IC, ID or IE as defined above, or a pharmaceutically acceptable salt thereof, and a pharmaceutically acceptable carrier.

(b) The pharmaceutical composition of (a), further comprising an effective amount of a β-lactam antibiotic and optionally further comprising an effective amount of a compound which is a class A β-lactamase inhibitor, class C β-lactamase inhibitor, and/or class D β-lactamase inhibitor.

(c) The pharmaceutical composition of (b), wherein the β-lactam antibiotic is selected from the group consisting of: (1) imipenem, (2) ertapenem, (3) meropenem, (4) doripenem, (5) biapenem, (6) panipenem, (7) ticarcillin, (8) ampicillin, (9) amoxicillin, (10) carbenicillin, (11) piperacillin, (12) azlocillin, (13) mezlocillin, (14) ticarcillin, (15) cefoperazone, (16) cefotaxime, (17) ceftriaxone, (18) cefipime, (19) ceftolozane, (20) ceftazidime, and (21) a pharmaceutically acceptable salt of any of (1)-(20), and the class A, C and D β-lactamase inhibitor is selected from the group consisting of relebactam or a pharmaceutically acceptable salt thereof, avibactam or a pharmaceutically acceptable salt thereof, vaborbactam or a pharmaceutically acceptable salt thereof, tazobactam or a pharmaceutically acceptable salt thereof, sulbactam or a pharmaceutically acceptable salt thereof, clavulanic acid or a pharmaceutically acceptable salt thereof, or CB-618 or a pharmaceutically acceptable salt thereof.

(d) The pharmaceutical composition of (b), wherein the β-lactam antibiotic is imipenem or a pharmaceutically acceptable salt thereof.

(e) The pharmaceutical composition of (b), wherein the β-lactam antibiotic is ceftazidime or a pharmaceutically acceptable salt thereof.

(f) The pharmaceutical composition of (h), wherein the β-lactam antibiotic is ceftolozane or a pharmaceutically acceptable salt thereof.

(g) The pharmaceutical composition of (b), wherein the β-lactam antibiotic is piperacillin or a pharmaceutically acceptable salt thereof.

(h) The pharmaceutical composition of (a), further comprising a compound which is a class A β-lactamase inhibitor, class C β-lactamase inhibitor, and/or class D β-lactamase inhibitor.

(i) The pharmaceutical composition of any of (b)-(h), wherein the β-lactamase inhibitor compound is relebactam or a pharmaceutically acceptable salt thereof.

(j) The pharmaceutical composition of any of (b)-(h), wherein the β-lactamase inhibitor compound is tazobactam or a pharmaceutically acceptable salt thereof.

(k) The pharmaceutical composition of (a), further comprising effective amounts of a β-lactam antibiotic, a renal dehydropeptidase (DHP) inhibitor, and optionally, a class A, C and D β-lactamase inhibitor.

(l) The pharmaceutical composition of (k), wherein the β-lactam antibiotic is imipenem or a pharmaceutically acceptable salt thereof, the DHP inhibitor is cilastatin or a pharmaceutically acceptable salt thereof, and the class A, C and D β-lactamase inhibitor is relebactam or a pharmaceutically acceptable salt thereof.

(m) A combination of effective amounts of a compound of Formula I as defined above, or a pharmaceutically acceptable salt thereof, a β-lactam antibiotic, and optionally, a class A, C and/or D β-lactamase inhibitor.

(n) The combination of (j), wherein the β-lactam antibiotic is selected from the group consisting of: (1) imipenem, (2) ertapenem, (3) meropenem, (4) doripenem, (5) biapenem, (6) panipenem, (7) ticarcillin, (8) ampicillin, (9) amoxicillin, (10) carbenicillin, (11) piperacillin, (12) azlocillin, (13) mezlocillin, (14) ticarcillin, (15) cefoperazone, (16) cefotaxime, (17) ceftriaxone, (18) cefipime, (19) ceftolozane, (20) ceftazidime, and (21) a pharmaceutically acceptable salt of any of (1)-(20).

(o) The combination of (n), wherein the β-lactam antibiotic is imipenem or a pharmaceutically acceptable salt thereof, optionally in combination with cilastatin or a pharmaceutically acceptable salt thereof, and the class A, C, D β-lactamase inhibitor is relebactam or a pharmaceutically acceptable salt thereof.

(p) The combination of (n), wherein the β-lactam antibiotic is ceftazidime or a pharmaceutically acceptable salt thereof and the class A, C, D β-lactamase inhibitor is avibactam or a pharmaceutically acceptable salt thereof.

(q) The combination of (n), wherein the β-lactam antibiotic is ceftolozane or a pharmaceutically acceptable salt thereof and the class A, C, D β-lactamase inhibitor is avibactam or a pharmaceutically acceptable salt thereof or relebactam or a pharmaceutically acceptable salt thereof.

(r) The combination of (n), wherein the β-lactam antibiotic is piperacillin or a pharmaceutically acceptable salt thereof.

(s) A combination of effective amounts of a compound of Formula I, IA, IB, IC, ID or IE as defined above, or a pharmaceutically acceptable salt thereof, and a class A, C and/or D β-lactamase inhibitor.

(t) A combination of effective amounts of a compound of Formula I, IA, IB, IC, ID or IE as defined above, or a pharmaceutically acceptable salt thereof, a β-lactam antibiotic, a DHP inhibitor, and optionally a class A, C and/or D β-lactamase inhibitor.

(u) The combination of (t), wherein the β-lactam antibiotic is imipenem, the DHP inhibitor is cilastatin or a pharmaceutically acceptable salt thereof, and the class A, C and D β-lactamase inhibitor is relebactam or a pharmaceutically acceptable salt thereof.

(v) A method for treating a bacterial infection which comprises administering to a subject in need of such treatment a therapeutically effective amount of a compound of Formula I, IA, IB, IC, ID or IE as defined above, or a pharmaceutically acceptable salt thereof, in combination with an effective amount of a β-lactam antibiotic and optionally in combination with a class A, C and D β-lactamase inhibitor.

(w) A method for treating a bacterial infection which comprises administering to a subject in need of such treatment a therapeutically effective amount of a compound of Formula I, IB, IC, ID or IE as defined above, or a pharmaceutically acceptable salt thereof, in combination with effective amounts of a β-lactam antibiotic and a DHP inhibitor, and optionally in combination with a class A, C and D β-lactamase inhibitor.

(x) A method for treating a bacterial infection which comprises administering to a subject in need of such treatment a therapeutically effective amount of the composition of (a), (b), (c), (d), (e), (f), (g), (h), (i), (j), (k), or (l).

(y) A method for treating a bacterial infection which comprises administering to a subject in need of such treatment a therapeutically effective amount of the combination of (m), (n), (O), (p), (q), (r), (s), (t), or (u).

(z) A method of treating a bacterial infection as set forth in (v), (w), (x), (y) or (z) wherein the bacterial infection is due to *Pseudomonas* spp., *Klebsiella* spp., *Enterobacter* spp., *Escherichia* spp.a, *Morganella* spp., *Citrobacter* spp., *Serratia*, spp. or *Acintetobacter* spp.

The present invention also includes a compound of Formula I, IA, IB, IC, ID or IE or a pharmaceutically acceptable salt thereof, (i) for use in, (ii) for use as a medicament for, or (iii) for use in the preparation (or manufacture) of a medicament for, inhibiting beta-lactamase activity or treating bacterial infection. In these uses, the compounds of the present invention can optionally be employed in combination with one or more β-lactam antibiotics, and may further be employed in combination with a class A, C, and/or D serine β-lactamase inhibitor and/or one or more DHP inhibitors.

Additional embodiments of the invention include the pharmaceutical compositions, combinations and methods set forth in (a)-(z) above and the uses set forth in the preceding paragraph, wherein the compound of the present invention employed therein is a compound of one of the embodiments, sub-embodiments, classes or sub-classes described above. The compound may optionally be used in the form of a pharmaceutically acceptable salt in these embodiments. In addition, the compound may optionally be used in the form of a prodrug that releases the active parent compound after dosing by intravenous or oral administration.

In the embodiments of the compounds and salts provided above, it is to be understood that each embodiment may be combined with one or more other embodiments, to the extent that such a combination provides a stable compound or salt and is consistent with the description of the embodiments. It is further to be understood that the embodiments of compositions and methods provided as (a) through (z) above are understood to include all embodiments of the compounds and/or salts, including such embodiments as result from combinations of embodiments.

Additional embodiments of the present invention include each of the pharmaceutical compositions, combinations, methods and uses set forth in the preceding paragraphs, wherein the compound of the present invention or its salt employed therein is substantially pure. With respect to a pharmaceutical composition comprising a compound of Formula I, IA, IB, IC, ID or IE or its salt and a pharmaceutically acceptable carrier and optionally one or more excipients, it is understood that the term "substantially pure" is in reference to a compound of Formula I, IA, IB, IC, ID or IE or its salt per se; i.e., the purity of the active ingredient in the composition.

Definitions and Abbreviations

The term "β-lactamase inhibitor" refers to a compound which is capable of inhibiting enzyme activity from β-lactamases. As used herein, inhibiting β-lactamase activity means inhibiting the activity of a class A, B, C, and/or D β-lactamase. For antimicrobial applications inhibition at a 50% inhibitory concentration is preferably achieved at or below about 100 micrograms/mL, or at or below about 50 micrograms/mL, or at or below about 25 micrograms/mL. The terms "class A", "class B", "class C", and "class D" β-lactamases are understood by those skilled in the art and are described in S. G. Waley, β-lactamase: mechanisms of action, in The Chemistry of β-Lactams, M. I. Page, Ed.; Chapman and Hall, London, (1992) 198-228.

The term "metallo-β-lactamase inhibitor" refers to a compound which is capable of inhibiting metallo-β-lactamase activity. As used herein, inhibiting metallo-β-lactamase activity means inhibiting the activity of a class B metallo-β-lactamase. For antimicrobial applications inhibition at a 50% inhibitory concentration is preferably achieved at or below about 100 μg/mL, or at or below about 50 μg/mL, or at or below about 25 μg/mL.

The term "metallo-β-lactamase" denotes a metalloprotein capable of inactivating a β-lactam antibiotic. The β-lactamase can be an enzyme which catalyzes the hydrolysis of the β-lactam ring of a β-lactam antibiotic. Of particular interest herein are microbial metallo-β-lactamases. The metallo-β-lactamase can be, for example, a zinc metallo-β-lactamase. β-Lactamases of interest include those disclosed in, e.g., S. G Waley, β-lactamase: mechanisms of action, in The Chemistry of β-Lactams, M. I. Page, Ed.; Chapman and Hall, London, (1992) 198-228. β-Lactamases of particular interest herein include a metallo-β-lactamases of *Escherichia coli* (Such as New Delhi Metallo-b-lactamase, NDM), *Serratia marcescens* (such as IMP), *Klebsiella* spp. (such as Verona integron-encoded metallo-β-lactamase, VIM and *Pseudomonas* spp (such as Verona integron-encoded metallo-β-lactamase, VIM)). Additional metallo-β-lactamases of interest herein include SPM-, GIM-, SIM-, KHM-, AIM-, DIM-, SMB-, TMB-, and FIM-type enzymes.

The term "antibiotic" refers to a compound or composition which decreases the viability of a microorganism, or which inhibits the growth or proliferation of a microorganism. The phrase "inhibits the growth or proliferation" means increasing the generation time (i.e., the time required for the bacterial cell to divide or for the population to double) by at least about 2-fold. Preferred antibiotics are those which can increase the generation time by at least about 10-fold or more (e.g., at least about 100-fold or even indefinitely, as in total cell death). As used in this disclosure, an antibiotic is further intended to include an antimicrobial, bacteriostatic, or bactericidal agent. Examples of antibiotics suitable for use with respect to the present invention include penicillins, cephalosporins and carbapenems.

The term "β-lactam antibiotic" refers to a compound with antibiotic properties that contains a β-lactam functionality. Non-limiting examples of β-lactam antibiotics useful with respect to the invention include penicillins, cephalosporins, penems, carbapenems, and monobactams and their pharmaceutically acceptable salts.

The term "about", when modifying the quantity (e.g., kg, L, or equivalents) of a substance or composition, or the value of a physical property, or the value of a parameter characterizing a process step (e.g., the temperature at which a process step is conducted), or the like refers to variation in the numerical quantity that can occur, for example, through typical measuring, handling and sampling procedures involved in the preparation, characterization and/or use of the substance or composition; through inadvertent error in these procedures; through differences in the manufacture, source, or purity of the ingredients employed to make or use the compositions or carry out the procedures; and the like. In certain embodiments, "about" can mean a variation of ±0.1, 0.2, 0.3, 0.4, 0.5, 1.0, 2.0, 3.0, 4.0, or 5.0 of the appropriate unit. In certain embodiments, "about" can mean a variation of ±1%, 2%, 3%, 4%, 5%, 10%, or 20%.

Another embodiment of the present invention is a compound of Formula I, IA, IB, IC, ID or IE, or a pharmaceutically acceptable salt thereof, as originally defined or as defined in any of the foregoing embodiments, sub-embodiments, aspects, classes or sub-classes, wherein the compound or its salt is in a substantially pure form. As used herein "substantially pure" means suitably at least about 60 wt. %, typically at least about 70 wt. %, preferably at least about 80 wt. %, more preferably at least about 90 wt. % (e.g., from about 90 wt. % to about 99 wt. %), even more preferably at least about 95 wt. % (e.g., from about 95 wt. % to about 99 wt. %, or from about 98 wt. % to 100 wt. %), and most preferably at least about 99 wt. % (e.g., 100 wt. %) of a product containing a compound of Formula I, IA, IB, IC, ID or IE, or its salt (e.g., the product isolated from a reaction mixture affording the compound or salt) consists of the compound or salt. The level of purity of the compounds and salts can be determined using a standard method of analysis such as thin layer chromatography, gel electrophoresis, high performance liquid chromatography, and/or mass spectrometry. If more than one method of analysis is employed and the methods provide experimentally significant differences in the level of purity determined, then the method providing the highest level of purity governs. A compound or salt of 100% purity is one which is free of detectable impurities as determined by a standard method of analysis.

With respect to a compound of the invention which has one or more asymmetric centers and can occur as mixtures of stereoisomers, a substantially pure compound can be either a substantially pure mixture of the stereoisomers or a substantially pure individual diastereomer or enantiomer unless expressly depicted otherwise. The present invention encompasses all stereoisomeric forms of the compounds of Formula I, IA, IB, IC, ID or IE. Unless a specific stereochemistry is indicated, the present invention is meant to comprehend all such isomeric forms of these compounds. Centers of asymmetry that are present in the compounds of Formula I, IA and IB can all independently of one another have (R) configuration or (S) configuration. When bonds to the chiral carbon are depicted as straight lines in the structural Formulas of the invention, it is understood that both the (R) and (S) configurations of the chiral carbon, and hence both enantiomers and mixtures thereof, are embraced within the Formula. Similarly, when a compound name is recited without a chiral designation for a chiral carbon, it is understood that both the (R) and (S) configurations of the chiral carbon, and hence individual enantiomers, diastereomers and mixtures thereof, are embraced by the name. The production of specific stereoisomers or mixtures thereof may be identified in the Examples where such stereoisomers or mixtures were obtained, but this in no way limits the inclusion of all stereoisomers and mixtures thereof from being within the scope of this invention.

The invention includes all possible enantiomers and diastereomers and mixtures of two or more stereoisomers, for example mixtures of enantiomers and/or diastereomers, in all ratios. Thus, enantiomers are a subject of the invention in enantiomerically pure form, both as levorotatory and as dextrorotatory antipodes, in the form of racemates and in the form of mixtures of the two enantiomers in all ratios. In the case of a cis/trans isomerism the invention includes both the cis form and the trans form as well as mixtures of these forms in all ratios. The preparation of individual stereoisomers can be carried out, if desired, by separation of a mixture by customary methods, for example by chromatography or crystallization, by the use of stereochemically uniform starting materials for the synthesis or by stereoselective synthesis. Optionally a derivatization can be carried out before a separation of stereoisomers. The separation of a mixture of stereoisomers can be carried out at an intermediate step during the synthesis of a compound of Formula I, IA, IB, IC, ID or IE or it can be done on a final racemic product. Absolute stereochemistry may be determined by X-ray crystallography of crystalline products or crystalline intermediates which are derivatized, if necessary, with a reagent containing a stereogenic center of known configuration. Unless a particular isomer, salt, solvate (including hydrates) or solvated salt of such racemate, enantiomer, or diastereomer is indicated, the present invention includes all such isomers, as well as salts, solvates (including hydrates) and solvated salts of such racemates, enantiomers, diastereomers and mixtures thereof.

"Alkyl" means saturated carbon chains which may be linear or branched or combinations thereof, unless the carbon chain is defined otherwise. Other groups having the prefix "alk", such as alkoxy and alkanoyl, also may be linear or branched, or combinations thereof, unless the carbon chain is defined otherwise. Examples of alkyl groups include methyl, ethyl, propyl, isopropyl, butyl, sec- and tert-butyl, pentyl, hexyl, heptyl, octyl, nonyl, and the like.

"Aminoalkyl" means saturated carbon chains which may be linear or branched or combinations thereof which are substituted with one amino group which may be terminal (—NH$_2$) or internal (—NH—).

"Hydroxyalkyl" means saturated carbon chains which may be linear or branched or combinations thereof which are substituted with one hydroxyl (—OH) group.

"Diaminoalkyl" means saturated carbon chains which may be linear or branched or combinations thereof which are substituted with two amino (—NH$_2$) groups.

"Dihydroxyalkyl" means saturated carbon chains which may be linear or branched or combinations thereof which are substituted with two hydroxyl (—OH) groups.

"Hydroxyaminoalkyl" means saturated carbon chains which may be linear or branched or combinations thereof which are substituted with one hydroxyl (—OH) group and one amino (—NH$_2$) group.

"Alkenyl" means carbon chains which contain at least one carbon-carbon double bond, and which may be linear or branched, or combinations thereof, unless otherwise defined. Examples of alkenyl include vinyl, allyl, isopropenyl, pentenyl, hexenyl, heptenyl, 1-propenyl, 2-butenyl, 2-methyl-2-butenyl, and the like.

"Aromatic ring system" means monocyclic, bicyclic or tricyclic aromatic ring or ring system containing 5-14 ring atoms, wherein at least one of the rings is aromatic. The term may be used to describe a carbocyclic ring fused to an aryl group. For example, a 5-7-membered cycloalkyl can be fused through two adjacent ring atoms to a 5-6-membered heteroaryl containing 1, 2, or 3 heteroatom ring atoms selected from N, O, and S. In other example, a heteromonocyclic ring is fused through two ring atoms to a phenyl or 5-6-membered heteroaryl containing 1, 2, or 3 heteroatoms selected from N, O, and S. In the case of a heteromonocyclic ring containing one or more N atoms, the N can be in the form of quarternary amine. In certain embodiments, a N ring atom can be in the form of an N-oxide.

"Aryl" means a monocyclic, bicyclic or tricyclic carbocyclic aromatic ring or ring system containing 5-14 carbon atoms, wherein at least one of the rings is aromatic. Examples of aryl include phenyl and naphthyl. In one embodiment of the present invention, aryl is phenyl.

"Cycloalkyl" means a saturated monocyclic, bicyclic or bridged carbocyclic ring, having a specified number of carbon atoms. Examples of cycloalkyl include cyclopropyl, cyclobutyl, cyclopentyl, cyclohexyl, cycloheptyl, indanyl, 1,2,3,4-tetrahydronaphthyl and the like. In one embodiment of the present invention, cycloalkyl is selected from: cyclopropane, cyclobutane, cyclopentane and cyclohexane.

"Cycloalkenyl" means a nonaromatic monocyclic or bicyclic carbocyclic ring containing at least one double bond. Examples of cycloalkenyl include cyclopropenyl, cyclobutenyl, cyclopentenyl, cyclohexenyl, cycloheptenyl, clyooxtenyl and the like.

"Cycloheteroalkyl" or "heterocycloalkyl" means a saturated or partly unsaturated non-aromatic monocyclic bicyclic (including spirocyclic) or bridged carbocyclic ring or ring system comprising 3 to about 11 ring atoms, containing at least one ring heteroatom selected from N, S and O and the remainder of the ring atoms are carbon atoms. The nitrogen or sulfur atom of the heterocycloalkyl can be optionally oxidized to the corresponding N-oxide, S-oxide or S-dioxide. A heterocycloalkyl group can be joined via a ring carbon, or ring nitrogen atom, unless specified otherwise. The cycloheteroalkyl ring may be substituted on the ring carbons and/or the ring nitrogen(s). In one embodiment, a heterocycloalkyl group is monocyclic and has from about 3 to about 7 ring atoms (a "3 to 7-membered monocyclic heterocycloalkyl" group). In another embodiment, a heterocycloalkyl group is monocyclic has from about 4 to about 7 ring atoms (a "4 to 7-membered monocyclic heterocycloalkyl" group). In other embodiments, the heterocycloalkyl group is bicyclic and has 7-10 ring atoms, 8-10 ring atoms, or 9 or 10 ring atoms (a "9 or 10-membered bicyclic heterocycloalkyl" group). In still another embodiment, a heterocycloalkyl group is monocyclic and has 5 or 6 ring atoms. In one embodiment, a heterocycloalkyl group is monocyclic. In another embodiment, a heterocycloalkyl group is bicyclic. There are no adjacent oxygen and/or sulfur atoms present in the ring system. Examples of cycloheteroalkyl include tetrahydrofuran, piperazine, piperidine, morpholine, oxetane, tetrahydropyran, indolinyl, isoindolinyl, azabicyclooctane, hexahydrofuro[3,2-b]furan, and 2,3, 3a,5,6,6a-hexahydrofuro[3,2-b]furan. Where the ring or ring system contains one or more N atoms, the N can be in the form of quarternary amine.

As used herein, a "nitrogen-linked heterocycloalkyl" refers to a nitrogen-containing heterocycloalkyl that is linked to the rest of the compound through a carbon-nitrogen bond to the 6-membered core ring containing $X_1$ and $X_2$. For example, the following compounds of the invention contain a nitrogen-linked heterocycloalkyl

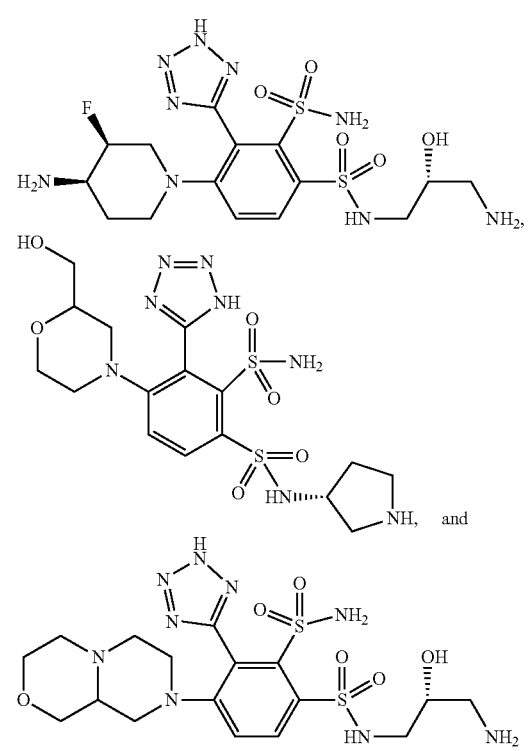

A nitrogen-linked heterocycloalkyl may be a 4-7 membered monocyclic ring, which may contain 0, 1, or 2, additional heteroatom ring atoms independently selected from N, O and S or a 6- to 12-membered bicyclic ring with 0, 1, 2, or 3 additional heteroatom ring atoms selected from N, O and S. A bicyclic nitrogen-linked heterocycloalkyl may be bridged, fused or spirocyclic. A nitrogen-linked heterocycloalkyl may optionally be substituted with one to three substituents as defined herein.

A "nitrogen-linked heterocycloalkenyl" refers to a nitrogen-containing heterocycloalkenyl that is linked to the rest of the compound through a carbon-nitrogen bond to the 6-membered core ring containing $X_1$ and $X_2$. For example, the following compounds of the invention contain a nitrogen-linked heterocycloalkenyl:

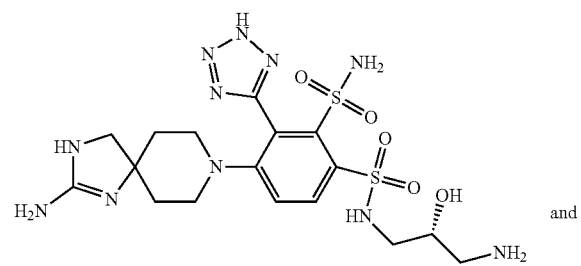

-continued

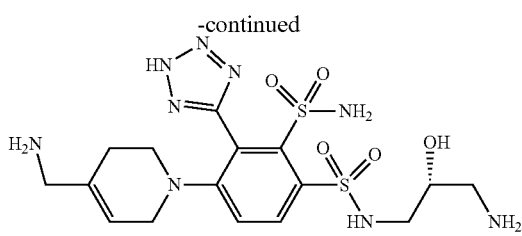

A nitrogen-linked heterocycloalkenyl may be a 4-7 membered monocyclic ring, which may contain 0, 1, or 2, additional heteroatom ring atoms independently selected from N, O and S or a 6- to 12-membered bicyclic ring with 0, 1, 2, or 3 additional heteroatom ring atoms selected from N, O and S. A bicyclic nitrogen-linked heterocycloalkenyl may be bridged, fused or spirocyclic. A nitrogen-linked heterocycloalkenyl may optionally be substituted with one to three substituents as defined herein.

"Heteroaryl" means monocyclic, bicyclic or tricyclic ring or ring system containing 5-14 carbon atoms and containing at least one ring heteroatom selected from N, S (including SO and $SO_2$) and O, wherein at least one of the heteroatom containing rings is aromatic. In the case of a heteroaryl ring system where one or more of the rings are saturated and contain one or more N atoms, the N can be in the form of quarternary amine. Examples of heteroaryl include pyrrolyl, isoxazolyl, isothiazolyl, pyrazolyl, pyridyl, oxazolyl, oxadiazolyl, thiadiazolyl, thiazolyl, imidazolyl, triazolyl, tetrazolyl, furanyl, triazinyl, thienyl, pyrimidyl, pyridazinyl, pyrazinyl, benzisoxazolyl, benzoxazolyl, benzothiazolyl, benzimidazolyl, benzopyrazolyl, benzofuranyl, benzothiophenyl (including S-oxide and dioxide), benzotriazolyl, furo(2,3-b)pyridyl, quinolyl, indolyl, isoquinolyl, quinazolinyl, dibenzofuranyl, and the like. Examples of bicyclic heteroaryl rings include:

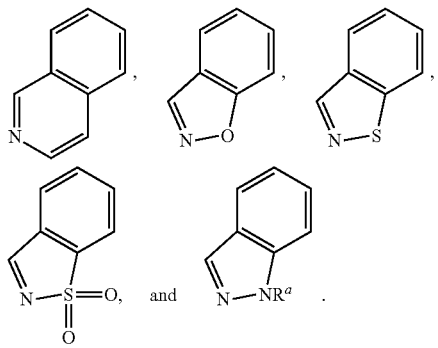

"Halogen" includes fluorine, chlorine, bromine and iodine.

"Oxo" means an oxygen atom connected to another atom by a double bond and is represented by "=O" herein.

Where any amine is present in the compound, the N atom may be optionally in the form of a quaternary amine having one or more appropriate additional substitutions, as further described herein.

When any ring atom is specified as being optionally substituted with, or in a specified form, for example, S substituted with oxo groups, or N in the form of a N-oxide, this does not preclude the substitution of any ring atom with the other listed optional substituents when not substituted with oxo groups or in the form of a N-oxide.

When any variable (e.g., n, $R^a$, $R^b$, etc.) occurs more than one time in any constituent or in Formula I, IA, TB, IC, ID or IE, its definition on each occurrence is independent of its definition at every other occurrence. Also, combinations of substituents and/or -variables are permissible only if such combinations result in stable compounds.

A wavy line ⌇⌇⌇⌇, as used herein, indicates a point of attachment to the rest of the compound. Lines drawn into a ring system, for example:

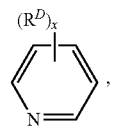

indicate that the bond may be attached to any of the substitutable ring atoms.

Under standard nomenclature used throughout this disclosure, the terminal portion of the designated side chain is described last, preceded by the adjacent functionality toward the point of attachment.

In choosing compounds of the present invention, one of ordinary skill in the art will recognize that the various substituents, i.e. $R^1$, $R^A$, etc., are to be chosen in conformity with well-known principles of chemical structure connectivity and stability.

The term "substituted" shall be deemed to include multiple degrees of substitution by a named substitutent. Where multiple substituent moieties are disclosed or claimed, the substituted compound can be independently substituted by one or more of the disclosed or claimed substituent moieties, singly or plurally. By independently substituted, it is meant that the (two or more) substituents can be the same or different.

In the compounds of Formula I, IA, IB, IC, ID or IE, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of Formula I, IA, IB, IC, ID or IE. For example, different isotopic forms of hydrogen (H) include protium ($^1H$) and deuterium ($^2H$ or D). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within Formula I, IA, IB, IC, ID or IE, can be prepared without undue experimentation by conventional techniques well known to those skilled in the art or by processes analogous to those described in the Schemes and Examples herein using appropriate isotopically-enriched reagents and/or intermediates.

Unless expressly stated to the contrary in a particular context, any of the various cyclic ring and ring system variables or substituents described herein may be attached to the rest of the compound at any ring atom (i.e., any carbon atom or any heteroatom) provided that a stable compound results.

Unless expressly stated to the contrary, all ranges cited herein are inclusive. For example, a heteroaromatic ring described as containing from "1 to 4 heteroatoms" means the ring can contain 1, 2, 3 or 4 heteroatoms. It is also to be understood that any range cited herein includes within its scope all of the sub-ranges within that range. Thus, for example, a heterocyclic ring described as containing from "1 to 4 heteroatoms" is intended to include as aspects thereof, heterocyclic rings containing 2 to 4 heteroatoms, 3 or 4 heteroatoms, 1 to 3 heteroatoms, 2 or 3 heteroatoms, 1 or 2 heteroatoms, 1 heteroatom, 2 heteroatoms, 3 heteroatoms, and 4 heteroatoms. Similarly, $C_1$-$C_6$ when used with a chain, for example an alkyl chain, means that the chain can contain 1, 2, 3, 4, 5 or 6 carbon atoms. It also includes all ranges contained therein including $C_1$-$C_5$, $C_1$-$C_4$, $C_1$-$C_3$, $C_1$-$C_2$, $C_2$-$C_6$, $C_3$-$C_6$, $C_4$-$C_6$, $C_5$-$C_6$ and all other possible combinations.

A "stable" compound is a compound which can be prepared and isolated and whose structure and properties remain or can be caused to remain essentially unchanged for a period of time sufficient to allow use of the compound for the purposes described herein (e.g., therapeutic administration to a subject). The compounds of the present invention are limited to stable compounds embraced by Formulas I, IA, IB, IC, ID or IE.

The term "compound" refers to the compound and, in certain embodiments, to the extent they are stable, any hydrate or solvate thereof. A hydrate is the compound complexed with water, and a solvate is the compound complexed with an organic solvent.

As indicated above, the compounds of the present invention can be employed in the form of pharmaceutically acceptable salts. Those skilled in the art will recognize those instances in which the compounds of the invention may form salts. The term "pharmaceutically acceptable salt" refers to a salt (including an inner salt such as a zwitterion) which possesses effectiveness similar to the parent compound and which is not biologically or otherwise undesirable (e.g., is neither toxic nor otherwise deleterious to the recipient thereof). Thus, an embodiment of the invention provides pharmaceutically acceptable salts of the compounds of the invention. The term "salt(s)", as employed herein, denotes any of the following: acidic salts formed with inorganic and/or organic acids, as well as basic salts formed with inorganic and/or organic bases. Salts of compounds of the invention may be formed by methods known to those of ordinary skill in the art, for example, by reacting a compound of the invention with an amount of acid or base, such as an equivalent amount, in a medium such as one in which the salt precipitates or in aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates ("mesylates"), naphthalenesulfonates, nitrates, oxalates, phosphates, propionates, salicylates, succinates, sulfates, tartarates, thiocyanates, toluenesulfonates (also known as tosylates) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use*. (2002) Zurich: Wiley-VOL S. Berge et al, *Journal of Pharmaceutical. Sciences* (1977) 66(1) 1-19; P. Gould, *International f of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamine, t-butyl amine, choline, and salts with amino acids such as arginine, lysine and the like. Basic nitrogen-containing groups may be quarternized with agents such as lower alkyl halides (e.g., methyl, ethyl, and butyl chlorides, bromides and iodides), dialkyl sulfates (e.g., dimethyl, diethyl, and dibutyl sulfates), long chain halides (e.g., decyl, lauryl, and stearyl chlorides, bromides and iodides), aralkyl halides (e.g., benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

In addition, when a compound of the invention contains both a basic moiety, such as, but not limited to an aliphatic primary, secondary, tertiary or cyclic amine, an aromatic or heteroaryl amine, pyridine or imidazole, and an acidic moiety, such as, but not limited to tetrazole or carboxylic acid, zwitterions ("inner salts") may be formed and are included within the terms "salt(s)" as used herein. It is understood that certain compounds of the invention may exist in zwitterionic form, having both anionic and cationic centers within the same compound and a net neutral charge. Such zwitterions are included within the invention.

The compounds of Formula I, IA, IB, IC, ID or IE may exist as rapidly interconverting tautomers with different points of attachment of hydrogen accompanied by one or more double bond shifts. The individual tautomers as well as mixtures thereof are encompassed by the present invention. The ratio between the tautomeric forms will vary depending on the conditions. As is well known to one of ordinary skill in the art, such compounds may be drawn and named in different ways. For example, the following structures depicted below show different ways that an illustrative compound of the invention may be drawn:

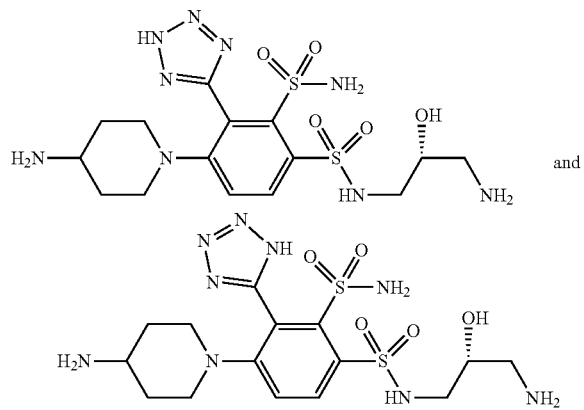

It is understood that all possible tautomeric forms of the compounds of Formula I, IA, IB, IC, ID and IE are contemplated as being within the scope of the instant invention, as well as mixtures thereof. It is further understood that while only one said tautomeric form of each example compound and embodiment of the invention may be depicted in the specification and appended claims, such depiction includes reference to all tautomeric forms of said compounds, which are included within the scope of the invention.

In the compounds of Formula I, IA, TB, IC, ID and IF, ring Z is a tetrazolyl group, depicted as:

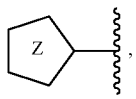

which is a 5-membered ring containing 4 nitrogen ring heteroatoms and one carbon atom, wherein Z is linked through a carbon to carbon bond to the six-membered core ring having $X_1$ and $X_2$ (see Formula I in the Summary of the Invention). As indicated above, all possible tautomeric forms of the compounds of Formula I, IA, B, IC, ID and IE are included within the scope of the invention. Thus, an indication of:

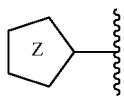

includes

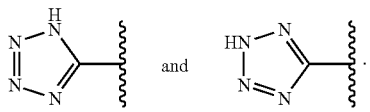

As set forth above, the present invention includes pharmaceutical compositions comprising a compound of Formula I, IA, IB, IC, ID or IE of the present invention, optionally one or more other active components (e.g., a β-lactam antibiotic), and a pharmaceutically acceptable carrier. The characteristics of the carrier will depend on the route of administration. By "pharmaceutically acceptable" is meant that the ingredients of the pharmaceutical composition must be compatible with each other, do not interfere with the effectiveness of the active ingredient(s), and are not deleterious (e.g., toxic) to the recipient thereof. Thus, compositions according to the invention may, in addition to the inhibitor, contain diluents, fillers, salts, buffers, stabilizers, solubilizers, and other materials well known in the art.

Also as set forth above, the present invention includes a method for treating a bacterial infection which comprises administering to a subject in need of such treatment a therapeutically effective amount of a compound of Formula I, IA, IB, IC, ID or IF, or a pharmaceutically acceptable salt thereof, in combination with a β-lactam antibiotic and optionally a DHP inhibitor. The term "subject" (or, alternatively, "patient") as used herein refers to an animal, preferably a mammal, and in particular a human or a non-human animal including livestock animals and domestic animals including, but not limited to, cattle, horses, sheep, swine, goats, rabbits, cats, dogs, and other mammals in need of treatment. In select embodiment, the subject is a human. In select embodiments, the subject has been the object of treatment, observation or experiment. The term "administration" and variants thereof (e.g., "administering" a compound) in reference to a compound of Formula I, IA, IB, IC, ID or IF mean providing the compound, or a pharmaceutically acceptable salt thereof, to the individual in need of treatment. When a compound or a salt thereof is provided in combination with one or more other active agents (e.g., a carbapenem antibiotic or a DHP inhibitor or both), "administration" and its variants are each understood to include provision of the compound or its salt and the other agents at the same time or at different times. When the agents of a combination are administered at the same time, they can be administered together in a single composition or they can be administered separately. It is understood that a "combination" of active agents can be a single composition containing all of the active agents or multiple compositions each containing one or more of the active agents. In the case of two active agents a combination can be either a single composition comprising both agents or two separate compositions each comprising one of the agents; in the case of three active agents a combination can be either a single composition comprising all three agents, three separate compositions each comprising one of the agents, or two compositions one of which comprises two of the agents and the other comprises the third agent; and so forth.

The compositions and combinations of the present invention are suitably administered in effective amounts. The term "effective amount," when used with a β-lactamase inhibitor (including a DHP inhibitor), means the amount of active compound sufficient to inhibit β-lactamase and thereby elicit the response being sought (i.e., an "inhibition effective amount") in a cell, tissue, system, animal or human. In one embodiment, the effective amount is a "therapeutically effective amount" for the alleviation of the symptoms of the disease or condition being treated (e.g., the healing of conditions associated with bacterial infection, and/or bacterial drug resistance) in combination with a β-lactam antibiotic. In another embodiment, the effective amount is a "prophylactically effective amount" for prophylaxis of the symptoms of the disease or condition being prevented. When the active compound (i.e., active ingredient) is administered as the salt, references to the amount of active ingredient are to the free acid or free base form of the compound. An "effective amount" of a β-lactam antibiotic is an amount sufficient to alleviate the symptoms of the disease or condition being treated (e.g., the healing of conditions associated with bacterial infection, and/or bacterial drug resistance).

The administration of a composition of the present invention is suitably parenteral, oral, sublingual, transdermal, topical, intranasal, intratracheal, intraocular, or intrarectal, wherein the composition is suitably formulated for administration by the selected route using formulation methods well known in the art, including, for example, the methods for preparing and administering formulations described in chapters 39, 41, 42, 44 and 45 in Remington—The Science and Practice of Pharmacy, 21$^{st}$ edition, 2006. In one embodiment, compounds of the invention are administered intravenously in a hospital setting. In another embodiment, administration is oral in the form of a tablet or capsule or the like. When administered systemically, a therapeutic composition is for example, suitably administered at a sufficient dosage to attain a blood level of inhibitor of at least about 1 µg/mL, and in additional embodiment at least about 10 µg/mL, and at least about 25 µg/mL. For localized administration, much lower concentrations than this may be effective, and much higher concentrations may be tolerated.

Intravenous administration of a compound of the invention can be conducted by reconstituting a powdered form of the compound with an acceptable solvent. Suitable solvents include, for example, saline solutions (e.g., 0.9% Sodium Chloride Injection) and sterile water (e.g., Sterile Water for Injection, Bacteriostatic Water for Injection with methylparaben and propylparaben or Bacteriostatic Water for Injection with 0.9% benzyl alcohol). The powdered form of the compound can be obtained by gamma-irradiation of the compound or by lyophilization of a solution of the compound, after which the powder can be stored (e.g., in a sealed vial) at or below room temperature until it is reconstituted. The concentration of the compound in the reconstituted IV solution can be, for example, in a range of from about 0.1 mg/mL to about 20 mg/mL.

The present invention also includes a method for inhibiting bacterial growth which comprises administering to a bacterial cell culture, or to a bacterially infected cell culture, tissue, or organism, an inhibition effective amount of a compound of Formula I, IA, IB, IC, ID or IE. Additional embodiments of the invention include the bacterial growth inhibiting method just described, wherein the compound of the present invention employed therein is a compound of one of the embodiments, sub-embodiments or classes described above. The compound may optionally be used in the form of a pharmaceutically acceptable salt in these embodiments. The method can involve administration of a compound of Formula I, IA, IB, IC, ID or IE to an experimental cell culture in vitro to prevent the growth of β-lactam resistant bacteria. The method can alternatively involve administration of a compound of I, IA, IB, IC, ID or IE to an animal, including a human, to prevent the growth of β-lactam resistant bacteria in vivo. In these cases, the compound of Formula I, IA, IB, IC, ID or IE is typically co-administered with a β-lactam antibiotic.

Compounds of the invention can be employed for the treatment, prophylaxis or inhibition of bacterial growth or infections due to bacteria that are resistant to β-lactam antibiotics in combination with a β-lactam antibiotic. More particularly, the bacteria can be metallo-β-lactamase positive strains that are highly resistant to β-lactam antibiotics. The terms "slightly resistant" and "highly resistant" are well-understood by those of ordinary skill in the art (see, e.g., Payne et al., *Antimicrobial Agents and Chemotherapy* 38:767-772 (1994); Hanaki el al., *Antimicrobial Agents and Chemotherapy* 30:11.20-11.26 (1995)). For the purposes of this invention, bacterial strains which are highly resistant to imipenem are those against which the MIC of imipenem is >16 µg/mL, and bacterial strains which are slightly resistant to imipenem are those against which the MIC of imipenem is >4 µg/mL.

Compounds of the invention can be used in combination with antibiotic agents for the treatment of infections caused by Class B-β-lactamase producing strains, in addition to those infections which are subsumed within the antibacterial spectrum of the antibiotic agent. Examples of class B-metallo-β-lactamase producing bacteria are *Pseudomonas aeruginosa, Pseudomonas putida, Enterobacter cloacae, Klebsiella pneumoniae, Klebsiella oxytoca, Escherichia coli, Serratia marcescens, Enterobacter aerogenes. Enterobacter asburiae, Citrobacter freundii, Proteus mirabilis, Morganella morganii Providencia rettgeri,* and *Acinetobacter baumannii.*

It is generally advantageous to use a compound of Formula I, IA, IB, IC, ID or IE in admixture or conjunction with a carbapenem, penicillin, cephalosporin, or other β-lactam antibiotic, or a prodrug thereof. It is advantageous to use a compound of Formula I, IA, IB, IC, ID or IE in combination with one or more β-lactam antibiotics because of the class B β-lactamase inhibitory properties of the compounds. It is also advantageous to use a compound of Formula I, IA, IB, IC, ID or IE in combination with one or more Class A, C, and D β-lactamase inhibitors to further limit β-lactam susceptibility. As already noted, the compound of Formula I, IA, IB, IC, ID or IF and the β-lactam antibiotic can be administered separately (at the same time or as different times) or in the form of a single composition containing both active ingredients.

Carbapenems, penicillins, cephalosporins and other β-lactam antibiotics suitable for use in the present invention include both those known to show instability to or to be otherwise susceptible to class B-β-lactamases.

When the compounds of Formula I, IA, IB, IC, ID or IE are combined with a carbapenem antibiotic, a dehydropeptidase (DHP) inhibitor can also be combined. Many carbapenems are susceptible to attack by a renal enzyme known as DHP. This attack or degradation may reduce the efficacy of the carbapenem antibacterial agent. Inhibitors of DHP and their use with carbapenems are disclosed in, e.g., U.S. Pat. Nos. 4,539,208; 4,616,038; 4,880,793; and 5,071,843. A preferred DHP inhibitor is 7-(L-2-amino-2-carboxyethylthio)-2-(2,2-dimethylcyclopropanecarboxamide)-2-heptenoic acid or a pharmaceutically acceptable salt thereof.

Carbapenems suitable for co-administration with compounds of the present invention include imipenem, ertapenem, meropenem, biapenem, (4R, 5S, 6S)-3-[3S, 5S)-5-(3-carboxyphenyl-carbamoyl)pyrrolidin-3-ylthio]-6-(1R)-1-hydroxyethyl]-4-methyl-7-oxo-1-azabicyclo[3.2.0]hept-2-ene-2-carboxylic acid, (1S, 5R, 6S)-2-(4-(2-(((carbamoylmethyl)-1,4-diazoniabicyclo[2.2.2]oct-1-yl)-ethyl(1,8-naphthosultam)methyl)-6-[1(R)-hydroxyethyl]-1-methylcarbapen-2-em-3-carboxylate chloride, BMS181139 ([4R-[4α,5β,6β(R*)]]-4-[2-[(aminoiminomethyl)amino]ethyl]-3-[(2-cyanoethyl)thio]-6-(1-hydroxyethyl)-7-oxo-1-azabicyclo[3.2.0]hept-2-ene-2-carboxylic acid), BO2727 ([4R-3[3S*,5S*(R*)], 4α,5β,6β(R*)]]-6-(1-hydroxyethyl)-3-[[5-[1-hydroxy-3-(methylamino)propyl]-3-pyrrolidinyl]thio]-4-methyl-7-oxo-1-azabicyclo[3.2.0]hept-2-ene-2-carboxylic acid monohydrochloride), E1010 ((1R, 5S, 6S)-6-[1(R)-hydroxymethyl]-2-[2(S)-[1(R)-hydroxy-[pyrrolidin-3 (R)-yl]methyl]pyrrolidin-4(S)-ylsulfanyl]-1-methyl-1-carba-2-penem-3-carboxylic acid hydrochloride) and S4661 ((1R,5S,6S)-2-[(3S,5S)-5-(sulfamoylaminomethyl) pyrrolidin-3-yl]thio-6-[(1R)-1-hydroxyethyl]-1-methylcarbapen-2-em-3-carboxylic acid), (1S,5R,6S)-1-methyl-2-{7-[4-(aminocarbonylmethyl)-1,4-diazoniabicyclo(2.2.2)octan-1yl]-methyl-fluoren-9-on-3-yl}-6-(1R-hydroxyethyl)-carbapen-2-em-3 carboxylate chloride.

Penicillins suitable for co-administration with compounds of the present invention include benzylpenicillin, phenoxymethylpenicillin, carbenicillin, azidocillin, propicillin, ampicillin, amoxicillin, epicillin, ticarcillin, cyclacillin, pirbenicillin, azlocillin, mezlocillin, piperacillin, and other known penicillins. The penicillins may be used in the form of pro-drugs thereof; for example as in vivo hydrolysable esters, for example the acetoxymethyl, pivaloyloxymethyl, α-ethoxycarbonyloxy-ethyl and phthalidyl esters of ampicillin, benzylpenicillin and amoxicillin; as aldehyde or ketone adducts of penicillins containing a 6-α-aminoacetamido side chain (for example hetacillin, metampicillin and analogous derivatives of amoxicillin); and as esters of carbenicillin and ticarcillin, for example the phenyl and indanyl α-esters.

Cephalosporins suitable for co-administration with compound of the present invention include cefatrizine, cephaloridine, cephalothin, cefazolin, cephalexin, cephacetrile, cephapirin, cephamandole nafate, cephradine, 4-hydroxycephalexin, cephaloglycin, cefoperazone, cefsulodin, ceftolozane, ceftazidime, cefuroxime, cefmetazole, cefotaxime, ceftriaxone, cefipime, and other known cephalosporins, all of which may be used in the form of pro-drugs thereof.

β-Lactam antibiotics other than penicillins and cephalosporins that may be co-administered with compounds of the present invention include aztreonam, latamoxef (MOXALACTAM), and other known β-lactam antibiotics such as carbapenems like imipenem, ertapenem, meropenem or (4R, 5S, 6S)-3-[3S,5S)-5-(3-carboxyphenylcarbamoyl)pyrrolidin-3-ylthio]-6-(1R)-1-hydroxyethyl]-4-methyl-7-oxo-1-azabicyclo[3.2.0]hept-2-ene-2-carboxylic acid, all of which may be used in the form of pro-drugs thereof.

In one embodiment, the antibiotic co-administered with a compound of the present invention is selected from the group consisting of imipenem, ertapenem, meropenem and (4R, 5S, 6S)-3-[(3S,5S)-5-(3-carboxyphenylcarbamoyl)pyrrolidin-3-ylthio]-6-(1R)-1-hydroxyethyl]-4-methyl-7-oxo-1-azabicyclo[3.2.0]hept-2-ene-2-carboxylic acid.

In another embodiment, the antibiotic co-administered with a compound of the present invention is selected from the group of penicillins consisting of ampicillin, amoxicillin, carbenicillin, piperacillin, azlocillin, mezlocillin, and ticarcillin. Such penicillins can optionally be used in the form of their pharmaceutically acceptable salts, for example their sodium salts. Ampicillin or amoxicillin can alternatively be employed in the form of fine particles of the zwitterionic form (generally as ampicillin trihydrate or amoxicillin trihydrate) for use in an injectable or infusable suspension. In an aspect of this embodiment, the penicillin co-administered with a compound of the present invention is amoxicillin, optionally in the form of its sodium salt or the trihydrate.

In another embodiment, the antibiotic co-administered with a compound of the present invention is selected from the group of cephalosporins consisting of cefotaxime, ceftriaxone, cefipime, and ceftazidime, which are optionally used in the form of their pharmaceutically acceptable salts, for example their sodium salts.

In certain embodiments of the invention, the compounds of the invention in combination with serine β-lactamase inhibitors (which can inhibit class A, C, D beta lactamases) in addition to β-lactam antibiotics. Serine β-lactamase inhibitors include but are not limited to avibactam, vaborbactam, relebactam, tazobactam, and clavulanic acid.

When co-administered with a β-lactam antibiotic, and optionally a β-lactamase inhibitor, the combination of the compound of the invention and the antibiotic can provide a synergistic effect. The terms "synergistic effect" and "synergy" indicate that the effect produced when two or more drugs are co-administered is greater than would be predicted based on the effect produced when the compounds are administered individually. While not wishing to be bound by theory, it is believed that the compounds of the present invention are β-lactamase inhibitors that act to prevent degradation of β-lactam antibiotics, thereby enhancing their efficacy and producing a synergistic effect.

Abbreviations employed herein include the following: Ac=acetyl=$CH_3C(=O)$; AcOH=acetic acid; ACN=MeCN=acetonitrile; aq=aqueous; BH3 DMS=borane dimethyl sulfide; BINAP=(2,2'-bis(diphenylphosphino)-1,1'-binaphthyl); BLI=β-lactamase inhibitor; Bn=benzyl; BOC (or Boc)=tert-butyloxycarbonyl; Boc anhydride=$Boc_2O$=di-tert-butyl dicarbonate; BrettPhos precatalyst generation 3=[(2-Di-cyclohexylphosphino-3,6-dimethoxy-2',4',6'-triisopropyl-1,1'-biphenyl)-2-(2'-amino-1,1'-biphenyl)]palladium(II) methanesulfonate; BPBD=N,N'-{bis(pyridin-2-yl)benzylidene}butane-1,4-diamine; CBZ (or Cbz)=carbobenzoxy (alternatively, benzyloxycarbonyl); $CH_3CN$=acetonitrile; CELITE=diatomaceous earth; conc.=concentrated; CV=column volume; DBU=1,8-diazabicyclo[5.4.0]undec-7-ene; DCM=dichloromethane; DEAD=diethyl azodicarboxylate; DIAD=diisopropyl azodicarboxylate; DIBAL-H=diisobutylaluminum hydride; DIEA=N,N-Diisopropylethylamine; DIPEA=diisopropylethylamine (or Hunig's base); DMA=dimethylacetamide; DMAP=4-dimethylaminopyridine or N,N-dimethylaminopyridine; DME=1,2-dimethoxyethane; DMF=N,N-dimethylformamide; DMSO=dimethyl sulfoxide; DPPA=diphenylphosphoryl azide; EA=AcOEt=EtOAc=ethyl acetate; EDC=1-ethyl-3-(3-dimethylaminopropyl) carbodiimide; Et=ethyl; EtOH=ethanol; HATU=(1-[Bis(dimethylamino)methylene]-1H-1,2,3-triazolo[4,5-b]pyridinium 3-oxid hexafluorophosphate); hex=hexane; HOAt=1-Hydroxy-7-azabenzotriazole; HPLC=high-performance liquid chromatography; h or hr or hrs=hours; i-Pr=isopropyl alcohol; KOAc=potassium acetate; LCMS=LC-MS=liquid chromatography/mass spectrometry; LDA=lithium di-isopropyl amide; mCPBA=meta-chloroperoxybenzoic acid; Me=methyl; MeCN=acetonitrile; MeOH=methanol; MIC=minimum inhibitory concentration; min or mins=minutes; MPLC=medium pressure liquid chromatography; Ms methanesulfonyl; MsCl=methane sulfonyl chloride; n-BuLi=n-butyllithium; NCS=N-Chlorosuccinimide; NIS=N-Iodosuccinimide; NMP=N-Methyl-2-pyrrolidone; NMR=nuclear magnetic resonance; PCy3 Pd G2=2nd Generation $PCy_3$ precatalyst=Chloro[(tricyclohexylphosphine)-2-(2'-aminobiphenyl)]palladium(II); $Pd_2(dba)_3$=Tris(dibenzylideneacetone)dipalladium, $Pd(dppf)Cl_2$=[1,1'-Bis(diphenylphosphino)ferrocene]dichloropalladium (II); PE=Pet. ether=petroleum ether; Ph=phenyl; PMB=p-Methoxybenzyl; $PPh_3$ precatalyst generation 2=$2^{nd}$ PPh3 precatalyst=Chloro(triphenylphosphine) [2-(2'-amino-1,1'-biphenyl)]palladium(II); prep-HPLC=preparative HPLC; RAC-BINAP-PD-G3=methanesulfonato[2,2'-bis(diphenylphosphino)-1,1'-binapthyl](2'-amino-1,1'-biphenyl-2-yl)palladium(II); RBF=round bottom flask; RPLC=reverse phase liquid chromatography; RT=room temp.=room temperature; sat'd=saturated; SFC=supercritical fluid chromatography; SM=starting material; TBAF=tetrabutylammonium fluoride; tBuXPhos precatalyst generation 3=[(2-Di-tert-butylphosphino-2',4',6'-triisopropyl-1,1'-biphenyl)-2-(2'-amino-1,1'-biphenyl)]palladium(II) methanesulfonate; TEA=triethylamine; TFA=trifluoroacetic acid; THF=tetrahydrofuran; TLC=thin layer chromatography; TMS=trimethylsilane; $TMSN_3$=azidotrimethylsilane; XPhos-Pd-2G or XPHOS Pd G2 precatalyst or Xphos precatalyst generation 2=Chloro(2-dicyclohexylphosphino-2',4',6'-triisopropyl-1,1'-biphenyl)[2-(2'-amino-1,1'-biphenyl)]palladium(II); X-Phos aminobiphenyl palladium chloride precatalyst; and Xantphos=4,5-Bis(diphenylphosphino)-9,9-dimethylxanthene.

The compounds of the present invention can be readily prepared according to the following reaction schemes and examples, or modifications thereof, using readily available starting materials, reagents and conventional synthesis procedures. In these reactions, it is also possible to make use of known variants. Other methods for preparing compounds of the invention will be readily apparent to the person of ordinary skill in the art in light of the following reaction schemes and examples.

Scheme I
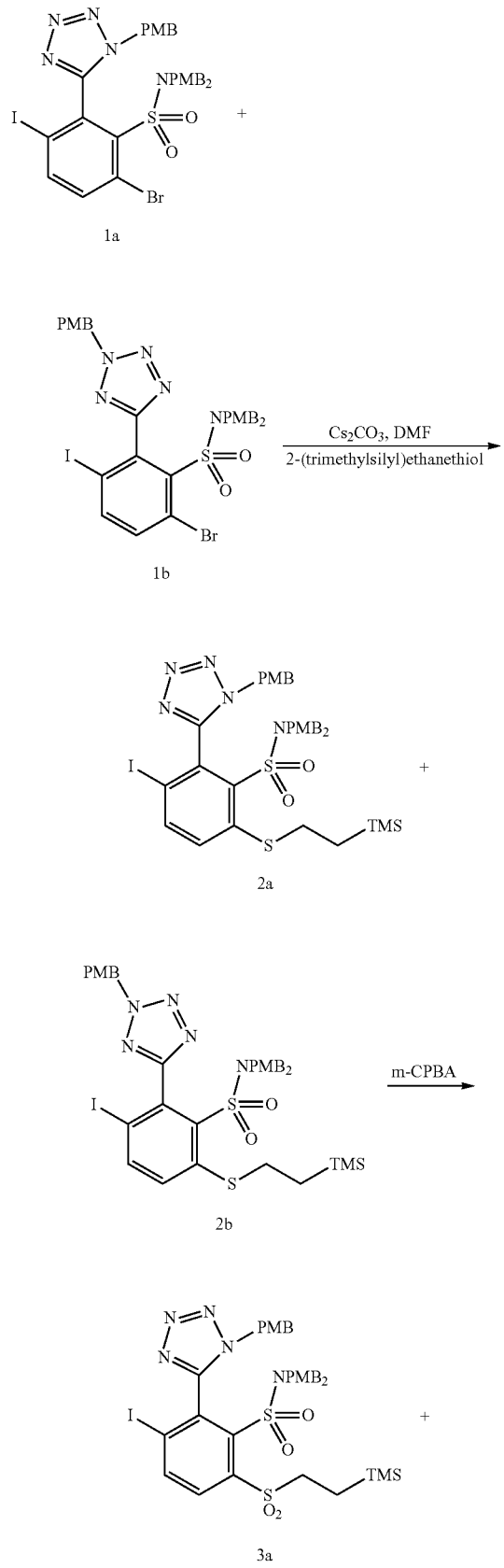
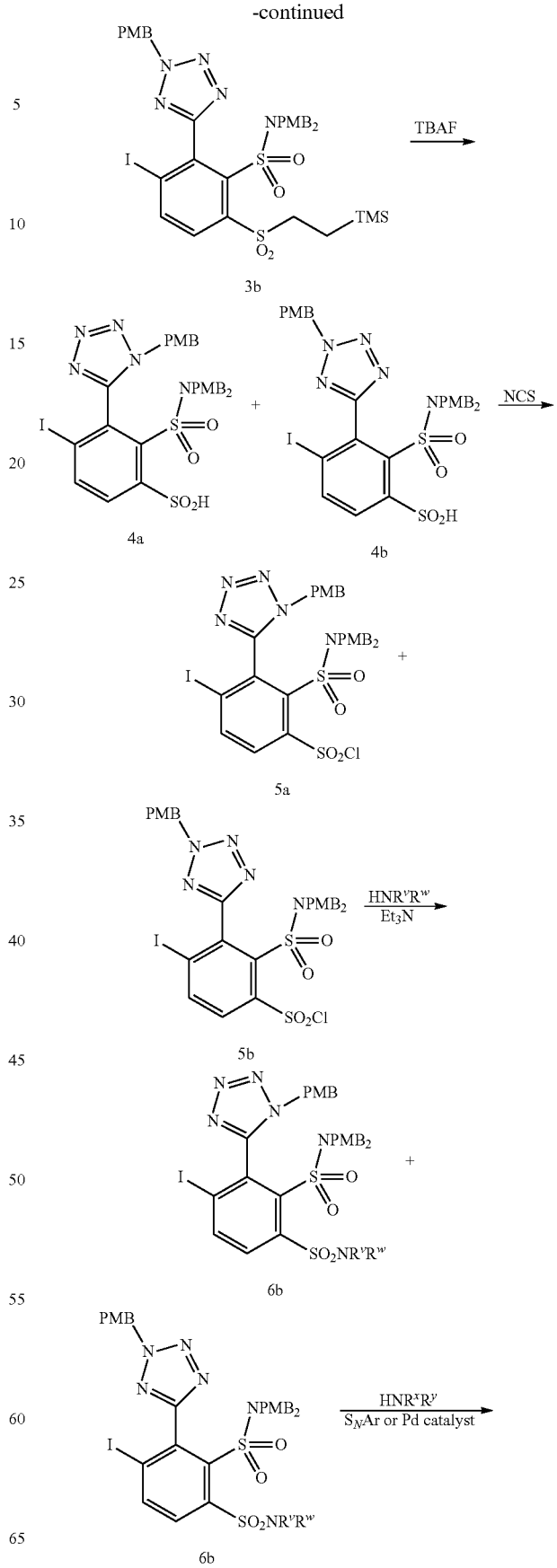

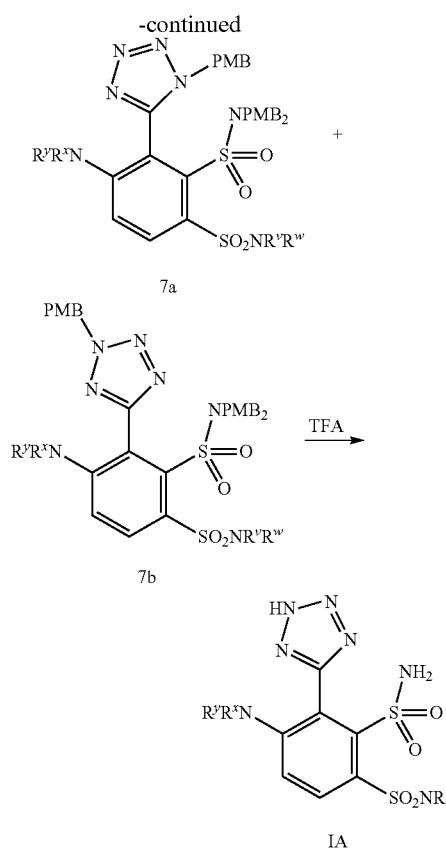

Sulfonamide compounds of the current invention, IA, may be prepared according to general Scheme I. According to the Scheme, bromide intermediates 1a and 1b (Scheme V) may be selectively reacted at the bromo position with 2(trimethylsilyl)enthanethiol in the presence of a base (such as cesium carbonate) to afford sulfides 2a and 2b. Oxidation, for example by using meta-chloroperoxybenzoic acid, gives sulfones 3a and 3b. Treatment with tetrabutylammonium fluoride (TBAF) gives the corresponding sulfinic acids 4a and 4b. The sulfinic acids may be converted to the corresponding sulfonyl chlorides 5a and 5b in a variety of ways, for example by treatment with N-chlorosuccinimide. Treatment of the sulfonyl chlorides 5a and 5b with a substituted or unsubstituted cyclic or acyclic amine ($R^v$ and $R^w$ can be independent substituents or combined or form a saturated heterocyclic ring) in the presence of a base such as triethyl amine affords the sulfonamides 6a and 6b. Alternatively, sulfinic acids 4a and 4b may be directly converted in one pot to the sulfonamides 6a and 6b by reaction with N-chlorosuccinimide in the presence of the above described amine reactant. Metal mediated C—N coupling, for example using palladium catalysts, or nucleophilic aromatic substitution ($S_NAr$) using a variety of nitrogen containing cyclic or acyclic saturated reagents ($R^x$ and $R^y$ can be independent substituents or combined to form a saturated heterocyclic ring) afford analogs 7a and 7b. Final PMB protective group removal can be achieved under acidic conditions such as by using TFA in the optional presence of a carbocation scavenger, such as anisole or triethylsilane, providing target compounds IA.

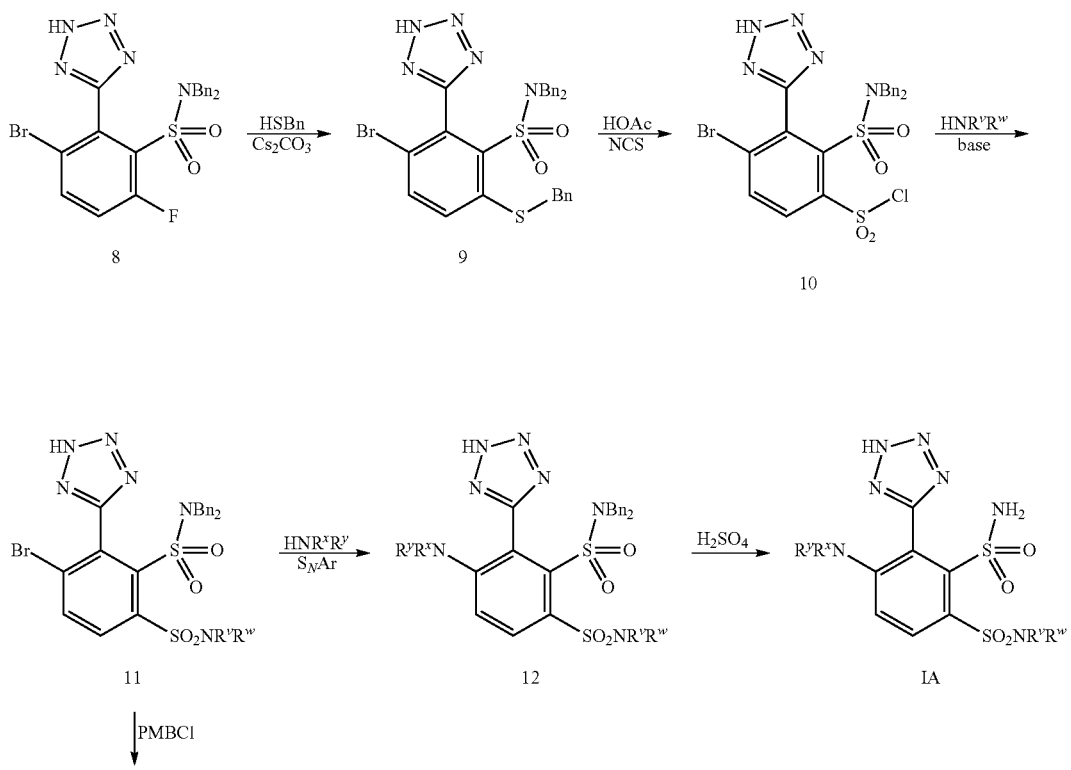

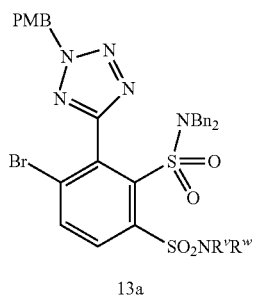 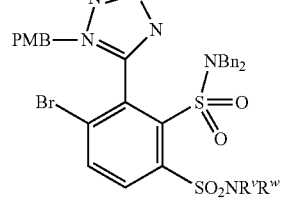 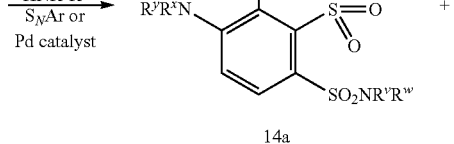

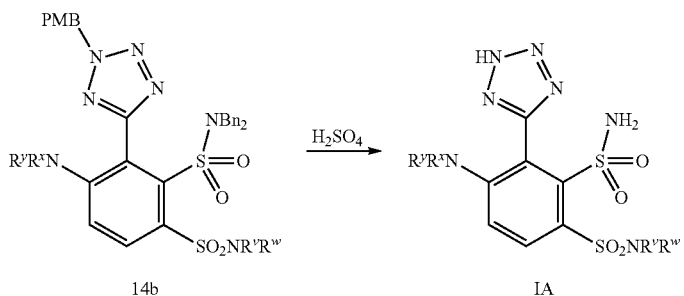

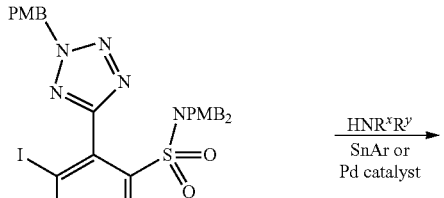

Alternatively as highlighted in Scheme II, fluoride intermediate 8 (Scheme VI) can be treated with a sulfide such as benzyl mercaptan in the presence of a base such as cesium carbonate to provide sulfide 9. Treatment of 9 with an oxidant such as N-chlorosuccinimide under acidic conditions will provide sulfonyl chloride 10. Treatment with an amine $HNR^xR^y$ (see Scheme I) in the presense of a base will provide sulfonamide 11. Treatment with various nitrogen containing cyclic or acyclic saturated reagents will provide intermediate 12. Finally cleavage of the benzyl groups can be accomplished after treatment with an appropriate acid such as sulfuric acid to provide target compounds IA, Alternatively the tetrazole of 11 can be protected with an appropriate protecting group such as para-methoxybenzyl to provide 13a and 13b. Subsequent metal mediated C—N coupling, for example using palladium catalysts, or nucleophilic aromatic substitution using a variety of nitrogen containing cyclic or acyclic saturated reagents will afford intermediates 14a and 14b. Final cleavage of the PMB and benzyl protecting groups can be achieved under acidic conditions such as by using sulfuric acid to provide target compounds IA.

Scheme III

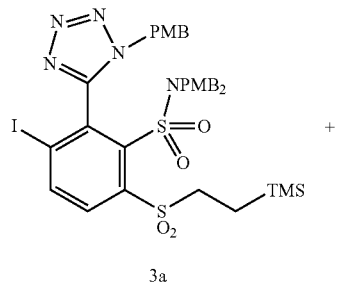

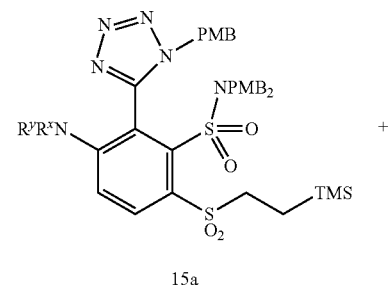

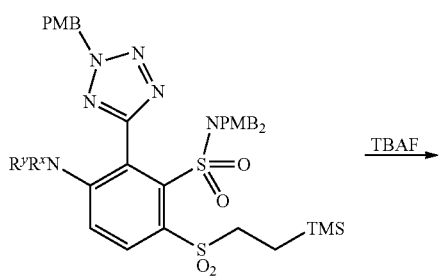

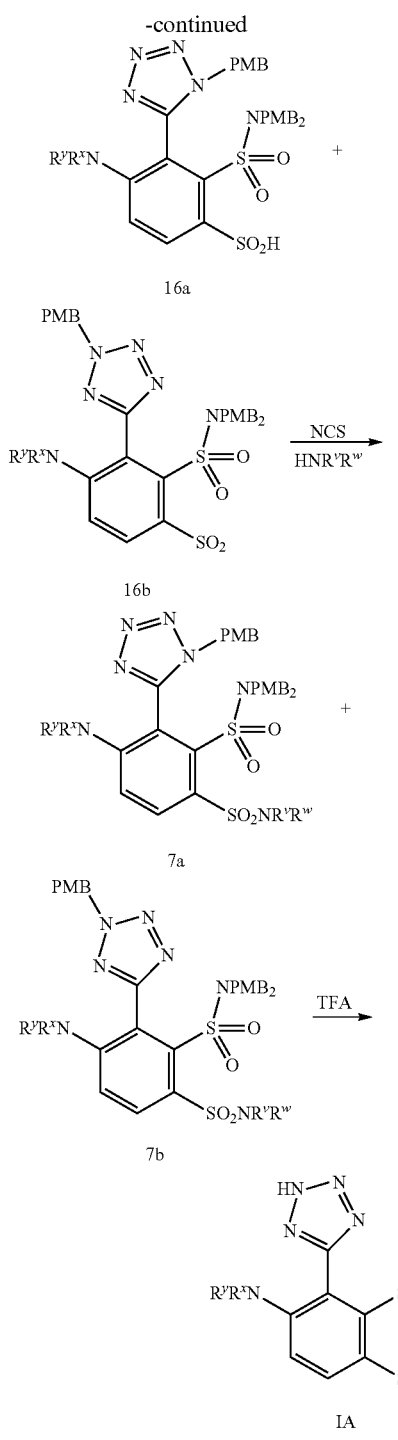

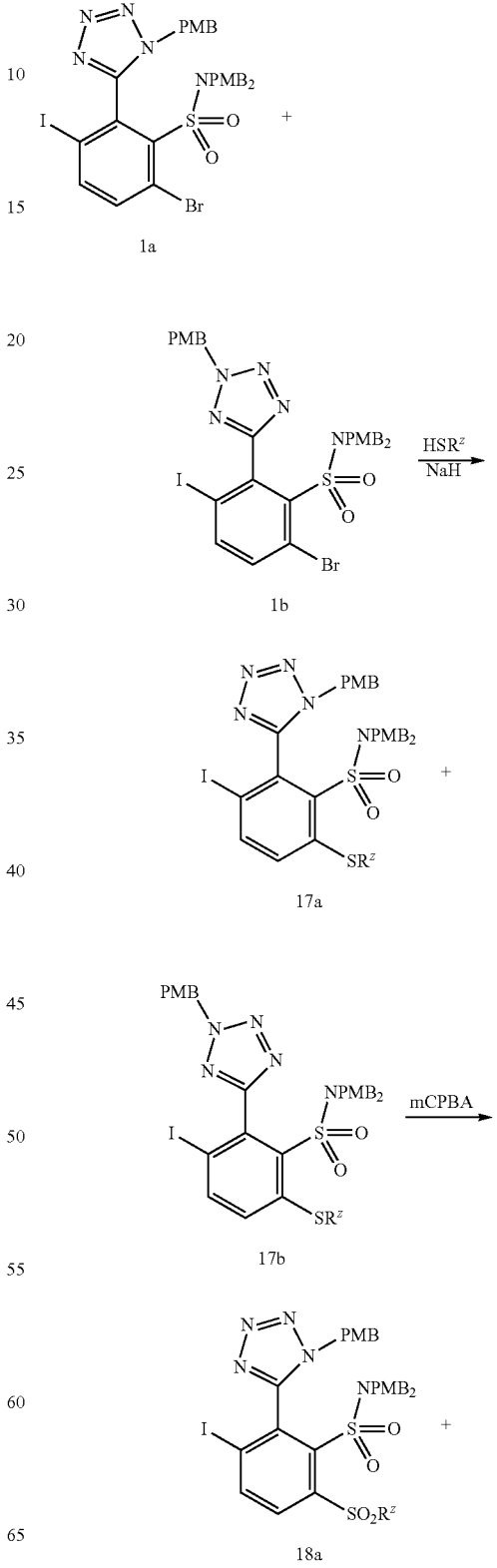

namides 7a and 7b. Finally cleavage of the protecting groups with an appropriate reagent such as TFA will provide target compounds IA.

Scheme IV

Alternatively as highlighted in Scheme III, the sequence of steps to provide target compounds IA can be modified. For example aryl iodides 3a and 3b can be treated with various nitrogen containing cyclic or acyclic saturated reagents under metal mediated C—N coupling or nucleophilic aromatic substitution conditions to provide intermediates 15a and 15b. Subsequent cleavage of the trimethylsilyl ethyl group with an appropriate reagent such as TBAF will provide sulfinic acids 16a and 16b. Conversion of the sulfinic acids to the sulfonyl chlorides for example using NCS in the presence of various amines will provide sulfo-

Scheme V

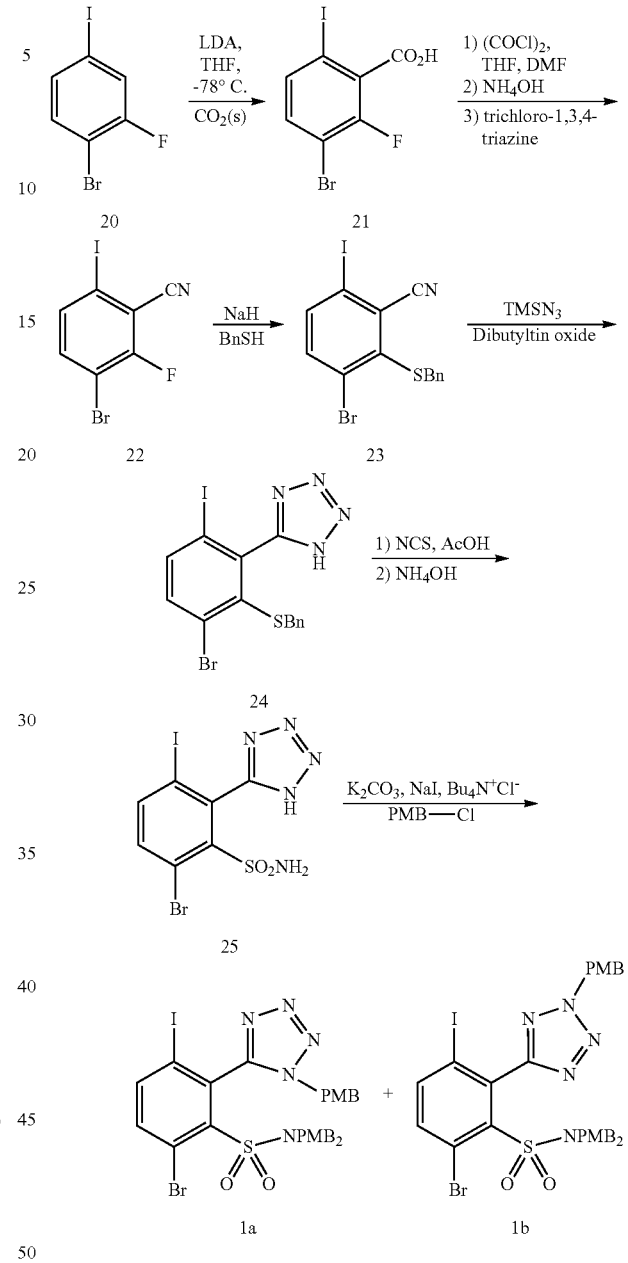

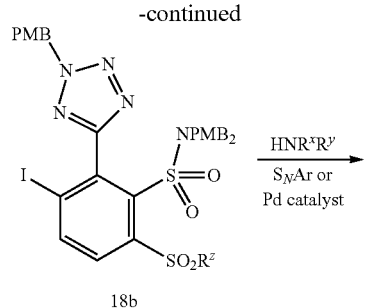
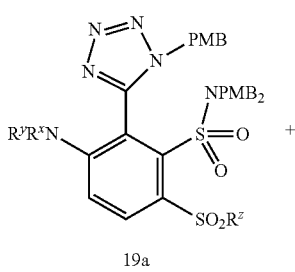
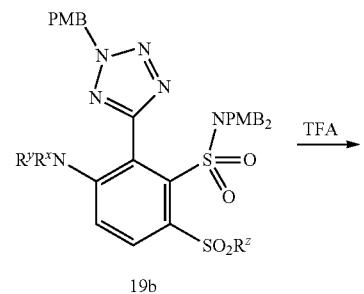
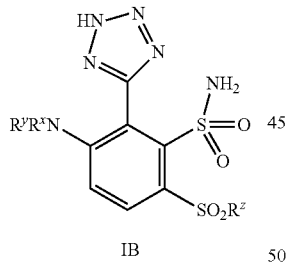

Sulfone compounds of the current invention, IB, may be prepared according to general Scheme IV. Bromides 1a and 1b (Scheme V) can be treated with various sulfides (where $R^z$ can be a substituted or unsubstituted saturated heterocycle or saturated acycle) in the presence of a base such as sodium hydride to afford sulfides 17a and 17b. Oxidation of the sulfides to sulfones 18a and 18b can be accomplished using an oxidant such as meta-chloroperoxybenzoic acid. Subsequent metal mediated C—N coupling, for example using palladium catalysts, or nucleophilic aromatic substitution using a variety of nitrogen containing cyclic or acyclic saturated reagents will afford intermediates 19a and 19b. Final cleavage of the PMB protecting groups can be achieved under acidic conditions such as by using trifluoroacetic acid to provide target compounds IB.

Intermediates 1a and 1b can be prepared according to Scheme V. According to the Scheme, commercially available aryl fluoride 20 can be converted to the carboxylic acid 21 by treatment with LDA, followed by dry ice. The carboxylic acid functionality can be transformed to the corresponding nitrile 22 in numerous ways known in the art. One approach involves conversion to the acid chloride, for example using oxalyl chloride, followed by treatment with ammonium hydroxide to afford the carboxamide, and finally, dehydration, for example using trichloro-1,3,5-triazine, to give the nitrile 22. Nucleophilic aromatic substitution of the fluoride using benzyl mercaptan and a base such as sodium hydride provides the sulfide 23. The nitrile present in 23 can be converted to the tetrazole 24 using one of several methods, for example by treatment with trimethylsilyl azide and dibutyltin oxide. Conversion of the benzyl sulfide to the sulfonyl chloride can be accomplished in several ways, for example, by treatment with N-chloro succinimide in acetic acid. Treatment with ammonium hydroxide then affords the sulfonamide 25. Concommittant protection of the tetrazole and sulfonamide to afford positional isomer mixture 1a and 1b can be achieved by treatment with excess of para-methoxybenzyl chloride in the presence of a base, such as potassium carbonate, and NaI and tetrabutyl ammonium chloride as catalysts. Typically 1a and 1b are used as a mixture of regioisomers, but the isomers can optionally be separated and used individually in the same way. In the examples below, it should be understood that the mixture of regioisomers or the individual regioisomers may be used interchangeably (occasionally only one isomer is shown for the sake of simplicity).

such as N-chlorosuccinimide. Treatment with dibenzylamine in the presense of a base such as triethyl amine will provide sulfonamide 31. The nitrile of 31 can be converted to a tetrazole under various conditions including treatment with sodium azide in the presence of zinc chloride to afford 38.

Note that in the experimental procedures below, the REFERENCE EXAMPLES and EXAMPLES can be used as the mixture of para-methoxylbenzyl tetrazole regioisomers. Alternatively, the two regioisomers may be separated and each can be used as described below in the same fashion. In some REFERENCE EXAMPLES and EXAMPLES below, both regioisomers are explicitly used; however, in other cases, for the sake of simplicity, only one regioisomers was, in fact, typically used.

Reference Example 1 tert-butyl (R)-(2-amino-3-hydroxypropyl)carbamate

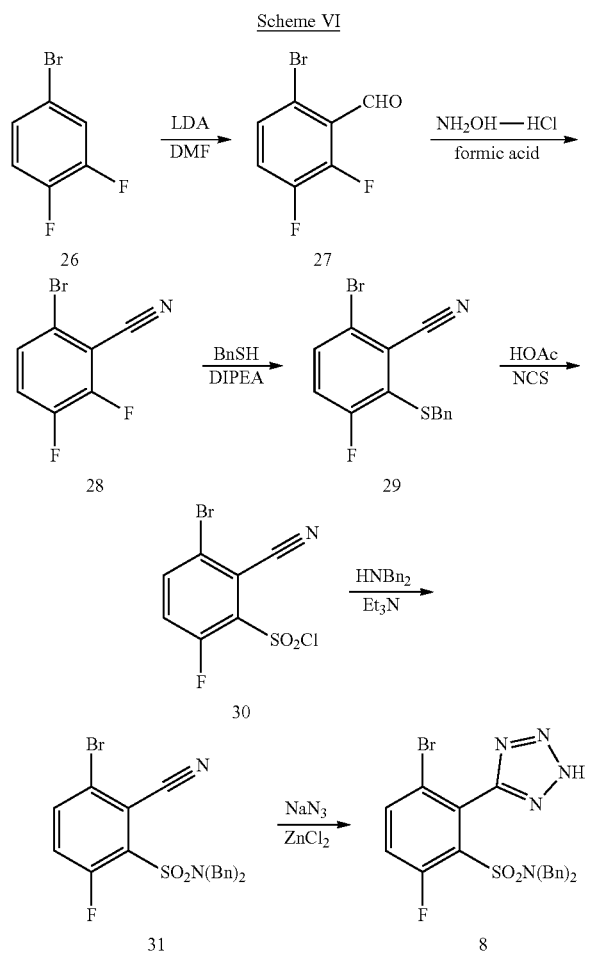

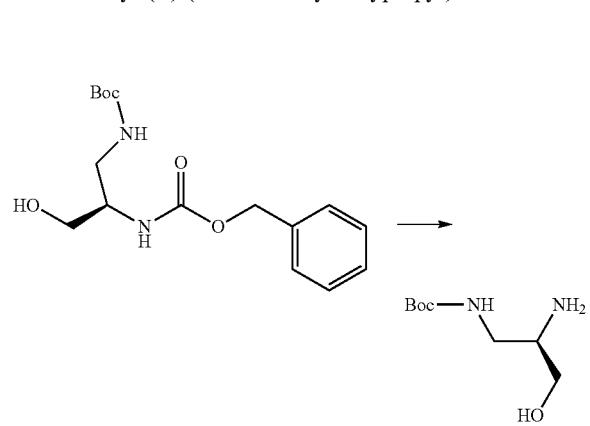

A solution of (R)-benzyl tert-butyl (3-hydroxypropane-1,2-dicarbamate (1.05 g, 3.24 mmol) in MeOH (15 mL) in a round bottom flask at RT under an atmosphere of N₂ was degassed by under reduced pressure followed by the replacement of the N₂ atmosphere. To the reaction mixture was added Pd—C (0.69 g, 0.65 mmol, 10% wt/wt) and the mixture was hydrogenated at 1 atmosphere (balloon pressure) overnight. The reaction mixture was filtered through a CELITE pad, washed the pad with EtOAc (3×50 mL). The filtrate was concentrated to afford the title product that was used without further purification.

Reference Example 2 tert-butyl (R)-(3-amino-2-hydroxypropyl)carbamate

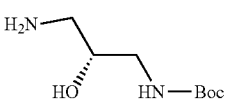

Intermediate 8 can be prepared according to Scheme VI. According to the Scheme, commercially available aryl fluoride 26 can be converted to the aldehyde 27 by treatment with LDA, followed the addition of N,N-dimethylformamide. The aldehyde can then be converted to the nitrile 28 under various conditions including treatment with hydroxylamine hydrochloride and formic acid. Selective displacement of the fluoride ortho to the nitrile with benzyl mercaptan can be accomplished with various bases including N,N-diisopropylethylamine to provide the sulfide 29. The benzyl sulfide can be converted to the sulfonyl chloride 30 upon treatment with acetic acid in the presence of an oxidant To a solution of epoxide (R)-tert-butyl (oxiran-2-ylmethyl)carbamate (2.0 g, 11.55 mmol) in ethanol (20 mL) was added ammonium hydroxide (20 mL, 114 mmol) at RT. The reaction mixture was stirred for 2 hours and concentrated in vacuo. The residue was dissolved in CH₂Cl₂ (40 mL), dried (MgSO₄), and concentrated in vacuo. The crude product was chromatographed over silica gel (40 g), eluting with 0-40% EtOAc/EtOH to give the title product. LC/MS [M+H]+: 191.

Reference Example 3 tert-butyl (S)-(3-amino-2-hydroxypropyl)carbamate

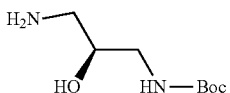

Synthesis of tert-butyl (S)-(3-amino-2-hydroxypropyl) carbamate was accomplished using the same procedure as described in REFERENCE EXAMPLE 2 from epoxide (S)-tert-butyl (oxiran-2-ylmethyl)carbamate. LC/MS [M+H]+: 191.

Reference Example 4 benzyl tert-butyl (3-aminopropane-1,2-diyl)(R)-dicarbamate

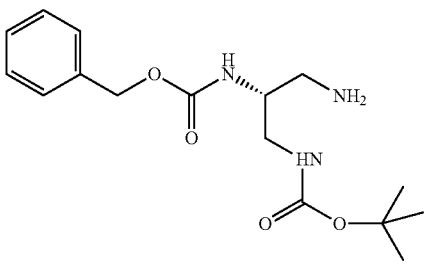 [SMILES: CC(C)(C)OC(=O)NC[C@@H](CN)NC(=O)OCc1ccccc1]

Step A. (M-benzyl tert-butyl (3-(1,3-dioxoisoindolin-2-yl)propane-1,2-diyl)dicarbamate Isoindoline-1,3-dione (1.583 g, 10.76 mmol) and triphenylphosphine (3.06 g, 11.65 mmol) were added to a stirred solution of (S)—N-2-benzyloxycarbonyl-N-3-t-butyloxycarbonyl-2,3-diaminopropanol (2.908 g, 8.97 mmol) in tetrahydrofuran (20 mL) at RT. (E)-diethyl diazene-1,2-dicarboxylate (1.84 mL, 11.65 mmol) was added slowly and the mixture was stirred at 0° C. for 30 min. The reaction mixture was concentrated in vacuo, the crude product was then titrated with 60 mL of 50% EtOAc in hexanes. The precipitate was filtered and the filtrate was collected and concentrated. The residue was chromatographed over silica gel, eluting with 0-50% EtOAc in hexanes to give the title compound. LC/MS [M+H]+: 454.

Step B. benzyl tert-butyl (3-aminopropane-1,2-diyl)(R)-dicarbamate

To a solution of (S)-benzyl tert-butyl (3-(1,3-dioxoisoindolin-2-yl)propane-1,2-diyl)dicarbamate (4 g, 8.82 mmol) in EtOH (100 mL) was added hydrazine (0.44 mL, 14.11 mmol) at 0° C. The reaction mixture was stirred at 60° C. for 2 hours. The reaction mixture was concentrated in vacuo. The residue was titrated with EtOAc (3×40 mL). The combined organic layers were concentrated to give the title compound, which was used without further purification. LC/MS [M+H]+: 324.

Reference Example 5 tert-butyl ((cis-3-hydroxypiperidin-4-yl)methyl)carbamate

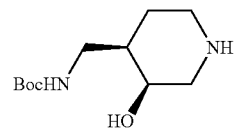 [SMILES: CC(C)(C)OC(=O)NC[C@H]1CCNC[C@H]1O]

Step A: benzyl cis-4-(((tert-butoxycarbonyl)amino)methyl)-3-hydroxypiperidine-1-carboxylate To cis-benzyl 4-(aminomethyl)-3-hydroxypiperidine-1-carboxylate (500 mg, 1.892 mmol) was added DCM (9.5 mL), DIPEA (0.99 mL, 5.67 mmol) and BOC anhydride (0.66 mL, 2.84 mmol). The reaction mixture was stirred at RT for 1.5 hours. The reaction mixture was concentrated and purified by silica gel column chromatography (gradient elution 100% hexane to 100% EtOAc) to give the title compound. LC/MS [M+H]$^+$: 365.28

Step B: tert-butyl ((cis-3-hydroxypiperidin-4-yl)methyl)carbamate

Benzyl cis-4-(((tert-butoxycarbonyl)amino)methyl)-3-hydroxypiperidine-1-carboxylate (501 mg, 1.375 mmol) was dissolved in MeOH (10 mL) and EtOAc (3 mL), followed by the addition of 10% Pd—C (345 mg, 3.24 mmol). The mixture was stirred at RT under 1 atmosphere of H$_2$ (balloon) for 3 hours. The reaction mixture was filtered and the filter cake was washed with EtOAc and MeOH. The filtrates were concentrated to give the title compound. LC/MS [M+H]$^+$: 231.28

The following REFERENCE EXAMPLES 6-9 were prepared as described for REFERENCE EXAMPLE 5 using the requisite amine intermediates as depicted below.

| Ref. Ex. | INTERMEDIATES | STRUCTURE/NAME | LC/MS [M + H]$^+$ |
|---|---|---|---|
| 6 | benzyl trans-4-(aminomethyl)-3-hydroxypiperidine-1-carboxylate | tert-butyl ((trans-3-hydroxypiperidin-4-yl)methyl)carbamate | 231.31 |

| Ref. Ex. | INTERMEDIATES | STRUCTURE/NAME | LC/MS [M + H]+ |
|---|---|---|---|
| 7 | benzyl cis-4-(aminomethyl)-3-fluoropiperidine-1-carboxylate | tert-butyl ((cis-3-fluoropiperidin-4-yl)methyl)carbamate | 233.32 |
| 8 | benzyl trans-4-(aminomethyl)-3-fluoropiperidine-1-carboxylate | tert-butyl ((trans-3-fluoropiperidin-4-yl)methyl)carbamate | 233.29 |
| 9 | ((1R,5S,6S)-3-benzyl-3-azabicyclo[3.1.0]hexan-6-yl)methanamine | tert-butyl ((1R,5S,6R)-3-azabicyclo[3.1.0]hexan-6-yl-methyl)carbamate | 213.29 |

Reference Example 10

1-(2-((tert-butyldimethylsilyl)oxy)ethyl)piperazin-2-one

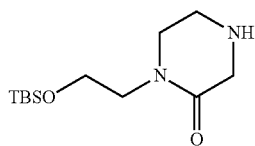 [SMILES: CC(C)(C)[Si](C)(C)OCCN1CCNCC1=O]

Step A: 1-(2-Hydroxyethyl)piperazin-2-one

A solution of tert-butyl 4-(2-((tert-butyldimethylsilyl)oxy)ethyl)-3-oxopiperazine-1-carboxylate (10.0 g, 27.93 mmol, prepared as described in US2006/211693 A1, 2006) in DCM (100 mL) and TFA (30 mL) was stirred at room temperature for 2 hours. The resulting mixture was concentrated under vacuum. The residue was purified by reverse phase column chromatography ($C_{18}$), eluting with 50% MeOH in water (5 mmol/L $NH_4HCO_3$) to afford 1-(2-hydroxyethyl)piperazin-2-one: LCMS [M+1]+: 145.

Step B: 1-(2-((Tert-butyldimethylsilyl)oxy)ethyl)piperazin-2-one

To a solution of 1-(2-hydroxyethyl)piperazin-2-one (1.50 g, 10.42 mmol) in THF (50 mL) was added tert-butylchlorodimethylsilane (1.60 g, 10.67 mmol) and 1H-imidazole (0.71 g, 10.44 mmol) at 0° C. The reaction mixture was stirred for 3 hours at RT. The resulting mixture was evaporated under vacuum. The residue was purified by a silica gel column chromatography, eluting with 40% EA in PE to afford 1-(2-((tert-butyldimethylsilyl)oxy)ethyl)piperazin-2-one: LCMS [M+1]+: 259.

Reference Example 11

1-(2-((tert-butyldimethylsilyl)oxy)ethyl)piperazin-2-one

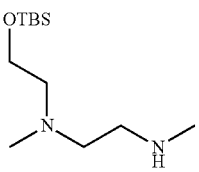

Step A: Tert-butyl (2-((2-((text-butyldimethylsilyl)oxy)ethyl)(methyl)amino)ethyl)(methyl) carbamate To a solution of tert-butyl methyl(2-(methylamino)ethyl)carbamate (5.10 g, 27.12 mmol) in acetonitrile (30 mL) was added (2-bromoethoxy) (tert-butyl)dimethylsilane (6.40 g, 26.78 mmol) and $K_2CO_3$ (5.50 g, 39.86 mmol) at RT. The reaction mixture was stirred for 2 hours at RT. The resulting mixture was diluted with water (100 mL), and then extracted with EA (3×60 mL). The combined organic layers were dried over anhydrous Na$_2$SO$_4$ and filtered. The filtrate was evaporated under vacuum. The residue was purified by a silica gel column chromatography, eluting with 35% EA in PE to afford the title compound: LCMS [M+1]$^+$: 347.

Step B: N1-(2-(((tert-butyldimethylsilyl)oxy)ethyl)-N1,N2-dimethylethane-1,2-diamine A solution of tert-butyl (2-((2-(((tert-butyldimethylsilyl)oxy)ethyl)(methyl) amino)ethyl)(methyl)carbamate (2.30 g, 6.65 mmol) in TFA (3 mL) was stirred for 1 hour at RT. After that time, the reaction was quenched with aqueous sat'd NaHCO$_3$ (30 mL) and extracted with EA (3×10 mL). The combined organic layers were concentrated under vacuum to afford the title compound. LCMS [M+1]$^+$: 247.

Reference Example 12 benzyl (2-(2-oxopiperazin-1-yl)ethyl)carbamate

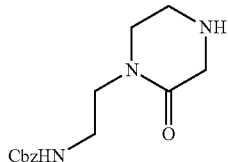 [SMILES: O=C(NCCN1CCNCC1=O)OCc1ccccc1]

Step A: Tert-butyl 4-(2-(((benzyloxy) carbonyl) amino)ethyl)-3-oxopiperazine-1-carboxylate To a mixture of NaH (4.39 g, 110 mmol, 60% in mineral oil) in DMF (100 mL) was added tert-butyl 3-oxopiperazine-1-carboxylate (10 g, 49.9 mmol) at 0° C. and the resultant mixture was stirred for 10 minutes. Benzyl (2-bromoethyl) carbamate (14.18 g, 54.9 mmol) was then added to the reaction and the mixture was stirred at RT for 6 hours. The resulting mixture was quenched with water (100 mL) and extracted with EA (100 mL×3). The organic layers were combined, dried over anhydrous MgSO$_4$ and filtered. The filtrate was concentrated under vacuum. The residue was purified by a silica gel column chromatography, eluting with 60% EA in PE to afford the title compound: LCMS [M+Na]$^+$: 400.

Step B: Benzyl (2-(2-oxopiperazin-1-yl)ethyl)carbamate

To a solution of tert-butyl 4-(2-(((benzyloxy)carbonyl) amino)ethyl)-3-oxopiperazine-1-carboxylate (4.20 g, 11.13 mmol) in DCM (5 mL) was added TFA (5 mL) at room temperature. The reaction mixture was stirred at RT for 2 hours. The resulting solution was quenched with aqueous sat'd NaHCO$_3$ (30 mL) and extracted with EA (3×10 mL). The combined organic layers were purified by a silica gel column chromatography, eluting with 10% MeOH in DCM to afford benzyl (2-(2 oxopiperazin-1-yl)ethyl)carbamate: LCMS [M+H]$^+$: 278.

Reference Example 13 benzyl (azepan-4-ylmethyl)carbamate

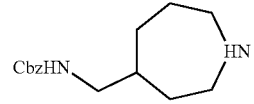

Step A: Tart-butyl 4-cyanoazepane-1-carboxylate

To a stirred mixture of tert-butyl 4-oxoazepane-1-carboxylate (5.00 g, 23.44 mmol) in DME (50 mL) was added 1-((isocyanomethyl)sulfonyl)-4-methylbenzene (9.15 g, 46.90 mmol), potassium 2-methylpropan-2-plate (26.3 g, 234 mmol) and t-BuOH (2 mL) under nitrogen at 0° C. The reaction mixture was stirred for 16 hours at RT. The resulting mixture was quenched with water (100 mL) and extracted with EA (3×80 mL). The combined organic layer was dried over anhydrous Na$_2$SO$_4$ and filtered. The filtrate was evaporated under vacuum. The residue was purified by a silica gel column chromatography, eluting with 16% EA in PE to afford the title compound: GCMS (EI) calc'd for C$_{12}$H$_{20}$N$_2$O$_2$[M]: 224, found 224; $^1$H NMR (300 MHz, CDCl$_3$) δ 3.70-3.20 (m, 4H), 2.90-2.78 (m, 1H), 2.11-1.70 (m, 6H), 1.47 (s, 9H)

Step 3: Tert-butyl 4-(aminomethyl)azepane-1-carboxylate

To a stirred solution of tert-butyl 4-cyanoazepane-1-carboxylate (1.00 g, 4.46 mmol) in MeOH (10 mL) were added ammonium hydroxide (2.92 g, 44.60 mmol) and Raney Ni (4.46 mmol) under nitrogen at RT. The flask was flushed with hydrogen three times. The mixture was stirred for 12 hours at RT under hydrogen (1.5 atm). The resulting mixture was filtered and the filtrate was concentrated under vacuum to afford the title compound, which was used in the next step without further purification: LCMS [M+H]$^+$: 229.

Step C: Tert-butyl 4-(((((benzyloxy)carbonyl)amino) methyl)azepane-1-carboxylate To the solution of tert-butyl 4-(aminomethyl)azepane-1-carboxylate (1.00 g, 4.38 mmol) in DCM (10 mL) were added benzyl chloroformate (1.49 g, 8.76 mmol) and triethylamine (0.89 g, 8.76 mmol) at room temperature. The reaction mixture was stirred at 25° C. for 2 hours. The resulting mixture was concentrated under vacuum. The residue was purified by a silica gel column chromatography, eluting with 90% EA in PE to afford the title compound: LCMS (ESI) calc'd for C$_{20}$H$_{30}$N$_2$O$_4$ [M+H]$^+$: 363, found 363.

Step D: Benzyl (azepan-4-ylmethyl)carbamate

To a stirred solution of tert-butyl 4-(((((benzyloxy)carbonyl)amino) methyl)azepane-1-carboxylate (1.20 g, 3.31 mmol) in DCM (8 mL) was added TFA (2 mL) under nitrogen at RT. The resulting mixture was stirred at RT for 1 hour. The resulting solution was quenched with aqueous sat'd NaHCO$_3$ (30 mL) and extracted with EA (3×10 mL). The combined organic layers were concentrated under vacuum to afford the title compound, which was used in the next step without further purification: LCMS [M+H]+: 263.

Reference Example 14 benzyl (2-(azepan-4-yl)ethyl)carbamate

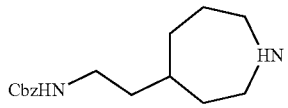 [SMILES: O=C(NCCC1CCCNCC1)OCc1ccccc1]

Step A: (Cyanomethyl)triphenylphosphonium bromide

To a solution of triphenylphosphine (32.8 g, 125.1 mmol) in Et₂O (50 mL) was added 2-bromoacetonitrile (12.0 g, 100 mmol) at RT. The reaction mixture was stirred at RT for 24 hours. The precipitate was filtered from the solution. The solid was washed with Et₂O (3×20 mL) and dried under vacuum to afford the title compound: LCMS [M−Br]+: 302.

Step B: Tert-butyl 4-(cyanomethylene)azepane-1-carboxylate

To a solution of potassium 2-m ethylpropan-2-olate (5.05 g, 45.00 mmol) in THF (5 mL) were added test-butyl 4-oxoazepane-1-carboxylate (6.40 g, 30 mmol) and (cyanomethyl)triphenylphosphonium bromide (17.21 g, 45 mmol) at RT under nitrogen. The reaction mixture was stirred at 70° C. for 3 hours. After cooling to RT, the reaction mixture was concentrated under vacuum. The residue was purified by a silica gel column chromatography, eluting with 20% EA in PE to afford tert-butyl 4-(cyanomethylene) azepane-1-carboxylate as an oil: GCMS (EI) 236; ¹H NMR (300 MHz, CDCl₃) δ 5.22 (s, 0.5H), 5.16 (s, 0.5H), 3.55-3.34 (m, 4H), 2.91-2.35 (m, 4H), 1.90-1.69 (m, 2H), 1.47 (s, 9H).

Step C: Tert-butyl 4-(2-aminoethyl)azepane-1-carboxylate

To a stirred solution of tert-butyl 4-(cyanomethylene) azepane-1-carboxylate (3.00 g, 12.70 mmol) in Mani (40 mL) was added Raney Ni (12.70 mmol) under nitrogen at RT. The reaction mixture was degassed with hydrogen three times. The reaction mixture was stirred for 12 hours at RT under hydrogen (1.5 atm). The resulting mixture was filtered and the filtrate was concentrated under vacuum to afford Teri-butyl 4-(2-aminoethyl)azepane-1-carboxylate as an oil. The crude product was used in the next step without further purification: LCMS [M+H]+: 243.

Step D: Tert-butyl 4-(2-(((benzyloxy)carbonyl) amino)ethyl)azepane-1-carboxylate To a solution of Tert-butyl 4-(2-aminoethyl)azepane-1-carboxylate (3.0 g, 12.4 mmol) in DCM (40 mL) were added benzyl chloroformate (3.88 g, 22.73 mmol) and triethylamine (2.30 g, 22.73 mmol) at room temperature. The reaction mixture was stirred at room temperature for 4 hours. The reaction mixture was evaporated under vacuum. The residue was purified by a silica gel column chromatography, eluting with 50% EA in PE to afford the title compounds: LCMS [M+H]+: 377.

Step E: Benzyl (2-(azepan-4-yl)ethyl)carbamate

To a stirred solution of tert-butyl 4-(2-(((benzyloxy)carbonyl)amino)ethyl) azepane-1-carboxylate (0.50 g, 1.33 mmol) in DCM (4 mL) was added TFA (1 mL) under nitrogen at RT. The reaction solution was stirred at RT for 1 hour. The resulting solution was quenched with aqueous sat'd NaHCO₃ (30 mL) and extracted with EA (3×10 mL). The combined organic layers were concentrated under vacuum to afford the title compound, which was used in the next step without further purification: LCMS [M+H]+: 277.

Reference Example 15 tert-butyl (2-((tert-butyldimethylsilyl)oxy)ethyl) (piperidin-4-ylmethyl) carbamate

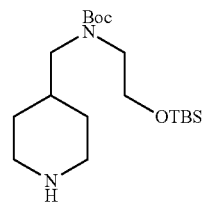 [SMILES: CC(C)(C)OC(=O)N(CCO[Si](C)(C)C(C)(C)C)CC1CCNCC1]

Step A: Benzyl 4-((tert-butoxycarbonyl)(2-((tert-butyldimethylsilyl)oxy)ethyl)amino) methyl)piperidine-1-carboxylate To a solution of benzyl 4-(((tert-butoxycarbonyl)amino) methyl) piperidine-1-carboxylate (3.48 g, 9.99 mmol, prepared as described in US 2003/119811) in DMF (30 mL) was added NaH (0.80 g, 19.90 mmol, 60% in mineral oil) at 0° C. under nitrogen. The reaction mixture was stirred for 0.5 hours at 0° C. Then (2-bromoethoxy)(tert-butyl)dimethylsilane (3.58 g, 14.98 mmol) was added in several portions. The reaction mixture was stirred for 16 hours at RT. The resulting mixture was quenched with water (50 mL) and extracted with EA (3×100 mL). The combined organic layers were washed with brine (100 mL), dried over anhydrous Na₂SO₄ and filtered. The filtrate was concentrated under reduced pressure. The residue was purified by a silica gel column chromatography, eluting with 30% EA in PE to afford the title compound: LCMS [M+Na]+: 529.

Step B: Tert-butyl (2-((tert-butyldimethylsilyl)oxy) ethyl)(piperidin-4-ylmethyl carbamate To a solution of benzyl 4-(((tert-butoxycarbonyl)(2-((tert-butyldimethylsilyl) oxy)ethyl)amino)methyl)piperidine-1-carboxylate (0.90 g, 1.78 mmol) in MeOH was added Pd/C (0.45 g, 0.42 mmol, 10% wt) at RT under nitrogen. The reaction mixture was degassed 3 times with hydrogen and stirred for 16 hours at RT under hydrogen (1.5 atm). The resulting mixture was filtered. The filtrate was concentrated under vacuum to afford the title compound, which was used without further purification: LCMS [M+H]+: 373.

Reference Example 16 tert-butyl (2-hydroxyethyl)(piperidin-4-yl)carbamate

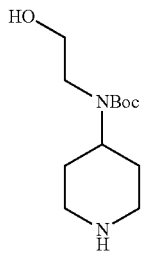

Step A: Tert-butyl (2-(2-(N,N-bis(4-methoxybenzyl)sulfamoyl)-4-iodo-3-(2-(4-methoxybenzyl)-2H-tetrazol-5-yl)phenylsulfonamido)ethyl)carbamate To a solution of benzyl 4-((2-hydroxyethyl)amino)piperidine-1-carboxylate (2.80 g, 10.06 mmol, prepared as described in WO 2005/113504) in DCM (20 mL) and water (20 mL) were added sodium hydrogencarbonate (1.69 g, 20.12 mmol) and di-tert-butyl dicarbonate (3.29 g, 15.09 mmol) at RT. The mixture was stirred for 16 hours at RT. The resulting mixture was extracted with DCM (3×50 mL). The combined organic layers were washed with brine (10 mL), dried over anhydrous $Na_2SO_4$, and filtered. The filtrate was concentrated under reduced pressure. The residue was purified by a silica gel column chromatography, eluting with 40% EA in PE to afford the title compound, which was used in the next step without further purification: LCMS (ESI) calc'd for $C_{20}H_{30}N_2O_5$ $[M+H]^+$: 379, found 379.

Step B: Tert-butyl (2-hydroxyethyl)(piperidin-4-yl)carbamate

To a solution of benzyl 4-((tert-butoxycarbonyl)(2-hydroxyethyl) amino)piperidine-1-carboxylate (3.30 g, 8.72 mmol) in MeOH (30 mL) was added $Pd(OH)_2/C$ (0.62 g, 0.88 mmol, 5% wt) at RT under nitrogen. The reaction mixture was degassed with hydrogen 3 times. The mixture was stirred for 16 hours at RT under hydrogen (1.5 atm). The solid was filtered off. The filtrate was concentrated under vacuum to afford the title compound, which was used without further purification: LCMS $[M+H]^+$: 245.

Reference Example 17

(1,4-diazepan-5-yl)methanol

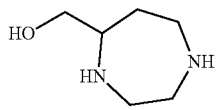

Step A: Methyl 1,4-dibenzyl-1,4-diazepane-5-carboxylate

To a stirred solution of N1,N2-dibenzylethane-1,2-diamine (11.20 g, 46.60 mmol) and TEA (13.00 mL, 93.20 mmol) in toluene (80 mL) was added the solution of methyl 2,4-dibromobutanoate (12.10 g, 46.60 mmol) in toluene (110 mL) dropwise at RT. The reaction mixture was stirred for 16 hours at 80° C. The resulting mixture was poured into aqueous sat'd $Na_2CO_3$ solution (60 mL) and extracted with EA (3×50 mL). The combined organic layers were washed with brine (3×80 mL), dried over anhydrous $Na_2SO_4$ and filtered. The filtrate was concentrated under vacuum. The residue was purified by a silica gel column chromatography, eluting with 20% EA in PE to afford the title compound: LCMS $[M+1]^+$: 339.

Step B: (1,4-Dibenzyl-1,4-diazepan-5-yl)methanol

To a solution of methyl 1,4-dibenzyl-1,4-diazepane-5-carboxylate (4.0 g, 11.82 mmol) in THF (50 mL) was added $LiAlH_4$ (0.67 g, 17.73 mmol) in several portions, and the temperature of the external bath was carefully maintained under 5° C. The resulting mixture was quenched with water (0.7 mL), followed by NaOH aqueous (0.7 mL, 15%) and water (2.1 MO. The solid was filtered off. The filtrate was concentrated under vacuum. The residue was dissolved in MeOH (15 mL) and purified by Preparative HPLC with the following conditions: Column: X Bridge Prep C18 OBD Column 19×250 mm, 10 µm; Mobile Phase A: water (10 mmol/L $NH_4HCO_3$), Mobile Phase B. ACN; Flow rate: 100 mL/min; Gradient: 30% B to 100% 13 in 15 min; Detector: UV 254/210 nm; Retention time: 3.54 min to afford the title compound: LCMS (EST) calc'd for $C_{20}H_{26}N_2O$ $[M+1]^+$: 311, found 311.

Step C: (1,4-Diazepan-5-yl)methanol

To a stirred solution of (1,4-dibenzyl-1,4-diazepan-5-yl)methanol (1.00 g, 3.22 mmol) in MeOH (15 mL) was added $Pd(OH)_2/C$ (0.50 g, 0.66 mmol, 20% wt). The reaction mixture was degassed with hydrogen three times and stirred at room temperature for 30 h under hydrogen (1.5 atm). The resulting mixture was filtered. The filtrate was evaporated under vacuum to afford the title compound, which was used without further purification: LCMS (ESI) calc'd for $C_6H_{14}N_2O$ $[M+1]^+$: 131, found 131.

Reference Example 18

3-((tert-butyldimethylsilyl)oxy)piperidin-2-one

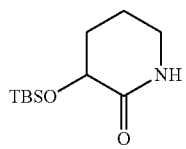

To a solution of 3-hydroxypiperidin-2-one (3.0 g, 26.1 mmol) and 1H-imidazole (1.95 g, 28.7 mmol) in DMF (30 mL) was slowly added TBSCl (5.11 g, 33.9 mmol) at RT. The reaction mixture was degassed with nitrogen 3 times and stirred at RT for 16 hours. The resulting mixture was poured into ice-water (100 mL) and extracted with EA (3×50 mL). The combined organic layers were washed with brine (3×30 mL), dried over anhydrous $Na_2SO_4$ and filtered. The filtrate was concentrated under vacuum. The residue was purified by a silica gel column chromatography, eluting with 50% of EA in PE to afford the title compound: LCMS $[M+1]^+$: 230.

Reference Example 19

2-(2-oxopiperidin-4-yl)methyl)isoindoline-1,3-dione

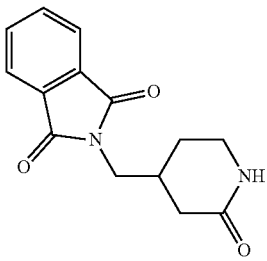 [SMILES: O=C1CC(CN2C(=O)c3ccccc3C2=O)CCN1]

Step A: (2-Oxopiperidin-4-yl)methyl methanesulfonate

To a solution of 4-(hydroxymethyl)piperidin-2-one (1.1 g, 8.13 mmol) and DMAP (0.20 g, 1.63 mmol) in DMF (10 mL) was added TEA (2.5 g, 24.39 mmol) and MsCl (1.7 g, 16.26 mmol) at 0° C. The reaction mixture was degassed with nitrogen three times and stirred for 6 hours at RT under nitrogen. The resulting solution was quenched with water (50 mL) and extracted with EA (3×50 mL). The combined organic layers were washed with brine (3×50 mL), dried over anhydrous $Na_2SO_4$ and filtered. The filtrate was concentrated under vacuum to afford the title compound, which was used in the next step without further purification: LCMS (ESI) calc'd for $C_7H_{13}NO_4S$ [M+1]$^+$: 208, found 208.

Step B: 2-((2-Oxopiperidin-4-yl)methyl)isoindoline-1,3-dione

To a solution of (2-oxopiperidin-4-yl)methyl methanesulfonate (1.70 g, 8.20 mmol) in DMF (20 mL) was added potassium 1,3-dioxoisoindolin-2-ide (4.60 g, 24.61 mmol) and $Cs_2CO_3$ (5.40 g, 16.41 mmol) at RT. The reaction mixture was degassed with nitrogen three times and stirred for 16 hours at 80° C. under nitrogen. After cooling to RT, the resulting mixture was quenched with water (50 mL) and extracted with EA (3×50 mL). The combined organic layers were washed with brine (3×50 mL), dried over anhydrous $Na_2SO_4$ and filtered. The filtrate was concentrated under vacuum. The residue was purified by a silica gel column chromatography, eluting with EA to afford the title compound: LCMS [M+1]$^+$: 259.

Reference Example 20

4-(((tert-butyldimethylsilyl)oxy)methyl)piperidin-2-one

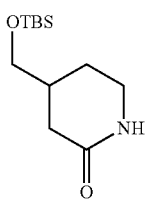

Step A: 4-(Hydroxymethyl)piperidin-2-one

To a solution of methyl 2-oxopiperidine-4-carboxylate (1.0 g, 6.36 mmol) in THF (8 mL) was added DIBAL-H (15.90 mL, 19.08 mmol, 1.2 M in THF) dropwise at −30° C. The reaction solution was stirred for 1 hour at RT. The resulting solution was quenched with MeOH (1 mL) in toluene (10 mL) and 30% $K_2CO_3$ (6 mL). The mixture was filtered and washed with EtOH (30 mL). The filtrate was concentrated under vacuum. The residue was purified by a silica gel column chromatography, eluting with 10% MeOH in DCM to afford the title compound: LCMS (ESI) calc'd for $C_6H_{11}NO_2$ [M+1]$^+$: 130, found 130.

Step B: 4-(((Tert-butyldimethylsilyl)oxy)methyl)piperidin-2-one

To a solution of 4-(hydroxymethyl)piperidin-2-one (0.60 g, 4.65 mmol) were added imidazole (0.95 g, 13.94 mmol) and TBS-Cl (2.8 g, 18.58 mmol) at RT. The reaction mixture was degassed with nitrogen three times and stirred for 16 hours at room temperature. The resulting mixture was poured into ice-water (20 mL) and extracted with EA (3×20 mL). The combined organic layers were washed with brine (3×30 mL), dried over $Na_2SO_4$ and filtered. The filtrate was concentrated under vacuum. The residue was purified by silica gel column chromatography, eluting with 60% EA in PE to afford the title compound: LCMS (ESI) calc'd for $C_{12}H_{25}NO_2Si$ [M+1]$^+$: 244, found 244.

Reference Example 21

4-((tert-butyldimethylsilyl)oxy)piperidin-2-one

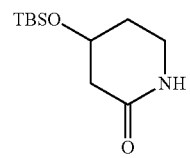

To a solution of 4-hydroxypiperidin-2-one (3.0 g, 26.1 mmol) were added imidazole (7.1 g, 104 mmol) and TBS-Cl (11.8 g, 78 mmol) at RT. The reaction mixture was degassed with nitrogen three times and stirred for 16 hours at RT. The resulting mixture was poured into ice water and extracted with EA (3×30 mL). The organic solution was washed with brine (5×50 mL), dried over anhydrous $Na_2SO_4$ and filtered. The filtrate was concentrated under vacuum. The residue was purified by a silica gel column chromatography, eluting with 75% EA in PE to afford the title compound: LCMS [M+1]$^+$: 230.

Reference Example 22

(R)-tert-butyl (2-((tert-butyldimethylsilyl)oxy)ethyl)(piperidin-3-yl) carbamate

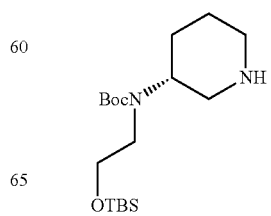

Step A: (R)-benzyl 3-((tert-butoxycarbonyl)amino) piperidine-1-carboxylate

To a solution of sodium bicarbonate (3.6 g, 42.7 mmol) and (R)-benzyl 3-aminopiperidine-1-carboxylate (5.0 g, 21.3 mmol) in DCM (30 mL) and water (20 mL) was added di-tert-butyl dicarbonate (9.3 g, 42.7 mmol). The reaction solution was stirred at RT for 16 hours. The resulting solution was diluted with water (100 mL), and then extracted with EA (3×50 mL). The organic layers were combined, washed with brine (2×100 mL), dried over anhydrous $Na_2SO_4$ and filtered. The filtrate was concentrated under vacuum. The residue was dissolved in EA (10 mL), and then PE (45 mL) was added. The slurry was stirred at RT for 16 hours. The mixture was filtered. The filter cake was dried over under vacuum to afford the title compound. LCMS (ESI) calc'd for $C_{18}H_{26}N_2O_4$ $[M+H]^+$: 335, found 335.

Step B: (R)-benzyl 3-((tert-butoxycarbonyl)(2-((tert-butyldimethylsilyl)oxy)ethyl)amino piperidine-1-carboxylate To a solution of (R)-benzyl 3-((tert-butoxycarbonyl) amino)piperidine-1-carboxylate (1.00 g, 2.99 mmol) in DMF (7 mL) was added NaH (0.36 g, 8.97 mmol, 60% in mineral oil) at 0° C. under nitrogen. The mixture was stirred at RT for 20 min under nitrogen, then (2-bromoethoxy)(tert-butyl) dimethylsilane (3.58 g, 14.95 mmol) was added at 0° C. The mixture was stirred at room temperature for 16 h. The resulting mixture was quenched with water (30 mL), then the mixture was extracted with EA (3×25 mL). The organic layers were combined, washed with brine (2×30 mL), dried over anhydrous $Na_2SO_4$ and filtered. The filtrate was concentrated under vacuum. The residue was purified by a silica gel column chromatography, eluting with 15% EA in PE to afford the title compound. LCMS $[M+H]^+$: 493.

Step C: (R)-tert-butyl (2-((tert-butyldimethylsilyl) oxy)ethyl)(piperidin-3-yl)carbamate To a solution of (R)-benzyl 3-((tert-butoxycarbonyl)(2-((tert-butyldimethylsilyl) oxy)ethyl)amino)piperidine-1-carboxylate (1.00 g, 2.03 mmol) in MeOH (8 mL) was added $Pd(OH)_2/C$ (0.4 g, 0.57 mmol, 5% wt) at RT. The mixture was degassed with hydrogen three times. The mixture was stirred 16 hours at RT under hydrogen (1.5 atm). The solid was filtered out. The filtrate was concentrated under vacuum to afford (R)-tert-butyl. (2-((tert-butyldimethylsilyl) oxy) ethyl)(piperidin-3-yl)carbamate: LCMS $[M+H]^+$: 359.

Reference Example 23

Benzyl ((1R, 5S,8r)-3-azabicyclo [3.2.1]octan-8-ylmethyl)carbamate

Step A: (1R,5S,8r)-tert-butyl ((benzyloxy)carbonyl) amino)methyl)-3-azabicyclo[3.2.1]octane-3-carboxylate To a solution of (1R,5S,8r)-tert-butyl 8-(aminomethyl)-3-azabicyclo[3.2.1] octane-3-carboxylate hydrochloride (0.500 g, 1.81 mmol) in DMF (5 mL) were added TEA (0.76 mL, 5.42 mmol) and benzyl carbonochloridate (0.37 g, 2.17 mmol) at 0° C. The reaction solution was stirred at RT for 1 hour. The resulting solution was diluted with water (20 mL) and extracted with DCM (3×10 mL). The organic layers were combined, washed with brine (2×15 mL), dried over anhydrous $Na_2SO_4$ and filtered. The filtrate was concentrated under reduced pressure. The residue was purified by a silica gel column chromatography, eluting with a gradient of 1%-40% EA in PE to afford (1R,5S,8r)-tert-butyl 8-((((benzyloxy)carbonyl)amino-3-azabicyclo[3.2.1]octane-3-carboxylate. LCMS $[M+1]^+$: 375.

Step B: Benzyl ((1R,5S,8r)-3-azabicyclo [3.2.1]octan-8-ylmethyl)carbamate

To a solution of (1R,5S,8r)-tert-butyl 8-((((benzyloxy)carbonyl)amino)methyl)-3-azabicyclo[3.2.1]octane-3-carboxylate (0.200 g, 0.53 mmol) in DCM (3 mL) was added TFA (1 mL) at 0° C. The reaction solution was stirred at 25° C. for 1 hour. The resulting solution was diluted with water (15 mL), then adjusted to pH 6-7 with a sat'd $NaHCO_3$ solution. The mixture was extracted with EA (3×40 mL). The organic layers were combined, washed with brine (2×20 mL), dried over anhydrous $Na_2SO_4$ and filtered. The filtrate was concentrated under reduced pressure to afford the title compound. LCMS $[M+1]^+$: 275.

Reference Example 24

2-(2,2-Dimethylpiperazin-1-yl)ethanol hydrochloride

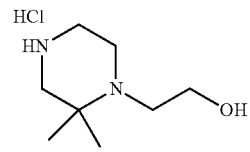

Step A: tert-Butyl 4-(2-(tert-butyldimethylsilyl)oxy) ethyl)-3,3-dimethylpiperazine-1-carboxylate To a stirred solution of tert-butyl 3,3-dimethylpiperazine-1-carboxylate (2.0 g, 9.33 mmol) and (2-bromoethoxy)(tert-butyl)dimethylsilane (3.35 g, 14.0 mmol) in ACN (5 mL) was added $K_2CO_3$ (3.87 g, 28.0 mmol) at RT. The reaction mixture was stirred at 70° C. for 16 hours. The resulting mixture was diluted with water (50 mL) and extracted with EA (3×50 mL). The combined organic layers were washed with brine (3×50 mL), dried over anhydrous $Na_2SO_4$ and filtered. The filtrate was concentrated under reduced pressure. The residue was purified by silica gel column chromatography, eluting with a gradient of 1-10% EA in PE to afford the title compound. LCMS (ESI) calc'd for $C_{19}H_{40}N_2O_3Si$ $[M+1]^+$: 373, found 373.

Step B: 2-(2,2-Dimethylpiperazin-1-yl)ethanol hydrochloride

To a solution of tert-butyl 4-(2-((tert-butyldimethylsilyl) oxy)ethyl)-3,3-dimethylpiperazine-1-carboxylate (1.50 g, 4.03 mmol) in DCM (5 mL) was added a solution of hydrogen chloride (4 M in dioxane) (2 mL, 8.0 mmol) at 25°

C. The reaction was stirred for 16 hours at 25° C. The reaction mixture was filtered. The filtrate was concentrated under reduced pressure to afford the title compound. LCMS [M+1−HCl]⁺: 159.

Reference Example 25

2-((2,5-Dihydro-1H-pyrrol-3-yl)methyl)isoindoline-1,3-dione

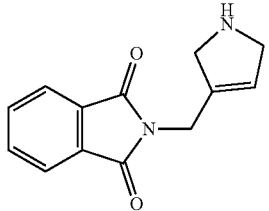 [SMILES: O=C1c2ccccc2C(=O)N1CC1=CCNC1]

Step A: tert-Buty 3-((1,3-dioxoisoindolin-2-yl)methyl)-2,5-dihydro-1H-pyrrole-1-carboxylate To a solution of tert-butyl 3-(chloromethyl)-2,5-dihydro-1H-pyrrole-1-carboxylate (0.800 g, 3.67 mmol, prepared as described in: Aponick et al. *European Organic Chemistry*, 2008, 25 4264-4276.) in DMF (15 mL) was added potassium 1,3-dioxoisoindolin-2-ide (1.02 g, 5.51 mmol). The reaction mixture was stirred at 80° C. for 5 hours, After cooling to room temperature, the resulting mixture was diluted with water (100 mL) and extracted with EA (2×20 mL). The combined organic layers were washed with brine (2×20 mL), dried over anhydrous $Na_2SO_4$ and filtered. The filtrate was concentrated under reduced pressure. The residue was purified by a silica gel column chromatography, eluting with a gradient of 1%-20% EA in PE to afford the title compound. LCMS [2×M+1]⁺: 657.

Step B: 2-((2,5-Dihydro-1H-pyrrol-3-yl)methyl)isoindoline-1,3-dione

To a solution of tert-butyl 3-((1,3-dioxoisoindolin-2-yl)methyl)-2,5-dihydro-1H-pyrrole-1-carboxylate (0.800 g, 2.436 mmol) in DCM (5 mL) was added TFA (5 mL). The reaction mixture was stirred at RT for 1 hour. The resulting solution was quenched with sat'd $NaHCO_3$ (30 mL) and extracted with EA (3×10 mL). The combined organic layers were concentrated under reduced pressure to afford the title compound, which was used in the next step without further purification. LCMS [M+1]⁺: 229.

Reference Example 26

Methyl 1,4-diazepane-5-carboxylate

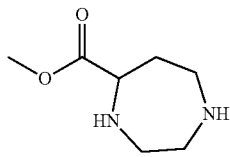

To a stirred solution of methyl 1,4-dibenzyl-1,4-diazepane-5-carboxylate (3.0 g, 8.86 mmol) in MeOH (20 mL) was added palladium hydroxide on carbon (0.900 g, 1.28 mmol, 20% wt). The reaction mixture was degassed with hydrogen three times and stirred at RT for 30 hours under hydrogen (5.0 atm). The resulting mixture was filtered. The filtrate was concentrated under reduced pressure to afford the title compound. LCMS [M+1]⁺: 159.

Reference Example 27 tert-Butyl ((1,4-diazepan-5-yl)methyl)carbamate

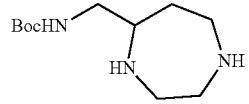

Step A: (4-Dibenzyl-1,4-diazepan-5-yl)methanamine

To a solution of 1,4-dibenzyl-1,4-diazepane-5-carboxamide (0.80 g, 2.47 mmol, prepared as described in U.S. Pat. No. 5,866,562) in THF (10 mL) was added $LiAlH_4$ (0.190 g, 4.95 mmol) in several portions at 0° C. The reaction mixture was stirred at 45° C. for 5 hours. The resulting mixture was quenched by water (0.2 mL), followed by aqueous NaOH (15%, 0.6 mL) and water (0.2 mL). The solid was filtered out. The filtrate was concentrated under reduced pressure to afford the title compound, which was used in the next step without further purification. LCMS (ESI) calc'd for $C_{20}H_{27}N_3$ [M+1]⁺: 310, found 310.

Step B: tert-Butyl ((1,4-dibenzyl-1,4-diazepan-5-yl)methyl)carbamate

To a solution of (1,4-dibenzyl-1,4-diazepan-5-yl)methanamine (0.70 g, 2.26 mmol) in DCM (8 mL) and water (8 mL) were added $Na_2CO_3$ (0.72 g, 6.79 mmol) and $(Boc)_2O$ (0.74 g, 3.39 mmol) at RT. The reaction mixture was stirred at RT for 16 hours. The resulting mixture was concentrated under reduced pressure. The residue was diluted with EA (50 mL), washed with brine (3×20 mL), dried over anhydrous $Na_2SO_4$ and filtered. The filtrate was concentrated under reduced pressure. The residue was purified by silica gel column chromatography, eluting with a gradient of 1%-20% EA in PE to afford the title compound. LCMS (ESI) calc'd for $C_{25}H_{35}N_3O_2$ [M+1]⁺: 410, found 410.

Step C: tert-Butyl ((1,4-diazepan-5-yl)methyl)carbamate

To a stirred solution of tert-butyl ((1,4-dibenzyl-1,4-diazepan-5-yl)methyl)carbamate (0.600 g, 1.47 mmol) in MeOH (10 mL) was added palladium hydroxide on carbon (0.300 g, 0.43 mmol, 20% wt). The reaction mixture was degassed with hydrogen for three times and stirred at room temperature for 16 hours under hydrogen (5 atm). The resulting mixture was filtered. The filtrate was concentrated under reduced pressure to afford the title compound. LCMS (ESI) calc'd for $C_{11}H_{23}N_3O_2$ [M+1]⁺: 230, found 230.

Reference Example 28

Benzyl ((1,2,3,6-tetrahydropyridin-4-yl)methyl)carbamate

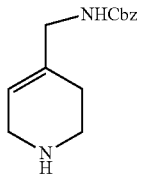

Step A: tert-Butyl 4-((benzyloxy)carbonyl)amino)methyl)-5,6-dihydropyridine-1(2H)-carboxylate To a solution of tert-Butyl 4-(aminomethyl)-5,6-dihydropyridine-1(2H)-carboxylate (3.0 g, 14.13 mmol, prepared as described in *Bioorganic and Medicinal Chemistry Letters*, 2016, 26, 228-234.) in DCM (30 mL) were added TEA (2.95 mL, 21.2 mmol) and benzyl chloroformate (2.42 mL, 17.0 mmol) at RT. The reaction mixture was stirred at RT for 16 hours. The resulting mixture was diluted with water (60 mL) and extracted with DCM (3×50 mL). The combined organic layers were washed with brine (3×10 mL), dried over anhydrous Na$_2$SO$_4$ and filtered. The filtrate was concentrated under reduced pressure. The residue was purified by a silica gel column chromatography, eluting with a gradient of 1%-40% EA in PE to afford the title compound. LCMS (ESI) calc'd for C$_{19}$H$_{26}$N$_2$O$_4$ [M+23]$^+$: 369, found 369.

Step B: Benzyl ((1,2,3,6-tetrahydropyridin-4-yl)methyl)carbamate

To the solution of tert-butyl 4-((((benzyloxy)carbonyl)amino)methyl)-5,6-dihydropyridine-1(2H)-carboxylate (1.0 g, 2.89 mmol) in DCM (5 mL) was added TFA (5 mL) at room temperature. The mixture was stirred at RT for 1 hour. The resulting solution was quenched with sat'd NaHCO$_3$ (30 mL) and extracted with DCM (3×50 mL). The combined organic layers were washed with brine (3×10 mL), dried over anhydrous Na$_2$SO$_4$ and filtered. The filtrate was concentrated under reduced pressure to afford benzyl ((1,2,3,6-tetrahydropyridin-4-yl) methyl)carbamate. LCMS [M+1]$^+$: 247.

Reference Example 29

1-(2-((tert-Butyldimethylsilyl)oxy)ethyl)-2-methylpiperazine

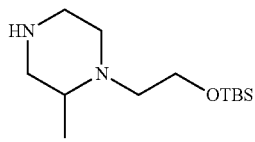 [SMILES: CC1CNCCN1CCO[Si](C)(C)C(C)(C)C]

Step A: tert-Butyl 4-(2-((tert-butyldimethylsilyl)oxy)ethyl)-3-methylpiperazine-1-carboxylate To a solution of tert-butyl 3-methylpiperazine-1-carboxylate (2.0 g, 9.99 mmol) in DMSO (20 mL) were added DIEA (8.72 mL, 49.9 mmol) and (2-bromoethoxy)(tert-butyl)dimethylsilane (7.17 g, 30.0 mmol) at RT. The reaction mixture was stirred at 70° C. for 18 hours. After cooling to RT, the resulting mixture was diluted with water (100 mL), and then extracted with EA (3×60 mL). The combined organic layers were washed with brine (3×50 mL), dried over anhydrous Na$_2$SO$_4$ and filtered. The filtrate was concentrated under reduced pressure. The residue was purified by a silica gel column chromatography, eluting with a gradient of 1%-35% EA in PE to afford tert-butyl 4-(2-((tert-butyldimethylsilyl)oxy)ethyl)-3-methylpiperazine-1-carboxylate. LCMS [M+1]$^+$: 359.

Step B: 1-(2-((tert-Butyldimethylsilyl)oxy)ethyl)-2-methylpiperazine

To a solution of tert-butyl 4-(2-((tert-butyldimethylsilyl)oxy)ethyl)-3-methylpiperazine-1-carboxylate (1.80 g, 5.02 mmol) in 1,4-dioxane (6 mL) was added HCl (gas) at room temperature. The reaction mixture was stirred at RT for 1 hour. The resulting mixture was quenched with sat'd NaHCO$_3$ (30 mL) and extracted with EA (3×10 mL). The combined organic layers were concentrated under reduced pressure to afford 1-(2-((tert-butyldimethylsilyl)oxy)ethyl)-2-methylpiperazine which was used in the next step without further purification. LCMS (ESI) calc'd for C$_{13}$H$_{30}$N$_2$OSi [M+1]$^+$: 259, found 259.

Reference Example 30

Benzyl (2-hydroxy-1-(piperidin-4-yl)ethyl) carbamate

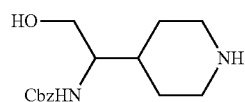

Step A: tert-Butyl 4-(1-(((benzyloxy)carbonyl) amino)-2-hydroxyethyl)piperidine-1-carboxylate To a solution of tert-butyl 4-(1-(((benzyloxy)carbonyl) amino)-2-methoxy-2-oxoethyl)piperidine-1-carboxylate (2.30 g, 5.66 mmol, prepared as described in US 2004/235896) in EtOH (20 mL) were added THF (20 mL) and NaBH$_4$ (1.10 g, 28.3 mmol) at room temperature. The reaction mixture was stirred at room temperature for 16 h. The resulting mixture was quenched with water (50 mL) and extracted with EA (3×30 mL). The combined organic layers were washed with brine (3×30 mL), dried over anhydrous Na$_2$SO$_4$ and filtered. The filtrate was concentrated under reduced pressure. The residue was purified by a silica gel column chromatography, eluting with a gradient of 1%-60% EA in PE to afford tert-butyl 4-(1-(((benzyloxy)carbonyl)amino)-2-hydroxyethyl) piperidine-1-carboxylate. LCMS [M+23]$^+$: 401.

Step B: Benzyl (2-hydroxy-1-(piperidin-4-yl)ethyl) carbamate

To a stirred solution of tert-butyl 4-(1-(((benzyloxy)carbonyl)amino)-hydroxyethyl) piperidine-1-carboxylate (0.40 g, 1.06 mmol) in DCM (4 mL) was added TFA (1 mL) at RT. The reaction solution was stirred at RT for 1 hour. The resulting mixture was quenched with sat'd NaHCO$_3$ (30 mL) and extracted with EA (3×10 mL). The combined organic layers were concentrated under reduced pressure to afford benzyl (2-hydroxy-1-(piperidin-4-yl)ethyl)carbamate, which was used for the next step without further purification. LCMS (ESI) calc'd for C$_{15}$H$_{22}$N$_2$O$_3$ [M+1]$^+$: 279, found 279.

Reference Examples 31 and 32

(S)-tert-butyl 4-(1-(((benzyloxy)carbonyl)amino)-2-hydroxyethyl) piperidine-1-carboxylate and (R)-tert-butyl 4-(1-(((benzyloxy)carbonyl)amino)-2-hydroxyethyl)piperidine-1-carboxylate

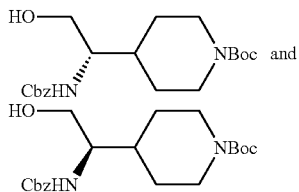

Preparation of tert-butyl 4-(1-(((benzyloxy)carbonyl)amino)-2-hydroxyethyl) piperidine-1-carboxylate, Enantiomers A and B

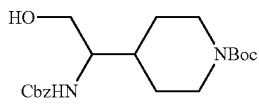

REFERENCE EXAMPLE 31
(Enantiomer A)

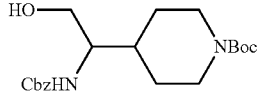

REFERENCE EXAMPLE 32
(Enantiomer B)

0.80 g of tert-butyl 4-(1-(((benzyloxy)carbonyl)amino)-2-hydroxyethyl) piperidine-1-carboxylate was separated by prep-SFC with following conditions: Column: EnantioPak A1-5, 2.12×25 cm, 5 µm; Mobile Phase A: CO$_2$: 80%; Mobile Phase B: IPA (2 mM NH$_3$-MeOH): 20%; Flow rate: 40 mL/min; 220 nm; Retention time 1: 4.42 min; Retention time 2: 5.26 min. The faster-eluting enantiomer afforded Enantiomer A of tert-butyl 4-(1-(((benzyloxy)carbonyl)amino)-2-hydroxyethyl)piperidine-1-carboxylate as an oil. LCMS (ESI) calc'd for C$_{20}$H$_{30}$N$_2$O$_5$ [M+23]$^+$: 401, found 401. The slower-eluting enantiomer afforded Enantiomer B of tert-butyl 4-(1-(((benzyloxy)carbonyl)amino)-2-hydroxyethyl)piperidine-1-carboxylate as an oil. LCMS (ESI) calc'd for C$_{20}$H$_{30}$N$_2$O$_5$ [M+23]$^+$: 401, found 401.

Reference Example 33

Benzyl ((4-aminopiperidin-4-yl)methyl)carbamate

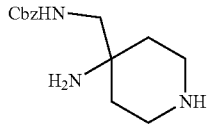

Step A: tert-Butyl 4-amino-4-((((benzyloxy)carbonyl)amino)methyl)piperidine-1-carboxylate To a stirred solution of tert-butyl 4-amino-4-(aminomethyl)piperidine-1-carboxylate (0.500 g, 2.180 mmol) in DCM (5 mL) were added benzyl carbonochloridate (0.93 g, 5.45 mmol) and TEA (0.66 g, 6.54 mmol) at RT. The reaction mixture was stirred at RT 3 hours. The resulting mixture was diluted with water (20 mL), and then extracted with EA (3×20 mL). The combined organic layers were dried over anhydrous Na$_2$SO$_4$ and filtered. The filtrate was concentrated under reduced pressure. The residue was purified by a silica gel column chromatography, eluting with a gradient of 1%-8% MeOH in DCM to afford tert-butyl 4-amino-4-((((benzyloxy)carbonyl)amino)methyl)piperidine-1-carboxylate. LCMS [M+1]$^+$: 364.

Step B: Benzyl ((4-aminopiperidin-4-yl)methyl)carbamate

To a stirred solution of tert-butyl 4-amino-4-((((benzyloxy)carbonyl)amino)methyl) piperidine-1-carboxylate (0.45 g, 1.24 mmol) in DCM (4 mL) was added TFA (1 mL) at RT. The reaction mixture was stirred at RT for 1 hour. The resulting solution was quenched with sat'd NaHCO$_3$ (30 mL) and extracted with EA (3×20 mL). The combined organic layer was concentrated under reduced pressure to afford benzyl ((4-aminopiperidin-4-yl)methyl)carbamate. LCMS [M+1]$^+$: 264.

Reference Example 34

2-(Piperazin-1-yl)propane-1,3-diol

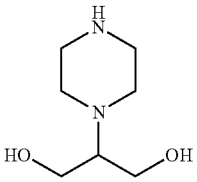

Prepared as described in EP 2295438 A1.

Reference Example 35

(S)-tert-butyl-(3-amino-2-hydroxypropyl)carbamate

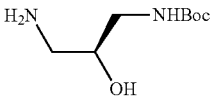

To a stirred solution of (R)-tert-butyl-(oxiran-2-ylmethyl) carbamate (1.50 g, 8.70 mmol) in EtOH (5 mL) was added 25% NH$_3$.H$_2$O (20 mL) at 0° C. The reaction solution was stirred for 2 hours at RT. The resulting solution was concentrated under vacuum to afford (S)-tert-butyl-(3-amino-2-hydroxypropyl) carbamate, which was used in the next step without further purification. LCMS (ESI) calc'd for C$_8$H$_{18}$N$_2$O$_3$ [M+1]$^+$: 191, found 191.

Reference Example 36

6-bromo-3-iodo-N,N-bis(4-methoxybenzyl)-2-(1-(4-methoxybenzyl)-1H-tetrazol-5-yl)benzenesulfonamide and 6-bromo-3-iodo-N,N-bis(4-methoxybenzyl)-2-(2-(4-methoxybenzyl)-2H-tetrazol-5-yl)benzenesulfonamide

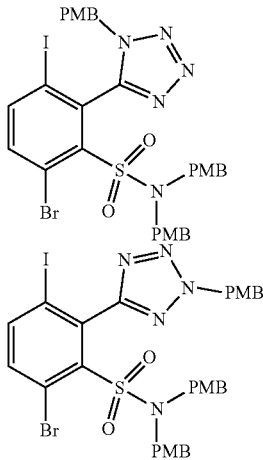

Step A: 3-bromo-2-fluoro-6-iodobenzoic acid

Into a 5000-mL 4-necked round-bottom flask purged and maintained with an inert atmosphere of nitrogen, was placed bis(propan-2-yl)amine (121.2 g, 1.20 mol, 1.20 equiv), tetrahydrofuran (1000 mL). This was followed by the addition of butyllithium (440 mL, 1.10 equiv, 2.5 N) dropwise with stirring at −78° C. in 20 min. 60 min later, to this was added a solution of 1-bromo-2-fluoro-4-iodobenzene (300 g, 997 mmol, 1.00 equiv) in tetrahydrofuran (2000 mL) dropwise with stirring at −78° C. in 30 min. The resulting solution was stirred for 2 hr at −78° C. in a liquid nitrogen bath. The reaction was then quenched by pouring into 5000 g of dry ice. After stirring for 2 hours, the resulting mixture was concentrated under vacuum. The residue was dissolved in 3000 mL of 4N sodium hydroxide. The resulting solution was extracted with 2×1000 mL of ether, and the aqueous layers combined. The pH of the solution was adjusted to 2-3 with hydrogen chloride (1 mmol/L). The resulting solution was extracted with 4×1000 mL of ethyl acetate, and the organic layers combined and dried over anhydrous sodium sulfate and concentrated under vacuum. The crude product was purified by re-crystallization from hexane.

Step B: 3-bromo-2-fluoro-6-iodobenzoyl

Into a 5000-mL 3-necked round-bottom flask purged and maintained with an inert atmosphere of nitrogen, was placed 3-bromo-2-fluoro-6-iodobenzoic acid (273 g, 791.52 mmol, 1.00 equiv), tetrahydrofuran (2730 mL), N,N-dimethylformamide (27.3 mL). This was followed by the addition of (COCl)₂ (110.9 g, 1.10 equiv) dropwise with stirring at 20° C. for 20 min. The resulting solution was stirred for 1 hour at RT. The resulting mixture was concentrated under vacuum.

Step C: 3-bromo-2-fluoro-6-iodobenzamide

Into a 5000-mL 4-necked round-bottom flask purged and maintained with an inert atmosphere of nitrogen, was placed MIAMI (1200 g). This was followed by the addition of a solution of 3-bromo-2-fluoro-6-iodobenzoyl chloride (280 g, 771 mmol, 1.00 equiv) in tetrahydrofuran (2800 mL) dropwise with stirring at 0° C. for 30 minutes. The resulting solution was stirred for 1 hr at room temperature. The resulting mixture was concentrated under vacuum. The solids were collected by filtration, and washed with H₂O to afford the title compound.

Step D: 3-bromo-2-fluoro-6-iodobenzonitrile

Into a 1.0000-ML 4-necked round-bottom flask purged and maintained with an inert atmosphere of nitrogen, was placed 3-bromo-2-fluoro-6-iodobenzamide (270 g, 785.07 mmol, 1.00 equiv), N,N-dimethylformamide (5400 mL). This was followed by the addition of trichloro-1,3,5-triazine (1014 g, 5.50 mol, 7.00 equiv), in portions at 0° C. The resulting solution was stirred for 2 hr at room temperature. The reaction was then quenched by the addition of 15000 mL of sodium bicarbonate aq. The solids were collected by filtration to afford the title compound.

Step E: 2-(benzylsulfanyl)-3-bromo-6-iodobenzonitrile

Into a 5000-mL 4-necked round-bottom flask purged and maintained with an inert atmosphere of nitrogen, was placed sodium hydride (34 g, 852 mmol, 1.20 equiv, 60%), 1,4-dioxane (700 mL). This was followed by the addition of a solution of phenylmethanethiol (88.7 g, 714.15 mmol, 1.00 equiv) in 1,4-dioxane (950 mL) dropwise with stirring at 10° C. for 15 minutes. 30 minutes later, a solution of 3-bromo-2-fluoro-6-iodobenzonitrile (230 g, 705.73 mmol, 1.00 equiv) in 1,4-dioxane (1800 mL) was added dropwise with stirring at 10° C. The resulting solution was stirred for 2 hours at RT. The reaction was then quenched by pouring into 5000 mL of water/ice. The resulting solution was extracted with 5×1000 mL of ethyl acetate and the organic layers combined. The resulting mixture was washed with 2×1000 mL of water and 2×1000 mL of sodium bicarbonate and 2×1000 mL of sodium chloride. The mixture was dried over anhydrous sodium sulfate and concentrated under vacuum. The crude product was purified by re-crystallization from ether to afford the title compound.

Step F: 5-[2-(benzylsulfanyl)-3-bromo-6-iodophenyl]-1H-1,2,3,4-tetrazole

Into a 2000-mL 4-necked round-bottom flask, was placed 2-(benzylsulfanyl)-3-bromo-6-iodobenzonitrile (66 g, 153.45 mmol, 1.00 equiv), toluene (660 mL), azidotrimethylsilane (44.2 g, 383.65 mmol, 2.50 equiv), dibutylstannanone (7.7 g, 30.93 mmol, 0.20 equiv). The resulting solution was stirred for 48 hours at 105° C. in an oil bath. The reaction mixture was cooled to RT. The resulting mixture was concentrated under vacuum. The residue was purified by silica gel column with tetrahydrofuran:PE (100:1) to afford the title compound.

Step G: 6-bromo-3-iodo-2-(1H-1,2,3,4-tetrazol-5-yl)benzene-1-sulfonyl chloride

Into a 2000-mL 3-necked round-bottom flask purged and maintained with an inert atmosphere of nitrogen, was placed 5-[2-(benzylsulfanyl)-3-bromo-6-iodophenyl]-1H-1,2,3,4-tetrazole (115.6 g, 244.33 mmol, 1.00 equiv), acetic acid (1156 mL), water (115.6 mL), NCS (81.74 g, 612.15 mmol, 150 equiv). The resulting solution was stirred overnight at RT in an ice/salt bath. The resulting mixture was concentrated under vacuum to afford the title compound.

Step H: 6-bromo-3-iodo-2-(1H-1,2,3,4-tetrazol-5-yl)benzene-1-sulfonamide

Into a 3000-mL 4-necked round-bottom flask purged and maintained with an inert atmosphere of nitrogen, was placed NH₄OH (1180 mL) and tetrahydrofuran (290 mL). This was followed by the addition of a solution of 6-bromo-3-iodo-2-(1H-1,2,3,4-tetrazol-5-yl)benzene-1-sulfonyl chloride (118 g, 262.54 mmol, 1.00 equiv) in tetrahydrofuran (300 mL) dropwise with stirring at 0° C. The resulting solution was stirred for 2 hours at 0-25° C. in an ice/salt bath (slowly warming to RT). The resulting mixture was concentrated under vacuum. The resulting solution was diluted with 500 mL of ether. After stirring for 30 minutes, the solids were collected by filtration to afford the title compound.

Step I: 6-bromo-3-iodo-N,N-bis[(4-methoxyphenyl) methyl]-2-[1-[(4-methoxyphenyl)methyl]-1H-1,2,3, 4-tetrazol-[5-yl]benzene-1-sulfonamide and 6-bromo-3-iodo-N,N-bis[(4-methoxyphenyl) methyl]-2-[2-[(4-methoxyphenyl)methyl]-2H-1,2,3, 4-tetrazol-[5-yl]benzene-1-sulfonamide Into a 3000-mL 4-necked round-bottom flask purged and maintained with an inert atmosphere of nitrogen, was placed 6-bromo-3-iodo-2-(1H-1,2,3,4-tetrazol-5-yl)benzene-1-sulfonamide (105 g, 244.17 mmol, 1.00 equiv), chloroform (1050 mL), potassium carbonate (168.9 g, 1.22 mol, 5.00 equiv), water (525 mL), NaI (11 g, 0.30 equiv), tetrabutyl (chloro)amine (20.4 g, 73.40 mmol, 0.30 equiv), 1-(chloromethyl)-4-methoxybenzene (230 g, 1.47 mol, 6.00 equiv). The resulting solution was stirred overnight at 50° C. in an oil bath. The reaction mixture was cooled to RT. The resulting solution was extracted with 2×1000 mL of dichloromethane and the organic layers combined and dried over anhydrous sodium sulfate and concentrated under vacuum to afford the title compounds. LC-MS: (ES, m/z): 790 [M+H]⁺; H-NMR: (300 MHz, CDCl₃, ppm): δ 7.956-7.928 (m, 0.5H), 7.852-7.824 (m, 1H), 7.656-7.612 (m, 1.5H), 7.323-7.282 (m, 1.5H), 7.195-7.224 (m, 2H), 6.944-6.908 (m, 6H), 6.822-6.760 (m, 9H), 5.791 (m, 1H), 5.570-5.521 (m, 1H), 5.149-5.100 (m, 1H), 4.769-4.718 (m, 2H), 4.232-4.221 (m, 2H), 3.900-3.848 (m, 2H), 3.789-3.742 (m, 14H).

Reference Example 37

3-iodo-N,N-bis(4-methoxybenzyl)-2-(2-(4-methoxybenzyl)-2H-tetrazol-5-yl)-6-((2-(trimethylsilyl)ethyl) sulfonyl)benzenesulfonamide and 3-iodo-N,N-bis(4-methoxybenzyl)-2-(1-(4-methoxybenzyl)-1H-tetrazol-5-yl)-6-((2-(trimethylsilyl)ethyl)sulfonyl) benzenesulfonamide

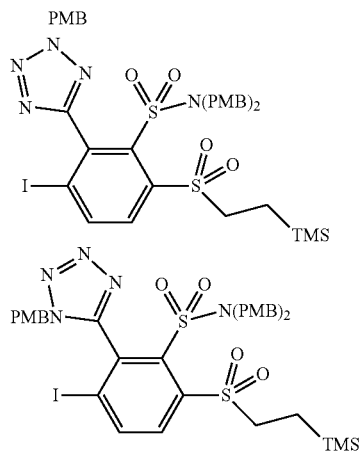

Step A: 3-iodo-N,N-bis(4-methoxybenzyl)-2-(2-(4-methoxybenzyl)-2H-tetrazol-5-yl)-6-(2-(trimethylsilyl)ethylthio)benzenesulfonamide and 3-iodo-N,N-bis(4-methoxybenzyl)-2-(1-(4-methoxybenzyl)-1H-tetrazol-5-yl)-6-((2-(trimethylsilyl)ethyl)thio) benzenesulfonamide 6-bromo-3-iodo-N,N-bis[(4-methoxyphenyl)methyl]-2-[1-[(4-methoxyphenyl)methyl]-1H-1,2,3,4-tetrazol-5-yl] benzene-1-sulfonamide, 6-bromo-3-iodo-N,N-bis[(4-methoxyphenyl)methyl]-2-[2-[(4-methoxyphenyl)methyl]-2H-1,2,3,4-tetrazol-5-yl]benzene-1-sulfonamide (500 mg, 0.633 mmol), 2-(trimethylsilyl)ethanethiol (170 mg, 1.265 mmol) and Cs₂CO₃ (618 mg, 1.898 mmol) were combined in DMF (1.5 mL). Then the mixture was stirred at RT for 5 hours. Then the mixture was poured onto ether (100 mL) with the organic layer collected and concentrated under vacuum to give the title compounds: LCMS [M+H]⁺: 844; ¹H NMR (300 MHz, CDCl₃): δ 4.71-4.40 (m, 1H), 4.13-4.00 (m, 1H), 3.83-3.67 (m, 1H), 2.81-2.72 (m, 1H), 2.32-2.21 (m, 2H), 2.08-1.74 (m, 2H), 1.44 (s, 9H).

Step B: 3-iodo-N,N-bis(4-methoxybenzyl)-2-(2-(4-methoxybenzyl)-2H-tetrazol-5-yl)-6-(2-(trimethylsilyl)ethylsulfonyl)benzenesulfonamide and 3-iodo-N,N-bis(1-methoxybenzyl)-2-(1-(4-methoxybenzyl)-1H-tetrazol-5-yl)-6-((2-(trimethylsilyl)ethyl) sulfonyl)benzenesulfonamide 3-iodo-N,N-bis(4-methoxybenzyl)-2-(2-(4-methoxybenzyl)-2H-tetrazol-5-yl)-6-((2-(trimethylsilyl)ethyl)thio)benzenesulfonamide (480 mg, 0.569 mmol) and m-CPBA (491 mg, 2.84 mmol) were combined in dichloromethane (2 mL). The mixture was stirred at RT for 4 hours. The resulting mixture was poured onto ether (200 mL) and washed with brine (150 mL). The organic layers were collected, dried over anhydrous Na₂SO₄, and concentrated under vacuum. The residue was applied on a silica gel column with EA/PE (1/3) to give the title compounds: LCMS [M+H]⁺: 876; ¹H NMR (300 MHz, CDCl₃): δ 8.62 (d, J=8.7 Hz, 1H), 8.26 (d, J=8.4 Hz, 1H), 7.90-7.88 (m, 1H), 7.69-7.68 (m, 0.5H), 7.56-7.53 (m, 0.5H), 7.27-7.20 (m, 2H), 6.91-6.79 (m, 12H), 5.44-5.39 (m, 1H), 5.20-5.15 (m, 1H), 4.58-4.53 (m, 2H), 3.98-3.79 (m, 2H), 3.75-3.66 (m, 9H), 2.50-2.48 (m, 2H), 1.19-1.03 (m, 1H), 0.83-0.82 (m, 1H), 0.01 (s, 9H).

Reference Example 38

2-(N,N-bis(4-methoxybenzyl)sulfamoyl)-4-iodo-3-(2-(4-methoxybenzyl)-1H-tetrazol-5-yl)benzenesulfinic acid and 2-(N,N-bis(4-methoxybenzyl)sulfamoyl)-4-iodo-3-(1-(4-methoxybenzyl)-1H-tetrazol-5-yl)benzenesulfinic acid

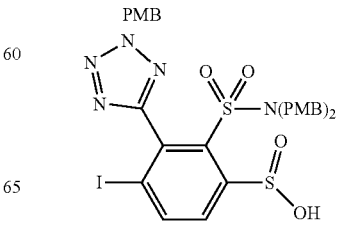

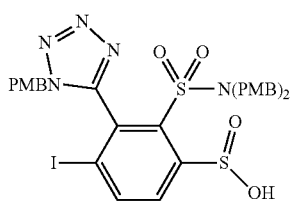

A solution of 3-iodo-N,N-bis(4-methoxybenzyl)-2-(2-(4-methoxybenzyl)-2H-tetrazol-5-yl)-6-((2-(trimethylsilyl)ethyl)sulfonyl)benzenesulfonamide (1.0 g, 1.14 mmol) in tetrahydrofuran (10 mL) was stirred with tetrabutylammonium fluoride (1.194 g, 4.57 mmol) at RT under $N_2$ for 0.5 hour. The mixture was diluted with ethyl acetate, washed with sat'd $KHSO_4$ aqueous, dried over $MgSO_4$, and concentrated under vacuum to get the crude product as a solid. The crude material was used directly for the next step: LCMS $[M+H]^+$: 776; $^1H$ NMR (300 MHz, $CDCl_3$): δ 4.87-4.60 (bs, 1H), 4.36-4.21 (bs, 1H), 3.96-3.90 (m, 1H), 2.87-2.83 (m, 1H), 2.46-2.2.9 (m, 2H), 2.27 (d, J=1.2 Hz, 3H), 1.95-1.91 (m, 1H), 1.43 (s, 9H).

Reference Example 39

2-(N,N-bis(4-methoxybenzyl)sulfamoyl)-4-iodo-3-(2-(4-methoxybenzyl)-2H-tetrazol-5-yl)benzenesulfonyl chloride and 2-(N,N-bis(4-methoxybenzyl)sulfamoyl)-4-iodo-3-(1-(4-methoxybenzyl)-1H-tetrazol-5-yl)benzenesulfonyl chloride

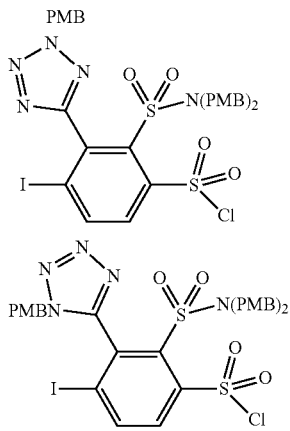

2-(N, N-bis(4-methoxybenzyl)sulfamoyl)-4-iodo-3-(2-(4-methoxybenzyl)-2H-tetrazol-5-yl)benzenesulfinic acid (800 mg, 1.031 mmol) in tetrahydrofuran (10 mL) was cooled to 0° C., 1-chloropyrrolidine-2,5-dione (275 mg, 2.063 mmol) in tetrahydrofuran (2 mL) was added over 5 minutes. The mixture was stirred at the same temperature for 30 minutes, then diluted with ethyl acetate, washed with sat'd $NaHCO_3$ and brine, dried over $MgSO_4$, and concentrated to get the crude product: LCMS $[M+H]^+$: 810.

Reference Example 40 tert-butyl (R)-3-((2-(N,N-bis(4-methoxybenzyl)sulfamoyl)-4-iodo-3-(1-(4-methoxybenzyl)-1H-tetrazol-5-yl)phenyl)sulfonamido)pyrrolidine-1-carboxylate and tert-butyl (R)-3-((2-(N,N-bis(4-methoxybenzyl)sulfamoyl)-4-iodo-3-(2-(4-methoxybenzyl)-2H-tetrazol-5-yl)phenyl)sulfonamido)pyrrolidine-1-carboxylate

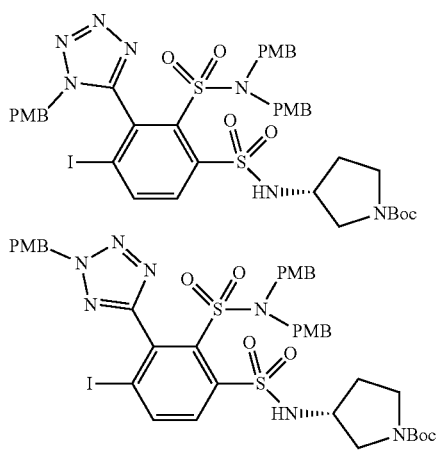

To a solution of 2-(N,N-bis(4-methoxybenzyl)sulfamoyl)-4-iodo-3-(2-(4methoxybenzyl-2H-tetrazol-5-yl)benzene-1-sulfonyl chloride and 2-(N,N-bis(4-methoxybenzyl)sulfamoyl)-4-iodo-3-(2-(4-methoxybenzyl)-1H-tetrazol-5-yl)benzene-1-sulfonyl chloride (0.46 g, 0.48 mmol) in tetrahydrofuran (10 mL) was added (T)-tert-butyl 3-aminopyrrolidine-1-carboxylate (90 mg, 0.48 mmol) at ambient temperature. The reaction was kept at 25° C. for 30 minutes. The mixture was concentrated under vacuum. The residue was diluted with EA (3×20 mL), and washed with brine (3×20 mL), dried over and filtered. The filtrate was concentrated under vacuum. The residue was applied onto silica gel column chromatography with ethyl acetate/petroleum ether (1:50 to 1:1) to give the title compound: LCMS (ESI) calc'd for $C_{40}H_{46}IN_7O_9S_2$: $[M+1]^+$ 960 found 960; $^1H$ NMR (400 MHz, DMSO-$d_6$) δ 8.52 (d, J=8.4 Hz, 1H), 8.29 (d, J=8.4 Hz, 1H), 7.29-7.25 (m, 2H), 6.83-6.69 (m, 10H), 5.95 (brs, 1H), 5.55-5.50 (m, 0.5H), 5.24-5.19 (m, 0.5H), 4.58-4.53 (m, 1H), 4.05-3.81 (m, 5H), 3.85 (s, 9H), 3.48-3.3 (m, 4H), 2.02-1.82 (m, 2H), 1.44 (s, 9H).

Reference Example 41 tert-butyl (2-((2-(N,N-bis(4-methoxybenzyl)sulfamoyl)-4-iodo-3-(1-(4-methoxybenzyl)-1H-tetrazol-5-yl)phenyl)sulfonamido)ethyl)carbamate and tert-butyl (2-((2-(N,N-bis(4-methoxybenzyl)sulfamoyl)-4-iodo-3-(2-(4-methoxybenzyl)-2H-tetrazol-5-yl)phenyl)sulfonamido)ethyl)carbamate

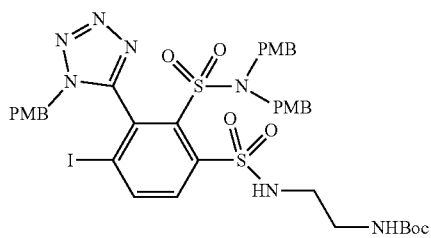

-continued

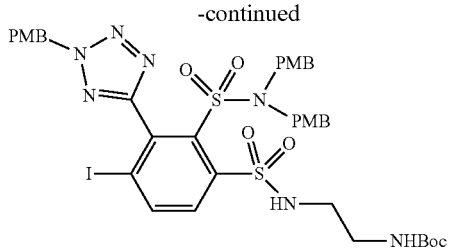

To a solution of 2-(N,N-bis(4-methoxybenzyl)sulfamoyl)-4-iodo-3-(2-(4-methoxybenzyl)-2H-tetrazol-5-yl)benzenesulfinic acid and 2-(N,N-bis(4-methoxybenzyl)sulfamoyl)-4-iodo-3-(1-(4-methoxybenzyl)-1H-tetrazol-5-yl)benzenesulfinic acid (3 g, 3.87 mmol) in THF (38.7 ml) was added tert-butyl (2-aminoethyl)carbamate (1.239 g, 7.74 mmol), triethylamine (1.078 ml, 7.74 mmol), and NCS (1.033 g, 7.74 mmol) in sequence at 0° C. under nitrogen. The mixture was stirred at the same temperature for 30 minutes. The reaction mixture was diluted with EtOAc, washed with NaHCO$_3$ solution and brine. The organic layer was dried over MgSO$_4$, evaporated, and the crude product was purified by silica gel column eluting with 0-100% EtOAc/hex to give the title compound. LC/MS [M+H]$^+$: 934.53.

Reference Example 42 tert-butyl (R)-(2-((2-(N,N-bis(4-methoxybenzyl)sulfamoyl)-4-iodo-3-(1-(4-methoxybenzyl)-1H-tetrazol-5-yl)phenyl)sulfonamido)propyl)carbamate and tert-butyl (R)-(2-((2-(N,N-bis(4-methoxybenzyl)sulfamoyl)-4-iodo-3-(2-(4-methoxybenzyl)-2H-tetrazol-5-yl)phenyl)sulfonamido)propyl)carbamate

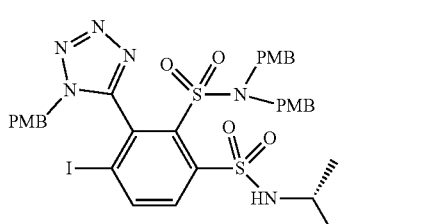

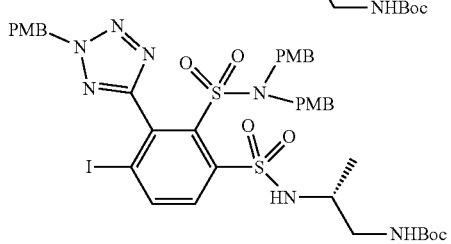

This intermediate was prepared in an analogous fashion to REFERENCE EXAMPLE 41 using tert-butyl (R)-(2-aminopropyl)carbamate. LC/MS [M+H]$^+$: 948.6.

Reference Example 43 tert-butyl (S)-(2-((2-(N,N-bis(4-methoxybenzyl)sulfamoyl)-4-iodo-3-(1-(4-methoxybenzyl)-1H-tetrazol-5-yl)phenyl)sulfonamido)propyl)carbamate and tert-butyl(S)-(2-((2-(N,N-bis(4-methoxybenzyl)sulfamoyl)-4-iodo-3-(2-(4-methoxybenzyl)-1H-tetrazol-5-yl)phenyl)sulfonamido)propyl)carbamate

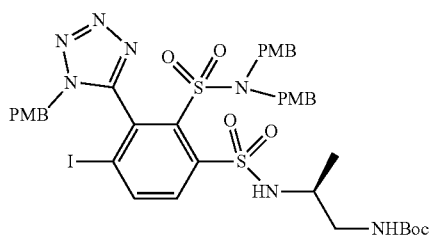

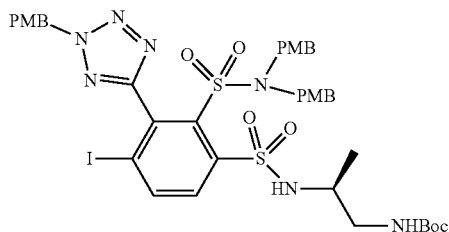

This intermediate was prepared in an analogous fashion to REFERENCE EXAMPLE 41 using tert-butyl (S)-(2-aminopropyl)carbamate. LC/MS [M+H]$^+$: 948.5.

Reference Example 44 tert-butyl (R)-(3-((2-(N,N-bis(4-methoxybenzyl)sulfamoyl)-4-iodo-3-(2-(4-methoxybenzyl)-2H-tetrazol-5-yl)phenyl)sulfonamido)-2-hydroxypropyl)carbamate

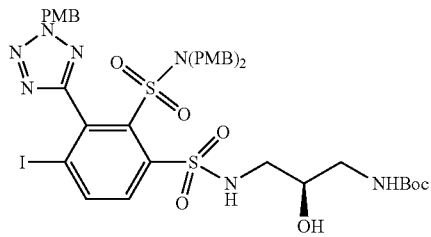

This intermediate was prepared as described for REFERENCE EXAMPLE 41 using tert-butyl (S)-(3-amino-2-hydroxypropyl)carbamate. LC/MS [M+H]$^+$: 9644.

Reference Example 45

(R)-tert-butyl (3-(2-(N,N-bis(4-methoxybenzyl)sulfamoyl)-4-iodo-3-(2-(4-methoxybenzyl)-2H-tetrazol-5-yl)phenylsulfonamido)-2-((tert-butyldimethylsilyl)oxy)propyl)carbamate

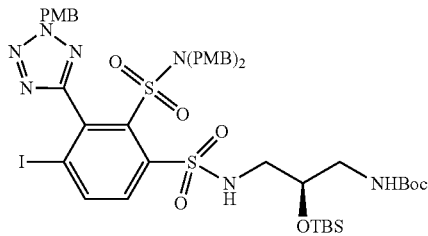

To a solution of (tert-butyl (R)-(3-((2-(N,N-bis(4-methoxybenzyl)sulfamoyl)-4-iodo-3-(2-(4-methoxybenzyl)-2H-tetrazol-5-yl)phenyl)sulfonamido)-2-hydroxypropyl)carbamate (REFERENCE EXAMPLE 44) (2.00 g, 2.07 mmol) in DMF (20 mL) were added 1H-imidazole (1.10 g, 1660 mmol) and TBS-Cl (1.90 g, 12.45 mmol) at RT. The reaction solution was stirred at RT for 16 hours. The resulting solution was diluted with water (50 mL), and then extracted with EA (3×40 mL). The organic layers were combined, washed with brine (2×30 mL), dried over anhydrous Na$_2$SO$_4$ and filtered. The filtrate was concentrated under vacuum. The residue was purified by a silica gel column chromatography, eluting with 50% EA in PE to afford (R)-tert-butyl 3-(2-(N,N-bis(4-methoxybenzyl)sulfamoyl)-4-iodo-3-(2-(4-methoxybenzyl)-2H-tetrazol-5-yl)phenylsulfonamido)-2-((tert-butyldimethylsilyl)oxy)propyl)carbamate as a solid: LCMS (ESI) calc'd for C$_{45}$H$_{60}$IN$_7$O$_{10}$S$_2$Si [M+H]$^+$: 1078, found 1078.

Reference Example 46 tert-butyl-((2-(N,N-bis(4-methoxybenzyl)sulfamoyl)-4-iodo-3-(1-(4-methoxybenzyl)-1H-tetrazol-5-yl)phenyl)sulfonyl)azetidine-1-carboxylate

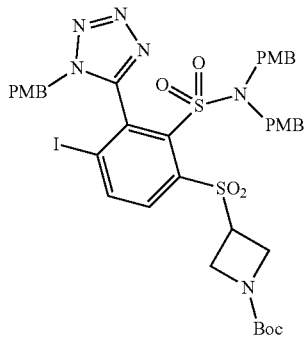

Step A: tert-butyl 3-((2-(N,N-bis(4-methoxybenzyl)sulfamoyl-4-iodo-3-(1-(4-methoxybenzyl)-1H-tetrazol-5-yl)phenyl)thio)azetidine-1-carboxylate To test-butyl 3-mercaptoazetidine-1-carboxylate (3.74 g, 19.74 mmol) in DMF (40 mL) was added sodium hydride (0.820 g, 20.49 mmol). The resulting mixture was stirred for 15 minutes at RT. 6-bromo-3-iodo-N,N-bis(4-methoxybenzyl)-2-(1-(4-methoxybenzyl)-1H-tetrazol-5-yl)benzenesulfonamide (REFERENCE EXAMPLE 36) (6.0 g, 7.59 mmol) in dimethylformamide (10 mL) was added at RT, and the reaction mixture was stirred at RT for 2 hours. The mixture was diluted with water (100 mL), extracted with acetate (2×100 mL). The combined organic phases were dried (MgSO$_4$), filtered and concentrated by reduced pressure. The residue was purified by column chromatography on silica gel 300 g, eluting with 0-100% EtOAc/isohexane for 1 hour to give the title product as a solid. LC/MS [M+H]+: 899.7.

Step B: 3-(2-amino-1H-benzol[d]imidazol-4-yl)-N,N-bis(4-methoxybenzyl)-2-(2-(4-methoxybenzyl)-2H-tetrazol-5-yl)-6-((2-(trimethylsilyl)ethyl)sulfonyl)benzenesulfonamide Sodium bicarbonate (1.12 g, 13.3 mmol) and 3-chlorobenzoperoxoic acid (5.75 g, 33.3 mmol) were added to a stirred solution of starting material tert-butyl 3-((2-(N,N-bis(4-methoxybenzyl)sulfamoyl)-4-iodo-3-(1-(4-methoxybenzyl)-1H-tetrazol-5-yl)phenyl)sulfinyl)azetidine-1-carboxylate (5.99 g, 6.66 mmol) in dichloromethane (40 mL) at RT, and the mixture was stirred at RT overnight. The mixture was diluted with Na$_2$S$_2$O$_3$ (3.0 g) in aqueous sodium bicarbonate (400 mL), and the mixture was extracted with ethyl acetate (2×400 mL). The residue was purified by column chromatography on silica gel 120 g, eluting with 0-70% EtOAc/isohexane for 45 minutes to give the title compound. LC/MS [M+H]+: 931.7.

Reference Example 47

(R)-tert-butyl (3-((2-(N,N-bis(4-methoxybenzyl)sulfamoyl)-4-iodo-3-(2-(4-methoxybenzyl)-2H-tetrazol-5-yl)phenyl)sulfonyl)-2-hydroxypropyl)carbamate

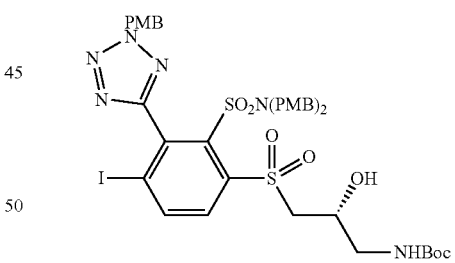

Step A: (R)-tert-butyl(3-((2-(N,N-bis(4-methoxybenzyl)sulfamoyl)-4-iodo-3-(2-(4-methoxy benzyl)-2H-tetrazol-5-yl)phenyl)thio)-2-((tert-butyldimethylsilyl)oxy)propyl) carbamate To a stirred solution of 6-bronco-3-iodo-N,N-bis(4-methoxybenzyl)-2-(2-(4-methoxybenzyl)-2H-tetrazol-5-yl)benzenesulfonamide (1.95 g, 2.47 mmol), (R)-tert-butyl-2-(tert-butyldimethylsilyloxy)-3-mercaptopropylcarbamate (1.59 g, 4.94 mmol) in DMF (15 mL) was added NaH (0.20 g, 8.21 mmol) at 0° C. under nitrogen. The reaction mixture was stirred at RT for 3 hours under nitrogen. The resulting mixture was quenched with water (100 mL) and extracted with EA (3×100 mL). The combined organic layers were washed with brine (3×100 mL), dried over anhydrous Na₂SO₄ and filtered. The filtrate was concentrated under vacuum. The residue was purified by silica gel column chromatography, eluting with 50% EA in PE to afford the title compound: LCMS [M+1]⁺: 1031.

Step B: (R)-tert-butyl (3-((2-(N,N-bis(4-methoxybenzyl)sulfamoyl)-4-iodo-3-(2-(4-methoxy benzyl)-2H-tetrazol-5-yl)phenyl)thio)-2-hydroxypropyl)carbamate To a solution of (R)-tert-butyl-3-(2-(N,N-bis(4-methoxybenzyl)sulfamoyl)-4-iodo-3-(2-(4-methoxybenzyl)-2H-tetrazol-5-yl)phenylthio)-2-(tert-butyldimethylsilyloxy)propylcarbamate (2.2 g, 2.14 mmol) in THF (40 mL) was added TBAF (6.4 mL, 6.40 mmol) at 0° C. The reaction mixture was stirred at RT for 1 hour. The resulting mixture was quenched with water (100 mL), extracted with EA (3×100 mL). The combined organic layers were washed with sat'd aqueous KHSO₄ (5×100 mL), brine (1×100 mL), dried over anhydrous MgSO₄ and filtered. The filtrate was concentrated under vacuum. The residue was purified by silica gel column chromatography, eluting with 70% EA in PE to afford the title compound: LCMS (ESI) calc'd for C₃₉H₄₅IN₆O₈S₂ [M+1]⁺: 917, found: 917.

Step C: (R)-tert-butyl(3-((2-(N,N-bis(4-methoxybenzyl)sulfamoyl)-4-iodo-3-(4-methoxy benzyl)-2H-tetrazol-5-yl)phenyl)sulfonyl)-2-hydroxypropyl)carbamate To a solution of (R)-tert-butyl(3-((2-(N,N-bis(4-methoxybenzyl)sulfamoyl)-4-iodo-3-(2-(4-methoxybenzyl)-2H-tetrazol-5-yl)phenyl)thio)-2-hydroxypropyl)carbamate (1.2 g, 1.31 mmol) in DCM (15 mL) was added m-CPBA (0.9 g, 5.23 mmol) at 0° C. The reaction mixture was stirred at RT for 16 hours. The resulting mixture was added into sat'd aqueous Na₂SO₃ (50 mL) and extracted with DCM (3×100 mL). The combined organic layers were washed with water (3×100 mL) and brine (3×100 mL), dried over anhydrous Na₂SO₄ and filtered. The filtrate was concentrated under vacuum. The residue was purified by silica gel column chromatography, eluting with 60% EA in PE to afford the title compound: LCMS (ESI) calc'd for C₃₉H₄₅IN₆O₁₀S₂ [M+1]⁺: 949, found: 949.

Reference Example 48

(R)-tert-butyl (3-((2-(N,N-bis(4-methoxybenzyl)sulfamoyl)-4-iodo-3-(2-(4-methoxybenzyl)-2H-tetrazol-5-yl)phenyl)sulfonyl)-2-((tert-butyldimethylsilyl)oxy)propyl)carbamate

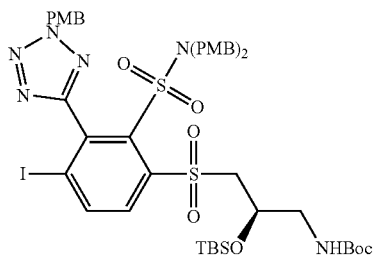

The title compound was prepared as described for REFERENCE EXAMPLE 41 using (R)-tert-butyl (3-((2-(N,N-bis(4-methoxybenzyl)sulfamoyl)-4-iodo-3-(2-(4-methoxybenzyl)-2H-tetrazol-5-yl)phenyl)sulfonyl)-2-hydroxypropyl)carbamate (REFERENCE EXAMPLE 44) to afford (R)-tert-butyl (3-((2-(N,N-bis(4-methoxybenzyl)sulfamoyl)-4-iodo-3-(2-(4-methoxybenzyl)-2H-tetrazol-5-yl)phenyl)sulfonyl)-2-((tert-butyldimethylsilyl)oxy)propyl)carbamate as a solid: LCMS [M+H]⁺: 1063.

Reference Example 49 tert-butyl (2-((2-(N,N-bis(4-methoxybenzyl)sulfamoyl)-4-iodo-3-(1-(4-methoxybenzyl)-1H-tetrazol-5-yl)phenyl)sulfonyl)ethyl)carbamate and tert-butyl (2-((2-(N,N-bis(4-methoxybenzyl)sulfamoyl)-4-iodo-3-(2-(4-methoxybenzyl)-2H-tetrazol-5-yl)phenyl)sulfonyl)ethyl)carbamate

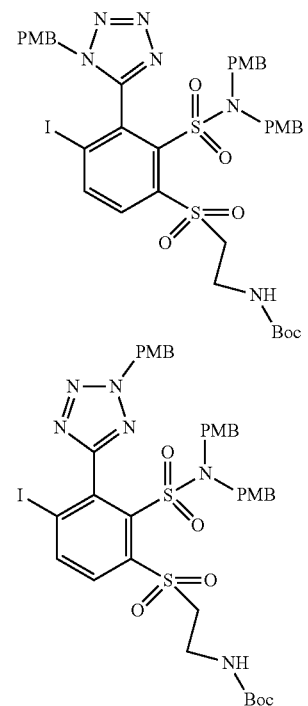

Step A: 2-fluoro-4-iodoaniline

Into a 20000-mL 4-necked round-bottom flask purged and maintained with an inert atmosphere of nitrogen, was placed 2-fluoroaniline (1256 g, 11.30 mol, 1.00 equiv), and CCl₄ (12560 mL). NIS (3992.8 g, 17.75 mol, 2.00 equiv) was then added in portions. The resulting solution was stirred overnight at room temperature. The reaction was then quenched by the addition of 5000 mL of water. The resulting mixture was washed with 3×2000 mL of H₂O. The resulting mixture was washed with 3×2000 mL of brine. The mixture was dried over anhydrous sodium sulfate and concentrated under vacuum. The residue was applied onto a silica gel column with ethyl acetate/petroleum ether (1:2) to afford the title compound.

Step B: 1-bromo-2-fluoro-4-iodobenzene

Into a 20000-mL 4-necked round-bottom flask purged and maintained with an inert atmosphere of nitrogen, was placed 2-fluoro-4-iodoaniline (1000 g, 4.22 mol, 1.00 equiv), water (1000 mL), and HBr (5000 mL). A solution of NaNO$_3$ (582 g, 2.00 equiv) in water (1900 mL) was then added dropwise with stirring at 0° C. To this was added CuBr (901 g) at 0° C. The resulting solution was stirred for 4 hr at 0° C. in an ice/salt bath. The resulting solution was extracted with 4×2000 mL of ethyl acetate and the organic layers combined. The resulting mixture was washed with 3×2000 mL of water and 3×2000 mL of brine. The mixture was dried over anhydrous sodium sulfate and concentrated under vacuum. The residue was applied onto a silica gel column with ethyl acetate/petroleum ether (1:7) to afford the title compound.

Step C: 3-bromo-2-fluoro-6-iodobenzoic acid

Into a 20000-mL 4-necked round-bottom flask, purged and maintained with an inert atmosphere of nitrogen, was placed LDA (2000 mL, 1.10 equiv) and tetrahydrofuran (5000 mL). A solution of 1-bromo-2-fluoro-4-iodobenzene (1090 g, 3.62 mol, 1.00 equiv) in tetrahydrofuran (5000 mL) was then added dropwise with stirring. The resulting solution was stirred for 2 hours at −78° C. in a liquid nitrogen bath: The reaction was then quenched by the addition of 20000 g of dry ice. The resulting mixture was concentrated under vacuum. The resulting solution was diluted with 10000 mL of 4N sodium hydroxide. The resulting solution was extracted with 3×3000 mL of ether and the aqueous layers combined. The pH of the solution was adjusted to 2-3 with hydrogen chloride (1 mol/L). The resulting solution was extracted with 5×3000 mL of ethyl acetate and the organic layers combined. The resulting mixture was washed with 2×3000 mL of brine. The mixture was dried over anhydrous sodium sulfate and concentrated under vacuum. The crude product was re-crystallized from hexane:EA in the ratio of 100:1 to afford the title compound.

Step D: 3-bromo-2-fluoro-6-iodobenzoyl chloride

Into a 10000-mL 4-necked round-bottom flask purged and maintained with an inert atmosphere of nitrogen, was placed 3-bromo-2-fluoro-6-iodobenzoic acid (600 g, 1.74 mol, 1.00 equiv), tetrahydrofuran (3000 mL), and N,N-dimethylformamide (60 mL). This was followed by the addition of (COCl)$_2$ (243.6 g, 1.10 equiv) dropwise with stirring at RT. The resulting solution was stirred for 1 hour at RT. The resulting mixture was concentrated under vacuum to afford the title compound.

Step E: 3-bromo-2-fluoro-6-iodobenzamide

Into a 20000-mL 4-necked round-bottom flask, purged and maintained with an inert atmosphere of nitrogen, was placed tetrahydrofuran (3000 mL) and NH$_4$OH (3100 mL). A solution of 3-bromo-2-fluoro-6-iodobenzoyl chloride (620 g, 1.71 mol, 1.00 equiv) in tetrahydrofuran (2000 mL) was then added dropwise with stirring at 0° C. The resulting solution was stirred for 1 hour at RT in an ice/salt bath. The resulting mixture was concentrated under vacuum. The solids were collected by filtration and washed with water to give the title compound.

Step F: 3-bromo-2-fluoro-6-iodobenzonitrile

Into a 20000-mL 4-necked round-bottom flask purged and maintained with an inert atmosphere of nitrogen, was placed 3-bromo-2-fluoro-6-iodobenzamide (1000 g, 2.91 mol, 1.00 equiv), and N,N-dimethylformamide (8000 mL). This was followed by the addition of trichloro-1,3,5-triazine (1070 g, 5.80 mol, 2.00 equiv) dropwise with stirring at 50° C. The resulting solution was stirred for 30 minutes at 60° C. The reaction was then quenched by the addition of 40000 mL of ice sodium bicarbonate. The solids were collected by filtration to provide the title compound.

Step G: 2-(benzylsulfanyl)-3-bromo-6-iodobenzonitrile

Into a 10000-mL 4-necked round-bottom flask, purged and maintained with an inert atmosphere of nitrogen, was placed 1,4-dioxane (2000 mL) and sodium hydride (62 g, 1.20 equiv). Phenylmethanethiol (162 g, 1.30 mol, 1.01 equiv) was then added dropwise with stirring. A solution of 3-bromo-2-fluoro-6-iodobenzonitrile (420 g, 1.29 mol, 1.00 equiv) in 1,4-dioxane (4300 mL) was then added dropwise with stirring at 10° C. for 1 hour. The resulting solution was stirred for 1 hour at 20° C. in a water/ice bath. The reaction was then quenched by the addition of 6000 mL of water/ice. The resulting solution was extracted with 5×1500 mL of ethyl acetate and the organic layers combined. The resulting mixture was washed with 3×1000 mL of sodium bicarbonate aq and 3×1000 mL of brine. The mixture was dried over anhydrous sodium sulfate and concentrated under vacuum. The crude product was purified by re-crystallization from ether to afford the title compound.

Step H: 5-[2-(benzylsulfanyl)-3-bromo-6-iodophenyl]-1H-1,2,3,4-tetrazole

Into a 3000-mL 4-necked round-bottom flask, purged and maintained with an inert atmosphere of nitrogen, was placed 2-(benzylsulfanyl)-3-bromo-6-iodobenzonitrile (150 g, 348.76 mmol, 1.00 equiv), toluene (1500 mL), azidotrimethylsilane (100.5 g, 872.33 mmol, 2.50 equiv), and dibutylstannanone (17.4 g, 69.90 mmol, 0.20 equiv). The resulting solution was stirred for 48 hours at 107° C. in an oil bath. The reaction mixture was cooled to 40° C. and concentrated under vacuum. The crude product was re-crystallized from ether:EA in the ratio of 1:1 to provide the title compound.

Step I: 6-bromo-3-iodo-2-(1H-tetrazol-5-yl)benzene-1-sulfonyl chloride

Into a 2000-mL 4-necked round-bottom flask purged and maintained with an inert atmosphere of nitrogen, was placed 542-(benzylsulfanyl)-3-bromo-6-iodophenyl]-1H-1,2,3,4-tetrazole (100 g, 211.36 mmol, 1.00 equiv), acetic acid (1000 mL), and water (100 mL). NCS (70.7 g, 529.47 mmol, 2.50 equiv) was then added in portions. The resulting solution was stirred for 2 hours at RT in a water/ice bath, then concentrated under vacuum. The resulting solution was diluted with 2000 mL of EA. The resulting mixture was washed with 2×1000 mL of water and 2×1000 mL of brine. The mixture was dried over anhydrous sodium sulfate and concentrated under vacuum to afford the title compound.

Step J: 6-bromo-3-iodo-2-(1H-1,2,3,4-tetrazol-5-yl)benzene-1-sulfonamide

Into a 2000-mL 4-necked round-bottom flask, purged and maintained with an inert atmosphere of nitrogen, was placed NH$_4$OH (850 mL) and tetrahydrofuran (100 mL): A solution of 6-bromo-3-iodo-2-(1H-1,2,3,4-tetrazol-5-yl)benzene-1-sulfonyl chloride (85 g, 189.12 mmol, 1.00 equiv) in tetrahydrofuran (325 mL) was then added dropwise with stirring at 0° C. The resulting solution was stirred overnight at RT. The resulting mixture was concentrated under vacuum. The resulting solution was diluted with 500 mL of H₂O. The resulting solution was extracted with 3×500 mL of ethyl acetate, and the aqueous layers combined. The pH of the solution was adjusted to 1-2 with hydrogen chloride (6 mol/L). The solids were collected by filtration. The filtrate was extracted with 2×500 mL of ethyl acetate, and the organic layers were combined, dried over anhydrous sodium sulfate and concentrated under vacuum to give the title compound.

Step K: 6-bromo-3-iodo-N,N-bis[(4-methoxyphenyl)methyl]-2-[1-[(4-methoxyphenyl)methyl]-1H-1,2,3,4-tetrazol-5-yl]benzene-1-sulfonamide and 6-bromo-3-iodo-N,N-bis[(4-methoxyphenyl)methyl]-2-[2-[(4-methoxyphenyl)methyl]-2H-1,2,3,4-tetrazol-5-yl]benzene-1-sulfonamide Into a 10000-mL 4-necked round-bottom flask, purged and maintained with an inert atmosphere of nitrogen, was placed 6-bromo-3-iodo-2-(1H-1,2,3,4-tetrazol-5-yl)benzene-1-sulfonamide (400 g, 930.19 mmol, 1.00 equiv), chloroform (4000 mL), water (2000 mL), potassium carbonate (643.3 g, 4.65 mol, 5.00 equiv), NaI (42 g, 0.30 equiv), tetrabutylazanium chloride (77.84 g, 280.08 mmol, 0.30 equiv), and PMBCl (873.3 g, 6.00 equiv). The resulting solution was stirred overnight at 50° C. in an oil bath. The reaction mixture was cooled to RT. The resulting solution was extracted with 1500 mL of dichloromethane, and the organic layers were combined, dried over anhydrous sodium sulfate and concentrated under vacuum. The residue was applied onto a silica gel column with ethyl acetate/petroleum ether (1:1) to afford the title compound.

Step L: tert-butyl N-[2-[(2-[bis[(4-methoxyphenyl)methyl]sulfamoyl]-4-iodo-3-[1-[(4-methoxyphenyl)methyl]-1H-1,2,3,4-tetrazol-5-yl]phenyl)sulfanyl]ethyl]carbamate Into a 5000-mL 4-necked round-bottom flask purged and maintained with an inert atmosphere of nitrogen, was placed 6-bromo-3-iodo-N,N-bis[(4-methoxyphenyl)methyl]-2-[1-[(4-methoxyphenyl)methyl]-1H-1,2,3,4-tetrazol-5-yl]benzene-1-sulfonamide (175 g, 221.39 mmol, 1.00 equiv), N,N-dimethylformamide (2100 mL), tert-butyl N-(2-sulfanylethyl)carbamate (43 g, 242.58 mmol, 1.10 equiv), and Cs₂CO₃ (215 g, 3.00 equiv). The resulting solution was stirred overnight at RT. The resulting solution was diluted with 3000 mL of ether. The resulting mixture was washed with 2×1500 mL of brine. The mixture was dried over anhydrous sodium sulfate and concentrated under vacuum to afford the title compound.

Step M: tert-butyl (2-((2-(N,N-bis(4-methoxybenzyl)sulfamoyl)-4-iodo-3-(1-(4-methoxybenzyl)-1H-tetrazol-5-yl)phenyl)sulfonyl)ethyl)carbamate and tert-butyl (2-((2-(N,N-bis(4-methoxybenzyl)sulfamoyl)-4-iodo-3-(2-(4-methoxybenzyl)-2H-tetrazol-5-yl)phenyl)sulfonyl)ethyl)carbamate Into a 3000-mL 4-necked round-bottom flask purged and maintained with an inert atmosphere of nitrogen, was placed tert-butyl N-[2-[(2-[bis[(4-methoxyphenyl)methyl]sulfamoyl]-4-iodo-3-[1-[(4-methoxyphenyl)methyl]-1H-1,2,3,4-tetrazol-5-yl]phenyl)sulfanyl]ethyl]carbamate (103 g, 116.15 mmol, 1.00 equiv), dichloromethane (1545 mL) and m-CPBA (125.3 g, 726.08 mmol, 5.00 equiv). The resulting solution was stirred overnight at RT. The resulting solution was diluted with 5000 mL, of ether. The resulting mixture was washed with 2×2000 mL of 0.5N sodium hydroxide and 2×1500 mL of brine. The mixture was dried over anhydrous sodium sulfate and concentrated under vacuum. The residue was applied onto a silica gel column with ethyl acetate/petroleum ether (1:2) to give the title compound.

Reference Example 50 tert-butyl (R)-3-((4-bromo-2-(N,N-dibenzylsulfamoyl)-3-(2H-tetrazol-5-yl)phenyl)sulfonamido)pyrrolidine-1-carboxylate

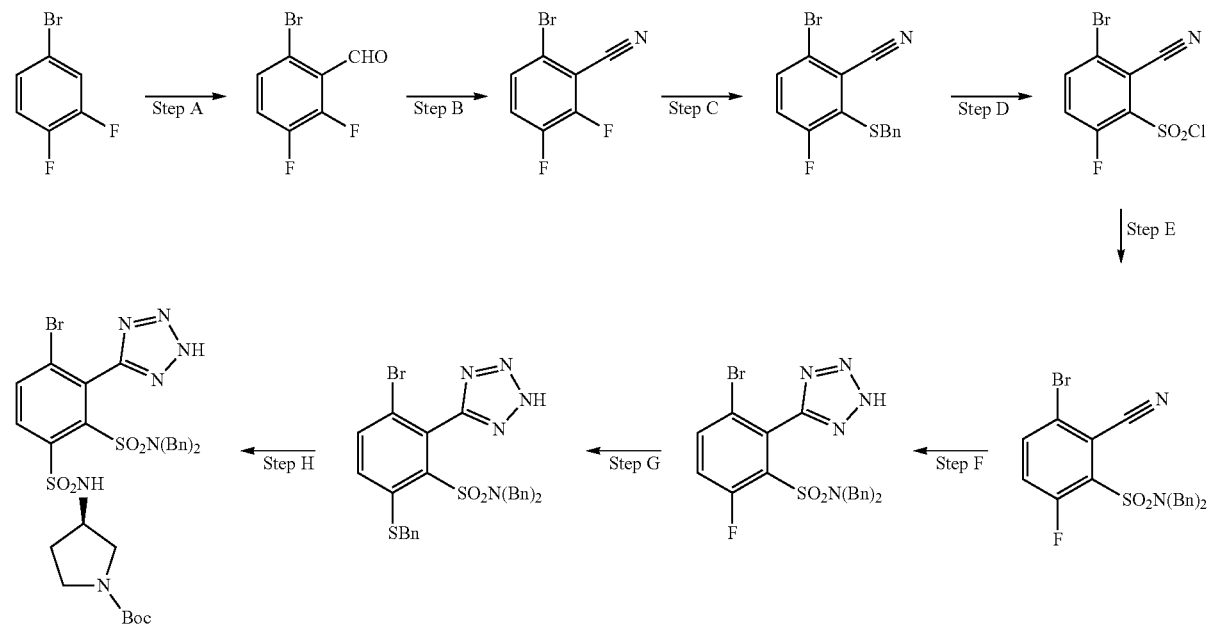

Step A: 6-bromo-2,3-difluorobenzaldehyde

To a 2000 mL, 3N RBF under nitrogen sweep, was added 1-bromo-3,4-difluorobenzene (60 mL, 531 mmol) and 600 mL THF. The reaction was cooled to −70° C. and lithium diisopropylamide (318 mL, 637 mmol) was added dropwise over ~1.5 hours while the temperature was maintained below −60° C. The reaction was then stirred for 15-20 minutes, then DMF (49.3 mL, 637 mmol) was added dropwise over 10 minutes while maintaining the temperature below −65° C. The mixture was stirred for an additional 30 minutes, then warmed to −20° C. The reaction mixture was quenched by the addition of water (75 mL) followed by the addition of 5N HCl (~400 mL) until pH 4 was achieved. The resultant mixture was stirred at RT and partitioned with 500 mL MTBE. The organic layer was washed with sat'd NaHCO$_3$ (200 mL) and brine (100 mL), dried over Na$_2$SO$_4$, filtered and concentrated in vacuo. The crude product was adsorbed on silica (~1 g/g of crude) and chromatographed (3 columns total, 330 g column, condition with hexanes, eluted ICV hexanes then gradient to 10% MTBE/hexanes over 4CV then hold for 4CV) to give 6-bromo-2,3-difluorobenzaldehyde.

Step B: 6-bronco-2,3-difluorobenzonitrile

To a 1000 mL 4N flask, internal thermometer and air condenser was added 6-bromo-2,3-difluorobenzaldehyde (96.14 g, 435 mmol), hydroxylamine hydrochloride (33.3 g, 479 mmol) and formic acid (492 mL, 13.1 mol). The reaction was heated to 90-95° C. and the mixture was stirred for 18 hours. The reaction mixture was cooled to RT, poured into water (1400 mL) and stirred vigorously for 20 minutes. The suspended solids were collected by filtration and washed with water (1000 mL). The filtrate was diluted with an additional 500 mL water and refiltered to give additional product. The solids were dried using a combination of vacuum and a flow of nitrogen for 18 hours to give 6-bromo-2,3-difluorobenzonitrile.

Step C: 2-(benzylthio)-6-bromo-3-fluorobenzonitrile

To a 1000 mL flask was added 6-bromo-2,3-difluorobenzonitrile (82.26 g, 377 mmol), N,N-diisopropylethylamine (99 mL, 566 mmol) and THF (400 mL). Neat benzyl mercaptan (44.9 mL, 383 mmol) was then added and the reaction was stirred at RT for 20 hours. The reaction was diluted with EtOAc (1200 mL), and washed sequentially with water (250 mL), 5N HCl (2×120 mL), sat'd NaHCO$_3$ (2×100 mL), brine (100 mL). The reaction mixture was then dried over Na$_2$SO$_4$, filtered and concentrated in vacuo. The crude product was suspended in 500 mL heptane and stirred vigorously for 30 minutes. The resultant solid was collected and washed with 200 mL heptane, then dried using a under vacuum followed by a nitrogen stream to give the title compound.

Step D: 3-bromo-2-cyano-6-fluorobenzene-1-sulfonyl chloride

To a 2000 mL RBF was added 2-(benzylthio)-6-bromo-3-fluorobenzonitrile (108.22 g, 336 mmol) and acetic acid. The mixture was stirred until the solid dissolved. Water (108 mL, 5995 mmol) was then added followed by N-chlorosuccinimide (112 g, 840 mmol) and the reaction mixture was stirred at RT for 2 hours. The reaction was then poured into 2200 mL water and stirred vigorously for 20 minutes. The resultant solid was collected by filtration, washed with water (2×200 mL), slurried and washed in hexanes (1×200 mL) and dried under a combination of vacuum and a flow of nitrogen to provide the title compound.

Step E: N,N-dibenzyl-3-bromo-2-cyano-6-fluorobenzenesulfonamide

To a 1000 mL RB flask was added triethylamine (28.0 mL, 201 mmol), dibenzylamine (21.26 mL, 111 mmol) and CH$_2$Cl$_2$ (300 mL). The reaction mixture was cooled in an ice/water bath and 3-bromo-2-cyano-6-fluorobenzene-1-sulfonyl chloride (30 g, 100 mmol) was added portionwise. The mixture was stirred for 10 minutes at 0° C., then 30 minutes at RT. The reaction was then taken up in 750 mL of EtOAc and the organic layer was washed sequentially with 1M HCl. (2×300 mL), sat NaHCO$_3$ (2×150 mL), sat'd brine (100 mL), dried over Na2SO4, filtered and concentrated in vacuo. The crude solid was slurried in hexanes, filtered, washed with hexanes, then dried under a combination of vacuum and a nitrogen stream to provide the title product.

Step F: N,N-dibenzyl-3-bromo-6-fluoro-2-(21H-tetrazol-5-yl)benzenesulfonamide To a 1000 mL 1N RB flask was added N,N-dibenzyl-3-bromo-2-cyano-6-fluorobenzenesulfonamide (40.5 g, 88 mmol), sodium azide (17.20 g, 265 mmol), zinc chloride (18.02 g, 132 mmol), and toluene (304 mL) followed by N,N,N',N'-tetramethylethylenediamine (21.15 mL, 141 mmol). The reaction was heated at 95° C. for 2 hours. The reaction was cooled to RT then 300 mL water was added followed by 300 mL hexanes. The resultant suspension was stirred for 1 hour. The suspension was filtered and the collected solid was washed with water (2×300 mL). To the wet solid was added 400 mL 1N HCl and 40 mL MeOH. The resultant mixture was stirred vigorously for 3 hours. The suspension was filtered, washed with 300 mL water and 200 mL hexanes then dried under a combination of vacuum along with a nitrogen stream overnight to provide the title product.

Step G: N,N-dibenzyl-6-(benzylthio)-3-bromo-2-(2H-tetrazol-5-yl)benzenesulfonamide To a 40 mL vial with stir bar was added N,N-dibenzyl-3-bromo-6-fluoro-2-(2H-tetrazol-5-yl)benzenesulfonamide (3.24 g, 6.45 mmol), Cs$_2$CO$_3$ (5.25 g, 16.12 mmol), NMP (16.20 mL) followed by benzyl mercaptan (1.134 mL, 9.67 mmol). The mixture was stirred at ambient temperature for 1.5 hours. The reaction mixture was taken up in 200 mL EtOAc, and the organic layer was washed sequentially with 1N HCl (2×50 mL), 10% LiCl (aq.) (2×50 mL) and brine (50 mL) then dried over Na$_2$SO$_4$, filtered and concentrated in vacuo. The crude product was purified by flash silica chromatography (column conditioned with hexanes then product eluted 0.5CV then gradient to 100% EtOAc over 12 CV then hold at 100% EtOAc for 6 CV) to give the title product: Calc, m/z 605.1 and 607.1 [M], Found m/z 606.2 and 608.2 [M+H]$^+$.

Step H: (R)-tert-butyl 3-(4-bromo-2-(N,N-dibenzylsulfamoyl)-3-(2H-tetrazol-5-yl)phenylsulfonamido)pyrrolidine-1-carboxylate To a 500 mL RBF containing N,N-dibenzyl-6-(benzylthio)-3-bromo-2-(2H-tetrazol-5-yl)benzenesulfonamide (22.67 g, 37.4 mmol) was added acetic acid (227 mL) followed by the addition of water (22.67 mL). The mixture was stirred at RT for 45 minutes. The reaction mixture was poured into 500 mL water and stirred for 30 minutes. The supernatant was decanted and an additional 300 mL water was added to the flask, mixed and decanted. The resultant gum was taken up in MTBE (500 mL,) washed with water (2×100 mL) and brine (2×100 mL), then dried over Na$_2$SO$_4$, filtered and concentrated in vacuo to provide the intermediate sulfonyl chloride. A solution of the sulfonyl chloride was added dropwise to a flask containing a cooled (0° C.) mixture of Et$_3$N (10.42 mL, 74.7 mmol) and (R)-1-BOC-3-aminopyrrolidine (6.97 mL, 41.1 mmol) in 100 mL of THF. The resultant mixture was stirred at 0° C. for 15 minutes followed by an additional 15 minutes at RT The reaction mixture was diluted with 500 mL EtOAc, then washed sequentially with 2×100 mL 1N HCl, 1×100 mL pH 7 buffer, and 1×100 mL sat'd brine, then dried over Na$_2$SO$_4$, filtered and concentrated in vacuo. The crude product was purified by flash silica chromatography (column conditioned with hexanes, loaded crude product in 30 mL DCM on to top of column, eluted 1 CV hexanes then gradient to 100% 3:1 EtOAc/EtOH over 6 CV) to provide the title compound, ESI MS Calc. m/z 731.1 and 733.1 [M], found m/z 732.4 and 734.4 [M+H]$^+$ Reference Example 51

(R)-tert-butyl (3-(4-bromo-2-(N,N-dibenzylsulfamoyl)-3-(2-(4-methoxybenzyl)-2H-tetrazol-5-yl) phenylsulfonamido)-2-((tert-butyldimethylsilyl) oxy)propyl)carbamate

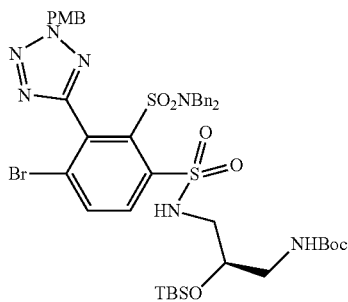

Step A: N,N-dibenzyl-3-bromo-2-(2H-tetrazol-5-yl)-6-((2-(trimethylsilyl)ethyl)thio) benzenesulfonamide To a mixture of NaH (10.5 g, 0.27 mol, 60% in mineral oil) in DMF (500 mL) was added 2-(trimethylsilyl)ethanethiol (30.10 g, 0.22 mol) at 0° C. under nitrogen. The mixture was stirred at 0° C. for 0.5 hours under nitrogen. Then N,N-dibenzyl-3-bromo-6-fluoro-2-(2H-tetrazol-5-yl) benzenesulfonamide (REFERENCE EXAMPLE 50—Step F) (45.0 g, 0.09 mol) was added slowly into the resulting mixture at RT. The reaction mixture was stirred at RT for 1 hour. The resulting mixture was used in the next step without further purification: LCMS [M+H]$^+$: 616, 618.

Step B: N,N-dibenzyl-3-bromo-2-(2-(4-methoxybenzyl)-5H-tetrazol-5-yl)-6-((2-(trimethylsilyl)ethyl) thio)benzenesulfonamide To resulting mixture above was added K$_2$CO$_3$ (37.0 g, 0.27 mol) at 0° C., and then it was added slowly to 1-(chloromethyl)-4-methoxybenzene (56.0 g, 0.36 mol) at 0° C. The mixture was stirred at RT for 16 hours. The resulting mixture was diluted with water (1 L), and then extracted with EA (3×500 mL). The organic layers were combined, washed with brine (2×300 mL), dried over anhydrous Na$_2$SO$_4$ and filtered. The filtrate was concentrated under vacuum. The residue was purified by a silica gel column chromatography, eluting with ethyl 40% EA in PE to afford N,N-dibenzyl-3-bromo-2-(2-(4-methoxybenzyl)-2H-tetrazol-5-yl)-6-((2-(trimethyl silyl)ethyl)thio)benzenesulfonamide as a solid: LCMS [M+H]$^+$: 736, 738.

Step C: N,N-dibenzyl-3-bromo-2-(2-(4-methoxybenzyl)-2H-tetrazol-5-yl)-6-((2-(trimethyl silyl)ethyl)sulfonyl)benzenesulfonamide To a solution of N,N-dibenzyl-3-bromo-2-(2-(4-methoxybenzyl)-2H-tetrazol-5-yl)-6-((2-(trimethylsilyl)ethyl)thio) benzenesulfonamide (33.0 g, 44.80 mmol) in DCM (300 mL) was added m-CPBA (31.0 g, 0.18 mol) slowly at RT. The mixture was stirred for 16 hours at RT. The solid was filtered out. The resulting solution was quenched with the addition of aqueous sat'd Na$_2$SO$_3$ (1500 mL) and extracted with of EA (3×800 mL). The organic layers were combined, washed with aqueous sat'd Na$_2$CO$_3$ (3×400 mL) and brine (2×300 mL), dried over anhydrous Na$_2$SO$_4$ and filtered. The filtrate was concentrated under vacuum. The residue was purified by a silica gel column chromatography, eluting with 20% EA in PE to afford N,N-dibenzyl-3-bromo-2-(2-(4-methoxybenzyl)-2H-tetrazol-5-yl)-6-((2-(trimethylsilyl) ethyl)sulfonyl)benzenesulfonamide as a solid: LCMS [M+H]$^+$: 768, 770.

Step D: 4-Bromo-2-(N,N-dipentylsulfamoyl)-3-(2-(4-methoxybenzyl)-2H-tetrazol-5-yl) benzenesulfinic acid To a solution of N,N-dibenzyl-3-bromo-2-(2-(4-methoxybenzyl)-2H-tetrazol-5-yl)-6-((2-(trimethylsilyl)ethyl)sulfonyl)benzenesulfonamide (20.0 g, 26.0 mmol) in THF (200 mL) was added TBAF.3H$_2$O (32.8 g, 0.10 mol) at 0° C. The reaction solution was stirred at RT for 1 hour. The resulting solution was diluted with water (600 mL) and extracted with EA (3×150 mL). The organic layers were combined, washed with aqueous sat'd KHSO$_4$ (4×300 mL) and brine (2×300 mL), dried over anhydrous MgSO$_4$ and filtered. The filtrate was concentrated under vacuum to afford 4-bromo-2-(N,N-dibenzylsulfamoyl)-3-(2-(4-methoxybenzyl)-2H-tetrazol-5-yl)benzenesulfinic acid as a solid which was used in the next step without further purification: LCMS [M+H]$^+$: 668, 670.

Step E: (R)-tert-butyl (3-(4-bromo-2-(N,N-dibenzylsulfamoyl)-3-(2-(4-methoxybenzyl)-2H-tetrazol-5-yl)phenylsulfonamido)-2-hydroxypropyl)carbamate To a solution of 4-bromo-2-(N,N-dibenzylsulfamoyl)-3-(2-(4-methoxybenzyl)-2H-tetrazol-5-yl)benzenesulfinic acid (18.1 g, 26.9 mmol) in THF (180 mL) were added (S)-tert-butyl (3-amino-2-hydroxypropyl)carbamate (7.68 g, 40.4 mmol) and TEA (5.63 mL, 40.4 mmol) at RT. The mixture was stirred at RT for 30 minutes. To the resulting solution was added 1-chloropyrrolidine-2,5-dione (7.19 g, 53.8 mmol). The reaction mixture was stirred at RT for 1 hour. The resulting solution was diluted with water (500 mL) and extracted with EA (3×300 mL). The organic layers were combined, washed with brine (2×200 mL), dried over anhydrous Na$_2$SO$_4$ and filtered. The filtrate was concentrated under vacuum. The residue was purified by a silica gel column chromatography, eluting with 50% EA in PE to afford of (R)-tert-butyl (3-(4-bromo-2-(N,N-dibenzylsulfamoyl)-3-(2-(4-methoxybenzyl)-2H-tetrazol-5-yl)phenylsulfonamido)-2-hydroxypropyl)carbamate as a solid: LCMS [M+H]$^+$: 856, 858.

Step F: (R)-tert-butyl (3-(4-bromo-2-(N,N-dibenzylsulfamoyl)-3-(2-(4-methoxybenzyl)-2H-tetrazol-5-yl)phenylsulfonamido)-2-((tert-butyldimethylsilyl)oxy)propyl)carbamate To a solution of (1)-tert-butyl (3-(4-bromo-2-(N,N-dibenzylsulfamoyl)-3-(2-(4-methoxybenzyl)-2H-tetrazol-5-yl) phenylsulfonamido)-2-hydroxypropyl)carbamate (20.0 g, 23.34 mmol) in DMF (200 mL) were added tert-butylchlorodimethylsilane (21.0 g, 0.14 mol) and 1H-imidazole (13.0 g, 0.19 mol) at RT. The reaction mixture was stirred at RT for 16 hours. The resulting solution was diluted with water (500 mL), and extracted with EA (3×250 mL). The organic layers were combined, washed with brine (2×100 mL), dried over anhydrous Na$_2$SO$_4$ and filtered. The filtrate was concentrated under vacuum. The residue was purified by a silica gel column chromatography, eluting with 30% EA in PE to afford (R)-tert-butyl (3-(4-bromo-2-(N,N-dibenzylsulfamoyl)-3-(2-(4-methoxybenzyl)-2H-tetrazol-5-yl) phenylsulfonamido)-2-((tert-butyldimethylsilyl)oxy) propyl) carbamate as a solid: LCMS [M+H]$^+$: 970, 972.

Reference Example 5.2 benzyl (S)-(2-((2-(N,N-bis(4-methoxybenzyl)sulfamoyl)-4-iodo-3-(2-(4-methoxybenzyl)-2H-tetrazol-5-yl)phenyl)sulfonamido)-3-((tert-butyldimethylsilyl)oxy)propyl)carbamate

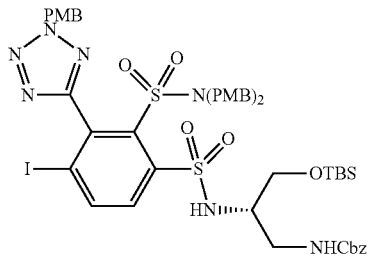

Step A: (S)-methyl 3-(((benzyloxy)carbonyl)amino)-2-((tert-butoxycarbonyl)amino) propanoate To a mixture of (S)-3-(((benzyloxy)carbonyl)amino)-2-((tert-butoxycarbonyl) amino)propanoic acid (5.00 g, 14.8 mmol) in DMF (50 mL) and K$_2$CO$_3$ (2.25 g, 16.3 mmol) was added iodomethane (6.29 g, 44.3 mmol) at RT. The reaction mixture was degassed with nitrogen three times and stirred at RT for 16 hours under nitrogen. The resulting mixture was diluted with water (150 mL) and extracted with EA (3×80 mL). The combined organic layer was washed with water (3×50 mL) and brine (3×100 mL), dried over anhydrous Na$_2$SO$_4$ and filtered. The filtrate was concentrated under reduced pressure. The residue was purified by a silica gel column chromatography, eluting with a gradient of 1%-50% EA in PE to afford (S)-methyl 3-(((benzyloxy)carbonyl) amino)-2-((tert-butoxycarbonyl)amino) propanoate as an oil. LCMS (ESI) calc'd for C$_{17}$H$_{24}$N$_2$O$_6$ [M+1]$^+$: 353, found 353.

Step B: (S)-benzyl tert-butyl (3-hydroxypropane-1,2-diyl)dicarbamate

To a solution of (S)-methyl 3-(((benzyloxy)carbonyl) amino)-2-((tert-butoxycarbonyl)amino)propanoate (4.50 g, 12.8 mmol) in THF (30 mL) was added LiBH$_4$ (1.39 g, 63.9 mmol) at 0° C. The reaction solution was stirred at 0° C. for 2 hours. The reaction was then quenched by the addition of water (150 mL) and extracted with EA (3×50 mL). The organic layers were combined, washed with brine (2×50 mL), dried over anhydrous Na$_2$SO$_4$ and filtered. The filtrate was concentrated under reduced pressure. The residue was purified by a silica gel column chromatography, eluting with a gradient of 1%-50% EA in PE to afford (S)-benzyl tert-butyl (3-hydroxypropane-1,2-diyl)dicarbamate as an oil. LCMS [M+1]$^+$: 325.

Step C: (5)-benzyl (2-amino-3-hydroxypropyl)carbamate 2,2,2-trifluoroacetate

To a solution of (S)-benzyl tert-butyl (3-hydroxypropane-1,2-diyl)dicarbamate (3.50 g, 10.8 mmol) in DCM (20 mL) was added TFA (10 mL) at 0° C. The reaction solution was warmed to RT and stirred for 1 hour. The resulting solution was concentrated under reduced pressure to afford (S)-benzyl (2-amino-3-hydroxypropyl)carbamate 2,2,2-trifluoroacetate as an oil. LCMS [M−114+1]$^+$: 225.

Step D: (S)-benzyl (2-(2-(N,N-bis(4-methoxybenzyl)sulfamoyl)-4-iodo-3-(2-(4-methoxybenzyl)-2H-tetrazol-5-yl)phenylsulfonamido)-3-hydroxypropyl)carbamate To a solution of 2-(N,N-bis(4-methoxybenzyl)sulfamoyl)-4-iodo-3-(2-(4-methoxybenzyl)-2H-tetrazol-5-yl) benzenesulfinic acid (2.00 g, 2.58 mmol) were added (S)-benzyl (2-amino-3-hydroxypropyl)carbamate 2,2,2-trifluoroacetate (2.49 g, 7.74 mmol) and TEA (7.19 mL, 51.6 mmol) at RT. The mixture was stirred at RT for 30 minutes. NCS (0.689 g, 5.16 mmol) was added to the reaction mixture at RT. The reaction mixture was stirred at RT for 16 hours. The resulting mixture was diluted with water (50 mL) and extracted with EA (3×50 mL). The organic layers were combined, washed with brine (2×50 mL), dried over anhydrous Na$_2$SO$_4$ and filtered. The filtrate was concentrated under reduced pressure. The residue was purified by a silica gel column chromatography, eluting with a gradient of 1%-50% EA in PE to afford (S)-benzyl (2-(2-(N,N-bis(4-methoxybenzyl)sulfamoyl)-4-iodo-3-(2-(4-methoxybenzyl)-2H-tetrazol-5-yl)phenylsulfonamido)-3-hydroxypropyl)carbamate as a solid, LCMS [M+1]$^+$: 998.

Step E: (S)-benzyl (2-(2-(N,N-bis(4-methoxybenzyl)sulfamoyl)-4-iodo-3-(2-(4-methoxybenzyl)-2H-tetrazol-5-yl)phenylsulfonamido)-3-((tert-butyldimethylsilyl) oxy)propyl)carbamate To a solution of (S)-benzyl (2-(2-(N,N-bis(4-methoxybenzyl)sulfamoyl)-4-iodo-3-(2-(4-methoxybenzyl)-2H-tetrazol-5-yl)phenylsulfonamido)-3-hydroxypropyl) carbamate (1.80 g, 1.80 mmol) in DCM (18 mL) were added 1H-imidazole (0.246 g, 3.61 mmol) and TBS-Cl (0.408 g, 2.71 mmol) at RT. The solution was stirred at RT for 16 hours. The resulting solution was diluted with water (50 mL) and extracted with EA (3×50 mL). The organic layers were combined, washed with brine (3×50 mL), dried over anhydrous $Na_2SO_4$ and filtered. The filtrate was concentrated under reduced pressure. The residue was purified by a silica gel column chromatography, eluting with a gradient of 1%-30% EA in PE to afford (S)-benzyl (2-(2-(N,N-bis(4-methoxybenzyl)sulfamoyl)-4-iodo-3-(2-(4-methoxybenzyl)-2H-tetrazol-5-yl) phenylsulfonamido)-3-((tert-butyldimethylsilyl) oxy)propyl)carbamate as a solid. LCMS (ESI) calc'd for $C_{48}H_{58}IN_7O_{10}S_2Si$ $[M+1]^+$: 1112, found 1112.

Reference Example 53

(S)-tert-butyl 2-carbamoylpiperazine-1-carboxylate

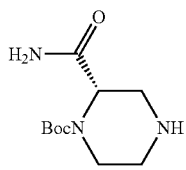

Step A: (S)-tert-butyl 2-carbamoylpiperazine-1-carboxylate

In a sealed tube, (S)-1-tert-butyl 2-methyl piperazine-1,2-dicarboxylate (1.00 g, 4.09 mmol) was dissolved in $NH_3$ (2 M in MeOH, 10 mL, 20.0 mmol) at RT. The reaction solution was stirred at 60° C. for 3 days. After cooling to RT, the resulting mixture was concentrated under reduced pressure to afford (S)-tert-butyl 2-carbamoylpiperazine-1-carboxylate as a solid. LCMS (ESI) calc'd for $C_{10}H_{19}N_3O_3$ $[M+1]^+$: 230, found 230.

Reference Example 54

(R)-tert-butyl 2-carbamoylpiperazine-1-carboxylate

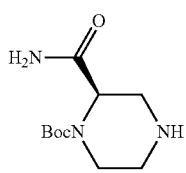

Step A: (R)-tert-butyl 2-carbamoylpiperazine-1-carboxylate

In a sealed tube, (R)-1-tert-butyl 2-methyl piperazine-1,2-dicarboxylate (1.00 g, 4.09 mmol) was dissolved in $NH_3$. (2 M in WOK 10 mL, 20.00 mmol) at RT. The reaction solution was stirred at 60° C. for 3 days. After cooling to RT, the resulting mixture was concentrated under reduced pressure to afford (R)-tert-butyl 2-carbamoylpiperazine-1-carboxylate as a solid. LCMS (ESI) calc'd for $C_{10}H_{19}N_3O_3$ $[M+1]^+$: 230, found 230.

Reference Example 55 benzyl (3-(piperidin-4-yl)propyl)carbamate

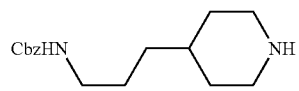 [SMILES: O=C(NCCCC1CCNCC1)OCc1ccccc1]

Step A: tert-Butyl 4-(3-(((benzyloxy)carbonyl)amino)propyl)piperidine-1-carboxylate To a solution of tert-butyl 4-(3-aminopropyl)piperidine-1-carboxylate (1.20 g, 4.95 mmol) in DCM (2 mL) were added Cbz-Cl (1.27 g, 7.43 mmol) and TEA (1.00 g, 9.90 mmol) at RT under nitrogen atmosphere. The reaction mixture was stirred at RT for 4 hours. The resulting mixture was concentrated under reduced pressure and the residue was purified by silica gel column chromatography, eluting with a gradient of 1%-30% EA in PE to afford tert-butyl 4-(3-(((benzyloxy)carbonyl)amino)propyl)piperidine-1-carboxylate as an oil. LCMS (ESI) calc'd for $C_{21}H_{32}N_2O_4$ $[M+1]^+$: 377, found 377.

Step B: Benzyl (3-(piperidin-4-yl)propyl)carbamate

To a solution of tert-butyl 4-(3-(((benzyloxy)carbonyl)amino)propyl) piperidine-1-carboxylate (1.05 g, 2.79 mmol) in DCM (5 mL) was added TFA (5 mL) at RT. The reaction mixture was stirred at RT for 2 hours. The resulting mixture was concentrated under reduced pressure and the residue was dissolved in DCM (5 mL) Then anhydrous $Na_2CO_3$ (0.250 g, 2.36 mmol) was added to the reaction. The mixture was stirred at RT for 1 hour. The resulting mixture was filtered and the filtrate was concentrated under reduced pressure to afford benzyl (3-(piperidin-4-yl)propyl)carbamate as an oil which was used in the next step without further purification. LCMS (ESI) calc'd for $C_{16}H_{24}N_2O_2$ $[M+1]^+$: 277, found 277.

Reference Example 56

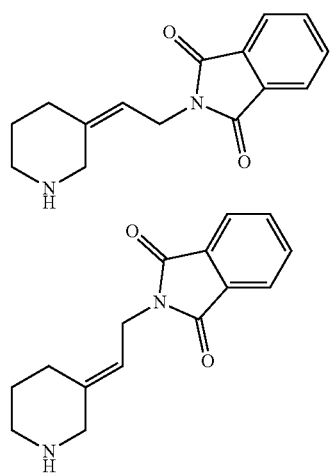

(Z) and (E)-2-(2-(piperidin-3-ylidene)ethyl)isoindoline-1,3-dione

Reference Examples 56a and 56b (Isomers A and B)

2-(2-(piperidin-3-ylidene)ethyl)isoindoline-1,3-dione (Isomers A and B)

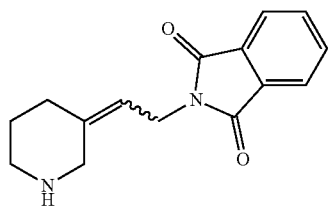

Isomers A and B

Step A: tert-Butyl 3-(2-methoxy-2-oxoethylidene)piperidine-1-carboxylate

To a solution of methyl 2-(dimethoxyphosphoryl)acetate (5.48 g, 30.1 mmol) in THF (10 mL) was added NaOH (1.20 g, 30.0 mmol). The reaction mixture was stirred at RT for 15 minutes. Then tert-butyl 3-oxopiperidine-1-carboxylate (4.00 g, 20.1 mmol) was added to the mixture. The reaction mixture was stirred at RT for 3 hours. The resulting mixture was concentrated under reduced pressure. The residue was purified by a silica gel column chromatography, eluting with a gradient of 1%-25% EA in PE to afford tert-butyl 3-(2-methoxy-2-oxoethylidene)piperidine-1-carboxylate as an oil. LCMS (ESI) calc'd for $C_{13}H_{21}NO_4$ [M+1]$^+$: 256, found 256.

Step B: tert-butyl 3-(2-hydroxyethylidene)piperidine-1-carboxylate (isomers A and B)

To a solution of tert-butyl 3-(2-methoxy-2-oxoethylidene)piperidine-1-carboxylate (4.50 g, 17.6 mmol) in THF (20 mL) was added DIBAL-H (1 M in THF, 70.5 mL, 70.5 mmol) at −50° C. under argon atmosphere. The reaction mixture was stirred at −50° C. for 1 hour. The resulting mixture was quenched with MeOH (20 mL) and water (2 mL) and stirred for 30 minutes. The resulting mixture was filtered. The filtrate was concentrated under reduced pressure. The residue was purified by a silica gel column chromatography, eluting with a gradient of 1%-43% EA in PE to afford tert-butyl 3-(2-hydroxyethylidene)piperidine-1-carboxylate (Isomer A). LCMS (ESI) calc'd for $C_{12}H_{21}NO_3$[M+1]$^+$: 228, found 228; and tert-butyl 3-(2-hydroxyethylidene)piperidine-1-carboxylate (isomer B). LCMS (ESI) calc'd for $C_{12}H_{21}NO_3$ [M+1]$^+$: 228, found 228.

Step C: tert-butyl 3-(2-(1,3-dioxoisoindolin-2-yl)ethylidene)piperidine-1-carboxylate (Isomers A and B)

To a solution of tert-butyl 3-(2-hydroxyethylidene)piperidine-1-carboxylate (0.900 g, 3.96 mmol) (Isomer A) in toluene (6 mL) were added isoindoline-1,3-dione (1.17 g, 7.92 mmol), PPh$_3$ (2.08 g, 7.92 mmol) and DIAD (1.54 mL, 7.92 mmol) at 0° C. under argon atmosphere. The reaction mixture was stirred at RT for 18 hours. The resulting mixture was concentrated under reduced pressure. The residue was purified by a silica gel column chromatography, eluting with a gradient of 1%-14% EA in PE to afford tert-butyl-dioxoisoindolin-2-yl)ethylidene) piperidine-1-carboxylate (Isomer A) as a solid. LCMS (ESI) calc'd for $C_{20}H_{24}N_2O_4$ [M+1]$^+$: 357, found 357; tert-butyl 3-(2-(1,3-dioxoisoindolin-2-yl)ethylidene)piperidine-1-carboxylate (Isomer B) was prepared in an analogous manner. LCMS (ESI) calc'd for $C_{20}H_{24}N_2O_4$[M+1]$^+$: 357, found 357.

Step D: 2-(2-(piperidin-3-ylidene)ethyl)isoindoline-1,3-dione (Isomers A and B)

To a solution of tert-butyl 3-(2-(1,3-dioxoisoindolin-2-yl)ethylidene)piperidine-1-carboxylate (Isomer A) (0.600 g, 1.68 mmol) in DCM (2 mL) was added TFA (2 mL) at room temperature. The reaction solution was stirred at room temperature for 1 h. The resulting solution was concentrated under reduced pressure to afford 2-(2-(piperidin-3-ylidene)ethyl)isoindoline-1,3-dione (Isomer A) as a solid which was used to next step without further purification. LCMS (ESI) calc'd for $C_{15}H_{16}N_2O_2$ [M+1]$^+$: 257, found 257; 2-(2-(piperidin-3-ylidene)ethyl)isoindoline-1,3-dione (Isomer B) was prepared in an analogous manner and obtained as a solid which was used without further purification. LCMS (ESI) calc'd for $C_{15}H_{16}N_2O_2$ [M+1]$^+$: 257, found 257.

Reference Example 57

4-(1H-imidazol-2-yl)piperidine hydrochloride

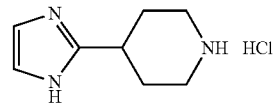

Prepared as described in WO2004/41777.

Reference Example 58

2-(piperidin-4-ylmethoxy)ethanol

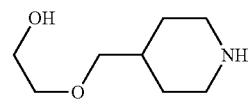

Prepared as described in EP1746095 A1.

Reference Example 59

(S)-tert-butyl (3-amino-2-((tert-butyldimethylsilyl)oxy)propyl)carbamate

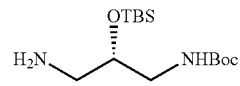

Step A: (S)-benzyl tert-butyl (2-hydroxypropane-1,3-diyl)dicarbamate

To a solution of (S)-tert-butyl (3-amino-2-hydroxypropyl) carbamate (2.0 g, 10.51 mmol) in DCM (20 mL) were added TEA (2.2 mL, 15.7 mmol) and CBZ-Cl (1.80 mL, 12.62 mmol). The reaction solution was stirred at RT for 16 hours. The resulting mixture was diluted with EA (50 mL) and washed with water (3×15 mL) and brine (3×10 mL). The organic layer was dried over anhydrous $Na_2SO_4$ and filtered. The filtrate was concentrated under reduced pressure and the residue was purified by a silica gel column chromatography, eluting with 1%-70% EA in PE to afford (S)-benzyl tert-butyl (2-hydroxypropane-1,3-diyl)dicarbamate as an oil: LCMS (ESI) calc'd for $C_{16}H_{24}N_2O_5$ $[M+1]^+$: 325, found 325.

Step B: (S)-benzyl tert-butyl (2-((tert-butyldimethylsilyl)oxy)propane-1,3-diyl)dicarbamate To a solution of (S)-benzyl tert-butyl (2-hydroxypropane-1,3-diyl)dicarbamate (1.8 g, 5.55 mmol) in DCM (10 mL) were added imidazole (0.57 g, 8.32 mmol) and TBS-Cl (1.0 g, 6.66 mmol). The reaction mixture was stirred at 40 for 16 hours. After cooling to RT, the resulting mixture was diluted with EA (50 mL) and washed with water (3×15 mL) and brine (3×10 mL). The organic layer was dried over anhydrous $Na_2SO_4$ and filtered. The filtrate was concentrated under reduced pressure and the residue was purified by a silica gel column chromatography, eluting with a gradient of 1%-40% EA in PE to afford (S)-benzyl tert-butyl (2-((tert-butyldimethylsilyl) oxy)propane-1,3-diyl)dicarbamate as an oil: LCMS $[M+1]^+$: 439.

Step C: (S)-tert-butyl (3-amino-2-((tert-butyldimethylsilyl)oxy)propyl)carbamate To a solution of (S)-benzyl tert-butyl (2-((tert-butyldimethylsilyl)oxy) propane-1,3-diyl)dicarbamate (2.1 g, 4.79 mmol) in MeOH (10 mL) was added palladium hydroxide on carbon (1.6 g, 2.28 mmol). The reaction mixture was degassed with hydrogen 3 times. The reaction mixture was stirred at RT for 16 hours under hydrogen. The resulting mixture was filtered and the filtrate was concentrated under reduced pressure to afford (S)-tert-butyl (3-amino-2-((tert-butyldimethylsilyl)oxy)propyl)carbamate as an oil: LCMS $[M+1]^+$: 305.

Reference Example 60 tert-butyl (R)-3-((4-bromo-2-(N,N-dibenzylsulfamoyl)-3-(1-(4-methoxybenzyl)-1H-tetrazol-5-yl)phenyl)sulfonamido)pyrrolidine-1-carboxylate intermediate

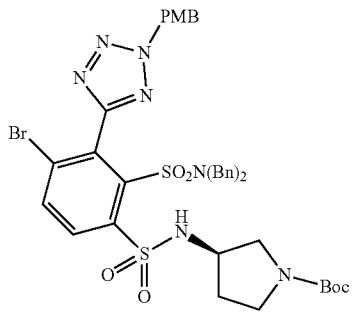

To a suspension of tert-butyl (R)-3-((4-bromo-2-(NV-dibenzylsulfamoyl)-3-(2H-tetrazol-5-yl)phenyl)sulfonamido)pyrrolidine-1-carboxylate (3.05 g, 4.16 mmol) in acetonitrile (41.6 ml) was added 4-methoxybenzyl chloride (0.734 ml, 5.41 mmol) and DIEA (1.818 ml, 10.41 mmol) and stirred at 25° C. for 16 hours. After that time, additional DIEA (1.818 ml, 10.41 mmol) and 4-methoxybenzyl chloride (0.734 ml, 5.41 mmol) was added, and the reaction mixture was stirred at RT for an additional 12 hours. The reaction mixture was diluted with DCM 100 mL and washed with water (30 ml) followed by brine (30 ml). The organic layer was dried over $Na_2SO_4$, filtered and concentrated in vacuo. The residue was purified by column chromatography on silica gel, eluting with a gradient of EtOAc in hexane 0 to 50% to afford the title compound.

Reference Example 61 tert-butyl (R)-3-((2-(N,N-bis(4-methoxybenzyl)sulfamoyl)-4-bromo-3-(2-(4-methoxybenzyl)-2H-tetrazol-5-yl)phenyl)sulfonamido)pyrrolidine-1-carboxylate

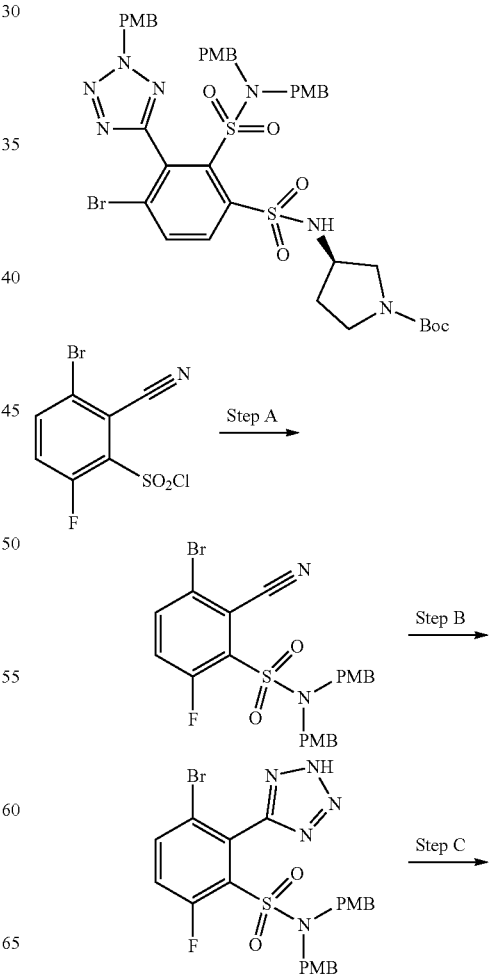

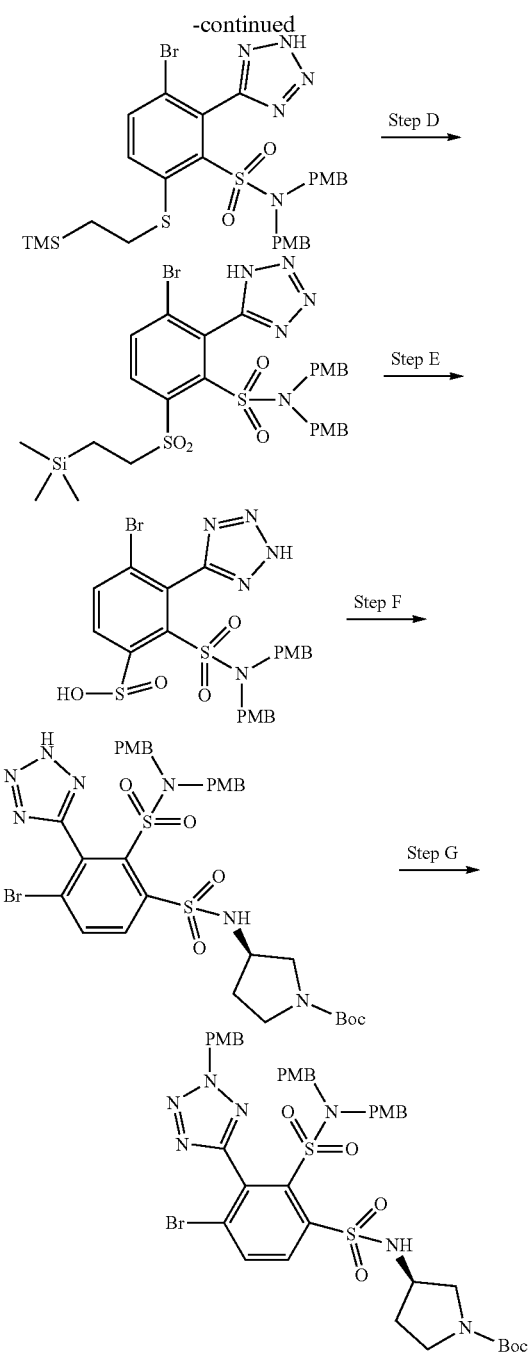

Step A: 3-bromo-2-cyano-6-fluoro-N,N-bis(4-methoxybenzyl)benzenesulfonamide

To a mixture of bis(4-methoxybenzyl)amine (18.18 g, 70.7 mmol) and triethylamine (17.91 ml, 128 mmol) in THF (200 ml) was added 3-bromo-2-cyano-6-fluorobenzene-1-sulfonyl chloride (from REFERENCE EXAMPLE 50 step D) (19.177 g, 64.2 mmol). The reaction mixture was stirred at RT for 18 hours. The reaction was diluted with MTBE (400 ml), 2M HOAc (150 ml) and water (100 ml). The organic layer was separated and washed with sat'd NaHCO$_3$ (2×50 ml) and brine (50 ml) then dried over Na$_2$SO$_4$, filtered and concentrated in vacuo. The material was titrated with MTBE/hexanes, filtered, washed with hexanes and dried under vacuum/nitrogen flow to afford the title compound.

Step B: 3-bromo-6-fluoro-N,N-bis(4-methoxybenzyl)-2-(2H-tetrazol-5-yl)benzenesulfonamide To a flask was added zinc chloride (9.45 g, 69.3 mmol), sodium azide (9.01 g, 139 mmol), 3-bronco-2-cyano-6-fluoro-N,N-bis(4-m ethoxybenzyl)benzenesulfonamide (24 g, 46.2 mmol), toluene (180 ml) followed by N,N,N',N'-tetramethylethylenediamine (11.09 ml, 73.9 mmol). The mixture was heated at 100° C. for 18 hours. After that time, the reaction was cooled to ~40° C., then diluted with 200 ml water and stirred vigorously for 30 minutes. The suspension was filtered, washed with 200 mL water followed by 200 mL hexanes and dried under vacuum. The solids were suspended in 300 ml 1N HCl and 30 ml MeOH was added. The mixture was stirred vigorously at RT for 2 hours, filtered, washed with water (2×100 mL), hexanes (100 mL) and dried under a combination of vacuum/nitrogen stream overnight to afford the title compound.

Step C: 3-bromo-N,N-bis(4-methoxybenzyl)-2-(2H-tetrazol-5-yl)-6-((2-(trimethylsilyl)ethyl) thio)benzenesulfonamide To a flask were added 3-bromo-6-fluoro-N,N-bis(4-methoxybenzyl)-2-(2H-tetrazol-5-yl)benzenesulfonamide (14.2 g, 25.2 mmol), cesium carbonate (16.45 g, 50.5 mmol) and NMP (71 ml) followed by 2-(trimethylsilyl)ethanethiol (6.06 ml, 37.9 mmol). The reaction mixture was stirred at RT for 36 hours. The reaction was poured into a mixture of 300 ml EtOAc, 100 ml 2N HOAc and 100 ml water. The organic layer was separated and washed sequentially with 2×100 ml 10% aq. LiCl, followed by brine then dried over Na$_2$SO$_4$, filtered and concentrated. The crude material was chromatographed on silica (gradient elution 0 to 100% EtOAc in hexanes) to provide the title compound.

Step D: 3-bromo-N,N-bis(4-methoxybenzyl)-2-(1H-tetrazol-5-yl)-6-((2-(trimethylsilyl)ethyl) sulfonyl)benzenesulfonamide To a flask were added 3-bromo-N,N-bis(4-methoxybenzyl)-2-(1H-tetrazol-5-yl)-6-((2-(trimethylsilyl)ethyl)thio)benzenesulfonamide (14.8 g, 21.87 mmol) and 150 ml DCM followed by the portionwise addition of 3-chloroperoxybenzoic acid (12.25 g, 54.7 mmol) over 20 minutes. The reaction mixture was stirred overnight at RT. After that time, the reaction was diluted with EtOAc (300 ml), then washed with sodium bisulfite (3×100 ml) and brine (100 ml). The organic layer was dried over Na$_2$SO$_4$, filtered and concentrated in vacuo. The crude material was purified by silica gel chromatography (gradient elution 0 to 100% EtOAc in hexanes) to provide the title compound.

Step E: 2-(N,N-bis(4-methoxybenzyl)sulfamoyl)-4-bromo-3-(2H-tetrazol-5-yl)benzenesulfinic acid To a flask were added 3-bromo-N,N-bis(4-methoxybenzyl)-2-(2H-tetrazol-5-yl)-6-((2-(trimethylsilyl)ethyl)sulfonyl)benzenesulfonamide (12 g, 16.93 mmol) and THF (48.0 ml). TBAF (50.8 ml, 50.8 mmol) was then added over 2.0 min at RT and the mixture was stirred for 3 days. The reaction mixture was partitioned between EtOAc (500 ml), water (300 ml) and 100 ml sat'd KHSO$_4$. The organic layer was separated and washed with sat'd KHSO$_4$ (4×100 ml), brine (75 ml) then dried over Na$_2$SO$_4$, filtered and concentrated in vacuo to afford the title compound, which was used without further purification.

Step F: (R)-tert-butyl 3-(2-(N,N-bis(4-methoxybenzyl)sulfamoyl)-4-bromo-3-(2H-tetrazol-5-yl)phenylsulfonamido)pyrrolidine-1-carboxylate To a flask was added a solution of the sulfinic acid from the previous step in 50 ml THF. The mixture was cooled to 0° C. then (R)-1-Boc-3-aminopyrrolidine (5.24 g, 28.1 mmol), triethylamine (3.92 ml, 28.1 mmol) and NCS (3.75 g, 28.1 mmol) were added in succession. The mixture was stirred for 20 minutes at 0° C. then partitioned between 250 ml EtOAc and 200 ml 2M aqueous HOAc. The organic layer was washed with sat'd brine (50 ml), dried over Na$_2$SO$_4$, filtered and concentrated in vacuo. The crude product was chromatographed on silica (gradient elution 0 to 10% MeOH in DCM) to provide the title compound.

Step G: tert-butyl (R)-3-((4-bromo-2-(N,N-dibenzylsulfamoyl)-3-(1-(4-methoxybenzyl)-1H-tetrazol-5-yl)phenyl)sulfonamido)pyrrolidine-1-carboxylate To a solution of tert-butyl (R)-3-((2-(N,N-bis(4-methoxybenzyl)sulfamoyl)-4-bromo-3-(1H-tetrazol-5-yl)phenyl)sulfonamido)pyrrolidine-1-carboxylate (1.0 g, 1.26 mmol) in acetonitrile 12.6 ml) were added 4-methoxybenzyl chloride (0.222 ml, 1.64 mmol) and DIEA (0.55 ml, 3.15 mmol). The reaction mixture was stirred at RT for 16 hours. Additional DIEA (0.55 ml, 3.15 mmol) and 4-methoxybenzyl chloride (0.222 ml, 1.64 mmol) were then added and the reaction was stirred for an additional 12 hours at RT. The reaction mixture was diluted with DCM 100 mL and washed with water (30 ml) and brine (30 ml). The organic layer was dried over Na$_2$SO$_4$, filtered and concentrated in vacuo. The crude product was purified by column chromatography on silica gel (gradient elution 0 to 70% EtOAc in hexanes) to afford the title compound.

Reference Example 62

(R)-di-tert-butyl (3-aminopropane-1,2-diyl)dicarbamate

Step A: (S)-di-tert-butyl (3-hydroxypropane-1,2-diyl)dicarbamate

To a solution of (S)-methyl 2,3-bis((tert-butoxycarbonyl)amino)propanoate (1.5 g, 4.71 mmol) in THF (15 mL) was added LiAlH$_4$ (0.27 g, 7.07 mmol) in several portions at 5° C. under nitrogen. The mixture was stirred for 2 hours at 5° C. under nitrogen. The resulting mixture was quenched with water (30 mL) and extracted with EA (3×30 mL). The combined organic layer was washed with brine (3×30 mL), dried over anhydrous Na$_2$SO$_4$ and filtered. The filtrate was concentrated under vacuum. The residue was purified by silica gel column chromatography, eluting with 30% EA in PE to afford (S)-di-tert-butyl (3-hydroxypropane-1,2-diyl) dicarbamate. LCMS (EST) calc'd for C$_{13}$H$_{26}$N$_2$O$_5$ [M+1]$^+$: 291, found 291.

Step B: (S)-2,3-bis((tert-butoxycarbonyl)amino)propyl methanesulfonate

To a solution of (S)-di-tert-butyl (3-hydroxypropane-L2-diyl)dicarbamate (0.8 g, 2.76 mmol) and TEA (0.84 g, 8.27 mmol) in DCM (8 mL) was added MsCl (0.47 g, 4.13 mmol) at 0° C. The reaction mixture was stirred at RT for 1 hour. The resulting mixture was quenched with water (50 mL) and extracted with EA (3×50 mL). The combined organic layers were washed with brine (3×50 mL), dried over anhydrous Na$_2$SO$_4$, and filtered. The filtrate was concentrated under vacuum to afford (5)-2,3-bis((tert-butoxycarbonyl)amino) propyl methanesulfonate as a solid, which was used in the next step without further purification: LCMS (ESI) calc'd for C$_{14}$H$_{28}$N$_2$O$_7$S [M+1]$^+$: 369, found 369.

Step C: (S)-di-tert-butyl (3-(1,3-dioxoisoindolin-2-yl)propane-1,2-diyl)dicarbamate To a solution of (S)-2,3-bis((tert-butoxycarbonyl)amino) propyl methanesulfonate (1.1 g, 2.99 mmol) in DMF (10 mL) was added potassium 1,3-dioxoisoindolin-2-ide (0.83 g, 4.48 mmol) at RT. Then the mixture was stirred at 60° C. for 16 hours. The reaction mixture was cooled to RT. The resulting mixture was quenched with water (50 mL) and extracted with EA (3×50 mL). The combined organic layers were washed with water (3×50 mL) and brine (3×50 mL), dried over anhydrous Na$_2$SO$_4$ and filtered. The filtrate was concentrated under vacuum. The residue was purified by silica gel column chromatography, eluting with 30% EA in PE to afford (S)-di-tert-butyl(3-(1,3-dioxoisoindolin-2-yl) propane-1,2-diyl) dicarbamate as a solid: LCMS (ESI) calc'd for C$_{21}$H$_{29}$N$_3$O$_6$ [M+1]$^+$: 420, found 420.

Step D: (R)-di-tert-butyl (3-aminopropane-1,2-diyl)dicarbamate

To a solution of (5')-di-tert-butyl (3-(1,3-dioxoisoindolin-2-yl)propane-1,2-diyl) dicarbamate (0.5 g, 1.19 mmol) in EtOH (5 mL) was added N$_2$H$_4$.H$_2$O (80%, 0.12 g, 3.58 mmol) at RT. The reaction was warmed to 80° C. The reaction mixture was stirred for 4 hours at 80° C. under nitrogen. The resulting mixture was cooled to RT. The mixture was filtered. The filter cake was washed with EtOH (2×50 mL). The filtrate was concentrated under vacuum to afford (R)-di-tert-butyl (3-aminopropane-1,2-diyl)dicarbamate as a solid, which was used for next step without further purification: LCMS (ESI) calc'd for C$_{13}$H$_{27}$N$_3$O$_4$ [M+1]$^+$: 290, found 290.

Reference Example 63

(S)-di-tert-butyl (3-(2-(N,N-bis(4-methoxybenzyl) sulfamoyl)-4-iodo-3-(2-(4-methoxy benzyl)-2H-tetrazol-5-yl)phenylsulfonamido)propane-1,2-diyl) dicarbamate

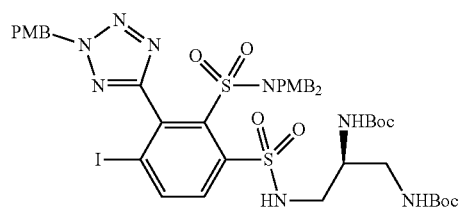

This reference example was prepared using a method similar to that described for REFERENCE EXAMPLE 41 using (R)-di-tert-butyl (3-aminopropane-1,2-diyl)dicarbamate (REFERENCE EXAMPLE 62).

Example 1

N[1]—((R)-3-amino-2-hydroxypropyl)-4-(cis-4-amino-3-fluoropiperidin-1-yl-3-2H-tetrazol-5-yl)benzene-1,2-disulfonamide

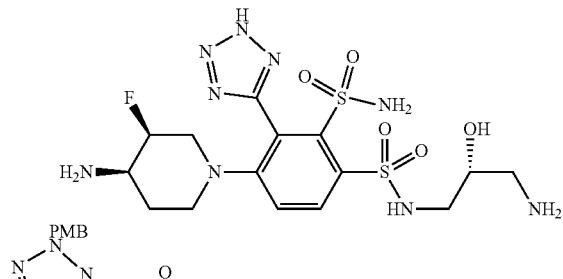

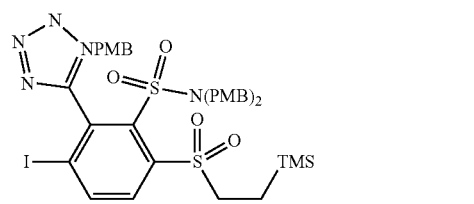

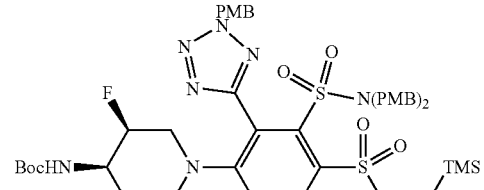

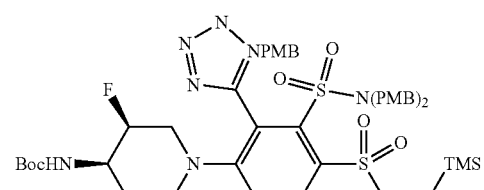

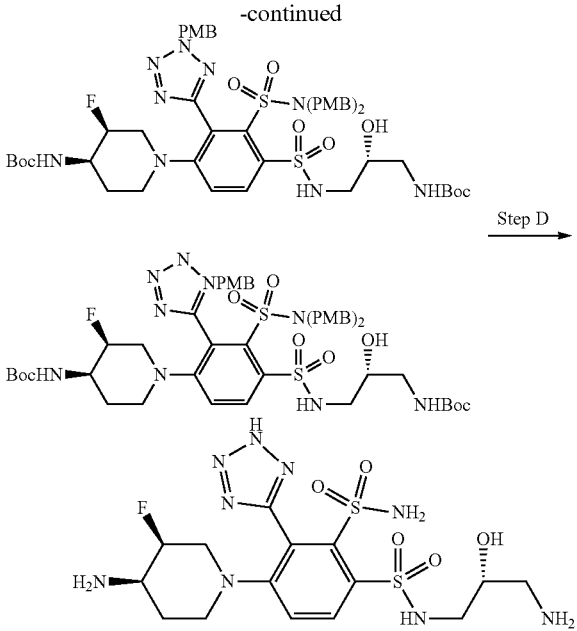

Step A: tert-butyl (cis-(3-(N,N-bis(4-methoxybenzyl)sulfamoyl)-2-(2-(4-methoxybenzyl)-2H-tetrazol-5-yl)-4-((2-(trimethylsilyl)ethyl)sulfonyl)phenyl)-3-fluoropiperidin-4-yl)carbamate and tert-butyl (cis-1-(3-(N,N-bis(4-methoxybenzyl)sulfamoyl)-2-(1-(4-methoxybenzyl-1H-tetrazol-5-yl)-4-((2-(trimethylsilyl)ethylsulfonyl)phenyl)-3-fluoropiperidin-4-yl)carbamate A flask was charged with 3-iodo-N,N-bis(4-methoxybenzyl)-2-(2-(4-methoxybenzyl)-2H-tetrazol-5-yl)-6-((2-(trimethylsilyl)ethyl)sulfonyl)benzenesulfonamide and 3-iodo-N,N-bis(4-methoxybenzyl)-2-(1-(4-methoxybenzyl)-1H-tetrazol-5-yl)-6-((2-(trimethylsilyl)ethyl)sulfonyl)benzenesulfonamide (REFERENCE EXAMPLE 37) (400 mg, 0.457 mmol), racemic tert-butyl (cis-3-fluoropiperidin-4-yl)carbamate (498 mg, 2.283 mmol) and DABCO (256 mg, 2.283 mmol). The vial was sealed, degassed with N$_2$, and filled with DMSO (3.1 mL). The resulting mixture was heated overnight at 110° C. The reaction mixture was concentrated and the residue was purified by silica gel column chromatography using (0-100)% EtOAc/hexane as mobile phase to afford the title compound. LC/MS [M+H]$^+$: 966.96.

Step B: 2-(N,N-bis(4-methoxybenzyl)sulfamoyl)-4-(cis-4-((tert-butoxycarbonyl)amino)-3-fluoropiperidin-1-yl)-3-(2-(4-methoxybenzyl)-2H-tetrazol-5-yl)benzenesulfinic acid and 2-(N,N-bis(4-methoxybenzyl)sulfamoyl)-4-(cis-4-((tert-butoxycarbonyl)amino)-3-fluoropiperidin-1-yl)-3-(1-(4-methoxybenzyl)-1H-tetrazol-5-yl)benzenesulfinic acid To a solution of tert-butyl (cis-1-(3-(N,N-bis(4-methoxybenzyl)sulfamoyl)-2-(2-(4-methoxybenzyl)-2H-tetrazol-5-yl)-4-((2-(trimethylsilyl)ethyl)sulfonyl)phenyl)-3-fluoropiperidin-4-yl)carbamate and tert-butyl (cis-1-(3-(N,N-bis(4-methoxybenzyl)sulfamoyl)-2-(1-(4-methoxybenzyl)-1H-tetrazol-5-yl)-4-((2-(trimethylsilyl)ethyl)sulfonyl)phenyl)-

3-fluoropiperidin-4-yl)carbamate (0.36 g, 0.373 mmol) in THF (3.73 mL) was added tetrabutylammonium fluoride (0.820 ml, 0.820 mmol) (1.0 M in THF) dropwise at 0° C. The reaction mixture was stirred at RT under $N_2$ for 0.5 hours. The reaction mixture was diluted with EtOAc, washed four times with sat'd aqeuous $KHSO_4$, twice with brine, dried over $MgSO_4$, and concentrated to afford the title compound. LC/MS $[M+H]^+$: 866.73.

Step C: tert-butyl (cis-1-(3-(N,N-bis(4-methoxybenzyl)sulfamoyl)-4-(N)—((R)-3-((tert-butoxycarbonyl)amino)-2-hydroxypropyl)sulfamoyl)-2-(2-(4-methoxybenzyl)-2H-tetrazol-5-yl)phenyl-3-fluoropiperidin-4-yl)carbamate and tert-butyl (cis-1-(3-(N,N-bis(4-methoxybenzyl)sulfamoyl)-4-(N—((R)-3-((tert-butoxycarbonyl)amino)-2-hydroxypropyl)sulfamoyl)-2-(1-(4-methoxybenzyl)-1H-tetrazol-5-yl)phenyl)-3-fluoropiperidin-4-yl)carbamate To a solution of 2-(N,N-bis(4-methoxybenzyl)sulfamoyl)-4-(cis-4-((tert-butoxycarbonyl)amino)-3-fluoropiperidin-1-yl)-3-(2-(4-methoxybenzyl)-2H-tetrazol-5-yl)benzenesulfinic acid and 2-(N,N-bis(4-methoxybenzyl)sulfamoyl)-4-(cis-4-((tert-butoxycarbonyl)amino)-3-fluoropiperidin-1-yl)-3-(1-(4-methoxybenzyl)-1H-tetrazol-5-yl)benzenesulfinic acid (0.32 g, 0.370 mmol) in THF (2.58 mL) were added (S)-tert-butyl (3-amino-2-hydroxypropyl)carbamate (0.141 g, 0.739 mmol), TEA (0.103 mL, 0.739 mmol), and NCS (0.099 g, 0.739 mmol) in sequence at 0° C. under nitrogen. The mixture was stirred at the same temperature for 30 minutes. The reaction mixture was diluted with EtOAc, washed with $NaHCO_3$ solution and brine. The organic layer was dried over $MgSO_4$, evaporated, and the crude product was purified by silica gel column chromatography eluting with 0-100% EtOAc/hexanes to give the title compound. LC/MS $[M+H]^+$: 1054.87.

Step D: $N^1$—((R)-3-amino-2-hydroxypropyl)-4-(cis-4-amino-3-fluoropiperidin-1-yl)-3-(2H-tetrazol-5-yl)benzene-1,2-disulfonamide To the solution of tert-butyl (cis-1-(3-(N,N-bis(4-methoxybenzyl)sulfamoyl)-4-(N—((R)-3-((tert-butoxycarbonyl)amino)-2-hydroxypropyl)sulfamoyl)-2-(2-(4-methoxybenzyl)-2H-tetrazol-5-yl)phenyl)-3-fluoropiperidin-4-yl)carbamate and tert-butyl (cis-1-(3-(N,N-bis(4-methoxybenzyl)sulfamoyl)-4-(N—((R)-3-((tert-butoxycarbonyl)amino)-2-hydroxypropyl)sulfamoyl)-2-(1-(4-methoxybenzyl)-1H-tetrazol-5-yl)phenyl)-3-fluoropiperidin-4-yl)carbamate (360 mg, 0.341 mmol) in DCM (2.5 mL) was added anisole (0.371 mL, 3.41 mmol) and TFA (2.63 mL, 34.1 mmol) at 0° C. The reaction mixture was stirred at 0° C. for 30 minutes. After removing the volatile, the residue was dissolved in TFA (5.26 mL, 68.2 mmol). The resulting mixture was stirred at 80° C. for 1.0 hour. After removing the volatile, the residue was purified by reverse phase HPLC (1-25% MeCN/water, 0.1% $NH_4OH$ as additive) to give the title compound. LC/MS $[M+H]^+$: 494.41.

EXAMPLES 2-3 were prepared according to the general procedures described above, using REFERENCE EXAMPLE 37, and requisite amine intermediates as depicted in the following table for step A and step C, respectively.

| EX. | INTERMEDIATES | STRUCTURE/NAME | LC/MS |
|---|---|---|---|
| 2 | tert-butyl (trans-3-fluoropiperidin-4-yl)carbamate and (S)-tert-butyl (3-amino-2-hydroxypropyl)carbamate | $N^1$-((R)-3-amino-2-hydroxypropyl)-4-(trans-4-amino-3-fluoropiperidin-1-yl)-3-(2H-tetrazol-5-yl)benzene-1,2-disulfonamide | $[M + H]^+$: 494.37 |
| 3 | tert-butyl ((4-fluoropiperidin-4-yl)methyl)carbamate and (S)-tert-butyl (3-amino-2-hydroxypropyl)carbamate | (R)-$N^1$-(3-amino-2-hydroxypropyl)-4-(4-(aminomethyl)-4-fluoropiperidin-1-yl)-3-(2H-tetrazol-5-yl)benzene-1,2-disulfonamide | $[M + H]^+$: 508.46 |

Example 4

N1-((R)-3-amino-2-hydroxypropyl)-4-(4-(aminomethyl)-2-methyl piperidin-1-yl)-3-(2H-tetrazol-5-yl)benzene-1,2-disulfonamide

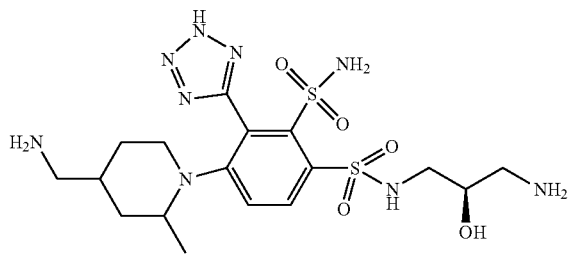 [SMILES: CC1CC(CN)CCN1c1ccc(S(=O)(=O)NC[C@H](O)CN)c(S(N)(=O)=O)c1-c1nn[nH]n1]

Step A: N,N-dibenzyl-3-(4-(((tert-butyldimethylsilyl)oxy)methyl)-2-methylpiperidin-1-yl)-2-(2-(4-methoxybenzyl)-2H-tetrazol-5-yl)-6-((2-(trimethylsilyl)ethyl)sulfonyl) benzenesulfonamide To a solution of 4-(((tert-butyldimethylsilyl)oxy)methyl)-2-methylpiperidine (0.63 g, 2.60 mmol, prepared as described in EP2913330 A1) in 1,4-dioxane (0.3 mL) was added KHMDS (0.5 g, 2.60 mmol) dropwise. The reaction solution was stirred at RT for 15 minutes, then N,N-dibenzyl-3-bromo-2-(2-(4-methoxybenzyl)-2H-tetrazol-5-yl)-6-((2-(trimethylsilyl)ethyl)sulfonyl)benzenesulfonamide (REFERENCE EXAMPLE 51 step C) (1.0 g, 1.30 mmol) was added to the reaction solution. The reaction solution was stirred at 140° C. for 3 days in a sealed tube. After cooling to RT, the resulting solution was quenched with sat'd NH$_4$Cl (5 mL) and extracted with EA (3×5 mL). The combined organic layer was washed with brine (3×5 mL) and dried over anhydrous Na$_2$SO$_4$, filtered and the filtrate was concentrated under reduced pressure. The residue was purified by flash gel column chromatography, eluting with a gradient of 1%-40% EA in PE to afford the title compound: LCMS [M+1]$^+$: 931.

Step B: 2-(N,N-dibenzylsulfamoyl)-4-(4-(hydroxymethyl)-2-methylpiperidin-1-yl)-3-(2-(4-methoxybenzyl)-2H-tetrazol-5-yl)benzenesulfinic acid To a solution of N,N-dibenzyl-3-(4-(((tert-butyldimethylsilyl)oxy)methyl)-2-methylpiperidin-1-yl)-2-(2-(4-methoxybenzyl)-2H-tetrazol-5-yl)-6-((2-(trimethylsilyl)ethyl)sulfonyl)benzenesulfonamide (0.40 g, 0.43 mmol) in THF (3 mL) was added TBAF (1.3 mL, 1.2.9 mmol). The reaction solution was stirred at 40° C. for 16 hours. The resulting solution was diluted by EA (50 ml) and washed with water (10×5 mL). The organic layer was dried over anhydrous MgSO$_4$, filtered and concentrated to afford the title compound which was used in the next step without further purification. LCMS [M+1]$^+$: 717.

Step C: tert-butyl ((2R)-2-((tert-butyldimethylsilyl)oxy)-3-(2-(N,N-dibenzylsulfamoyl)-4-(4-(hydroxymethyl)-2-methylpiperidin-1-yl)-3-(2-(4-methoxy benzyl)-2H-tetrazol-5-yl)phenylsulfonamido)propyl)carbamate To a solution of 2-(N,N-dibenzylsulfamoyl)-4-(4-(hydroxymethyl)-2-methylpiperidin-1-yl)-3-(2-(4-methoxybenzyl)-2H-tetrazol-5-yl)benzenesulfinic acid (0.30 g, 0.42 mmol) in THF (5 mL) were added TEA (0.12 mL, 0.84 mmol) and (S)-tert-butyl (3-amino-2-((tert-butyldimethylsilyl)oxy)propyl)carbamate (0.26 g, 0.84 mmol)). The reaction mixture was stirred at 0° C. for 15 minutes, then NCS (83.6 mg, 0.63 mmol) was added to the reaction mixture. The reaction mixture was stirred at RT for 1 hour. The resulting mixture was diluted with water (8 mL) and extracted with EA (3×10 mL). The organic layers were combined, washed with brine (2×10 mL), dried over anhydrous Na$_2$SO$_4$ and filtered. The filtrate was concentrated under reduced pressure. The residue was purified by silica gel column chromatography, eluting with a gradient of 1%-80% EA in PE to afford the title compound. LCMS (ESI) calc'd for C$_{50}$H$_{70}$N$_8$O$_9$S$_2$Si [M+1]$^+$: 1019, found 1019.

Step D: (1-(4-(N—((R)-3-((tert-butoxycarbonyl)amino)-2-((tert-butyldimethylsilyl) oxy)propyl)sulfamoyl)-3-(N,N-dibenzylsulfamoyl)-2-(2-(4-methoxybenzyl)-2H-tetrazol-5-yl)phenyl)-2-methyl)-2-methylpiperidin-4-yl)methyl methanesulfonate The title compound was prepared as described for EXAMPLE 208 step B using tert-butyl ((2R)-2-((tert-butyldimethylsilyl)oxy)-3-(2-(N,N-dibenzylsulfamoyl)-4-(4-(hydroxymethyl)-2-methylpiperidin-1-yl)-3-(2-(4-methoxybenzyl)-2H-tetrazol-5-yl) phenylsulfonamido)propyl)carbamate (0.57 g, 0.56 mmol). The product was used in the next step without further purification. LCMS [M+1]$^+$: 1097.

Step E: tert-butyl ((2R)-3-(4-(4-(azidomethyl)-2-methylpiperidin-1-yl)-2-(N,N-dibenzylsulfamoyl)-3-(2-(4-methoxybenzyl)-2H-tetrazol-5-yl)phenylsulfonamido)-2-((tert-butyldimethylsilyl)oxy)propyl) carbamate To a solution of (1-(4-(N—((R)-3-((tert-butoxycarbonyl)amino)-2-((tert-butyldimethylsilyl)oxy)propyl)sulfamoyl)-3-(N,N-dibenzylsulfamoyl)-2-(2-(4-methoxybenzyl)-2H-tetrazol-5-yl)phenyl)-2-methylpiperidin-4-yl)methyl methanesulfonate (0.52 g, 0.474 mmol) in DMSO (3 mL) were added sodium azide (61.6 mg, 0.948 mmol) and KI (15.73 mg, 0.095 mmol). The reaction mixture was stirred at 100° C. for 4 hours. The resulting mixture was diluted with EA (50 mL) and washed with water (3×5 mL) and brine (3×5 mL). The organic layer was dried over anhydrous Na$_2$SO$_4$ and filtered. The filtrate was concentrated under reduced pressure and the residue was purified by silica gel column chromatography, eluting with a gradient of 1%-50% EA in PE to afford the title compound. LCMS [M+1]$^+$: 1044.

Step F: tert-butyl ((2R)-3-(4-(4-(aminomethyl)-2-methylpiperidin-1-yl)-2-(N,N-dibenzylsulfamoyl)-3-(2-(4-methoxybenzyl)-2H-tetrazol-5-yl)phenylsulfonamido)-2-((tert-butyldimethylsilyl)oxy)propyl) carbamate The title compound was prepared as described for EXAMPLE 208 step D from tert-butyl ((2R)-3-(4-(4-(azidomethyl)-2-methylpiperidin-1-yl)-2-(N,N-dibenzyl sulfamoyl)-3-(2-(4-methoxybenzyl)-2H-tetrazol-5-yl)phenylsulfonamido)-2-((tert-butyldimethylsilyl)oxy)propyl) carbamate (0.39 g, 0.373 mmol). LCMS [M+1]$^+$: 1019.

Step G: N1-((R)-3-amino-2-hydroxypropyl)-4-(4-(aminomethyl)-2-methylpiperidin-1-yl)-3-(2H-tetrazol-5-yl)benzene-1,2-disulfonamide The title compound was prepared as described for EXAMPLE 164 step B using tert-butyl ((R)-3-(4-(4-(aminomethyl)-2-methylpiperidin-1-yl)-2-(N,N-dibenzyl sulfamoyl)-3-(2-(4-methoxybenzyl)-2H-tetrazol-5-yl)phenylsulfonamido)-2-((tert-butyldimethylsilyl)oxy)propyl) carbamate (0.300 g, 0.29 mmol) to afford the crude product. The crude product was purified by Column: XBridge Shield RP$_{18}$ OBD Column 19×250 mm, 10 μm; Mobile Phase A: Water (10 mmol/L NH$_4$HCO$_3$), Mobile Phase B: ACN; Flow rate: 20 mL/min; Gradient: 3% B to 9% B in 13 min; 254 nm and 210 nm; Retention time: 11.47 min. to afford the title compound. LCMS [M+1]$^+$: 504. $^1$H NMR (400 MHz, Deuterium Oxide) δ 8.14 (d, J=8.9, 1H), 7.37 (d, J=8.9 Hz, 1H), 3.86-3.75 (m, 1H), 3.22-2.81 (m, 6H), 2.80-2.63 (m, 3H), 1.89-1.87 (m, 1H), 1.63-1.61 (m, 1H), 1.24-1.22 (m, 1H), 1.16-1.06 (m, 1H), 0.80-0.67 (m, 4H).

EXAMPLES 5-8 were prepared according to the general procedures described above, using REFERENCE EXAMPLE 37, and requisite amine intermediates as depicted in the following table for step A and step C, respectively.

| Ex. | INTERMEDIATES | STRUCTURE/NAME | LC/MS |
|---|---|---|---|
| 5 | racemic tert-butyl (cis-3-fluoropiperidin-4-yl)carbamate and tert-butyl (R)-(2-aminopropyl)carbamate | 4-((cis-4-amino-3-fluoropiperidin-1-yl)-N$^1$-((R)-1-aminopropan-2-yl)-3-(2H-tetrazol-5-yl)benzene-1,2-disulfonamide | [M + 1]$^+$: 478.37 |
| 6 | racemic tert-butyl ((cis-3-fluoropiperidin-4-yl)methyl)carbamate and (S)-tert-butyl (3-amino-2-hydroxypropyl)carbamate | N$^1$-((R)-3-amino-2-hydroxypropyl)-4-(cis-4-(aminomethyl)-3-fluoropiperidin-1-yl)-3-(2H-tetrazol-5-yl)benzene-1,2-disulfonamide | [M + 1]$^+$: 508.41 |
| 7 | racemic tert-butyl ((cis-3-fluoropiperidin-4-yl)methyl)carbamate and tert-butyl (R)-3-aminopyrrolidine-1-carboxylate | 4-(cis-4-(aminomethyl)-3-fluoropiperidin-1-yl)-N$^1$-((R)-pyrrolidin-3-yl)-3-(2H-tetrazol-5-yl)benzene-1,2-disulfonamide | [M + 1]$^+$: 504.41 |

| Ex. | INTERMEDIATES | STRUCTURE/NAME | LC/MS |
|---|---|---|---|
| 8 | racemic tert-butyl ((cis-3-fluoropiperidin-4-yl)methyl)carbamate and tert-butyl (R)-(2-aminopropyl)carbamate | 4-(cis-4-(aminomethyl)-3-fluoropiperidin-1-yl)-$N^1$-((R)-1-aminopropan-2-yl)-3-(2H-tetrazol-5-yl)benzene-1,2-disulfonamide | $[M + 1]^+$: 492.42 |

Example 9

$N^1$—((R)-3-amino-2-hydroxypropyl)-4-(cis-4-(aminomethyl)-3-hydroxypiperidin-1-yl)-3-(2H-tetrazol-5-yl)benzene-1,2-disulfonamide

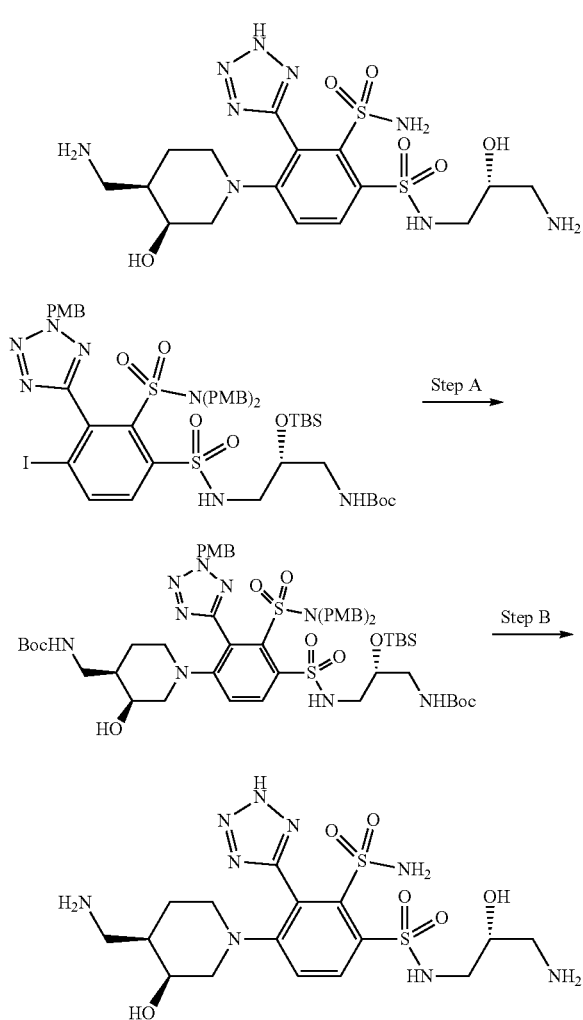

Step A: tert-butyl ((cis-1-(3-(N,N-bis(4-methoxybenzyl)sulfamoyl)-4-(N—((R)-3-((tert-butoxycarbonyl)amino)-2-((tert-butyldimethylsilyl)oxy)propyl)sulfamoyl)-2-(2-(4-methoxybenzyl)-2H-tetrazol-5-yl)phenyl)-3-hydroxypiperidin-4-yl)methyl)carbamate tert-Butyl (R)-(3-((2-(N,N-bis(4-methoxybenzyl)sulfamoyl)-4-iodo-3-(2-(4-methoxybenzyl)-2H-tetrazol-5-yl)phenyl)sulfonamido)-2-((tert-butyldimethylsilyl)oxy)propyl)carbamate (REFERENCE EXAMPLE 45) (200 mg, 0,186 mmol), tert-butyl ((cis-3-hydroxypiperidin-4-yl)methyl)carbamate (299 mg, 1299 mmol), and 1,4-diazabicyclo[2.2.2]octane (146 mg, 1.299 mmol) were dissolved in DMSO and heated at 110° C. under $N_2$ overnight. The reaction mixture was purified by silica gel column chromatography (100% hexane to 80% EtOAc/Hexane) to give the title product. $[M+H]^+$: 1180.88.

Step B: $N^1$—((R)-3-amino-2-hydroxypropyl)-4-(cis-4-(aminomethyl)-3-hydroxypiperidin-1-yl)-3-(2H-tetrazol-5-yl)benzene-1,2-disulfonamide tert-Butyl ((cis-1-(3-(N,N-bis(4-methoxybenzyl)sulfamoyl)-4-(N—((R)-3-((tert-butoxycarbonyl)amino)-2-((tert-butyldimethylsilyl)oxy)propyl)sulfamoyl)-2-(2-(4-methoxybenzyl)-2H-tetrazol-5-yl)phenyl)-3-hydroxypiperidin-4-yl)methyl)carbamate (135 mg, 0.114 mmol) was dissolved in DCM (2 mL) followed by addition of TFA (1 mL). The reaction mixture was stirred at RT for 1 hour. The reaction mixture was then concentrated and co-evaporated with toluene. The residue was heated in TFA (2 mL) and water (0.15 mL) at 80° C. for 1 hour. After concentration, the residue was purified with RP-HPLC (C18 column) (0-40% $CH_3CN$/water with 0.1% $NH_4OH$) and later with RP-HPLC (C18 column) (0-40% $CH_3CN$/water with 0.1% TFA). The pure fractions were concentrated and lyophilized to give the title product. LC/MS $[M+H]^+$: 506.18.

EXAMPLES 10-14 were prepared according to the general procedures described for EXAMPLE 9, using REFERENCE. EXAMPLE 44, and requisite amines listed in the following table in step A.

| Ex. | Amine | STRUCTURE/NAME | LC/MS [M + H]+ |
|---|---|---|---|
| 10 | tert-butyl ((trans-3-hydroxypiperidin-4-yl)methyl)carbamate | $N^1$-((R)-3-amino-2-hydroxypropyl)-4-(trans-4-(aminomethyl)-3-hydroxypiperidin-1-yl)-3-(2H-tetrazol-5-yl)benzene-1,2-disulfonamide | 506.40 |
| 11 | tert-butyl ((1R,5S,6r)-3-azabicyclo[3.1.0]hexan-6-yl-methyl)carbamate | $N^1$-((R)-3-amino-2-hydroxypropyl)-4-((1R,5S,6S)-6-(aminomethyl)-3-azabicyclo[3.1.0]hexan-3-yl)-3-(2H-tetrazol-5-yl)benzene-1,2-disulfonamide | 488.36 |
| 12 | benzyl 6-azaspiro[2.5]octan-1-ylcarbamate | $N^1$-((R)-3-amino-2-hydroxypropyl)-4-(1-amino-6-azaspiro[2.5]octan-6-yl)-3-(2H-tetrazol-5-yl)benzene-1,2-disulfonamide | 502.33 |

Example 13

$N^1$—((R)-3-amino-2-hydroxypropyl)-4-(trans-4-(aminomethyl)-3-fluoropiperidin-1-yl)-3-(2H-tetrazol-5-yl)benzene-1,2-disulfonamide

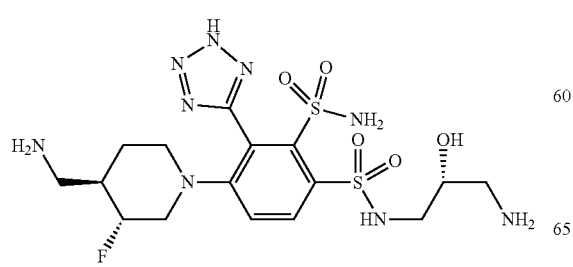

-continued

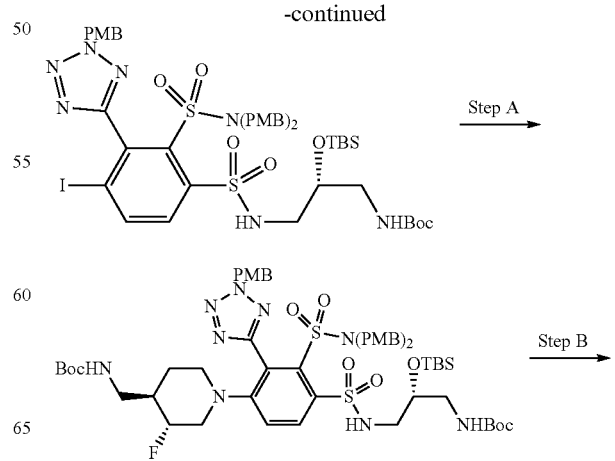

115
-continued

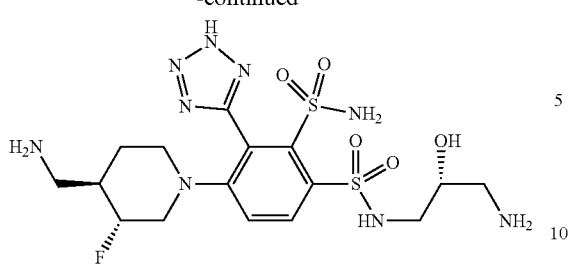

Step A: tert-butyl ((trans-1-(3-(N,N-bis(4-methoxy-benzyl)sulfamoyl)-4-(N—((R)-3-((tert-butoxycarbo-nyl)amino)-2-((tert-butyldimethylsilyl)oxy)propyl) sulfamoyl-2-(2-(4-methoxybenzyl)-2H-tetrazol-5-yl) phenyl)-3-fluoropiperidin-4-yl)methyl)carbamate tert-Butyl (R)-3-((2-(N,N-bis(4-methoxybenzyl)sulfa-moyl)-4-iodo-3-(2-(4-methoxybenzyl)-2H-tetrazol-5-yl) phenyl)sulfonamido)-2-((tert-butyldimethylsilyl)oxy)pro-pyl)carbamate (REFERENCE EXAMPLE 45) (850 mg, 0.788 mmol), tert-butyl ((trans-3-fluoropiperidin-4-yl) methyl)carbamate (366 mg, 1.577 mmol), cesium carbonate (771 mg, 2.365 mmol), rac-BINAP-G3 precatalyst (156 mg, 0.158 mmol) were placed in a microwave vial. After addition of DME (7.9 mL), the reaction mixture was sealed, degassed, and heated at 80° C. overnight. The reaction mixture was concentrated, and the residue was purified by silica gel column chromatography (100% hexane to 70% EtOAc/Hexane) to afford the title compound. [M+H]⁺: 1182.78.

Step B: N¹—((R)-3-amino-2-hydroxypropyl)-4-(trans-4-(aminomethyl)-3-fluoropiperidin-1-yl)-3-(2H-tetrazol-5-yl)benzene-1,2-disulfonamide tert-Butyl ((trans-1-(3-(N,N-bis(4-methoxybenzyl)sulfa-moyl)-4-(N—((R)-3-((tert-butoxycarbonyl)amino)-2-((tert-butyldimethylsilyl)oxy)propyl)sulfamoyl)-2-(2-(4-methoxybenzyl)-2H-tetrazol-5-yl)phenyl)-3-fluoropiperidin-4-yl)methyl)carbamate (157 mg, 0.133 mmol) was dissolved in DCM (2 mL), followed by addition of TFA (1 mL). After stirring at RT for 45 minutes, the reaction mixture was concentrated and co-evaporated with toluene. The residue was dissolved in TFA (2 mL) and heated at 80° C. for 1 hour. Then water (0.15 mL) was added and the reaction mixture was continued to heat at 80° C. for 30 minutes. After concentration, the residue was purified with RP-HPLC (0-40% CH₃CN/water as eluent with 0.1% NH₄OH as additive) on C18 column. The pure fractions were concentrated and lyophilized from CH₃CN/water to give title compound. LC/MS [M+H]⁺: 508.29.

116
Examples 14-15

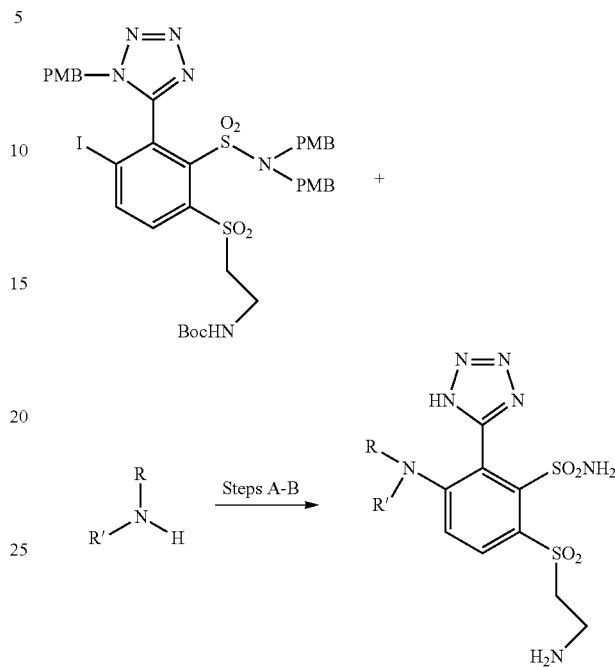

Parallel Preparation Method:

Step A:

To a set of vials containing the requisite amines (see table below) (0.544 mmol) was added 1.0 mL of a solution of tert-butyl (((2-(N,N-bis(4-methoxybenzyl)sulfamoyl)-4-iodo-3-(1-(4-methoxybenzyl)-1H-tetrazol-5-yl)phenyl) sulfonyl)ethyl)carbamate from REFERENCE EXAMPLE 49 (100 mg, 0.109 mmol) in DMF. The vials were capped and heated at 150° C. with stirring for 1 hour. After that time, the vials were cooled to RT, the reaction was added to EtOAc and the mixture was washed with water, brine, and dried over magnesium sulfate, filtered and concentrated. The crude products were used in the next step without further purification.

Step B:

To the residues from Step A were each added DCM 0.4 mL and TFA 0.4 mL followed by anisole (0.3 mL). The vials were shaken at ambient temperature for 2 hours. Solvent was removed under reduced pressure. To each vial was then added 1 mL TFA and the reaction mixtures were heated to 80° C. for 1 hour. The crude products were purified by mass triggered reverse phase HPLC using the following conditions: [column: Waters XBridge C18, or Waters Sunfire C18, 5 μm, 19×100 mm; solvent: gradient range 3-28% initial to 45-95% final MeCN (0.1% TFA) in water (0.1% TFA) 50 or 70 mL/min; 8 min run time] to afford EXAMPLES 14-15 (see table below).

| EX. NO. | RR'NH | STRUCTURE | NAME | LC/MS m/e [M + H]+ |
|---|---|---|---|---|
| 14 |  | 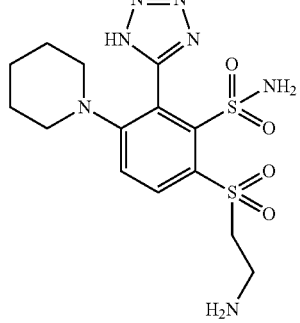 | 6-((aminomethyl)sulfonyl)-3-(piperidin-1-yl)-2-(1H-tetrazol-5-yl)benzenesulfonamide | 416.3 |
| 15 |  | 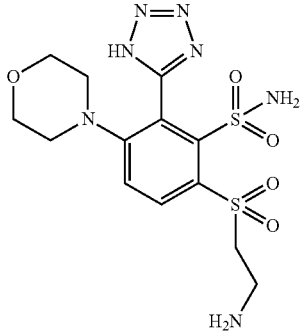 [SMILES: NCCS(=O)(=O)c1ccc(N2CCOCC2)c(-c2nnn[nH]2)c1S(N)(=O)=O] | 6-((2-aminomethyl)sulfonyl)-3-morpholino-2-(1H-tetrazol-5-yl)benzenesulfonamide | 418.3 |

Example 16

(R)-4-(4-(2-aminoethyl)piperidin-1-yl)-N$^1$-(pyrrolidin-3-yl)-3-(2H-tetrazol-5-yl)benzene-1,2-disulfonamide

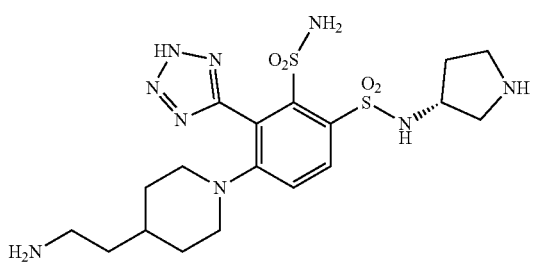 [SMILES: NCCC1CCN(c2ccc(S(=O)(=O)N[C@@H]3CCNC3)c(S(N)(=O)=O)c2-c2nn[nH]n2)CC1]

Step A: Preparation of tert-butyl (R)-3-(4-(4-(2-((tert-butoxycarbonyl)amino)ethyl)piperidin-1-yl)-2-(N,N-dibenzylsulfamoyl)-3-(2-(4-methoxybenzyl)-2H-tetrazol-5-yl)phenyl)sulfonamido)pyrrolidine-1-carboxylate To a solution of (R)-tert-butyl 3-(4-bromo-2-(N,N-dibenzylsulfamoyl)-3-(2H-tetrazol-5-yl)phenylsulfonamido)pyrrolidine-1-carboxylate (REFERENCE EXAMPLE 50) (600 mg, 0.819 mmol) in DMF (5 ml) was added tert-butyl (2-(piperidin-4-yl)ethyl)carbamate (280 mg, 1.228 mmol) and 1,4-diazabicyclo[2.2.2]octane (138 mg, 1.228 mmol) under nitrogen. The reaction mixture was stirred and heated at 110° C. overnight. The reaction mixture was concentrated in vacuo, then was chromatographed over silica gel (0-100% EtOAc in hexanes) to give the title product. LCMS [M+H]+ 880.66.

Step B: (R)-4-(4-(2-aminoethyl)piperidin-1-yl)-N$^1$-(pyrrolidin-3-yl)-3-(2H-tetrazol-5-yl)benzene-1,2-disulfonamide To a 20 mL RBF was added a solution of (R)-tert-butyl 3-(4-(4-(2-((tert-butoxycarbonyl)amino)ethyl)piperidin-1-yl)-2-(N,N-dibenzylsulfamoyl)-3-(2H-tetrazol-5-yl)phenylsulfonamido)pyrrolidine-1-carboxylate (180 mg, 0.180 mmol), anisole (195 mg, 1.8 mmol) and trifluoroacetic acid (1.03 g, 9.00 mmol) at 0 DC under nitrogen. The reaction mixture was stirred for 30 minutes. The reaction mixture was concentrated in vacuo and the residue was dissolved in 2 ml of methanol, then was filtered through ion-exchange resin (Agilent, BE-SCX 2 g) with 20 mL of methanol (containing 7N ammonia) as elutent. The filtrate was collected and concentrated. The residue was dissolved in sulfuric acid (0.48 mL, 9.00 mmol). The reaction mixture was stirred at RT overnight. The reaction mixture was cooled to 0° C. To the reaction mixture was added 20 ml of ammonia in methanol (7.0 N) to give a suspension. The mixture was filtered and the filtrate was concentrated. The residue was dissolved in 2 ml of DMSO, then was purified by reverse phase HPLC (gradient 0-30% acetonitrile in water, containing 0.1% NH$_4$OH) to give the title compound. LC-MS [M+H]+ 500.4.

Example 17

N$^{1}$-(2-aminoethyl)-4-(4-(aminomethyl)-4-hydroxypiperidin-1-yl)-3-(2H-tetrazol-5-benzene-1,2-disulfonamide

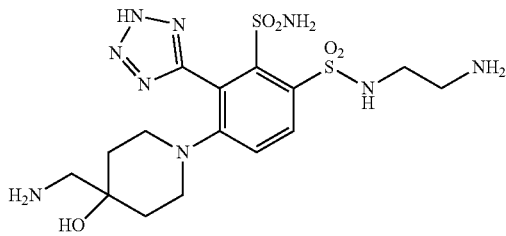 [SMILES: NCCNS(=O)(=O)c1ccc(N2CCC(O)(CN)CC2)c(-c2nn[nH]n2)c1S(N)(=O)=O]

Step A: tert-butyl((1-(3-(N,N-bis(4-methoxybenzyl)sulfamoyl)-4-(N-(2-((tert-butoxycarbonyl)amino)ethyl)sulfamoyl)-2-(2-(4-methoxybenzyl)-2H-tetrazol-5-yl)phenyl)-4-hydroxypiperidin-4-yl)methyl)carbamate To a solution of tert-butyl (2-(2-(N,N-bis(4-methoxybenzyl)sulfamoyl)-4-iodo-3-(2-(4-methoxybenzyl)-2H-tetrazol-5-yl)phenylsulfonamido)ethyl)carbamate (REFERENCE EXAMPLE 41) (200 mg, 0.214 mmol) in DMF (10 ml) was added tert-butyl ((4-hydroxypiperidin-4-yl)methyl)carbamate (99 mg, 0.428 mmol) and 1,4-diazabicyclo[2.2.2]octane (0.035 ml, 0.321 mmol). The reaction mixture was heated at 120 DC under nitrogen overnight. The reaction mixture was cooled to RT, diluted with 10 mL of EtOAc, filtered through a CELITE pad. The filtrate was dried (MgSO$_4$), concentrated and chromatographed over silica gel with 0-10% MeOH in DCM as eluent to give the title compound. LC-MS 1036.7.

Step B: N$^{1}$-(2-aminoethyl)-4-(4-(aminomethyl)-4-hydroxypiperidin-1-yl)-3-(2H-tetrazol-5-yl)benzene-1,2-disulfonamide To a flask was added a solution of tert-butyl ((1-(3-(N,N-bis(4-methoxybenzyl)sulfamoyl)-4-(N-(2-((tert-butoxycarbonyl)amino)ethyl)sulfamoyl)-2-(2-(4-methoxybenzyl)-2H-tetrazol-5-yl)phenyl)-4-hydroxypiperidin-4-yl)methyl)carbamate (140 mg, 0.135 mmol) in DCM (0.5 ml). After concentration in vacuo, the residue was treated by sequential addition of anisole (146 mg, 1.351 mmol) and 2,2,2-trifluoroacetic acid (770 mg, 6.76 mmol) at 0° C. under N$_2$. The reaction mixture was stirred at RT for 30 minutes. The mixture was concentrated in vacuo and the residue was dissolved in 3 ml of methanol, then was filtered through ion-exchange resin (Agilent, BE-SCX 2 g) with 20 ml of methanol (containing 7N ammonia) as eluent. The filtrate was collected and concentrated. The residue was dissolved in 2,2,2-trifluoroacetic acid (770 mg, 6.76 mmol) in a 20 ml RBF and heated at 80° C. for 1 hour. After removing the volatiles, the residue was dissolved in 2 mL of DMSO and purified by reverse phase HPLC with 0-30% acetonitrile in water as eluent to give the title compound. LC-MS [M+H]$^+$ 476.45.

EXAMPLES 18-19 were prepared as described for EXAMPLE 17, starting from commercially available amines and REFERENCE EXAMPLES 42 and 43.

| EX. NO. | RR'NH Step A | STRUCTURE | NAME | LC/MS [M + H]$^+$ |
|---|---|---|---|---|
| 18 | ![] | ![] | (S)-4-(4-(aminomethyl)-4-hydroxypiperidin-1-yl)-N1-(1-aminopropan-2-yl)-3-(2H-tetrazol-5-yl)benzene-1,2-disulfonamide | 490.3 |
| 19 | ![] | ![] | (R)-N1-(1-aminopropan-2-yl)-4-(4-(hydroxymethyl)-4-methoxypiperidin-1-yl)-3-(2H-tetrazol-5-yl)benzene-1,2-disulfonamide | 505.4 |

Example 20

N¹—((R)-3-amino-2-hydroxypropyl)-4-(2-(hydroxymethyl)morpholino)-3-(2H-tetrazol-5-yl)benzene-1,2-disulfonamide

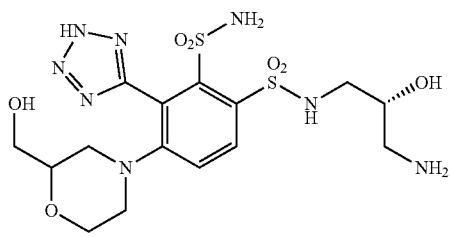 [SMILES: NC[C@@H](O)CNS(=O)(=O)c1ccc(N2CCOC(CO)C2)c(-c2nn[nH]n2)c1S(N)(=O)=O]

Step A: Preparation of 3-(2-(hydroxymethyl)morpholino)-N,N-bis(4-methoxybenzyl-2-(2-(4-methoxybenzyl)-2H-tetrazol-5-yl)-6-((2-(trimethylsilyl)ethyl)sulfonyl)benzenesulfonamide To a solution of 3-iodo-N,N-bis(4-methoxybenzyl)-2-(2-(4-methoxybenzyl)-2H-tetrazol-5-yl)-6-((2-(trimethylsilyl)ethyl)sulfonyl)benzenesulfonamide (REFERENCE EXAMPLE 37) (500 mg, 0.571 mmol) in DMF (5 ml) was added morpholin-2-ylmethanol (201 mg, 1.713 mmol) and 1,4-diazabicyclo[2.2.2]octane (96 mg, 0.856 mmol) under nitrogen. The reaction mixture was stirred and heated at 110° C. overnight. The reaction mixture was concentrated in vacuo, then was chromatographed over silica gel with 0-10% MeOH in DCM as eluent to give the desired product 3-(2-(hydroxymethyl)morpholino)-N,N-bis(4-methoxybenzyl)-2-(2-(4-methoxybenzyl)-2H-tetrazol-5-yl)-6-((2-(trimethylsilyl)ethyl)sulfonyl), LC-MS [M+H]⁺ 865.64.

Step B: Preparation of 2-(N,N-bis(4-methoxybenzyl)sulfamoyl)-4-(2-(hydroxymethyl)morpholino)-3-(2-(4-methoxybenzyl)-2H-tetrazol-5-yl)benzenesulfinic acid To a solution of 3-(2-(hydroxymethyl)morpholino)-N,N-bis(4-methoxybenzyl)-2-(2-(4-methoxybenzyl)-2H-tetrazol-5-yl)-6-(2-(trimethylsilyl)ethyl)sulfonyl)benzenesulfonamide (134 mg, 0.155 mmol) in THF (10 ml) was added tetrabutylammonium fluoride (0.341 ml, 0.341 mmol) (1.0 M in THF) at 0° C. under N₂ for 0.5 hours. The mixture was diluted with 10 mL of ethyl acetate, washed with 3 portions of 1 ml of sat'd. aqueous KHSO₄, 5 ml of brine, dried over MgSO₄, and concentrated in vacuo to give the desired product 2-(N,N-bis(4-methoxybenzyl)sulfamoyl)-4-(2-(hydroxymethyl)morpholino)-3-(2-(4-methoxybenzyl)-2H-tetrazol-5-yl)benzenesulfinic acid, LC-MS [M+H]⁺ 765.60.

Step C: Preparation of sulfonamide tert-butyl ((2R)-3-(2-(N,N-bis(4-methoxybenzyl)sulfamoyl)-4-(2-(hydroxymethyl)morpholino)-3-(2-(4-methoxybenzyl)-2H-tetrazol-5-yl)phenylsulfonamido)-2-hydroxypropyl)carbamate To a solution of 2-(N,N-bis(4-methoxybenzyl)sulfamoyl)-4-(2-(hydroxymethyl)morpholino)-3-(2-(4-methoxybenzyl)-2H-tetrazol-5-yl)benzenesulfinic acid (118 mg, 0.154 mmol) in 20 ml of —CH₂Cl₂ was added tert-butyl (S)-(3-amino-2-hydroxypropyl)carbamate (REFERENCE EXAMPLE 3) (58.7 mg, 0.309 mmol), triethylamine (46.8 mg, 0.463 mmol), N,N-dimethylpyridin-4-amine (9.42 mg, 0.077 mmol) and 1-chloropyrrolidine-2,5-dione (41.2 mg, 0.309 mmol) sequentially at 0° C. under N₂. After stirring for 0.5 hours, the mixture was washed with 10 ml of sat'd. aqueous NaHCO₃, dried over MgSO₄. The crude product was chromatographed over silica gel with 0-10% MeOH in DCM as eluent to give the title compound. LC-MS [M+H]⁺ 963.98.

Step D: N¹—((R)-3-amino-2-hydroxypropyl)-4-(2-(hydroxymethyl)morpholino)-3-(2H-tetrazol-5-yl)benzene-1,2-disulfonamide To a 10 ml RBF was added a solution of tert-butyl ((2R)-3-(2-(N,N-bis(4-methoxybenzyl)sulfamoyl)-4-(2-(hydroxymethyl)morpholino)-3-(2-(4-methoxybenzyl)-2H-tetrazol-5-yl)phenyl sulfonamido)-2-hydroxypropyl)carbamate (70 mg, 0.073 mmol) in DCM (0.5 ml). After concentration in vacuo, the residue was treated by sequential addition of anisole (79 mg, 0.734 mmol) and 2,2,2-trifluoroacetic acid (419 mg, 3.67 mmol) at 0° C. under N₂. The reaction mixture was stirred at RT for 30 minutes. The volatile was removed, and the residue was dissolved in 3 ml of methanol, then was filtered through ion-exchange resin (Agilent, BE-SCX 2 g) with 30 ml of methanol (containing 7N ammonia) as eluent. The filtrate was collected and concentrated. The residue was dissolved in 2,2,2-trifluoroacetic acid (419 mg, 3.67 mmol) in a 20 ml RBF and heated at 80° C. for 1 hour. After removing the volatile, the residue was dissolved in 2 mL of DMSO) and purified by Reverse phase HPLC directly with 0-30% acetonitrile in water as eluent to give the title compound. LC-MS [M+H]⁺ 493.03.

EXAMPLES 21-27 were prepared as described for EXAMPLE 20 starting from commercially available amines and REFERENCE EXAMPLES 3 and 37.

| EX. | RR'NH | STRUCTURE | NAME | LC/MS m/e [M + H]⁺ |
|---|---|---|---|---|
| 21 | (structure with piperidine, OMe, CH₂OH) | (structure) | (R)-N¹-(3-amino-2-hydroxypropyl)-4-(4-(hydroxymethyl)-4-methoxypiperidin-1-yl)-3-(2H-tetrazol-5-yl)benzene-1,2-disulfonamide | 521.4 |

| EX. | RR'NH | STRUCTURE | NAME | LC/MS m/e [M + H]+ |
|---|---|---|---|---|
| 22 | | 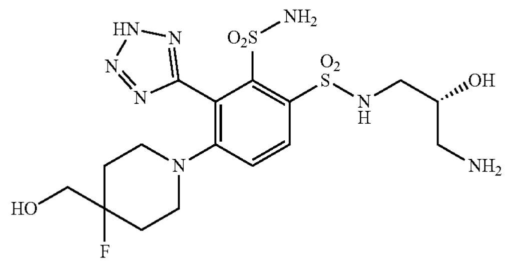 [SMILES: NC[C@@H](O)CNS(=O)(=O)c1ccc(N2CCC(F)(CO)CC2)c(-c2nn[nH]n2)c1S(N)(=O)=O] | (R)-N¹-(3-amino-2-hydroxypropyl)-4-(4-fluoro-4-(hydroxymethyl)piperidin-1-yl)-3-(2H-tetrazol-5-yl)benzene-1,2-disulfonamide | 509.3 |
| 23 | | 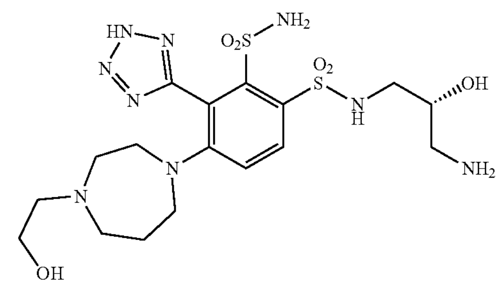 [SMILES: NC[C@@H](O)CNS(=O)(=O)c1ccc(N2CCCN(CCO)CC2)c(-c2nn[nH]n2)c1S(N)(=O)=O] | (R)-N¹-(3-amino-2-hydroxypropyl)-4-(4-(2-hydroxyethyl)-1,4-diazepan-1-yl)-3-(2H-tetrazol-5-yl)benzene-1,2-disulfonamide | 520.5 |
| 24 | | 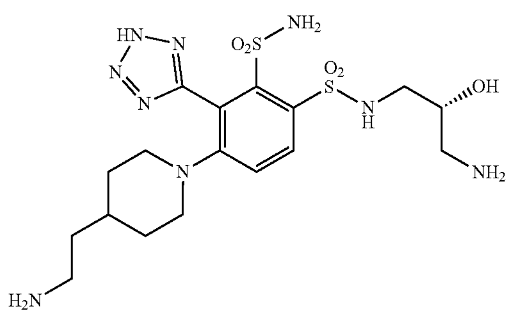 [SMILES: NCCC1CCN(c2ccc(S(=O)(=O)NC[C@H](O)CN)c(S(N)(=O)=O)c2-c2nn[nH]n2)CC1] | (R)-N¹-(3-amino-2-hydroxypropyl)-4-(4-(2-aminoethyl)piperidin-1-yl)-3-(2H-tetrazol-5-yl)benzene-1,2-disulfonamide | 504.4 |
| 25 | | 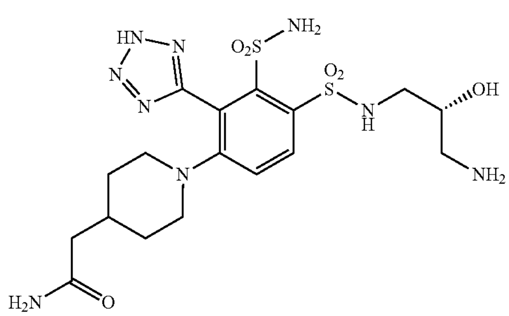 [SMILES: NC[C@@H](O)CNS(=O)(=O)c1ccc(N2CCC(CC(N)=O)CC2)c(-c2nn[nH]n2)c1S(N)(=O)=O] | (R)-2-(1-(4-(N-(3-amino-2-hydroxypropyl)sulfamoyl)-3-sulfamoyl-2-(2H-tetrazol-5-yl)phenyl)piperidin-4-yl)acetamide | 518.3 |
| 26 | | 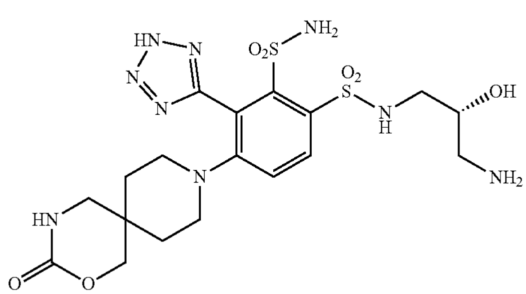 [SMILES: NC[C@@H](O)CNS(=O)(=O)c1ccc(N2CCC3(CC2)CNC(=O)OC3)c(-c2nn[nH]n2)c1S(N)(=O)=O] | (R)-N¹-(3-amino-2-hydroxypropyl)-4-(3-oxo-2-oxa-4,9-diazaspiro[5.5]undecan-9-yl)-3-(2H-tetrazol-5-yl)benzene-1,2-disulfonamide | 506.5 |

| EX. | RR'NH | STRUCTURE | NAME | LC/MS m/e [M + H]+ |
|---|---|---|---|---|
| 27 | ![piperidine-pyrazole] | ![structure] | (R)-4-(4-(2-(1H-pyrazol-1-yl)ethyl)piperidin-1-yl)-N¹-(3-amino-2-hydroxypropyl)-3-(2H-tetrazol-5-yl)benzene-1,2-disulfonamide | 555.6 |

Example 28

(R)-3-(3-aminopiperidin-1-yl)-6-(azetidin-3-ylsulfonyl)-2-(1H-tetrazol-5-yl)benzenesulfonamide

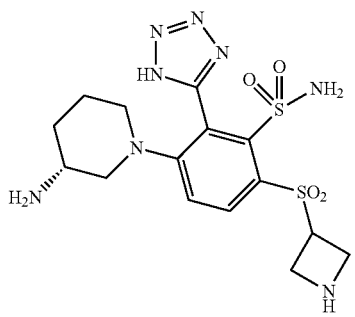 [SMILES: N[C@@H]1CCCN(c2ccc(S(=O)(=O)C3CNC3)c(S(N)(=O)=O)c2-c2nnn[nH]2)C1]

Step A: tert-butyl (R)-3-((2-(N,N-bis(4-methoxybenzyl)sulfamoyl)-4-(3-((tert-butoxycarbonyl)amino)piperidin-1-yl)-3-(1-(4-methoxybenzyl)-1H-tetrazol-5-yl)phenyl)sulfonyl)azetidine-1-carboxylate A solution of REFERENCE EXAMPLE 46 (150 mg, 0.161 mmol) and (R)-tert-butyl piperidin-3-ylcarbamate (161 mg, 0.806 mmol) in DMF (1.5 ml) in a microwave vial was heated at 150° C. for 60 minutes in a microwave reactor. The mixture was then diluted with brine (30 mL) and extracted with ethyl acetate (2×30 mL). The combined organic layers were concentrated. The residue was purified by column chromatography on silica gel, eluting with 0-80% EtOAc/isohexane in 30 min to give the title compound as a solid. LC/MS [M+H]+: 1004.

Step B: (R)-3-(3-aminopiperidin-1-yl)-6-(azetidin-3-ylsulfonyl)-N-(4-methoxybenzyl)-2-(1-(4-methoxybenzyl)-1H-tetrazol-5-yl)benzenesulfonamide TFA (2 ml, 26.0 mmol) and 1,4-dimethoxybenzene (165 mg, 1.196 mmol) were added to a stirred solution of starting material tert-butyl 3-(2-(N,N-bis(4-methoxybenzyl)sulfamoyl)-4-((R)-3-((tert-butoxycarbonyl)amino)piperidin-1-yl)-3-(1-(4-methoxybenzyl)-1H-tetrazol-5-yl)phenyl)sulfonyl)azetidine-1-carboxylate (120 mg, 0.120 mmol) in dichloromethane (2 mL) at RT, and the mixture was stirred at RT for 2 hours. The mixture was concentrated under reduced pressure to provide the title product, which was used without further purification. LC/MS [M+H]+: 683.5.

Step C: (R)-3-(3-aminopiperidin-1-yl)-6-(azetidin-3-ylsulfonyl)-2-(1H-tetrazol-5-yl)benzenesulfonamide TFA (2 ml, 26.0 mmol) was added to 3-((R)-3-aminopiperidin-1-yl)-6-(azetidin-3-ylsulfonyl)-N-(4-methoxybenzyl)-2-(1-(4-methoxybenzyl)-1H-tetrazol-5-yl)benzenesulfonamide (82 mg, 0.120 mmol) at RT, and the mixture was stirred at 80° C. for 2 hours. The reaction mixture was concentrated. The residue was purified by preparative HPLC reverse phase (C18), eluting with 0-20% acetonitrile/water with 0.1% TFA to give EXAMPLE 28 after lyophilization. LC/MS [M+H]+: 443

EXAMPLES 29-33 were prepared as described for EXAMPLE 28, starting from tert-butyl 3-((2-(N,N-bis(4-methoxybenzyl)sulfamoyl)-4-iodo-3-(1-(4-methoxybenzyl)-1H-tetrazol-5-yl)phenyl)sulfonyl)azetidine-1-carboxylate (REFERENCE EXAMPLE 46) and the requisite amine as shown in the table.

| EX. NO | STRUCTURE | NAME | AMINE | LC/MS [M + H]+ |
|---|---|---|---|---|
| 29 | 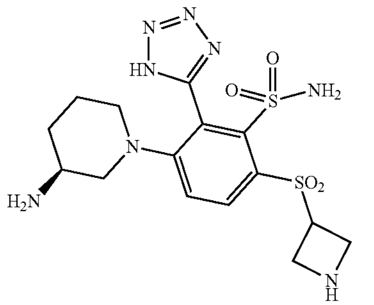 [SMILES: N[C@H]1CCCN(c2ccc(S(=O)(=O)C3CNC3)c(S(N)(=O)=O)c2-c2nnn[nH]2)C1] | (S)-3-(3-aminopiperidin-1-yl)-6-(azetidin-3-ylsulfonyl)-2-(1H-tetrazol-5-yl)benzenesulfonamide | | 443 |
| 30 | 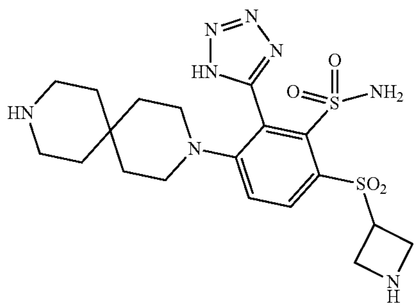 [SMILES: NS(=O)(=O)c1c(S(=O)(=O)C2CNC2)ccc(N2CCC3(CCNCC3)CC2)c1-c1nnn[nH]1] | 6-(azetidin-3-ylsulfonyl)-3-(3,9-diazaspiro[5.5]undecan-3-yl)-2-(1H-tetrazol-5-yl)benzenesulfonamide | | 497 |
| 31 | 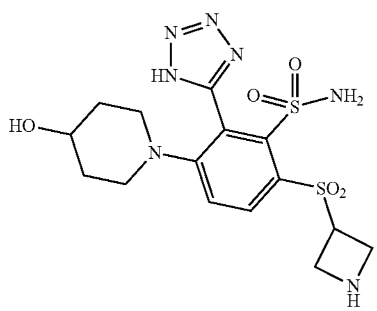 [SMILES: NS(=O)(=O)c1c(S(=O)(=O)C2CNC2)ccc(N2CCC(O)CC2)c1-c1nnn[nH]1] | 6-(azetidin-3-ylsulfonyl)-3-(4-hydroxypiperidin-1-yl)-2-(1H-tetrazol-5-yl)benzenesulfonamide | | 444 |
| 32 | 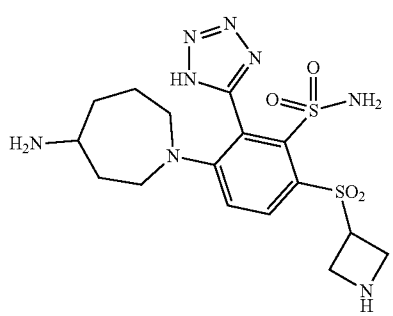 [SMILES: NC1CCCN(c2ccc(S(=O)(=O)C3CNC3)c(S(N)(=O)=O)c2-c2nnn[nH]2)CC1] | 3-(4-aminoazepan-1-yl)-6-(azetidin-3-ylsulfonyl)-2-(1H-tetrazol-5-yl)benzenesulfonamide | | 457 |
| 33 | 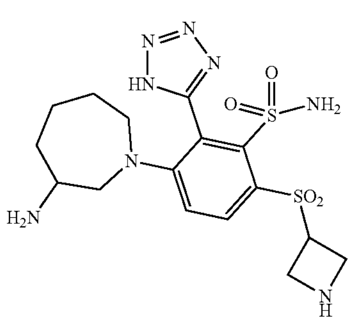 [SMILES: NC1CCCCN(c2ccc(S(=O)(=O)C3CNC3)c(S(N)(=O)=O)c2-c2nnn[nH]2)C1] | 3-(3-aminoazepan-1-yl)-6-(azetidin-3-ylsulfonyl)-2-(1H-tetrazol-5-yl)benzenesulfonamide | | 457 |

Example 34

(R)—N1-(3-amino-2-hydroxypropyl)-4-(4-(aminomethyl)piperidin-1-yl)-3-1H-tetrazol-5-yl)benzene-1,2-disulfonamide

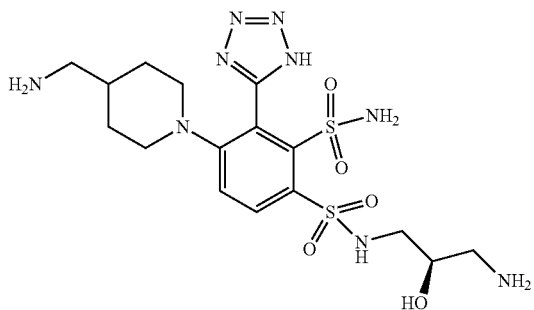 [SMILES: NCC1CCN(c2ccc(S(=O)(=O)NC[C@H](O)CN)c(S(N)(=O)=O)c2-c2nnn[nH]2)CC1]

Step A: tert-butyl ((1-(3-(N,N-bis(4-methoxybenzyl)sulfamoyl)-2-(1-(4-methoxybenzyl)-1H-tetrazol-5-yl)-4-((2-(trimethylsilyl)ethyl)sulfonyl)phenyl)piperidin-4-yl)methyl carbamate Tera-butyl (piperidin-4-ylmethyl)carbamate (890 mg, 4.15 mmol) and DABCO (466 mg, 4.15 mmol) were added to a stirred solution of 3-iodo-N,N-bis(4-methoxybenzyl)-2-(1-(4-methoxybenzyl)-1H-tetrazol-5-yl)-6-((2-(trimethylsilyl)ethyl)sulfonyl)benzenesulfonamide (REFERENCE EXAMPLE 37) (606 mg, 0.692 mmol) in dimethylsulfoxide at RT, and the mixture was stirred at 110° C. overnight. The mixture was washed diluted with water (30 mL), extracted with EtOAc (2×30 mL). The combined organic phases were dried (MgSO$_4$), concentrated. The residue was purified by column chromatography on silica gel, eluting with 0-60% EtOAc/Hexane to give the title compound. LC/MS [M+H]+: 962.

Step B: 2-(N,N-bis(4-methoxybenzyl)sulfamoyl)-4-(4-(((tert-butoxycarbonyl)amino)methyl)piperidin-1-yl)-3-(1-(4-methoxybenzyl)-1H-tetrazol-5-yl)benzenesulfinic acid TBAF (1.429 ml, 1.429 mmol) was added to a stirred solution of tert-butyl ((1-(3-(N,N-bis(4-methoxybenzyl)sulfamoyl)-2-(1-(4-methoxybenzyl)-1H-tetrazol-5-yl)-4-((2-(trimethylsilyl)ethyl)sulfonyl)phenyl)piperidin-4-yl)methyl)carbamate (625 mg, 0.650 mmol) in tetrahydrofuran (6 mL) at RT and the mixture was stirred at RT for 45 minutes. The mixture was diluted with sat'd KHSO$_4$ (50 mL), extracted with ethyl acetate (2×50 mL). The combined organic phases were washed with an aqueous solution of KHSO$_4$ (2×). The organic phases were combined and concentrated to afford the title compound. LC/MS [M+H]+: 862.

Step C: tert-butyl (R)-((1-(3-(N,N-bis(4-methoxybenzyl)sulfamoyl)-4-(N-(3-((tert-butoxycarbonyl)amino)-2-hydroxypropyl)sulfamoyl)-2-(1-(4-methoxybenzyl)-1H-tetrazol-5-yl)phenyl)piperidin-4-yl)methyl)carbamate TEA (0.146 ml, 1.044 mmol) and (S)-tert-butyl (3-amino-2-hydroxypropyl)carbamate (REFERENCE EXAMPLE 3) (132 mg, 0.696 mmol) were added to a stirred solution of 2-(N,N-bis(4-methoxybenzyl)sulfamoyl)-4-(4-(((tert-butoxycarbonyl)amino)methyl)piperidin-1-yl)-3-(1-(4-methoxybenzyl)-1H-tetrazol-5-yl)benzenesulfinic acid (300 mg, 0.348 mmol) in CH$_2$Cl$_2$ at 0° C. NCS (102 mg, 0.766 mmol) was then added, and the mixture was stirred at 0° C. for 30 minutes. The mixture was diluted with water (50 mL), extracted with ethyl acetate (2×50 mL). The combined organic phases were washed with brine, dried (MgSO$_4$) and concentrated under reduced pressure. The residue was purified by column chromatography on silica gel, eluting with 0 to 70% heptane/ethanol to give the title compound. LC/MS [M+H]+: 1050.

Step D: (R)—N1-(3-amino-2-hydroxypropyl)-4-(4-(aminomethyl)piperidin-1-yl)-N2-(4-methoxybenzyl)-3-(1-(4-methoxybenzyl)-1H-tetrazol-5-yl)benzene-1,2-disulfonamide TFA (3 ml, 38.9 mmol) and 1,4-dimethoxybenzene (374 mg, 2.70 mmol) were added to a stirred solution of starting material (284 mg, 0.270 mmol) in dichloromethane (3 mL) at RT, and the mixture was stirred at RT for 1 hour. The mixture was concentrated under reduced pressure. The residue crude product was used without further purification. LC/MS [M+H]+: 930.

Step E: (R)—N1-(3-amino-2-hydroxypropyl)-4-(4-(aminomethyl)piperidin-1-yl)-3-(1H-tetrazol-5-yl)benzene-1,2-disulfonamide TFA (3 nil, 38.9 mmol) and 1,4-dimethoxybenzene (373 mg, 2.70 mmol) were added to a stirred solution of starting material N1-((R)-3-amino-2-hydroxypropyl)-4-(4-(aminomethyl)piperidin-1-yl)-N2-(4-methoxybenzyl)-3-(1-(4-methoxybenzyl)-1H-tetrazol-5-yl)benzene-1,2-disulfonamide (197 mg, 0.270 mmol) in TFA (3 mL) at RT, and the mixture was stirred at 80° C. for 90 minutes. The mixture was diluted with water (20 mL), extracted with ethyl acetate (20 mL). The water phases were concentrated under reduced pressure. The residue was purified by preparative HPLC reverse phase (C18), eluting with 0-30% acetonitrile/water with 0.05% NH$_3$ to give (R)—N1-(3-amino-2-hydroxypropyl)-4-(4-(aminomethyl)piperidin-1-yl)-3-(1H-tetrazol-5-yl)benzene-1,2-disulfonamide.

EXAMPLES 35-52 were prepared in an analogous fashion to that described for EXAMPLE 34 using the requisite amines shown below.

| EX NO | STRUCTURE | NAME | LEFT SIDE AMINE | RIGHT SIDE AMINE | LC/MS [M + H]+ |
|---|---|---|---|---|---|
| 35 | 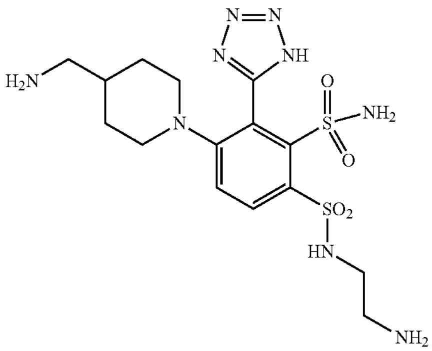 [SMILES: NCCNS(=O)(=O)c1ccc(N2CCC(CN)CC2)c(-c2nnn[nH]2)c1S(N)(=O)=O] | N1-(2-aminoethyl)-4-(4-(aminomethyl)piperidin-1-yl)-3-(1H-tetrazol-5-yl)benzene-1,2-disulfonamide | | | 460 |
| 36 | 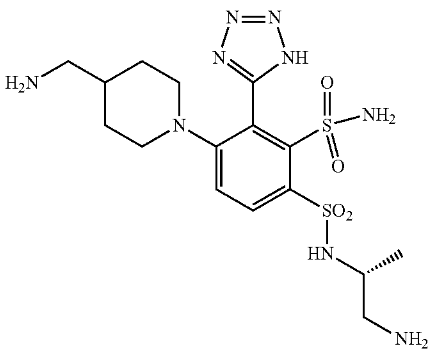 [SMILES: C[C@H](CN)NS(=O)(=O)c1ccc(N2CCC(CN)CC2)c(-c2nnn[nH]2)c1S(N)(=O)=O] | (R)-4-(4-(aminomethyl)piperidin-1-yl)-N1-(1-aminopropan-2-yl)-3-(1H-tetrazol-5-yl)benzene-1,2-disulfonamide | | | 474 |
| 37 | 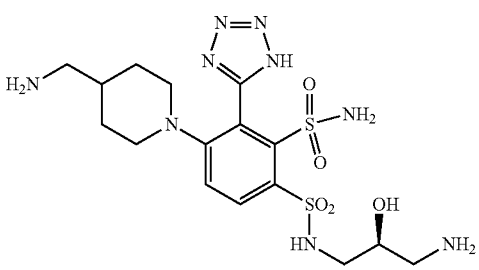 [SMILES: NCC1CCN(c2ccc(S(=O)(=O)NC[C@@H](O)CN)c(S(N)(=O)=O)c2-c2nnn[nH]2)CC1] | (S)-N1-(3-amino-2-hydroxypropyl)-4-(4-(aminomethyl)piperidin-1-yl)-3-(1H-tetrazol-5-yl)benzene-1,2-disulfonamide | | | 490 |
| 38 | 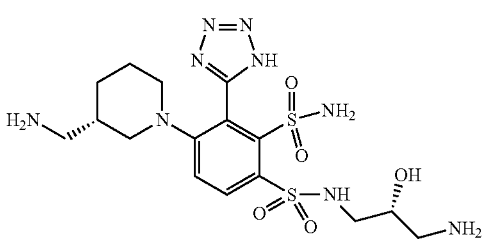 [SMILES: NC[C@@H](O)CNS(=O)(=O)c1ccc(N2CCC[C@@H](CN)C2)c(-c2nnn[nH]2)c1S(N)(=O)=O] | N1-((R)-3-amino-2-hydroxypropyl)-4-((S)-3-(aminomethyl)piperidin-1-yl)-3-(1H-tetrazol-5-yl)benzene-1,2-disulfonamide | | | 490 |
| 39 | 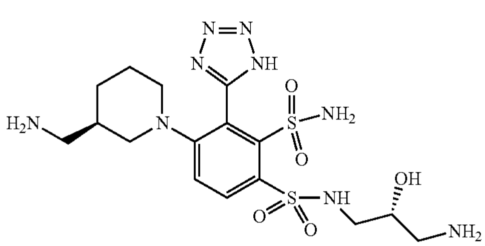 [SMILES: NC[C@@H](O)CNS(=O)(=O)c1ccc(N2CCC[C@H](CN)C2)c(-c2nnn[nH]2)c1S(N)(=O)=O] | N1-((R)-3-amino-2-hydroxypropyl)-4-((R)-3-(aminomethyl)piperidin-1-yl)-3-(1H-tetrazol-5-yl)benzene-1,2-disulfonamide | | | 490 |

-continued

| EX NO | STRUCTURE | NAME | LEFT SIDE AMINE | RIGHT SIDE AMINE | LC/MS [M + H]+ |
|---|---|---|---|---|---|
| 40 | 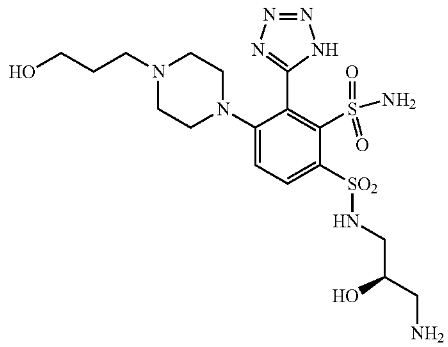 [SMILES: NC[C@@H](O)CNS(=O)(=O)c1ccc(N2CCN(CCCO)CC2)c(-c2nnn[nH]2)c1S(N)(=O)=O] | (R)-N1-(3-amino-2-hydroxypropyl)-4-(4-(3-hydroxypropyl)piperazin-1-yl)-3-(1H-tetrazol-5-yl)benzene-1,2-disulfonamide | | | 520 |
| 41 | 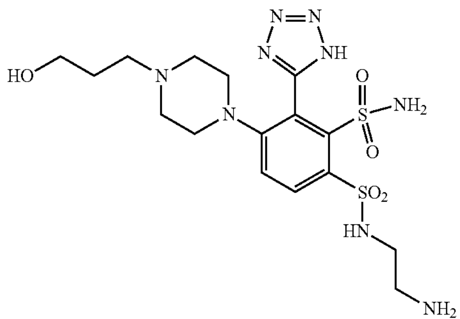 [SMILES: NCCNS(=O)(=O)c1ccc(N2CCN(CCCO)CC2)c(-c2nnn[nH]2)c1S(N)(=O)=O] | N1-(2-aminoethyl)-4-(4-(3-hydroxypropyl)piperazin-1-yl)-3-(1H-tetrazol-5-yl)benzene-1,2-disulfonamide | | | 490 |
| 42 | 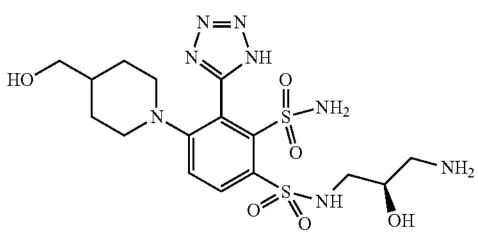 [SMILES: NC[C@@H](O)CNS(=O)(=O)c1ccc(N2CCC(CO)CC2)c(-c2nnn[nH]2)c1S(N)(=O)=O] | (R)-N1-(3-amino-2-hydroxypropyl)-4-(4-(hydroxymethyl)piperidin-1-yl)-3-(1H-tetrazol-5-yl)benzene-1,2-disulfonamide | | | 491 |
| 43 | 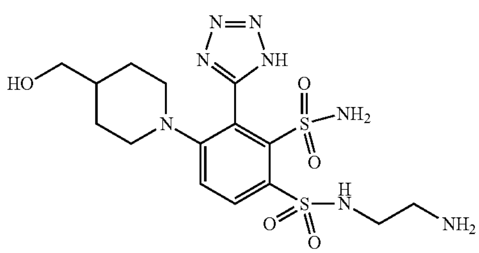 [SMILES: NCCNS(=O)(=O)c1ccc(N2CCC(CO)CC2)c(-c2nnn[nH]2)c1S(N)(=O)=O] | N1-(2-aminoethyl)-4-(4-(hydroxymethyl)piperidin-1-yl)-3-(1H-tetrazol-5-yl)benzene-1,2-disulfonamide | | | 461 |
| 44 | 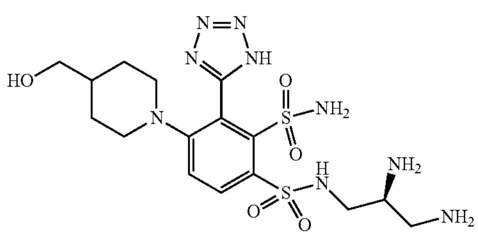 [SMILES: NC[C@H](N)CNS(=O)(=O)c1ccc(N2CCC(CO)CC2)c(-c2nnn[nH]2)c1S(N)(=O)=O] | (S)-N1-(2,3-diaminopropyl)-4-(4-(hydroxymethyl)piperidin-1-yl)-3-(1H-tetrazol-5-yl)benzene-1,2-disulfonamide | | | 490 |

-continued

| EX NO | STRUCTURE | NAME | LEFT SIDE AMINE | RIGHT SIDE AMINE | LC/MS [M + H]+ |
|---|---|---|---|---|---|
| 45 | 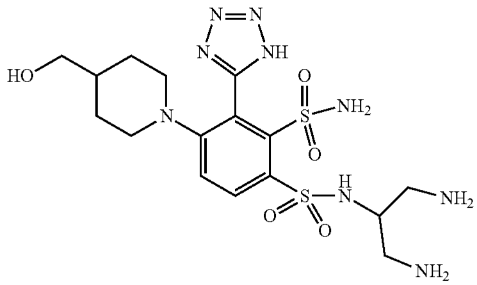 [SMILES: NCC(CN)NS(=O)(=O)c1ccc(N2CCC(CO)CC2)c(-c2nnn[nH]2)c1S(N)(=O)=O] | N1-(1,3-diaminopropan-2-yl)-4-(4-(hydroxymethyl)piperidin-1-yl)-3-(1H-tetrazol-5-yl)benzene-1,2-disulfonamide | | | 490 |
| 46 | 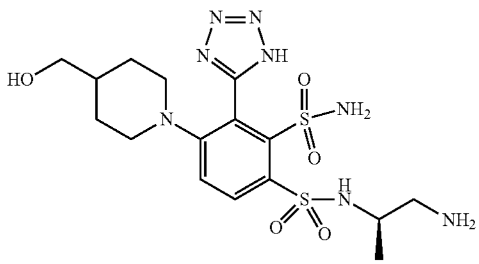 [SMILES: C[C@H](CN)NS(=O)(=O)c1ccc(N2CCC(CO)CC2)c(-c2nnn[nH]2)c1S(N)(=O)=O] | (R)-N1-(1-aminopropan-2-yl)-4-(4-(hydroxymethyl)piperidin-1-yl)-3-(1H-tetrazol-5-yl)benzene-1,2-disulfonamide | | | 475 |
| 47 | 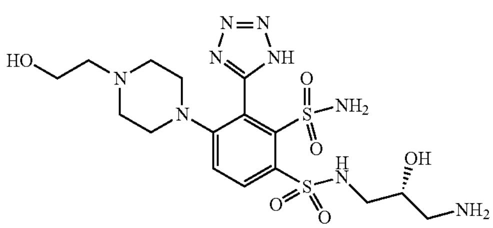 [SMILES: NC[C@@H](O)CNS(=O)(=O)c1ccc(N2CCN(CCO)CC2)c(-c2nnn[nH]2)c1S(N)(=O)=O] | (R)-N1-(3-amino-2-hydroxypropyl)-4-(4-(2-hydroxyethyl)piperazin-1-yl)-3-(1H-tetrazol-5-yl)benzene-1,2-disulfonamide | | | 506 |
| 48 | 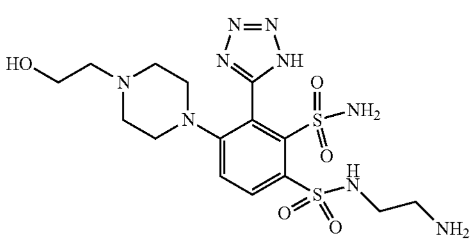 [SMILES: NCCNS(=O)(=O)c1ccc(N2CCN(CCO)CC2)c(-c2nnn[nH]2)c1S(N)(=O)=O] | N1-(2-aminoethyl)-4-(4-(2-hydroxyethyl)piperazin-1-yl)-3-(1H-tetrazol-5-yl)benzene-1,2-disulfonamide | | | 476 |
| 49 | 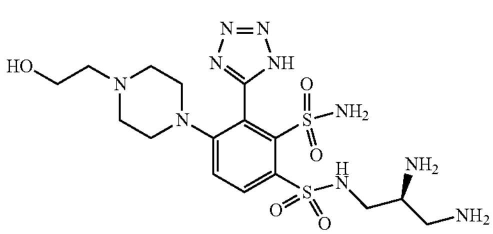 [SMILES: NC[C@H](N)CNS(=O)(=O)c1ccc(N2CCN(CCO)CC2)c(-c2nnn[nH]2)c1S(N)(=O)=O] | (S)-N1-(2,3-diaminopropyl)-4-(4-(2-hydroxyethyl)piperazin-1-yl)-3-(1H-tetrazol-5-yl)benzene-1,2-disulfonamide | | | 505 |

-continued

| EX NO | STRUCTURE | NAME | LEFT SIDE AMINE | RIGHT SIDE AMINE | LC/MS [M + H]+ |
|---|---|---|---|---|---|
| 50 | 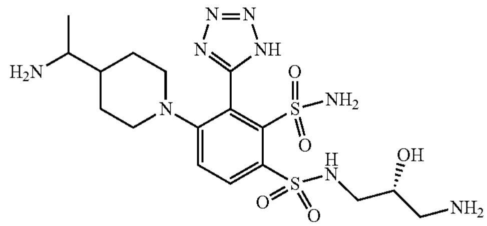 [SMILES: CC(N)C1CCN(c2ccc(S(=O)(=O)NC[C@H](O)CN)c(S(N)(=O)=O)c2-c2nnn[nH]2)CC1] | N1-((R)-3-amino-2-hydroxypropyl)-4-(4-(1-aminoethyl)piperidin-1-yl)-3-(1H-tetrazol-5-yl)benzene-1,2-disulfonamide | | | 504 |
| 51 | 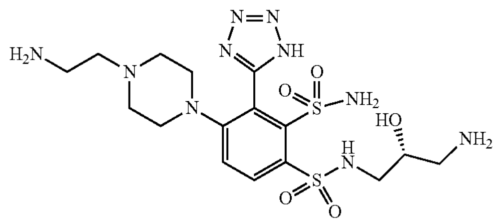 [SMILES: NCCN1CCN(c2ccc(S(=O)(=O)NC[C@H](O)CN)c(S(N)(=O)=O)c2-c2nnn[nH]2)CC1] | (R)-N1-(3-amino-2-hydroxypropyl)-4-(4-(2-aminoethyl)piperazin-1-yl)-3-(1H-tetrazol-5-yl)benzene-1,2-disulfonamide | | | 505 |
| 52 | 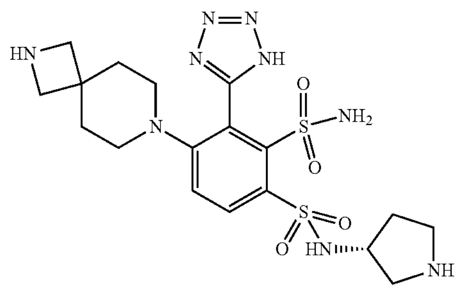 [SMILES: NS(=O)(=O)c1c(S(=O)(=O)N[C@@H]2CCNC2)ccc(N2CCC3(CC2)CNC3)c1-c1nnn[nH]1] | (R)-N1-(pyrrolidin-3-yl)-4-(2,7-diazaspiro[3.5]nonan-7-yl)-3-(1H-tetrazol-5-yl)benzene-1,2-disulfonamide | | | 498 |

Examples 53-62

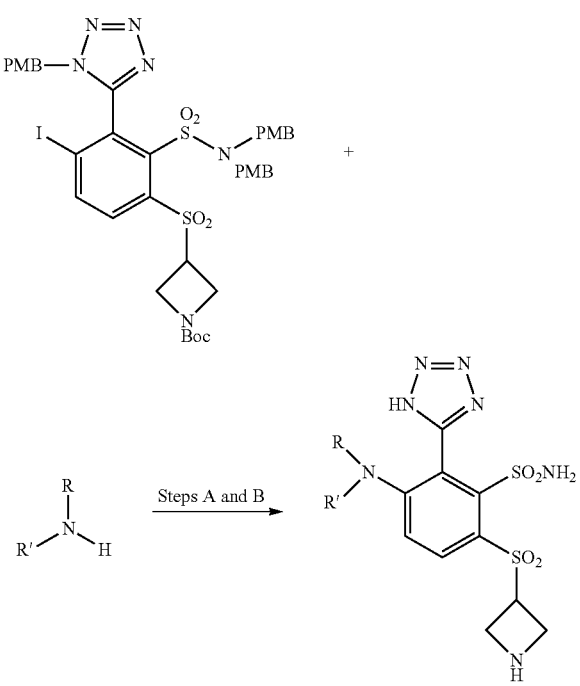

Parallel Synthesis of EXAMPLES 53-62

Step A:

To a set of vials each containing the requisite amine shown in the table below (0.129 mmol) were added 1.0 mL of a solution of tert-butyl 3-((2-(N,N-bis(4-methoxybenzyl)sulfamoyl)-4-iodo-3-(1-(4-methoxybenzyl)-1H-tetrazol-5-yl)phenyl)sulfonyl)azetidine-1-carboxylate from REFERENCE EXAMPLE 46 (40 mg, 0.043 mmol) in 1,4-dioxane and DIEA (0.04 mL, 0.22 mmol). The vials were capped and heated at 80° C. with stirring for 12 hours. The vials were cooled to RT, then the solvent was removed in vacuo.

Step B:

To the residues from Step A were each added DCM 0.4 mL and TFA 0.4 mL followed by anisole (0.3 mL). The vials were shaken at 25° C. for 3 hours. The reaction mixtures were then concentrated under reduced pressure. To each of the intermediates was added 1 mL TFA and the reaction mixtures were agitated at 55° C. for 4 hours. The reaction mixtures were then concentrated. The residues were dissolved in DMSO. Each crude mixture was filtered, then purified by mass triggered reverse phase HPLC using the following conditions: [column: Waters XBridge C18, or Waters Sunfire C18, 5 μm, 19×100 mm; solvent: gradient range 3-28% initial to 45-95% final MeCN (0.1% TFA) in water (0.1% TFA) 50 or 70 mL/min; 8 min run time] to afford EXAMPLES 53-62.

| EX. | RR'NH | STRUCTURE | NAME | LC/MS m/e [M + H]+ |
|---|---|---|---|---|
| 53 | 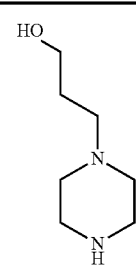 | 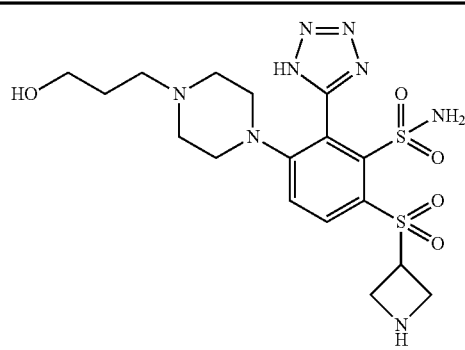 | 6-(azetidin-3-ylsulfonyl)-3-[4-(3-hydroxypropyl)piperazin-1-yl]-2-(1H-tetrazol-5-yl)benzenesulfonamide | 487.1 |
| 54 | 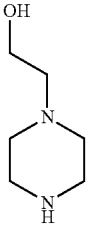 | 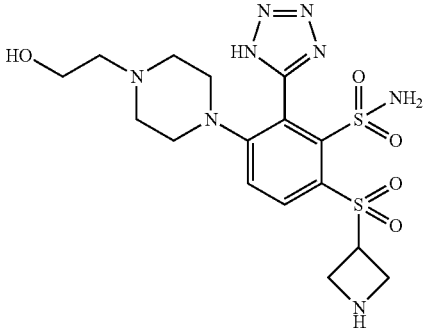 [SMILES: NS(=O)(=O)c1c(S(=O)(=O)C2CNC2)ccc(N2CCN(CCO)CC2)c1-c1nnn[nH]1] | 6-(azetidin-3-ylsulfonyl)-3-[4-(2-hydroxyethyl)piperazin-1-yl]-2-(1H-tetrazol-5-yl)benzenesulfonamide | 473.1 |
| 55 | 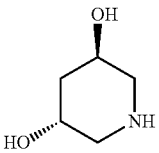 | 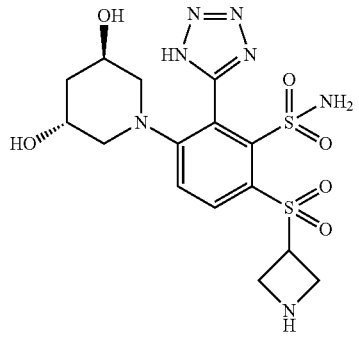 [SMILES: NS(=O)(=O)c1c(S(=O)(=O)C2CNC2)ccc(N2C[C@H](O)C[C@@H](O)C2)c1-c1nnn[nH]1] | 6-(azetidin-3-ylsulfonyl)-3-[(3R,5R)-3,5-dihydroxypiperidin-1-yl]-2-(1H-tetrazol-5-yl)benzenesulfonamide | 460.1 |
| 56 | 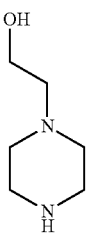 | 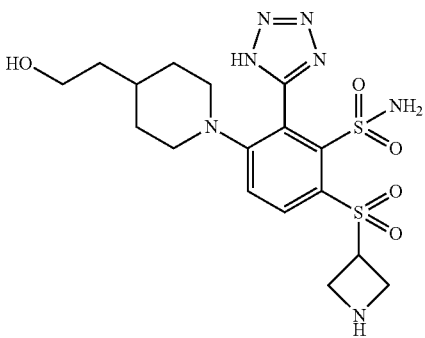 | 6-(azetidin-3-ylsulfonyl)-3-[4-(2-hydroxyethyl)piperidin-1-yl]-2-(1H-tetrazol-5-yl)benzenesulfonamide | 472.1 |

-continued

| EX. | RR'NH | STRUCTURE | NAME | LC/MS m/e [M + H]+ |
|---|---|---|---|---|
| 57 | 3-(hydroxymethyl)piperidine | 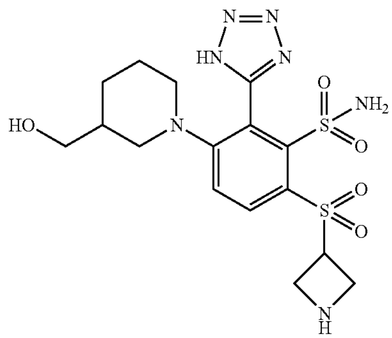 [SMILES: NS(=O)(=O)c1c(S(=O)(=O)C2CNC2)ccc(N2CCCC(CO)C2)c1-c1nnn[nH]1] | 6-(azetidin-3-ylsulfonyl)-3-[3-(hydroxymethyl)piperidin-1-yl]-2-(1H-tetrazol-5-yl)benzenesulfonamide | 458.1 |
| 58 | 4-(hydroxymethyl)piperidine | 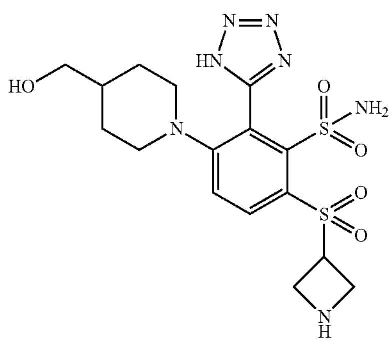 [SMILES: NS(=O)(=O)c1c(S(=O)(=O)C2CNC2)ccc(N2CCC(CO)CC2)c1-c1nnn[nH]1] | 6-(azetidin-3-ylsulfonyl)-3-[4-(hydroxymethyl)piperidin-1-yl]-2-(1H-tetrazol-5-yl)benzenesulfonamide | 458.1 |
| 59 | 3-hydroxy-3-methylpiperidine | 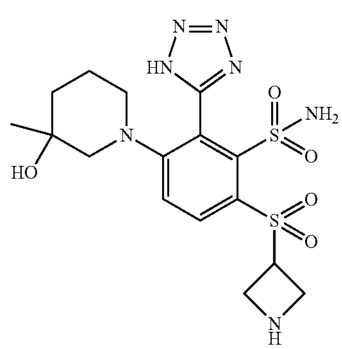 [SMILES: CC1(O)CCCN(c2ccc(S(=O)(=O)C3CNC3)c(S(N)(=O)=O)c2-c2nnn[nH]2)C1] | 6-(azetidin-3-ylsulfonyl)-3-(3-hydroxy-3-methylpiperidin-1-yl)-2-(1H-tetrazol-5-yl)benzenesulfonamide | 458.1 |
| 60 | (3S)-3-hydroxypiperidine | 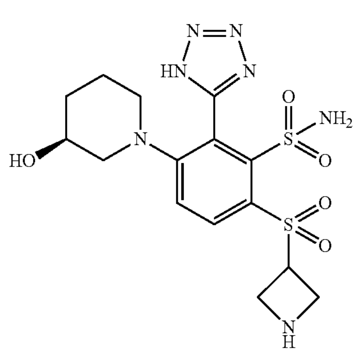 [SMILES: NS(=O)(=O)c1c(S(=O)(=O)C2CNC2)ccc(N2CCC[C@H](O)C2)c1-c1nnn[nH]1] | 6-(azetidin-3-ylsulfonyl)-3-[(3S)-3-hydroxypiperidin-1-yl]-2-(1H-tetrazol-5-yl)benzenesulfonamide | 444.1 |

-continued

| EX. | RR'NH | STRUCTURE | NAME | LC/MS m/e [M + H]+ |
|---|---|---|---|---|
| 61 | 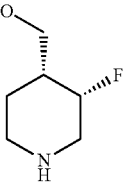 | 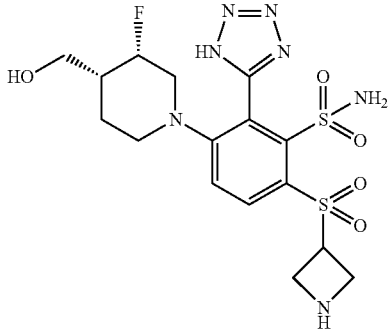 [SMILES: NS(=O)(=O)c1c(S(=O)(=O)C2CNC2)ccc(N2CC[C@H](CO)[C@H](F)C2)c1-c1nnn[nH]1] | 6-(azetidin-3-ylsulfonyl)-3-[(3S,4R)-3-fluoro-4-(hydroxymethyl)piperidin-1-yl]-2-(1H-tetrazol-5-yl)benzenesulfonamide | 476.1 |
| 62 | 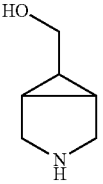 | 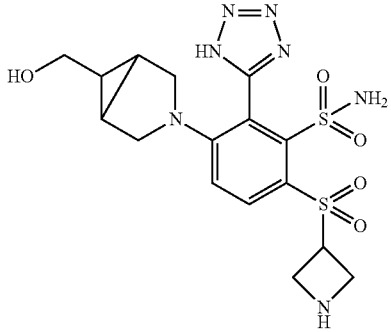 [SMILES: NS(=O)(=O)c1c(S(=O)(=O)C2CNC2)ccc(N2CC3C(CO)C3C2)c1-c1nnn[nH]1] | 6-(azetidin-3-ylsulfonyl)-3-[6-(hydroxymethyl)-3-azabicyclo[3.1.0]hex-3-yl]-2-(1H-tetrazol-5-yl)benzenesulfonamide | 456.1 |

Examples 63-93

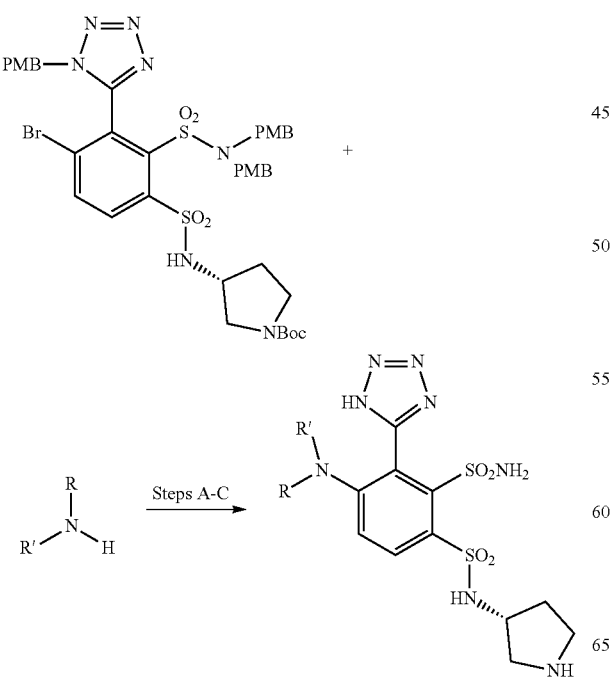

EXAMPLES 63-93 were prepared in parallel using the method described to prepare EXAMPLES 53-62 using tea-butyl (R)-3-((2-(N,N-bis(4-methoxybenzyl)sulfamoyl)-4-bromo-3-(1-(4-methoxybenzyl)-2H-tetrazol-5-yl)phenyl)sulfonamido)pyrrolidine-1-carboxylate (REFERENCE EXAMPLE 61) The crude products were purified by mass triggered reverse phase HPLC using the following conditions: [column: Waters XBridge C18, or Waters Sunfire C18, 5 μm, 19×100 mm; solvent: gradient range 3-28% initial to 45-95% final MeCN (0.1% TFA) in water (0.1% TFA) 50 or 70 mL/min; 8 min run time] or [C18 gradient 8-20% MeCN (0.1% NH₄OH) in water (0.1% NH₄OH)] to afford EXAMPLES 63-93.

| EX. NO. | RR'NH | STRUCTURE | NAME | LC/MS m/e [M + H]+ |
|---|---|---|---|---|
| 63 | (4-hydroxypiperidine) | 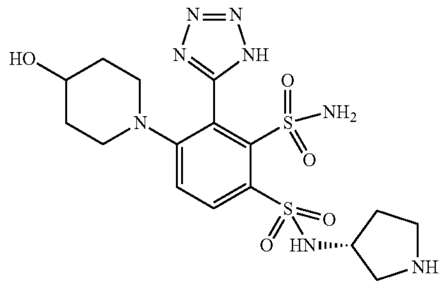 [SMILES: NS(=O)(=O)c1c(S(=O)(=O)N[C@@H]2CCNC2)ccc(N2CCC(O)CC2)c1-c1nnn[nH]1] | 4-(4-hydroxypiperidin-1-yl)-N1-[(3R)-pyrrolidin-3-yl]-3-(1H-tetrazol-5-yl)benzene-1,2-disulfonamide | 473.1 |
| 64 | (2-morpholinoethylamine) | 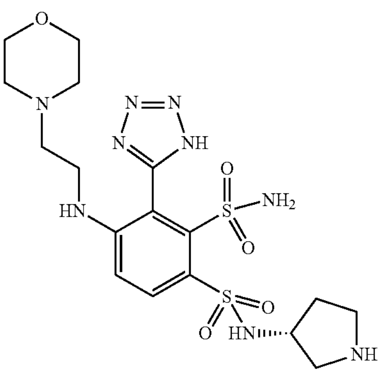 [SMILES: NS(=O)(=O)c1c(S(=O)(=O)N[C@@H]2CCNC2)ccc(NCCN2CCOCC2)c1-c1nnn[nH]1] | 4-[(2-morpholin-4-ylethyl)amino]-N1-[(3R)-pyrrolidin-3-yl]-3-(1H-tetrazol-5-yl)benzene-1,2-disulfonamide | 502.2 |
| 65 | (1-methyl-2-oxopiperazine) | 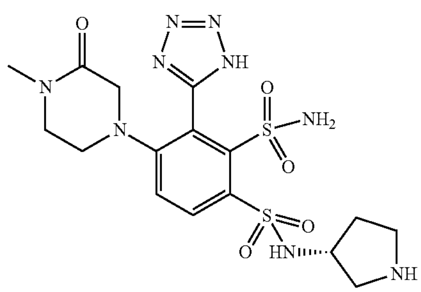 [SMILES: CN1CCN(c2ccc(S(=O)(=O)N[C@@H]3CCNC3)c(S(N)(=O)=O)c2-c2nnn[nH]2)CC1=O] | 4-(4-methyl-3-oxopiperazin-1-yl)-N1-[(3R)-pyrrolidin-3-yl]-3-(1H-tetrazol-5-yl)benzene-1,2-disulfonamide | 486.1 |
| 66 | (4-aminotetrahydropyran) | 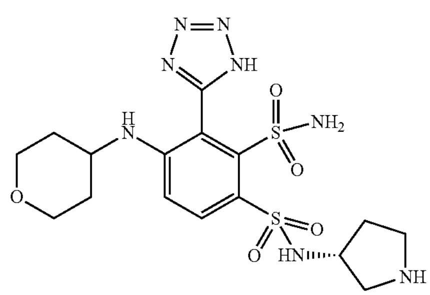 [SMILES: NS(=O)(=O)c1c(S(=O)(=O)N[C@@H]2CCNC2)ccc(NC2CCOCC2)c1-c1nnn[nH]1] | N1-[(3R)-pyrrolidin-3-yl]-4-(tetrahydro-2H-pyran-4-ylamino)-3-(1H-tetrazol-5-yl)benzene-1,2-disulfonamide | 473.1 |
| 67 | (3S)-3-(dimethylamino)pyrrolidine | 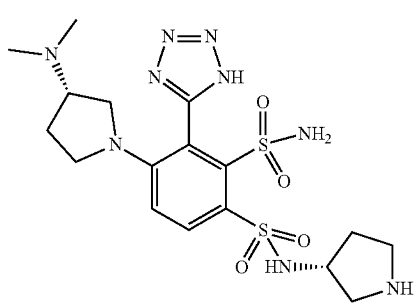 [SMILES: CN(C)[C@H]1CCN(c2ccc(S(=O)(=O)N[C@@H]3CCNC3)c(S(N)(=O)=O)c2-c2nnn[nH]2)C1] | 4-[(3S)-3-(dimethylamino)pyrrolidin-1-yl]-N1-[(3R)-pyrrolidin-3-yl]-3-(1H-tetrazol-5-yl)benzene-1,2-disulfonamide | 486.2 |

-continued

| EX. NO. | RR'NH | STRUCTURE | NAME | LC/MS m/e [M + H]+ |
|---|---|---|---|---|
| 68 | | 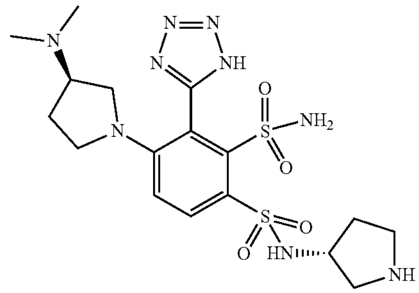 [SMILES: CN(C)[C@@H]1CCN(c2ccc(S(=O)(=O)N[C@@H]3CCNC3)c(S(N)(=O)=O)c2-c2nnn[nH]2)C1] | 4-[(3R)-3-(dimethylamino)pyrrolidin-1-yl]-N1-[(3R)-pyrrolidin-3-yl]-3-(1H-tetrazol-5-yl)benzene-1,2-disulfonamide | 486.2 |
| 69 | | 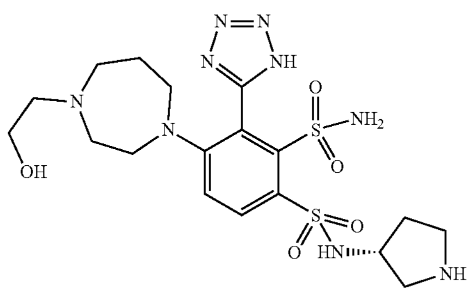 [SMILES: NS(=O)(=O)c1c(S(=O)(=O)N[C@@H]2CCNC2)ccc(N2CCCN(CCO)CC2)c1-c1nnn[nH]1] | 4-[4-(2-hydroxyethyl)-1,4-diazepan-1-yl]-N1-[(3R)-pyrrolidin-3-yl]-3-(1H-tetrazol-5-yl)benzene-1,2-disulfonamide | 516.2 |
| 70 | | 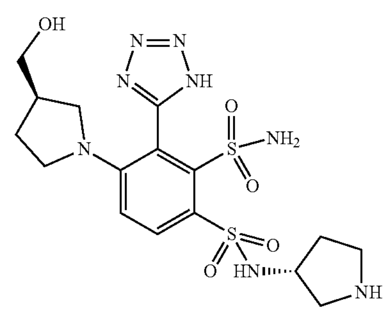 [SMILES: NS(=O)(=O)c1c(S(=O)(=O)N[C@@H]2CCNC2)ccc(N2CC[C@@H](CO)C2)c1-c1nnn[nH]1] | 4-[(3R)-3-(hydroxymethyl)pyrrolidin-1-yl]-N1-[(3R)-pyrrolidin-3-yl]-3-(1H-tetrazol-5-yl)benzene-1,2-disulfonamide | 473.1 |
| 71 | | 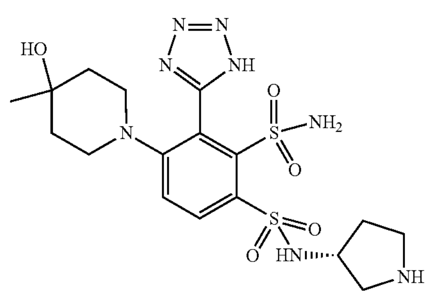 [SMILES: CC1(O)CCN(c2ccc(S(=O)(=O)N[C@@H]3CCNC3)c(S(N)(=O)=O)c2-c2nnn[nH]2)CC1] | 4-(4-hydroxy-4-methylpiperidin-1-yl)-N1-[(3R)-pyrrolidin-3-yl]-3-(1H-tetrazol-5-yl)benzene-1,2-disulfonamide | 487.2 |
| 72 | | 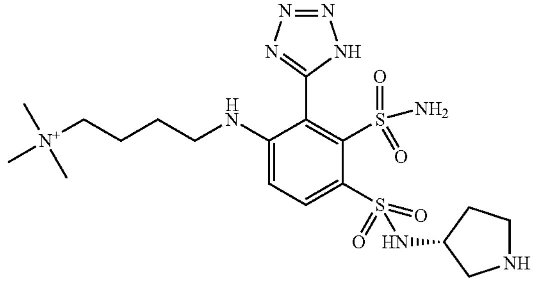 [SMILES: C[N+](C)(C)CCCCNc1ccc(S(=O)(=O)N[C@@H]2CCNC2)c(S(N)(=O)=O)c1-c1nnn[nH]1] | N,N,N-trimethyl-4-({4-[(3R)-pyrrolidin-3-ylsulfamoyl]-3-sulfamoyl-2-(1H-tetrazol-5-yl)phenyl}amino)butan-1-aminium | 503.2 |

| EX. NO. | RR'NH | STRUCTURE | NAME | LC/MS m/e [M + H]+ |
|---|---|---|---|---|
| 73 | 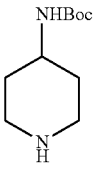 | 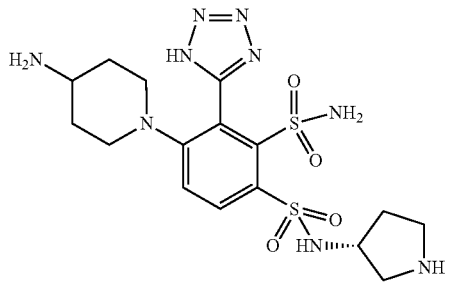 [SMILES: NC1CCN(c2ccc(S(=O)(=O)N[C@@H]3CCNC3)c(S(N)(=O)=O)c2-c2nnn[nH]2)CC1] | 4-(4-aminopiperidin-1-yl)-N1-[(3R)-pyrrolidin-3-yl]-3-(1H-tetrazol-5-yl)benzene-1,2-disulfonamide | 472.2 |
| 74 | 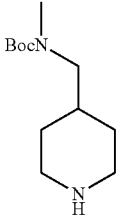 | 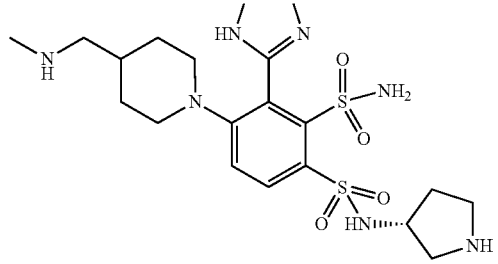 | 4-{4-[(methylamino)methyl]piperidin-1-yl}-N1-[(3R)-pyrrolidin-3-yl]-3-(1H-tetrazol-5-yl)benzene-1,2-disulfonamide | 500.2 |
| 75 | 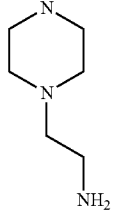 | 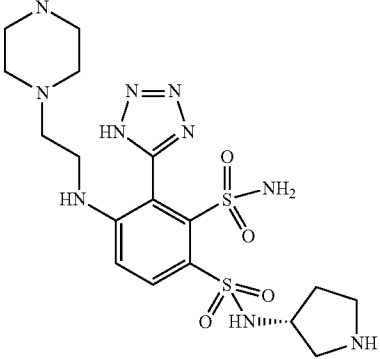 | 4-[(2-piperazin-1-ylethyl)amino]-N1-[(3R)-pyrrolidin-3-yl]-3-(1H-tetrazol-5-yl)benzene-1,2-disulfonamide | 501.2 |
| 76 | 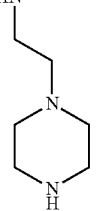 | 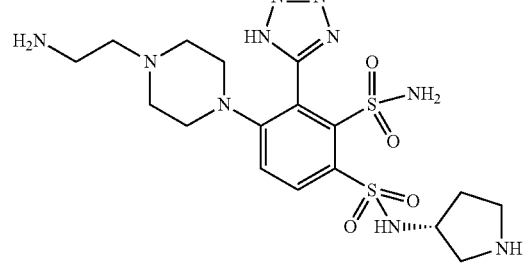 | 4-[4-(2-aminoethyl)piperazin-1-yl]-N1-[(3R)-pyrrolidin-3-yl]-3-(1H-tetrazol-5-yl)benzene-1,2-disulfonamide | 501.2 |
| 77 | 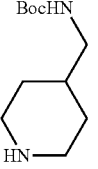 | 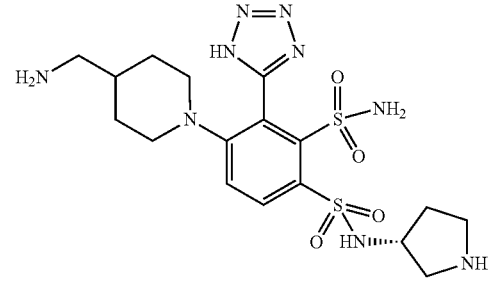 [SMILES: NCC1CCN(c2ccc(S(=O)(=O)N[C@@H]3CCNC3)c(S(N)(=O)=O)c2-c2nnn[nH]2)CC1] | 4-[4-(aminomethyl)piperidin-1-yl]-N1-[(3R)-pyrrolidin-3-yl]-3-(1H-tetrazol-5-yl)benzene-1,2-disulfonamide | 486.2 |

-continued

| EX. NO. | RR'NH | STRUCTURE | NAME | LC/MS m/e [M + H]+ |
|---|---|---|---|---|
| 78 | | 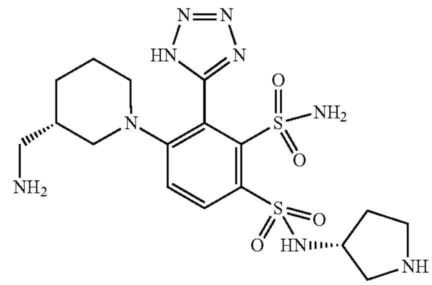 [SMILES: NC[C@@H]1CCCN(c2ccc(S(=O)(=O)N[C@@H]3CCNC3)c(S(N)(=O)=O)c2-c2nnn[nH]2)C1] | 4-[(3S)-3-(aminomethyl)piperidin-1-yl]-N1-[(3R)-pyrrolidin-3-yl]-3-(1H-tetrazol-5-yl)benzene-1,2-disulfonamide | 486.2 |
| 79 | | 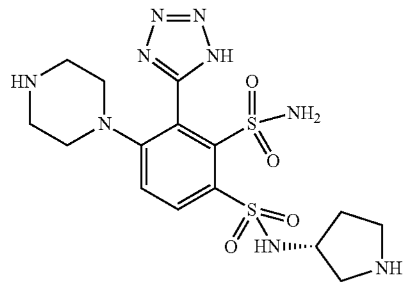 [SMILES: NS(=O)(=O)c1c(S(=O)(=O)N[C@@H]2CCNC2)ccc(N2CCNCC2)c1-c1nnn[nH]1] | 4-piperazin-1-yl-N1-[(3R)-pyrrolidin-3-yl]-3-(1H-tetrazol-5-yl)benzene-1,2-disulfonamide | 458.1 |
| 80 | | 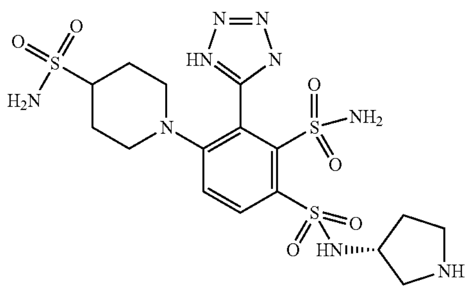 [SMILES: NS(=O)(=O)c1c(S(=O)(=O)N[C@@H]2CCNC2)ccc(N2CCC(S(N)(=O)=O)CC2)c1-c1nnn[nH]1] | N1-[(3R)-pyrrolidin-3-yl]-4-(4-sulfamoylpiperidin-1-yl)-3-(1H-tetrazol-5-yl)benzene-1,2-disulfonamide | 536.1 |
| 81 | | 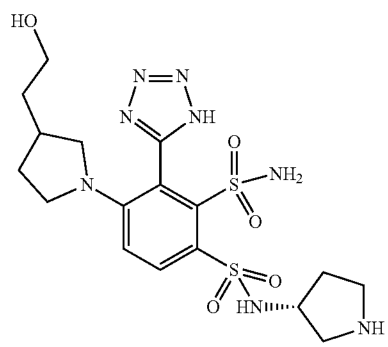 [SMILES: NS(=O)(=O)c1c(S(=O)(=O)N[C@@H]2CCNC2)ccc(N2CCC(CCO)C2)c1-c1nnn[nH]1] | 4-[3-(2-hydroxyethyl)pyrrolidin-1-yl]-N1-[(3R)-pyrrolidin-3-yl]-3-(1H-tetrazol-5-yl)benzene-1,2-disulfonamide | 487.2 |
| 82 | | 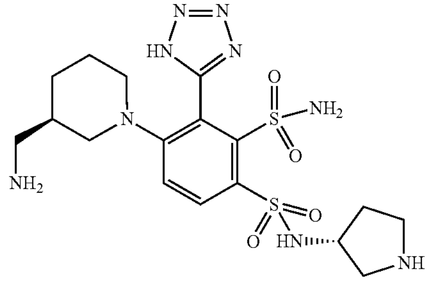 [SMILES: NC[C@H]1CCCN(c2ccc(S(=O)(=O)N[C@@H]3CCNC3)c(S(N)(=O)=O)c2-c2nnn[nH]2)C1] | 4-[(3R)-3-(aminomethyl)piperidin-1-yl]-N1-[(3R)-pyrrolidin-3-yl]-3-(1H-tetrazol-5-yl)benzene-1,2-disulfonamide | 486.2 |

| EX. NO. | RR'NH | STRUCTURE | NAME | LC/MS m/e [M + H]+ |
|---|---|---|---|---|
| 83 | | 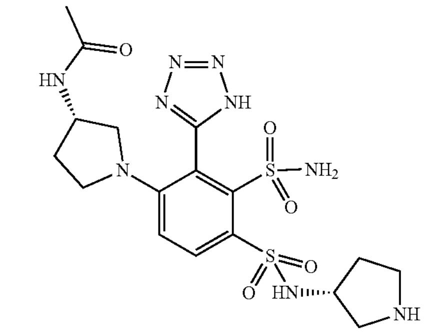 [SMILES: CC(=O)N[C@H]1CCN(c2ccc(S(=O)(=O)N[C@@H]3CCNC3)c(S(N)(=O)=O)c2-c2nnn[nH]2)C1] | N-[(3S)-1-{4-[(3R)-pyrrolidin-3-ylsulfamoyl]-3-sulfamoyl-2-(1H-tetrazol-5-yl)phenyl}pyrrolidin-3-yl]acetamide | 500.1 |
| 84 | | 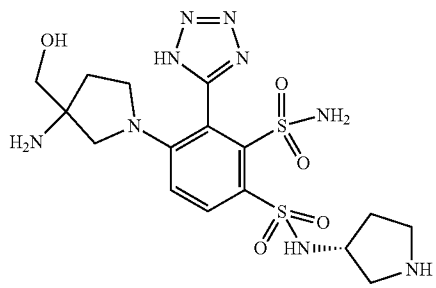 [SMILES: NC1(CO)CCN(c2ccc(S(=O)(=O)N[C@@H]3CCNC3)c(S(N)(=O)=O)c2-c2nnn[nH]2)C1] | 4-[3-amino-3-(hydroxymethyl)pyrrolidin-1-yl]-N1-[(3R)-pyrrolidin-3-yl]-3-(1H-tetrazol-5-yl)benzene-1,2-disulfonamide | 488.1 |
| 85 | | 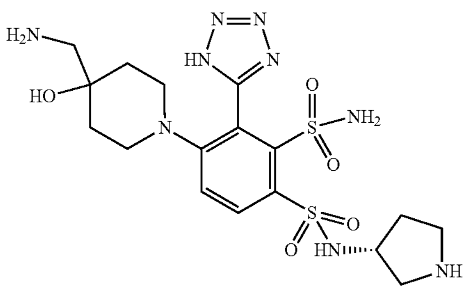 [SMILES: NCC1(O)CCN(c2ccc(S(=O)(=O)N[C@@H]3CCNC3)c(S(N)(=O)=O)c2-c2nnn[nH]2)CC1] | 4-[4-(aminomethyl)-4-hydroxypiperidin-1-yl]-N1-[(3R)-pyrrolidin-3-yl]-3-(1H-tetrazol-5-yl)benzene-1,2-disulfonamide | 502.2 |
| 86 | | 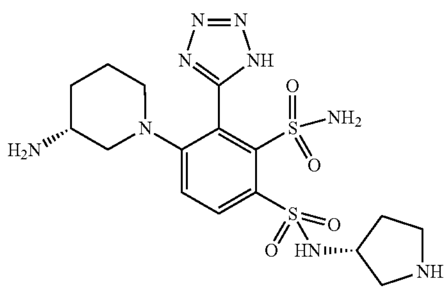 [SMILES: N[C@@H]1CCCN(c2ccc(S(=O)(=O)N[C@@H]3CCNC3)c(S(N)(=O)=O)c2-c2nnn[nH]2)C1] | 4-[(3R)-3-aminopiperidin-1-yl]-N1-[(3R)-pyrrolidin-3-yl]-3-(1H-tetrazol-5-yl)benzene-1,2-disulfonamide | 472.2 |
| 87 | | 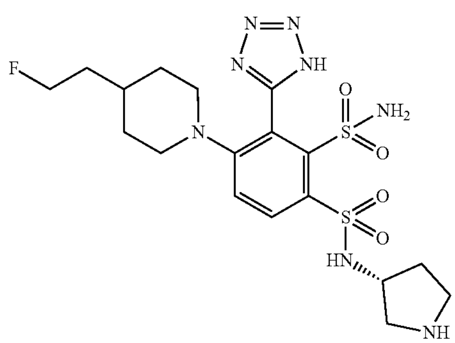 [SMILES: NS(=O)(=O)c1c(S(=O)(=O)N[C@@H]2CCNC2)ccc(N2CCC(CCF)CC2)c1-c1nnn[nH]1] | 4-[4-(2-fluoroethyl)piperidin-1-yl]-N1-[(3R)-pyrrolidin-3-yl]-3-(1H-tetrazol-5-yl)benzene-1,2-disulfonamide | 503.2 |

-continued

| EX. NO. | RR'NH | STRUCTURE | NAME | LC/MS m/e [M + H]+ |
|---|---|---|---|---|
| 88 | 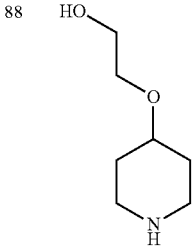 | 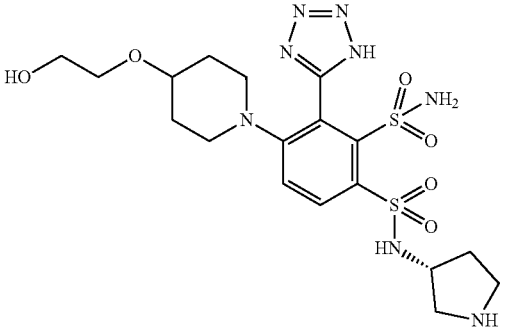 [SMILES: NS(=O)(=O)c1c(S(=O)(=O)N[C@@H]2CCNC2)ccc(N2CCC(OCCO)CC2)c1-c1nnn[nH]1] | 4-[4-(2-hydroxyethoxy)piperidin-1-yl]-N1-[(3R)-pyrrolidin-3-yl]-3-(1H-tetrazol-5-yl)benzene-1,2-disulfonamide | 517.2 |
| 89 | 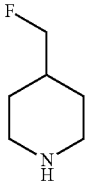 | 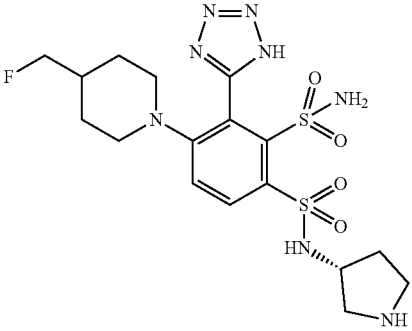 [SMILES: NS(=O)(=O)c1c(S(=O)(=O)N[C@@H]2CCNC2)ccc(N2CCC(CF)CC2)c1-c1nnn[nH]1] | 4-[4-(fluoromethyl)piperidin-1-yl]-N1-[(3R)-pyrrolidin-3-yl]-3-(1H-tetrazol-5-yl)benzene-1,2-disulfonamide | 489.2 |
| 90 | 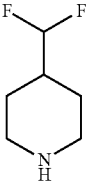 | 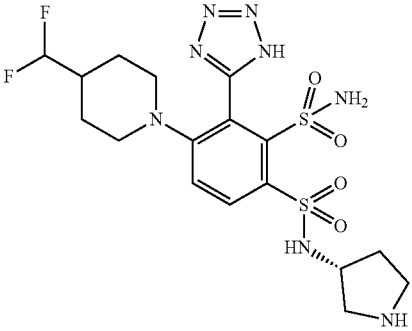 [SMILES: NS(=O)(=O)c1c(S(=O)(=O)N[C@@H]2CCNC2)ccc(N2CCC(C(F)F)CC2)c1-c1nnn[nH]1] | 4-[4-(difluoromethyl)piperidin-1-yl]-N1-[(3R)-pyrrolidin-3-yl]-3-(1H-tetrazol-5-yl)benzene-1,2-disulfonamide | 507.1 |
| 91 | 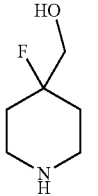 | 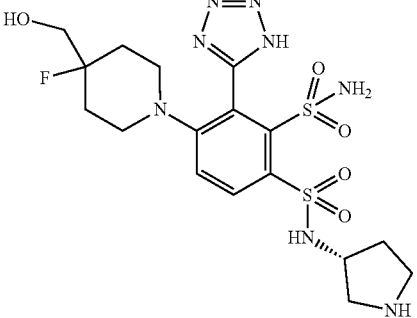 | 4-[4-fluoro-4-(hydroxymethyl)piperidin-1-yl]-N1-[(3R)-pyrrolidin-3-yl]-3-(1H-tetrazol-5-yl)benzene-1,2-disulfonamide | 505.1 |

| EX. NO. | RR'NH | STRUCTURE | NAME | LC/MS m/e [M + H]+ |
|---|---|---|---|---|
| 92 | H₂N-C(=O)-pyrrolidine | (structure shown) | 1-{4-[(3R)-pyrrolidin-3-ylsulfamoyl]-3-sulfamoyl-2-(1H-tetrazol-5-yl)phenyl}pyrrolidine-3-carboxamide | 486.1 |
| 93 | HO-(CH₂)₃-piperazine | (structure shown) | 4-[4-(3-hydroxypropyl)piperazin-1-yl]-N1-[(3R)-pyrrolidin-3-yl]-3-(1H-tetrazol-5-yl)benzene-1,2-disulfonamide | 516.2 |

Examples 94-101

Parallel Preparation of Examples 94-101

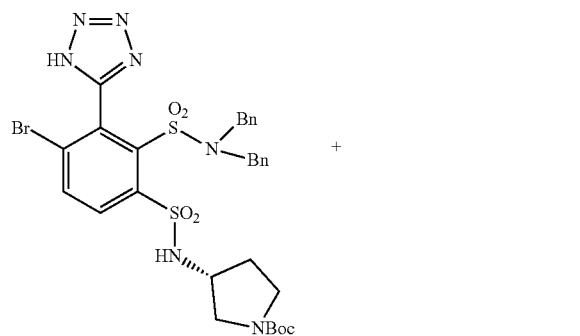

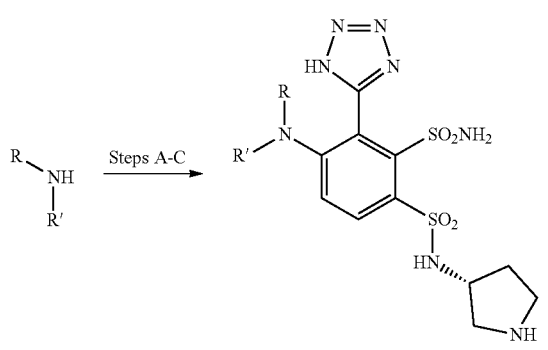

Step A:

To a set of one dram vials each containing the requisite amines (0.143 mmol) were added 1.0 mL of a solution of tert-butyl (R)-3-((4-bromo-2-(N,N-dibenzylsulfamoyl)-3-(1H-tetrazol-5-yl)phenyl)sulfonamido)pyrrolidine-1-carboxylate from REFERENCE EXAMPLE 50 (35 mg, 0.048 mmol) in DMSO and 1,4-diazabicyclo[2,2,2]octane (16 mg, 0.143 mmol). The vials were capped and heated at 100° C. with stirring for 12 hours. The vials were cooled to then the solvent was removed in vacuo.

Step B:

The residues from Step A were each added DCM 0.4 mL, TFA 0.4 mL alone with thioanilsole (0.3 mL). The vials were shaken at 25° C. for 3 hours. The solvent was removed under reduced pressure.

Step C:

In 2 dram vials containing the intermediates from the last step was added 0.2 mL sulfuric acid, and the mixtures were agitated at 25° C. for 2 hours. To each reaction mixture, 1 mL of prechilled 7N NH₃/MeOH solution was slowly added. The mixtures were filtered and washed with 2 mL MeOH. The solvent was removed in vacuo The residues were dissolved in DMSO. Each crude mixture was filtered and the crude products were purified by mass triggered reverse phase HPLC using the following conditions: [column: Waters XBridge C18, or Waters Sunfire C18, 19×100 mm; solvent: gradient range 3-28% initial to 45-95% final MeCN (0.1% TFA) in water (0.1% TFA) 50 or 70 ml/min: 8 min run time] to afford Examples 94-101.

| EX. NO. | RR'NH | STRUCTURE | NAME | LC/MS m/e [M + H]+ |
|---|---|---|---|---|
| 94 | | 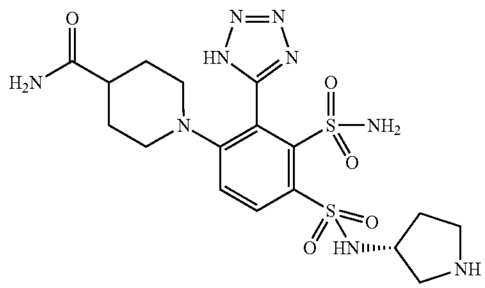 [SMILES: NC(=O)C1CCN(c2ccc(S(=O)(=O)N[C@@H]3CCNC3)c(S(N)(=O)=O)c2-c2nnn[nH]2)CC1] | 1-{4-[(3R)-pyrrolidin-3-ylsulfamoyl]-3-sulfamoyl-2-(1H-tetrazol-5-yl)phenyl}piperidine-4-carboxamide | 500.1 |
| 95 | | 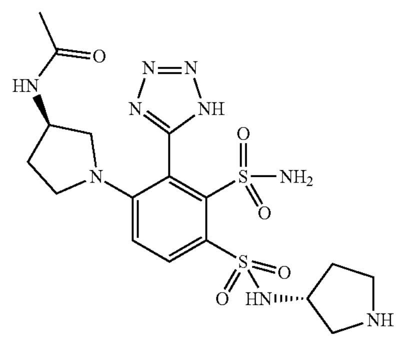 [SMILES: CC(=O)N[C@@H]1CCN(c2ccc(S(=O)(=O)N[C@@H]3CCNC3)c(S(N)(=O)=O)c2-c2nnn[nH]2)C1] | N-[(3R)-1-{4-[(3R)-pyrrolidin-3-ylsulfamoyl]-3-sulfamoyl-2-(1H-tetrazol-5-yl)phenyl}pyrrolidin-3-yl]acetamide | 500.1 |
| 96 | | 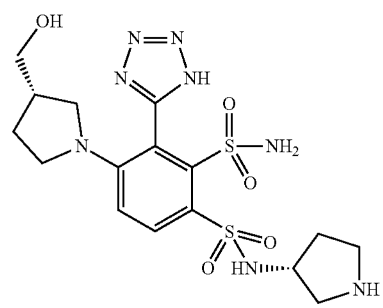 [SMILES: NS(=O)(=O)c1c(S(=O)(=O)N[C@@H]2CCNC2)ccc(N2CC[C@H](CO)C2)c1-c1nnn[nH]1] | 4-[(3S)-3-(hydroxymethyl)pyrrolidin-1-yl]-N1-[(3R)-pyrrolidin-3-yl]-3-(1H-tetrazol-5-yl)benzene-1,2-disulfonamide | 473.1 |
| 97 | | 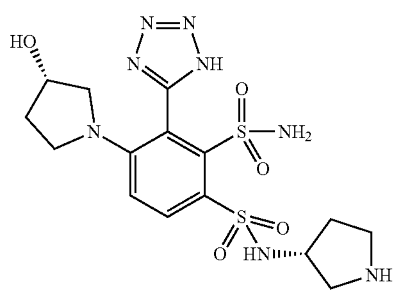 [SMILES: NS(=O)(=O)c1c(S(=O)(=O)N[C@@H]2CCNC2)ccc(N2CC[C@H](O)C2)c1-c1nnn[nH]1] | 4-[(3S)-3-hydroxypyrrolidin-1-yl]-N1-[(3R)-pyrrolidin-3-yl]-3-(1H-tetrazol-5-yl)benzene-1,2-disulfonamide | 459.1 |
| 98 | | 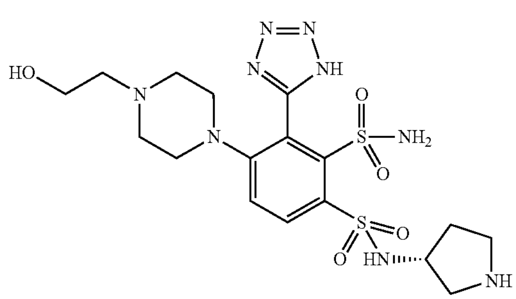 [SMILES: NS(=O)(=O)c1c(S(=O)(=O)N[C@@H]2CCNC2)ccc(N2CCN(CCO)CC2)c1-c1nnn[nH]1] | 4-[4-(2-hydroxyethyl)piperidin-1-yl]-N1-[(3R)-pyrrolidin-3-yl]-3-(1H-tetrazol-5-yl)benzene-1,2-disulfonamide | 501.2 |

-continued

| EX. NO. | RR'NH | STRUCTURE | NAME | LC/MS m/e [M + H]+ |
|---|---|---|---|---|
| 99 | | 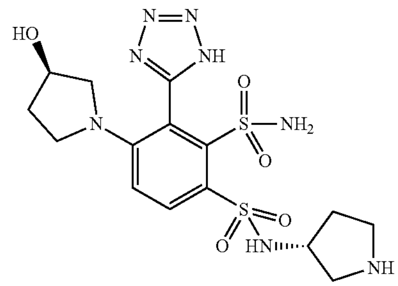 [SMILES: NS(=O)(=O)c1c(S(=O)(=O)N[C@@H]2CCNC2)ccc(N2CC[C@@H](O)C2)c1-c1nnn[nH]1] | 4-[(3R)-3-hydroxypyrrolidin-1-yl]-N1-[(3R)-pyrrolidin-3-yl]-3-(1H-tetrazol-5-yl)benzene-1,2-disulfonamide | 459.1 |
| 100 | | 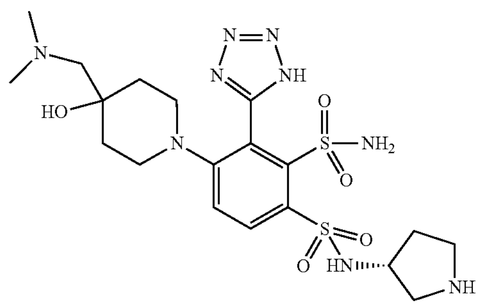 [SMILES: CN(C)CC1(O)CCN(c2ccc(S(=O)(=O)N[C@@H]3CCNC3)c(S(N)(=O)=O)c2-c2nnn[nH]2)CC1] | 4-{4-[(dimethylamino)methyl]-4-hydroxypiperidin-1-yl}-N1-[(3R)-pyrrolidin-3-yl]-3-(1H-tetrazol-5-yl)benzene-1,2-disulfonamide | 530.2 |
| 101 | | 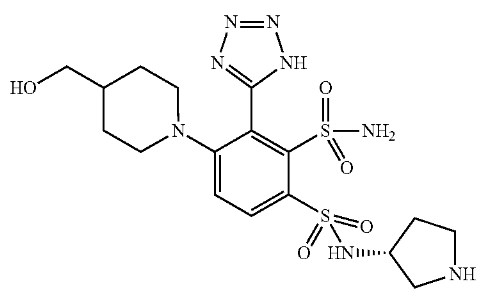 [SMILES: NS(=O)(=O)c1c(S(=O)(=O)N[C@@H]2CCNC2)ccc(N2CCC(CO)CC2)c1-c1nnn[nH]1] | 4-[4-(hydroxymethyl)piperidin-1-yl]-N1-[(3R)-pyrrolidin-3-yl]-3-(1H-tetrazol-5-yl)benzene-1,2-disulfonamide | 487.2 |

Examples 102-116

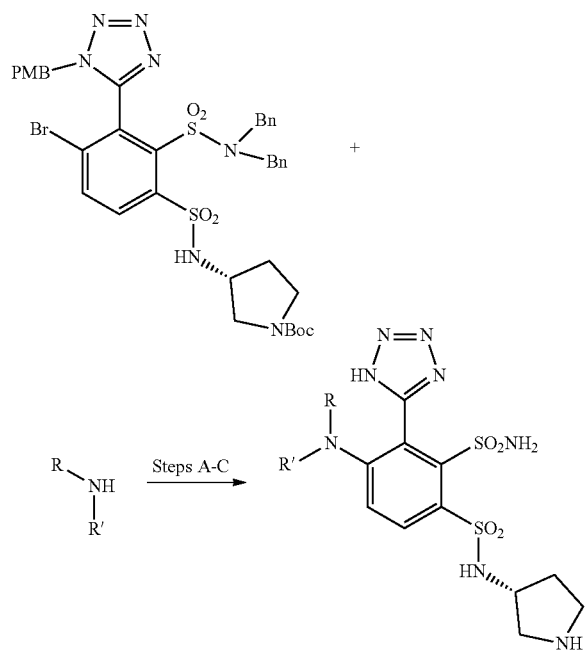

Step A:

To a set of 1-dram vials each containing the requisite amine (see table below) (0.188 mmol) were added 1.0 mL of a solution of tert-butyl (R)-3-((4-bromo-2-(N,N-dibenzylsulfamoyl)-3-(1-(4-methoxybenzyl)-1H-tetrazol-5-yl)phenyl)sulfonamido)pyrrolidine-1-carboxylate from REFERENCE EXAMPLE 60 (40 mg, 0.047 mmol) in DME and DIEA (0.041 mL, 0.235 mmol). The vials were capped and heated at 100° C. with stirring for 12 hours. The vials were cooled to RT and the solvent was removed in vacuo.

Step B:

To the residues from Step A were each added DCM 0.4 mL, TFA 0.4 mL along with thioanilsole (0.3 mL). The vials were shaked at 25° C. for 3 hours. Solvent was removed under reduced pressure.

Step C:

To a set of 2-dram vials containing the intermediates from last step, was added 0.2 mL, sulfuric acid and the reaction mixtures were agitated at 25° C. for 2 hours. After that time, 1 mL of prechilled 7N NH$_3$/MeOH solution was slowly added into each reaction. The mixtures were filtered and washed with 2 mL MeOH. The solvent from each reaction was removed in vacuo. The residues were dissolved in 1 DMSO and filtered. The crude products were purified by mass triggered reverse phase HPLC using the following conditions: [column: Waters XBridge C18, or Waters Sunfire C18, 5 μm, 19×100 mm; solvent: gradient range 3-28% initial to 45-95% final MeCN (0.1% TFA) in water (0.1% TFA) 50 or 70 ml/min; 8 min run time] to afford EXAMPLES 102-116.

| EX. NO. | RR'NH | STRUCTURE | NAME | LC/MS m/e [M + H]+ |
|---|---|---|---|---|
| 102 | 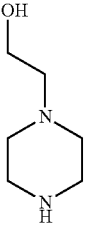 | 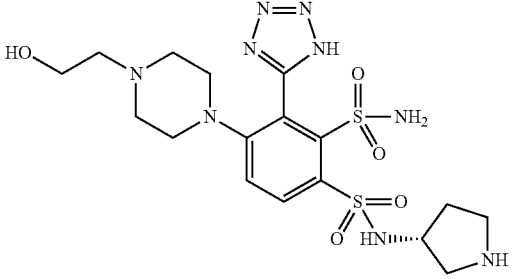 [SMILES: NS(=O)(=O)c1c(S(=O)(=O)N[C@@H]2CCNC2)ccc(N2CCN(CCO)CC2)c1-c1nnn[nH]1] | 4-[4-(2-hydroxyethyl)piperazin-1-yl]-N1-[(3R)-pyrrolidin-3-yl]-3-(1H-tetrazol-5-yl)benzene-1,2-disulfonamide | 502.2 |
| 103 | 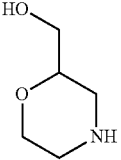 | 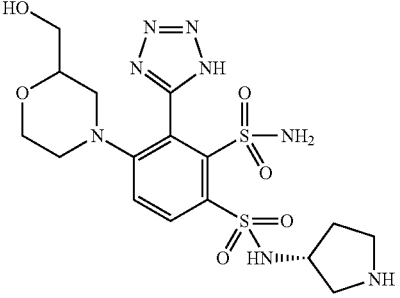 [SMILES: NS(=O)(=O)c1c(S(=O)(=O)N[C@@H]2CCNC2)ccc(N2CCOC(CO)C2)c1-c1nnn[nH]1] | 4-[2-(hydroxymethyl)morpholin-4-yl]-N1-[(3R)-pyrrolidin-3-yl]-3-(1H-tetrazol-5-yl)benzene-1,2-disulfonamide | 489.1 |
| 104 | 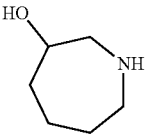 | 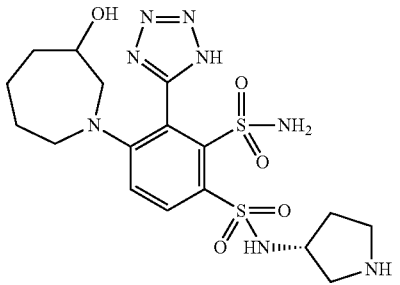 [SMILES: NS(=O)(=O)c1c(S(=O)(=O)N[C@@H]2CCNC2)ccc(N2CCCCC(O)C2)c1-c1nnn[nH]1] | 4-(3-hydroxyazepan-1-yl)-N1-[(3R)-pyrrolidin-3-yl]-3-(1H-tetrazol-5-yl)benzene-1,2-disulfonamide | 487.2 |
| 105 | 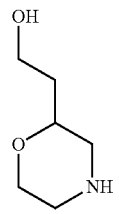 | 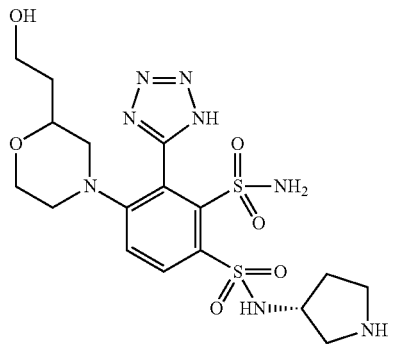 [SMILES: NS(=O)(=O)c1c(S(=O)(=O)N[C@@H]2CCNC2)ccc(N2CCOC(CCO)C2)c1-c1nnn[nH]1] | 4-[2-(2-hydroxyethyl)morpholin-4-yl]-N1-[(3R)-pyrrolidin-3-yl]-3-(1H-tetrazol-5-yl)benzene-1,2-disulfonamide | 503.1 |

| EX. NO. | RR'NH | STRUCTURE | NAME | LC/MS m/e [M + H]+ |
|---|---|---|---|---|
| 106 | | 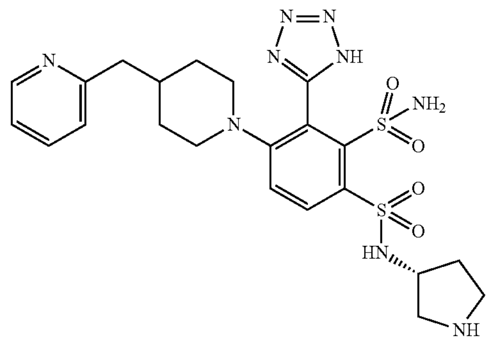 [SMILES: NS(=O)(=O)c1c(S(=O)(=O)N[C@@H]2CCNC2)ccc(N2CCC(Cc3ccccn3)CC2)c1-c1nnn[nH]1] | 4-[4-(pyridin-2-ylmethyl)piperidin-1-yl]-N1-[(3R)-pyrrolidin-3-yl]-3-(1H-tetrazol-5-yl)benzene-1,2-disulfonamide | 548.2 |
| 107 | | 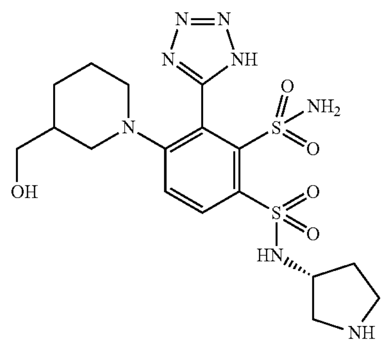 [SMILES: NS(=O)(=O)c1c(S(=O)(=O)N[C@@H]2CCNC2)ccc(N2CCCC(CO)C2)c1-c1nnn[nH]1] | 4-[3-(hydroxymethyl)piperidin-1-yl]-N1-[(3R)-pyrrolidin-3-yl]-3-(1H-tetrazol-5-yl)benzene-1,2-disulfonamide | 487.2 |
| 108 | | 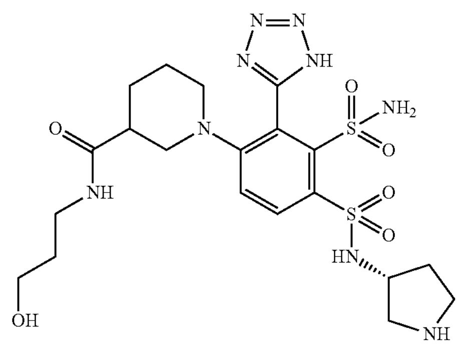 [SMILES: NS(=O)(=O)c1c(S(=O)(=O)N[C@@H]2CCNC2)ccc(N2CCCC(C(=O)NCCCO)C2)c1-c1nnn[nH]1] | N-(3-hydroxypropyl)-1-{4-[(3R)-pyrrolidin-3-ylsulfamoyl]-3-sulfamoyl-2-(1H-tetrazol-5-yl)phenyl}piperidine-3-carboxamide | 558.2 |
| 109 | | 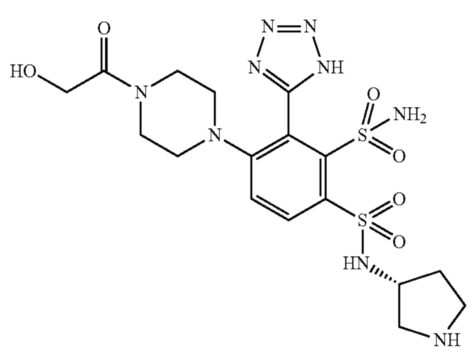 [SMILES: NS(=O)(=O)c1c(S(=O)(=O)N[C@@H]2CCNC2)ccc(N2CCN(C(=O)CO)CC2)c1-c1nnn[nH]1] | 4-[4-(hydroxyacetyl)piperazin-1-yl]-N1-[(3R)-pyrrolidin-3-yl]-3-(1H-tetrazol-5-yl)benzene-1,2-disulfonamide | 516.1 |

| EX. NO. | RR'NH | STRUCTURE | NAME | LC/MS m/e [M + H]+ |
|---|---|---|---|---|
| 110 | 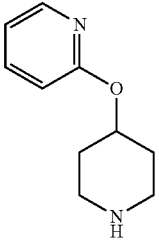 | 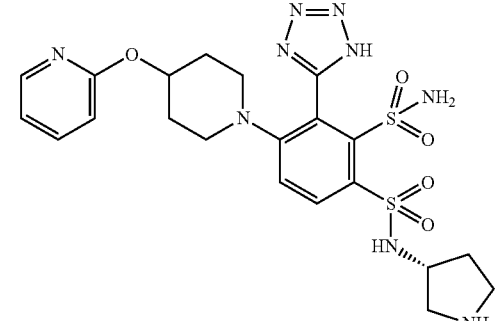 | 4-[4-(pyridin-2-yloxy)piperidin-1-yl]-N1-[(3R)-pyrrolidin-3-yl]-3-(1H-tetrazol-5-yl)benzene-1,2-disulfonamide | 550.2 |
| 111 | 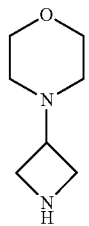 | 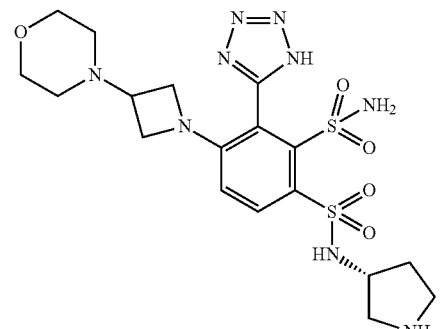 | 4-(3-morpholin-4-ylazetidin-1-yl)-N1-(3R)-pyrrolidin-3-yl]-3-(1H-tetrazol-5-yl)benzene-1,2-disulfonamide | 514.2 |
| 112 | 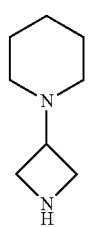 | 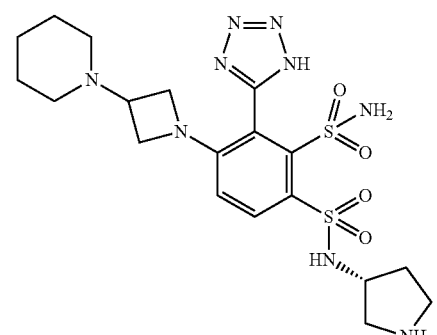 | 4-(3-piperidin-1-ylazetidin-1-yl)-N1-[(3R)-pyrrolidin-3-yl]-3-(1H-tetrazol-5-yl)benzene-1,2-disulfonamide | 512.2 |
| 113 |  | 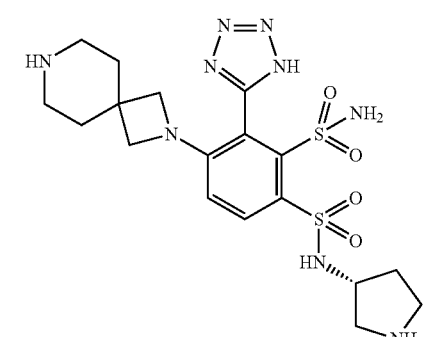 | 4-(2,7-diazaspiro[3.5]non-2-yl)-N1-[(3R)-pyrrolidin-3-yl]-3-(1H-tetrazol-5-yl)benzene-1,2-disulfonamide | 498.2 |

-continued

| EX. NO. | RR'NH | STRUCTURE | NAME | LC/MS m/e [M + H]+ |
|---|---|---|---|---|
| 114 | | 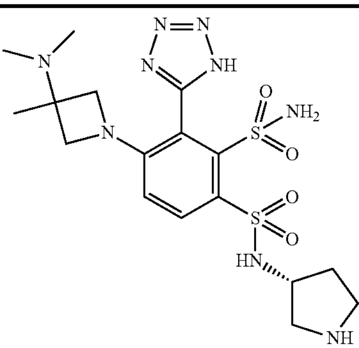 | 4-[3-(dimethylamino)-3-methylazetidin-1-yl]-N1-[(3R)-pyrrolidin-3-yl]-3-(1H-tetrazol-5-yl)benzene-1,2-disulfonamide | 486.2 |
| 115 | | 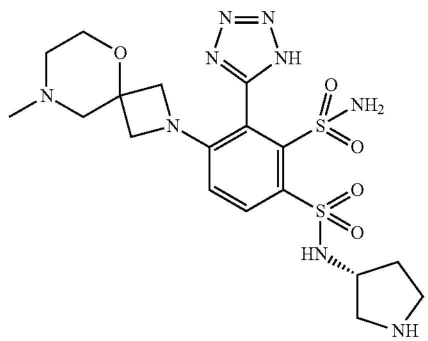 [SMILES: CN1CCOC2(C1)CN(c1ccc(S(=O)(=O)N[C@@H]3CCNC3)c(S(N)(=O)=O)c1-c1nnn[nH]1)C2] | 4-(8-methyl-5-oxa-2,8-diazaspiro[3.5]non-2-yl)-N1-[(3R)-pyrrolidin-3-yl]-3-(1H-tetrazol-5-yl)benzene-1,2-disulfonamide | 514.2 |
| 116 | | 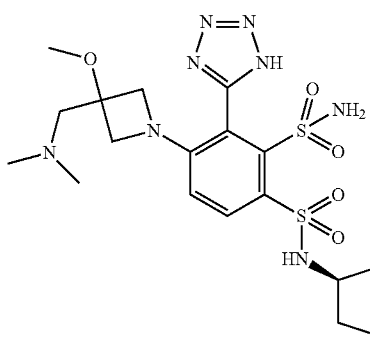 | 4-{3-[(dimethylamino)methyl]-3-methoxyazetidin-1-yl}-N1-[(3R)-pyrrolidin-3-yl]-3-(1H-tetrazol-5-yl)benzene-1,2-disulfonamide | 516.2 |

Example 117

(R)—N1-(3-amino-2-hydroxypropyl)-4-(4-(2-(methylsulfonyl)ethyl) piperazin-1-yl)-3-(2H-tetrazol-5-yl)benzene-1,2-disulfonamide

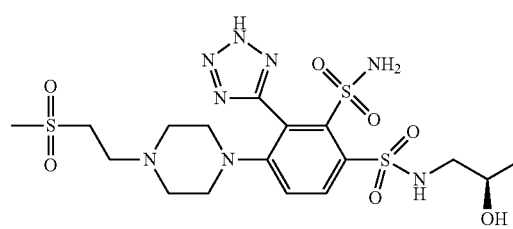

Step A: (R)-tert-butyl (3-(2-(N,N-bis(4-methoxybenzyl)sulfamoyl)-3-(2-(4-methoxybenzyl)-2H-tetrazol-5-yl)-4-(4-(2-(methylsulfonyl)ethyl)piperazin-1-yl)phenylsulfonamido)-2-((tert-butyldimethylsilyl)oxy)propyl)carbamate To a solution of (R)-tert-butyl (3-(2-(N,N-bis(4-methoxybenzyl)sulfamoyl)-4-iodo-3-(2-(4-methoxybenzyl)-2H-tetrazol-5-yl)phenylsulfonamido)-2-((tert-butyldimethylsilyl)oxy)propyl)carbamate (REFERENCE EXAMPLE 45) (0.60 g, 0.56 mmol) in DME (4 mL) were added 1-(2-(methylsulfonyl)ethyl)piperazine (0.32 g, 1.67 mmol, prepared as described in WO 2010/104899) and DIEA (0.29 mL, 1.67 mmol). The mixture was stirred for 50 hours at 100° C. After cooling to RT the resulting mixture was diluted with water (20 mL) and extracted with EA (3×20 mL). The combined organic layers were washed with brine (2×20 mL), dried over anhydrous Na$_2$SO$_4$ and filtered. The filtrate was concentrated under vacuum. The residue was purified by a silica gel column chromatography, eluting with 50% EA in PE to afford the title compound. LCMS (ESI) calc'd for $C_{52}H_{75}N_9O_{12}S_3Si$ [M+H]$^+$: 1142, found 1142.

Step B: (R)—N1-(3-amino-2-hydroxypropyl)-4-(4-(2-(methylsulfonyl)ethyl)piperazin-1-yl)-3-(2H-tetrazol-5-yl)benzene-1,2-disulfonamide To a solution of (R)-tert-butyl (3-(2-(N,N-bis(4-methoxybenzyl) sulfamoyl)-3-(2-(4-methoxybenzyl)-2H-tetrazol-5-yl)-4-(4-(2-(methylsulfonyl)ethyl) piperazin-1-yl)phenylsulfonamido)-2-((tert-butyldimethylsilyl)oxy)propyl) carbamate (0.14 g, 0.15 mmol) in $CH_2Cl_2$ (4 mL) was added TFA (4 mL, 51.9 mmol) at RT. The reaction solution was stirred at RT for 1 hour. The solution was concentrated under vacuum. The residue was co-evaporated with anisole (3×5 mL). The residue was used in the next step without further purification. The residue was dissolved in TFA (5 mL, 64.9 mmol) at room temperature, and then the solution was stirred at 80° C. for 1 h. The solution was concentrated under vacuum. The residue was dissolved in EA (5 mL), and then extracted with 1 N HCl (3×5 mL). The aqueous layers were combined and concentrated under reduced pressure. The crude product was purified by Prep-HPLC with the following conditions: Column: XBridge Shield RP18 OBD Column 19×250 mm, 10 μm; Mobile Phase A: water (10 mmol/L $NH_4HCO_3$), Mobile Phase B: ACN; Flow rate: 20 mL/min; Gradient: 1% B to 36% B in 11 min; Detector: UV 254/210 nm; Retention time: 9.55 min. to afford the title compound. LCMS [M+H]$^+$: 568; $^1$H NMR (400 MHz, DMSO-d$_6$) δ 8.05 (d, J=8.8 Hz, 1H), 7.32 (br, 3H), 7.30 (d, J=8.8 Hz, 1H), 3.79-3.81 (m, 1H), 3.23 (t, J=6.7 Hz, 2H), 3.07-3.02 (m, 2H), 3.00 (s, 3H), 2.98-2.87 (m, 2H), 2.78-2.57 (m, 6H), 2.22 (m, 4H).

Example 118

1-(4-(N—((R)-3-amino-2-hydroxypropyl)sulfamoyl)-3-sulfamoyl-2-(2H-tetrazol-5-yl)phenyl)pyrrolidine-3-carboxamide

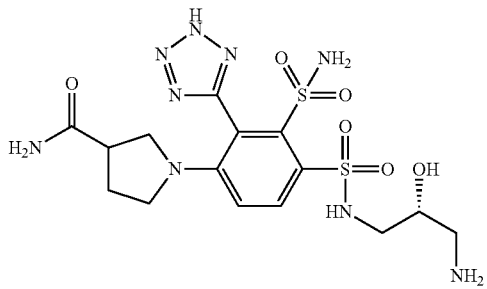 [SMILES: NC[C@@H](O)CNS(=O)(=O)c1ccc(N2CCC(C(N)=O)C2)c(-c2nn[nH]n2)c1S(N)(=O)=O]

Step A: Methyl 1-(3-(N,N-bis(4-methoxybenzyl) sulfamoyl-4-(N—((R)-3-((tert-butoxycarbonyl) amino)-2-((tert-butyldimethylsilyl)oxy)propyl)sulfamoyl)-2-(2-(4-methoxybenzyl)-2H-tetrazol-5-yl) phenyl)pyrrolidine-3-carboxylate Under argon atmosphere, to a solution of (R)-tert-butyl (3-(2-(N,N-bis(4-methoxybenzyl)sulfamoyl)-4-iodo-3-(2-(4-methoxybenzyl)-2H-tetrazol-5-yl)phenylsulfonamido)-2-((tert-butyldimethylsilyl)oxy)propyl) carbamate (REFERENCE EXAMPLE 45) (1.10 g, 1.02 mmol) in DME (5 mL) were added methyl pyrrolidine-3-carboxylate (0.66 g, 5.10 mmol) and DIEA (0.66 g, 5.10 mmol) at RT. The reaction mixture was stirred at 100° C. for 60 hours. After cooling to RT, the resulting mixture was concentrated under vacuum. The residue was purified by a silica gel column chromatography, eluting with EA/PE (3:1) to afford the title compound, LCMS [M+H]$^+$: 1079.

Step B: 1-(3-(N,N-bis(4-methoxybenzyl)sulfamoyl)-4-(N—((R)-3-((tert-butoxycarbonyl) amino)-2-((tert-butyldimethylsilyl)oxy)propyl)sulfamoyl)-2-(2-(4-methoxybenzyl)-2H-tetrazol-5-yl)phenyl) pyrrolidine-3-carboxylic acid To a solution of methyl 1-(3-(N,N-bis(4-methoxybenzyl) sulfamoyl)-4-(N—((R)-3-((tert-butoxycarbonyl)amino)-2-((tert-butyldimethylsilyl)oxy)propyl)sulfamoyl)-2-(2-(4-methoxybenzyl)-2H-tetrazol-5-yl)pyrrolidine-3-carboxylate (0.60 g, 0.56 mmol) in MeOH (5 mL) was added KOH (62 mg, 1.11 mmol) at RT. The reaction mixture was stirred at RT for 30 minutes. The reaction mixture was evaporated under vacuum. The residue was diluted with water (20 mL), and pH was adjusted to 4 with 1N HCl. The aqueous solution was extracted with DCM (5×20 mL). The combined organic layers were dried over anhydrous $MgSO_4$ and filtered. The filtrate was removed under vacuum to afford the title compound, which was used in the next step without further purification: LCMS [M+H]$^+$: 1065.

Step C: Tert-butyl((2R-3-(2-(N,N-bis(4-methoxybenzyl)sulfamoyl)-4-(3-carbamoylpyrrolidin-1-yl)-3-(2-(4-methoxybenzyl)-2H-tetrazol-5-yl)phenylsulfonamido)-2-((tert-butyl dimethylsilyl)oxy)propyl) carbamate To a solution of 1-(3-(N,N-bis(4-methoxybenzyl)sulfamoyl-4-(N—((R)-3-((tert-butoxycarbonyl)amino)-2-((tert-butyldimethylsilyl)oxy)propyl)sulfamoyl)-2-(2-(4-methoxybenzyl)-2H-tetrazol-5-yl)phenyl)pyrrolidine-3-carboxylic acid (0.55 g, 0.52 mmol) in THF (10 mL) were added HATU (0.39 g, 1.03 mmol), sat'd. ammonia in THF (1 mL) and triethylamine (1.05 g, 10.33 mmol) at RT. The reaction mixture was stirred at RT for 6 hours. The reaction mixture was evaporated under vacuum. The residue was purified by a silica gel column chromatography, eluting with 90% EA in PE to afford the title compound. LCMS [M+H]$^+$: 1064.

Step D: 1-(4-(N—((R)-3-amino-2-hydroxypropyl) sulfamoyl)-3-sulfamoyl-2-(2H-tetrazol-5-yl) phenyl) pyrrolidine-3-carboxamide The title compound was prepared as described for EXAMPLE 117 step B using tert-butyl((2R)-3-(2-(N,N-bis (4-methoxybenzyl)sulfamoyl)-4-(3-carbamoylpyrrolidin-1-yl)-3-(2-(4-methoxybenzyl)-2H-tetrazol-5-yl)phenylsulfonamido)-2-((tert-butyldimethylsilyl)oxy)propyl) carbamate (REFERENCE EXAMPLE 45) to afford the crude product. The crude product was purified by Prep-HPLC with the following conditions: Column: XBridge C18 OBD Prep Column, 100 Å, 5 μm, 19 mm×250 mm; Mobile Phase A: water (10 mmol/L $NH_4HCO_3$), Mobile Phase B: ACN; Flow rate: 20 mL/min; Gradient: 3% B to 40% B in 10 min; Detector: UV 254/210 nm; Retention time: 5.7 min to give the title compound. LCMS [M+H]$^+$: 490, $^1$H NMR (300 MHz, D$_2$O) δ 7.98 (d, J=9.2 Hz, 1H), 7.01 (d, J=9.2 Hz, 1H), 3.95-3.83 (m, 1H), 3.17-2.93 (m, 3R), 2.93-2.52 (m, 6H), 2.01-1.71 (m, 2H).

Example 119

(R)—N1-(3-amino-2-hydroxypropyl)-4-(4-(2-aminoacetyl)piperazin-1-yl)-3-(2H-tetrazol-5-yl)benzene-1,2-disulfonamide

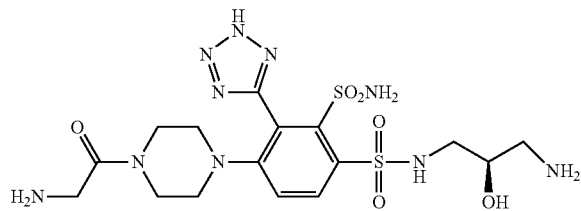 [SMILES: NCC(=O)N1CCN(c2ccc(S(=O)(=O)NC[C@H](O)CN)c(S(N)(=O)=O)c2-c2nn[nH]n2)CC1]

Step A: (R)-tert-butyl (3-(2-(N,N-bis(4-methoxybenzyl)sulfamoyl)-3-(2-(4-methoxybenzyl)-2H-tetrazol-5-yl)-4-(piperazin-1-yl)phenylsulfonamido)-2-((tert-butyldimethylsilyl) oxy)propyl)carbamate The title compound was prepared as described for EXAMPLE 117 Step A using (R)-tert-butyl (3-(2-(N,N-bis(4-methoxybenzyl)sulfamoyl)-4-iodo-3-(2-(4-methoxybenzyl)-2H-tetrazol-5-yl)phenylsulfonamido)-2-((tert-butyldimethylsilyl)oxy)propyl) carbamate (REFERENCE EXAMPLE 45) to afford (R)-tert-butyl (3-(2-(N,N-bis(4-methoxybenzyl) sulfamoyl)-3-(2-(4-methoxybenzyl)-2H-tetrazol-5-yl)-4-(piperazin-1-yl)phenylsulfonamido)-2-((tert-butyldimethylsilyl)oxy)propyl)carbamate: LCMS [M+H]⁺: 1036.

Step B: tert-butyl (R)-(3-((4-(4-(((benzyloxy)carbonyl)glycyl)piperazin-1-yl)-2-(N,N-bis(4-methoxybenzyl)sulfamoyl)-3-(2-(4-methoxybenzyl)-2H-tetrazol-5-yl)phenyl)sulfonamido)-2-((tert-butyldimethylsilyl)oxy)propyl)carbamate To a solution of 2-(((benzyloxy)carbonyl)amino)acetic acid (45 mg, 0.22 mmol) in DMF (1 mL) were added HATU (0.11 g, 0.29 mmol) and DIEA (37 mg, 0.29 mmol) at RT. The reaction solution was stirred at 30° C. for 0.5 hours. Then (R)-tert-butyl(3-(2-(N,N-bis(4-methoxybenzyl)sulfamoyl)-3-(2-(4-methoxybenzyl)-2H-tetrazol-5-yl)-4-(piperazin-1-yl)phenylsulfonamido)-2-((tert-butyldimethylsilyl) oxy)propyl)carbamate (0.15 g, 0.15 mmol) was added into the resulting solution. The reaction solution was stirred at RT for 4 hours, then diluted with water (10 mL), and extracted with EA (3×6 mL). The organic layers were combined, washed with brine (2×20 mL), dried over anhydrous Na₂SO₄ and filtered. The filtrate was concentrated under vacuum. The residue was purified by Preperative TLC, eluting with 50% EA in RE to afford the title compound: LCMS [M+H]⁺: 1227.

Step C: (R)—N1-(3-amino-2-hydroxypropyl)-4-(4-(2-aminoacetyl)piperazin-1-yl)-3-(2H-tetrazol-5-yl) benzene-1,2-disulfonamide The title compound was prepared as described for EXAMPLE 117 Step using tert-butyl (R)-(3-((4-(4-(((benzyloxy)carbonyl)glycyl)piperazin-1-yl)-2-(N,N-bis(4-methoxybenzyl)sulfamoyl)-3-(2-(4-methoxybenzyl)-2H-tetrazol-5-yl)phenyl)sulfonamido)-2-((tert-butyldimethylsilyl)oxy)propyl)carbamate to afford the crude product. The crude product was purified by Prep-HPLC with the following conditions: Column: XBridge Shield RP18 OBD Column, 19×250 mm, 10 μm; Mobile Phase A: water (10 mmol/L NH₄HCO₃), Mobile Phase B: ACN; Flow rate: 20 mL/min; Gradient: 0% B to 30% B in 11 min; Detector: UV 254/210 nm; Retention time: 9.38 min to give the title compound. LCMS [M+H]⁺: 519; ¹H NMR (300 MHz, CD₃OD) δ 8.25 (d, J=8.7 Hz, 1H), 7.39 (d, J=8.7 Hz, 1H), 3.86-3.77 (m, 1H), 3.54 (s, 2H), 3.40-3.34 (m, 2H), 3.15-2.92. (m, 5H), 2.87-2.75 (m, 5H).

EXAMPLES 120-126 were prepared in an analogous fashion to EXAMPLE 117, starting from (R)-tert-butyl (3-(2-(N,N-bis(4-methoxybenzyl)sulfamoyl)-4-iodo-3-(2-(4-methoxybenzyl)-2H-tetrazol-5-yl)phenylsulfonamido)-2-((tert-butyldimethylsilyl)oxy)propyl) carbamate (REFERENCE EXAMPLE 45) and the requisite amines, which were prepared as described herein, or which were available from commercial sources.

| EX. | STRUCTURE | NAME | LC/MS [M + H]⁺ |
|---|---|---|---|
| 120 | 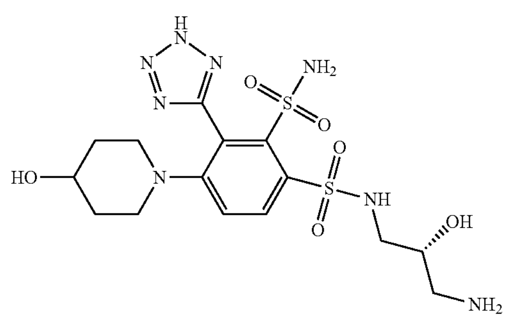 [SMILES: NC[C@@H](O)CNS(=O)(=O)c1ccc(N2CCC(O)CC2)c(-c2nn[nH]n2)c1S(N)(=O)=O] | (R)-N1-(3-amino-2-hydroxypropyl)-4-(4-hydroxypiperidin-1-yl)-3-(2H-tetrazol-5-yl)benzene-1,2-disulfonamide | 477 |
| 121 | 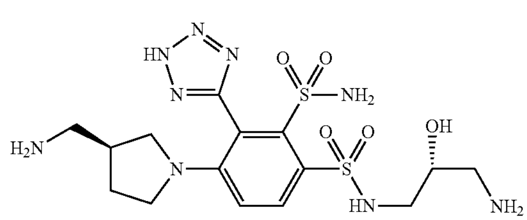 [SMILES: NC[C@@H](O)CNS(=O)(=O)c1ccc(N2CC[C@@H](CN)C2)c(-c2nn[nH]n2)c1S(N)(=O)=O] | N1-((R)-3-amino-2-hydroxypropyl)-4-((S)-3-(aminomethyl)pyrrolidin-1-yl)-3-(2H-tetrazol-5-yl)benzene-1,2-disulfonamide | 476 |

-continued

| EX. | STRUCTURE | NAME | LC/MS [M + H]+ |
|---|---|---|---|
| 122 | 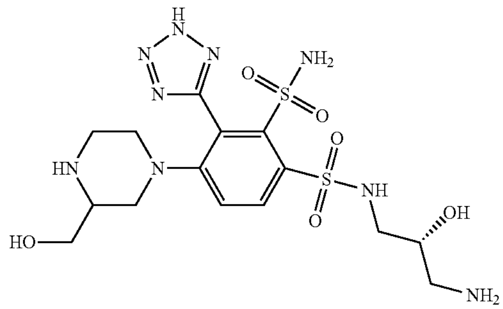 [SMILES: NC[C@@H](O)CNS(=O)(=O)c1ccc(N2CCNC(CO)C2)c(-c2nn[nH]n2)c1S(N)(=O)=O] | N1-((R)-3-amino-2-hydroxypropyl)-4-(3-(hydroxymethyl)piperazin-1-yl)-3-(2H-tetrazol-5-yl)benzene-1,2-disulfonamide | 492 |
| 123 | 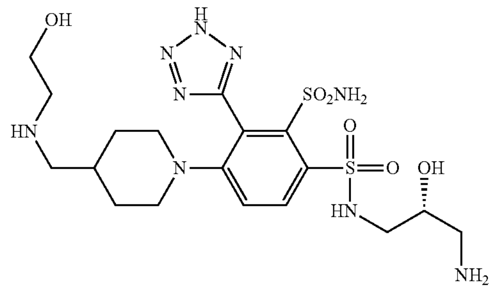 [SMILES: NC[C@@H](O)CNS(=O)(=O)c1ccc(N2CCC(CNCCO)CC2)c(-c2nn[nH]n2)c1S(N)(=O)=O] | (R)-N1-(3-amino-2-hydroxypropyl)-4-(4-(((2-hydroxyethyl)amino)methyl)piperidin-1-yl)-3-(2H-tetrazol-5-yl)benzene-1,2-disulfonamide | 534 |
| 124 | 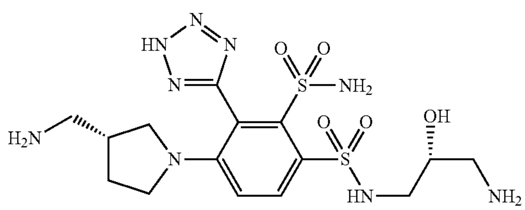 [SMILES: NC[C@@H](O)CNS(=O)(=O)c1ccc(N2CC[C@H](CN)C2)c(-c2nn[nH]n2)c1S(N)(=O)=O] | N1-((R)-3-amino-2-hydroxypropyl)-4-((R)-3-(aminomethyl)pyrrolidin-1-yl)-3-(2H-tetrazol-5-yl)benzene-1,2-disulfonamide | 475 |
| 125 | 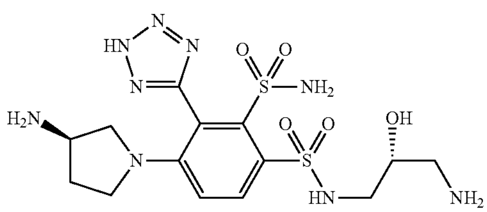 [SMILES: NC[C@@H](O)CNS(=O)(=O)c1ccc(N2CC[C@@H](N)C2)c(-c2nn[nH]n2)c1S(N)(=O)=O] | N1-((R)-3-amino-2-hydroxypropyl)-4-((R)-3-aminopyrrolidin-1-yl)-3-(2H-tetrazol-5-yl)benzene-1,2-disulfonamide | 462 |
| 126 | 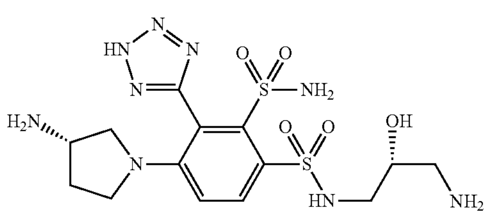 [SMILES: NC[C@@H](O)CNS(=O)(=O)c1ccc(N2CC[C@H](N)C2)c(-c2nn[nH]n2)c1S(N)(=O)=O] | N1-((R)-3-amino-2-hydroxypropyl)-4-((S)-3-aminopyrrolidin-1-yl)-3-(2H-tetrazol-5-yl)benzene-1,2-disulfonamide | 462 |

EXAMPLE 120: $^1$H NMR (400 MHz, DMSO-d$_6$+D$_2$O) δ 7.99 (d, J=8.9 Hz, 1H), 7.27 (d, J=9.0 Hz, 1H), 3.82-3.77 (m, 1H), 3.45-3.38 (m, 1H), 3.02-2.98 (m, 1H), 2.95-2.86 (m, 4H), 2.71-2.65 (m, 1H), 2.49-2.45 (m, 2H), 1.49-1.40 (m, 2H), 1.15-1.03 (m, 2H). EXAMPLE 121: $^1$H NMR (400 MHz, CD$_3$OD+DCl): δ 8.26 (d, J=9.2 Hz, 1H), 7.28 (d, J=9.3 Hz, 1H), 4.01-3.92 (m, 1H), 3.29-2.62 (m, 10H), 2.53-2.47 (m, 1H), 2.13-2.00 (m, 1H), 1.72-1.65 (m, 1H). EXAMPLE 122: $^1$H NMR (300 MHz, CD$_3$OD) δ 8.29 (d, J=8.8 Hz, 1H), 7.43 (d, J=8.8 Hz, 1H), 3.86-3.80 (m, 1H), 3.45-3.35 (m, 2H), 3.15-2.94 (m, 5H), 2.83-2.65 (m, 3H), 2.58-2.47 (m, 3H). EXAMPLE 123: $^1$H NMR (300 MHz, CD$_3$OD+DCl) δ 8.40 (d, J=8.7 Hz, 1H), 7.66 (d, J=8.7 Hz, 1H), 3.99-3.92 (m, 1H), 3.81-3.77 (m, 2H), 3.13-3.07 (m, 7H), 2.93-2.85 (m, 3H), 2.70-2.68 (m, 2H), 1.71-1.65 (m, 3H), 0.95-0.90 (m, 2H). EXAMPLE 124: $^1$H NMR (300 MHz, D$_2$O) δ 8.00 (d, J=9.3 Hz, 1H), 7.02 (d, J=9.3 Hz, 1H), 3.85-3.83 (m, 1H), 3.15-2.84 (m, 4H), 2.84-2.54 (m, 5H), 2.30-2.26 (m, 2H), 1.91-1.88 (m, 1H), 1.47-1.44 (m, 1H). EXAMPLE 125: $^1$H NMR (300 MHz, CD$_3$OD+DCl): δ 8.29 (d, J=9.3 Hz, 1H), 7.32 (d, J=9.3 Hz, 1H), 4.09-3.90 (m, 1H), 3.87-3.73 (m, 1H), 3.16-3.06 (m, 6H), 3.00-2.88 (m, 1H), 2.82-2.72 (m, 1H) 2.49-2.18 (m, 1H), 2.16-1.89 (m, 1H). EXAMPLE 126: ¹H NMR (300 MHz, CD₃OD+DCl): δ 8.14 (d, J=9.2 Hz, 1H), 7.05 (d, J=9.2 Hz, 1H), 3.86-3.80 (m, 1H), 3.50-3.39 (m, 1H), 3.13-2.74 (m, 7H), 2.48-2.58 (m, 1H), 2.05-1.99 (m, 1H), 1.73-1.62 (m, 1H).

Example 127

4-(5-(hydroxymethyl)-1,4-diazepan-1-yl)-N1-((R)-pyrrolidin-3-yl)-3-(2H-tetrazol-5-yl)benzene-1,2-disulfonamide

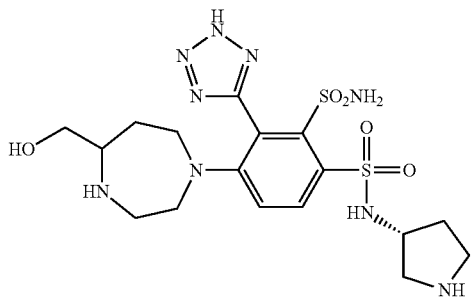 [SMILES: NS(=O)(=O)c1c(S(=O)(=O)N[C@@H]2CCNC2)ccc(N2CCNC(CO)CC2)c1-c1nn[nH]n1]

Step A: (3R)-tert-butyl 3-(2-(N,N-bis(4-methoxybenzyl)sulfamoyl)-4-(5-(hydroxymethyl)-1,4-diazepan-1-yl)-3-(2-(4-methoxybenzyl)-2H-tetrazol-5-yl) phenylsulfonamido) pyrrolidine-1-carboxylate The title compound was prepared as described for EXAMPLE 117 Step A using (R)-tert-butyl 3-(2-(N,N-bis (4-methoxybenzyl)sulfamoyl)-4-iodo-3-(2-(4-methoxy benzyl)-2H-tetrazol-5-yl)phenylsulfonamido)pyrrolidine-1-carboxylate (REFERENCE EXAMPLE 40) and (1,4-diazepan-5-yl)methanol. LCMS [M+1]⁺: 962.

Step B: 4-(5-(Hydroxymethyl)-1,4-diazepan-1-yl)-N1-((R)-pyrrolidin-3-yl)-3-(2H-tetrazol-5-yl)benzene-1,2-disulfonamide The title compound was prepared as described for EXAMPLE 117 Step B using (3R)-tert-butyl 3-(2-(N,N-bis (4-methoxybenzyl)sulfamoyl)-4-(5-(hydroxymethyl)-1,4-diazepan-1-yl)-3-(2-(4-methoxybenzyl)-2H-tetrazol-5-yl) phenylsulfonamido) pyrrolidine-1-carboxylate to afford the crude product. The crude product was purified by Prep-HPLC with the following conditions: Column: X Bridge Prep C18 OBD Column 19×250 min 10 μm; Mobile Phase A: water with 10 mmol/L NH₄HCO₃, Mobile Phase B: ACN; Flow rate: 25 mL/min; Gradient: 1% B to 15% B in 12 min; Detector: UV 254 nm; Retention time: 10.78 min to give the title compound. LCMS [M+1]⁺: 502; ¹H NMR (300 MHz, CD₃OD+DCl) δ 8.51 (d, J=8.8 Hz, 1H), 7.85 (d, J=8.9 Hz, 1H), 4.30-4.15 (m, 1H), 3.77-3.68 (m, 1H), 3.55-3.35 (m, 7H), 3.27-2.75 (m, 5H), 2.31-2.17 (m, 1H), 2.06-1.89 (m, 1H), 1.84-1.60 (m, 2H).

Example 128

(R)-6-((3-amino-2-hydroxypropyl)sulfonyl)-3-(4-(aminomethyl)piperidin-1-yl)-2-(2H-tetrazol-5-yl) benzenesulfonamide

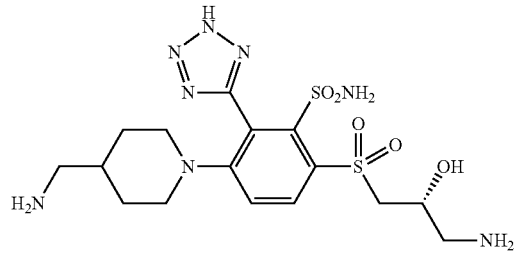 [SMILES: NCC1CCN(c2ccc(S(=O)(=O)C[C@H](O)CN)c(S(N)(=O)=O)c2-c2nn[nH]n2)CC1]

Step A: tert-butyl (R)-(3-((2-(N,N-bis(4-methoxybenzyl)sulfamoyl)-4-(4-(((tert-butoxycarbonyl) amino)methyl)piperidin-1-yl)-3-(2-(4-methoxybenzyl)-2H-tetrazol-5-yl)phenyl)sulfonyl)-2-((tert-butyldimethylsilyl)oxy)propyl)carbamate To a solution of (R)-tert-butyl (3-((2-(N,N-bis(4-methoxybenzyl)sulfamoyl)-4-iodo-3-(2-(4-methoxybenzyl)-2H-tetrazol-5-yl)phenyl)sulfonyl)-2-((tert-butyldimethylsilyl)oxy)propyl)carbamate (REFERENCE EXAMPLE 45) (0.45 g, 0.42 mmol) in DMSO (5 mL) were added DABCO (0.14 g, 1.27 mmol) and tert-butyl (piperidin-4-ylmethyl)carbamate (0.14 g, 0.63 mmol) at RT. The reaction solution was stirred at 110° C. for 18 hours. The resulting solution was diluted with water (15 mL), and then extracted with EA (3×10 mL). The organic layers were combined, washed with brine (2×20 mL), dried over anhydrous Na₂SO₄ and filtered. The filtrate was concentrated under vacuum. The residue was purified by Prep-HPLC with the following conditions: Column: C18; Mobile Phase A: water (10 mmol/L NH₄HCO₃), Mobile Phase B: ACN; Flow rate: 20 mL/min; Gradient: 70% B to 100% B in 30 min; Detector: UV 254/22.0 nm; Retention time: 23-25 min to afford the title compound: LCMS [M+H]⁺: 1150.

Step B: (R)-6-((3-amino-2-hydroxypropyl)sulfonyl)-3-(4-(aminomethyl)piperidin-1-yl)-2H-tetrazol-5-yl) benzenesulfonamide The title compound was prepared as described for EXAMPLE 117 Step B using tert-butyl(R)-(3-((2-(N,N-bis (4-methoxybenzyl)sulfamoyl)-4-(4-(((tert-butoxycarbonyl) amino)methyl)piperidin-1-yl)-3-(2-(4-methoxybenzyl)-2H-tetrazol-5-yl)phenyl)sulfonyl)-2-((tert-butyldimethylsilyl) oxy)propyl)carbamate to afford the crude product. The crude product was purified by Prep-HPLC with the following conditions: Column: Atlantis Prep T3 OBD Column, 19×250 mm; 10 μm; Mobile Phase A: water (10 mmol/L NH₄HCO₃), Mobile Phase B: ACN; Flow rate: 20 Gradient: 3% B to 30% B in 13 min; Detector: LTV 254/210 nm; Retention time: 11.48 min to give the title compound. LCMS [M+H]⁺: 475; ¹H NMR (300 MHz, CD₃OD+DCl) δ 8.46 (d, J=8.8 Hz, 1H), 7.67 (d, J=8.8 Hz, 1H), 4.55-4.45 (m, 1H), 4.05-4.05 (m, 1H), 3.92-3.87 (m, 1H), 3.23-3.20 (m, 1H), 3.13-2.94 (m, 3H), 2.80-2.61 (m, 4H), 1.80-1.66 (m, 3H), 1.03-0.75 (m, 2H).

Example 129

N1-((R)-3-amino-2-hydroxypropyl)-4-(hexahydropyrazino [2,1-c][1,4] oxazin-8(1H)-yl)-3-(2H-tetrazol-5-yl)benzene-1,2-disulfonamide 2,2,2-trifluoroacetate

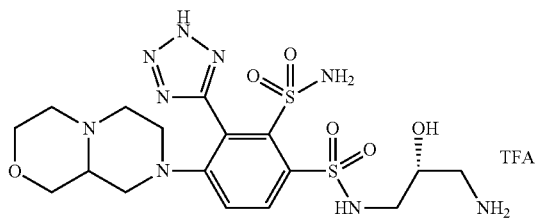 [SMILES: NC[C@@H](O)CNS(=O)(=O)c1ccc(N2CCN3CCOCC3C2)c(-c2nn[nH]n2)c1S(N)(=O)=O]

Step A: Tert-butyl ((2R)-2-((tert-butyldimethylsilyl)oxy)-3-(N,N-dibenzylsulfamoyl)-4-(hexahydropyrazino[2,1-c][1,4]oxazin-8(1H)-yl)-3-(2-(4-methoxybenzyl)-2H-tetrazol-5-yl)phenylsulfonamido)propyl)carbamate To a solution of (R)-tert-butyl (3-(4-bromo-2-(N,N-dibenzylsulfamoyl)-3-(2-(4-methoxybenzyl)-2H-tetrazol-5-yl)phenylsulfonamido)-2-((tert-butyldimethyl silyl)oxy)propyl)carbamate (REFERENCE EXAMPLE 60) (0.40 g, 0.41 mmol) in DMSO) (3 mL) were added octahydropyrazino[2,1-c][1,4]oxazine (0.18 g, 1.24 mmol) and DABCO (0.23 mL, 2.06 mmol) at RT. The reaction solution was stirred at 110° C. for 16 hours. The resulting solution was diluted with water (20 mL), and then extracted with EA (3×8 mL). The combined organic layers were washed with brine (2×20 mL), dried over anhydrous Na$_2$SO$_4$ and concentrated under vacuum. The residue was purified by Prep-TLC, eluting with 33% EA in PE to afford tert-butyl ((2R)-2-((tert-butyldimethylsilyl)oxy)-3-(2-(N,N-dibenzylsulfamoyl)-4-(hexahydropyrazino [2,1-c][1,4]oxazin-8(1H)-yl)-3-(2-(4-methoxybenzyl)-2H-tetrazol-5-yl)phenyl sulfonamido)propyl)carbamate as an oil: LCMS [M+H]$^+$: 1032.

Step B: N1-((R)-3-amino-2-hydroxypropyl)-4-(hexahydropyrazino[2,1-c][1,4]oxazin-8(1H)-yl)-3-(2H-tetrazol-5-yl)benzene-1,2-disulfonamide 2,2,2-trifluoroacetate To a solution tut-butyl 42R)-2-((tert-butyldimethylsilyl)oxy)-3-(2-(N,N-dibenzylsulfamoyl)-4-(hexahydropyrazino [2,1-c][1,4]oxazin-8(1H)-yl)-3-(2-(4-methoxybenzyl)-2H-tetrazol-5-yl)phenylsulfonamido)propyl)carbamate (0.10 g, 0.10 mmol) in DCM (1 mL) was added TFA (2 mL) at 0° C. The reaction solution was stirred at RT for 1 hour. The resulting solution was concentrated under vacuum. The residue was co-evaporated with anisole (3×2 mL) under vacuum and used in the next step without further purification. The crude product was dissolved into H$_2$SO$_4$ (1 mL) at 0° C. The solution was stirred at 0° C. for 1 hour. Then water (1 mL) was added at 0° C. The solution was warmed to 80° C. and stirred at 80° C. for 1 hour. The reaction solution was cooled to RT. The resulting solution diluted with water (15 mL), then extracted with EA (10 mL). The aqueous layer was adjusted to pH 7 with 28% ammonium hydroxide. The aqueous layer was concentrated under vacuum to reduce to one third. The slurry was filtered out. The filtrate was purified by Prep-HPLC with the following conditions: Column: XBridge Shield RP18 OBD Column 19×250 mm, 10 μm; Mobile Phase A: water (10 mmol/L NH$_4$HCO$_3$), Mobile Phase B: ACN; Flow rate: 20 mL/min; Gradient: 4% B to 19% B in 11 min; Detector: UV 254/210 nm; Retention time: 7.93 min to afford crude product. The crude product was re-purified by Prep-HPLC with the following conditions: Column: XBridge C18 OBD Prep Column 100 Å, 10 μm, 19 mm×250 mm; Mobile Phase A: water (0.05% TFA), Mobile Phase B: ACN; Flow rate: 20 mL/min; Gradient: 3% B to 10% B in 10 min; Detector: UV 254/220 nm; Retention time: 6.55 min to afford the title compound. LCMS [M+H–TFA]$^+$: 518; $^1$H NMR (300 MHz, CD$_3$OD) δ 8.44 (d, J=8.6 Hz, 1H), 7.73 (d, J=8.6 Hz, 1H), 4.03-3.72 (m, 4H), 3.55-3.40 (m, 1H), 3.40-3.30 (m, 2H), 3.21-3.05 (m, 7H), 2.97-2.82 (m, 3H), 2.72-2.68 (m, 1H). $^{19}$F NMR (282 MHz, CD$_3$OD) δ −77.15 (s, 3F).

EXAMPLES 130-133 were prepared in an analogous fashion as EXAMPLE 129, starting from (R)-tert-butyl (3-(4-bromo-2-(N,N-dibenzylsulfamoyl)-3-(2-(4-methoxybenzyl)-2H-tetrazol-5-yl) phenylsulfonamido)-2-((tert-butyldimethylsilyl)oxy)propyl)carbamate (REFERENCE EXAMPLE 60) and the requisite amines, which were prepared as described herein, or which were available from commercial sources.

| EX. | STRUCTURE | NAME | LC/MS [M + H]$^+$ |
|---|---|---|---|
| 130 | (structure shown) | N1-((R)-3-amino-2-hydroxypropyl)-4-((R)-3-((2-hydroxyethyl)amino)piperidin-1-yl)-3-(2H-tetrazol-5-yl)benzene-1,2-disulfonamide bis(2,2,2-trifluoroacetate) | 520 |

| EX. | STRUCTURE | NAME | LC/MS [M + H]+ |
|---|---|---|---|
| 131 | H₂N—\NH—S(=O)₂—[piperidine]—N—[benzene with tetrazole, SO₂NH₂, SO₂NH-CH₂-CH(OH)-CH₂-NH₂]  2 TFA | (R)-N1-(3-amino-2-hydroxypropyl)-4-(4-(N-(2-aminoethyl)sulfamoyl)piperidin-1-yl)-3-(2H-tetrazol-5-yl)benzene-1,2-disulfonamide | 583 |
| 132 | H₂N—CH(OH)—[piperidine]—N—[benzene with tetrazole, SO₂NH₂, SO₂NH-CH₂-CH(OH)-CH₂-NH₂] | 4-(4-(2-amino-1-hydroxyethyl)piperidin-1-yl)-N1-((R)-3-amino-2-hydroxypropyl)-3-(2H-tetrazol-5-yl)benzene-1,2-disulfonamide | 520 |
| 133 | HN—[spirocycle]—N—[benzene with tetrazole, SO₂NH₂, SO₂NH-CH₂-CH(OH)-CH₂-NH₂]  2 TFA | N1-((R)-3-amino-2-hydroxypropyl)-4-(3-(hydroxymethyl)piperazin-1-yl)-3-(2H-tetrazol-5-yl)benzene-1,2-disulfonamide di-trifluoroacetic acid | 502 |

EXAMPLE 130: ¹H NMR (300 MHz, CD₃OD) δ 8.40 (d, J=8.7 Hz, 1H), 7.65 (d, J=8.7 Hz, 1H), 3.96-3.88 (m, 1H), 3.77 (t, J=5.1 Hz, 2H), 3.39 (d, J=7.8 Hz, 1H), 3.16-2.99 (m, 5H), 2.96-2.82 (m, 2H), 2.77-2.64 (m, 3H), 2.08-1.99 (m, 1H), 1.63-1.59 (m, 1H), 1.49-1.35 (m, 1H), 1.32-1.16 (m, 1H), ¹⁹F NMR (282 MHz, CD₃OD) δ −77.00 (s, 6F). EXAMPLE 131: ¹H NMR (300 MHz, CD₃OD) δ 8.37 (d, J=8.7 Hz, 1H), 7.61 (d, J=8.7 Hz, 1H), 4.00-3.86 (m, 1H), 3.31-3.29 (m, 2H), 3.13-2.82 (m, 9H), 2.76-2.66 (m, 2H), 1.95-1.91 (m, 2H), 1.42-1.26 (m, 2H); ¹⁹F NMR (282 MHz, CD₃OD) δ −77.01 (s, 6F), EXAMPLE 132: ¹H NMR (300 MHz, CD₃OD) δ 8.36 (d, J=8.7 Hz, 1H), 7.61 (d, J=8.7 Hz, 1H), 3.98-3.89 (m, 1H), 3.46-3.34 (m, 1H), 3.16-2.82 (m, 7H), 2.79-2.58 (m, 3H), 1.73-1.70 (m, 1H), 1.47-1.38 (m, 2H), 0.96-0.92 (s, 2H). EXAMPLE 133: ¹H NMR (400 MHz, CD₃OD) δ 8.22 (d, J=9.0 Hz, 1H), 7.20 (d, J=9.0 Hz, 1H), 4.89-4.86 (m, 1H), 3.14-3.08 (m, 6H), 2.97-2.79 (m, 6H), 1.94-1.87 (m, 4H); ¹⁹F NMR (282 MHz, CD₃OD) δ −77.04 (s, 6F).

Example 134

4-(1-oxo-2,8-diazaspiro[4.5]decan-2-yl)-3-(2H-tetrazol-5-yl)benzene-1,2-disulfonamide

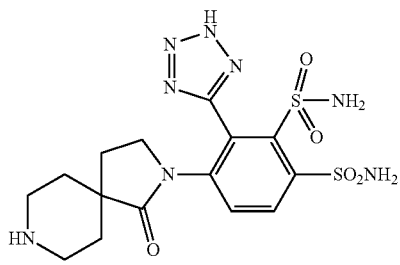 [SMILES: NS(=O)(=O)c1ccc(N2CCC3(CCNCC3)C2=O)c(-c2nn[nH]n2)c1S(N)(=O)=O]

Step A: tert-butyl 2-(3-(N,N-bis(4-methoxybenzyl)sulfamoyl)-2-(2-(4-methoxybenzyl)-2H-tetrazol-5-yl)-4-((2-(trimethylsilyl)ethyl)sulfonyl)phenyl)-1-oxo-2,8-diazaspiro[4.5]decane-8-carboxylate A mixture of 3-iodo-N,N-bis(4-methoxybenzyl)-2-(2-(4-methoxybenzyl)-2H-tetrazol-5-yl)-6-((2-(trimethylsilyl)ethyl)sulfonyl)benzenesulfonamide (REFERENCE EXAMPLE 37) (0.2 g, 0.228 mmol), tert-butyl 1-oxo-2,8-diazaspiro[4.5]decane-8-carboxylate (0.116 g, 0.457 mmol), Pd₂(dba)₃ (0.021 g, 0.023 mmol), xantphos (0.026 g, 0.046 mmol) and cesium carbonate (0.223 g, 0.685 mmol) in toluene (15 ml) was heated under N₂ overnight. The mixture was diluted with EtOAc. The organic layer was separated, washed with brine, dried over MgSO₄, and concentrated. The crude material was purified by silica gel chromatography (0-100% EtOAc in hexane) to give tert-butyl 2-(3-(N,N-bis(4-methoxybenzyl)sulfamoyl)-2-(2-(4-methoxybenzyl)-2H-tetrazol-5-yl)-4-((2-(trimethylsilyl)ethyl)sulfonyl)phenyl)-1-oxo-2,8-diazaspiro[4.5]decane-8-carboxylate. LCMS 1003.03.

Step B: tert-butyl 2-(3-(N,N-bis(4-methoxybenzyl)sulfamoyl)-2-(2-(4-methoxybenzyl)-2H-tetrazol-5-yl)-4-sulfamoylphenyl)-1-oxo-2,8-diazaspiro[4.5]decane-8-carboxylate Under N₂, to a solution of tert-butyl 2-(3-(N,N-bis(4-methoxybenzyl)sulfamoyl)-2-(2-(4-methoxybenzyl)-2H-tetrazol-5-yl)-4-((2-(trimethylsilyl)ethyl)sulfonyl)phenyl)-1-oxo-2,8-diazaspiro[4.5]decane-8-carboxylate (0.090 g, 0.090 mmol) in THF (40 ml) was added TBAF (9.13 ml, 9.13 mmol). The mixture was stirred at RT for 1 hour. Sodium acetate (1.873 g, 22.83 mmol) in water (10 ml) was added followed by solid (aminooxy)sulfonic acid (2.58 g, 22.83 mmol). The resultant mixture was stirred at RT under $N_2$ for 3 days. The reaction mixture was diluted with EtOAc. The organic layer was separated, washed with brine, dried ($MgSO_4$) and concentrated. The crude material was purified by silica gel chromatography (gradient 0-100% EtOAc in hexane) to give tert-butyl 2-(3-(N,N-bis(4-methoxybenzyl)sulfamoyl)-2-(2-(4-methoxybenzyl)-2H-tetrazol-5-yl)-4-sulfamoylphenyl)-1-oxo-2,8-diazaspiro[4.5]decane-8-carboxylate. LCMS 917.89

Step C: 4-(1-oxo-2,8-diazaspiro[4.5]decan-2-yl)-3-(2H-tetrazol-5-yl)benzene-1,2-disulfonamide A solution of tert-butyl 2-(3-(N,N-bis(4-methoxybenzyl)sulfamoyl)-2-(2-(4-methoxybenzyl)-2H-tetrazol-5-yl)-4-sulfamoylphenyl)-1-oxo-2,8-di azaspiro[4.5]decane-8-carboxylate (35 mg, 0.038 mmol)) and in dichloromethane (4 ml) was stirred at RT for 2 hours with 2 ml TFA, and concentrated. The residue was heated at 80° C. in 2 ml TFA in the presence of two drops of anisole for 40 minutes. TFA was removed, and the crude material was purified by reverse phase HPLC (5-50% acetonitrile in water with 0.05% TFA) to give solid 4-(1-oxo-2,8-diazaspiro[4.5]decan-2-yl)-3-(2H-tetrazol-5-yl)benzene-1,2-disulfonamide. LCMS 457.40.

Example 135

(R)-4-(4-(aminomethyl)piperidin-1-yl)-N1-(pyrrolidin-3-yl)-3-(2H-tetrazol-5-yl)benzene-1,2-disulfonamide dihydrochloride

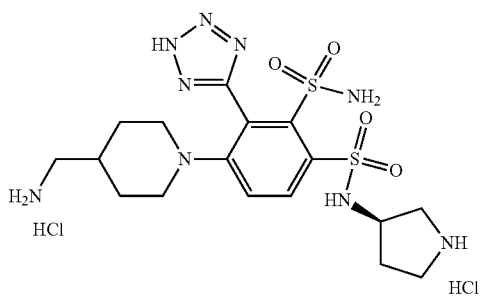 [SMILES: NCC1CCN(c2ccc(S(=O)(=O)N[C@@H]3CCNC3)c(S(N)(=O)=O)c2-c2nn[nH]n2)CC1 ; Cl ; Cl]

Step A: (R)-tert-butyl 3-(2-(N,N-bis(4-methoxybenzyl)sulfamoyl)-4-(4-(((tert-butoxycarbonyl) amino)methyl)piperidin-1-yl)-3-(2-(4-methoxybenzyl)-2H-tetrazol-5-yl)phenyl sulfonamido)pyrrolidine-1-carboxylate To a solution of (R)-tert-butyl 3-(2-(N,N-bis(4-methoxybenzyl)sulfamoyl)-4-iodo-3-(2-(4-methoxybenzyl)-2H-tetrazol-5-yl)phenylsulfonamido)pyrrolidine-1-carboxylate (REFERENCE EXAMPLE 40) (7.00 g, 7.29 mmol) in DMSO (45 mL) were added tert-butyl (piperidin-4-ylmethyl)carbamate (4.69 g, 21.88 mmol) and 1,4-diazabicyclo[2.2.2]octane (4.09 g, 36.5 mmol) at RT. The reaction solution was stirred at 110° C. for 16 hours. The resulting solution was diluted with water (200 mL), and then extracted with EA (3×80 mL). The combined organic layers were washed with brine (2×30 mL), dried over anhydrous $Na_2SO_4$ and filtered. The filtrate was concentrated under vacuum. The residue was purified by a silica gel column chromatography, eluting with 30% EA in PE to afford the title compound. LCMS [M+H]$^+$: 1046.

Step B: (R)-4-(4-(aminomethyl)piperidin-1-yl)-N1-(pyrrolidin-3-yl)-3-(2H-tetrazol-5-yl) benzene-1,2-disulfonamide To a solution of (R)-tert-butyl 3-(2-(N,N-bis(4-methoxybenzyl)sulfamoyl)-4-(4-(((tert-butoxycarbonyl)amino)methyl)piperidin-1-yl)-3-(2-(4-methoxybenzyl)-2H-tetrazol-5-yl)phenylsulfonamido)pyrrolidine-1-carboxylate (1.50 g, 1.43 mmol) in DCM (5 mL) was added TFA (15 mL) at 0° C. The reaction solution was stirred at RT for 1 hour. The resulting solution was concentrated under vacuum. The residue was co-evaporated with anisole (3×10 mL) under vacuum and used in the next step without further purification. The crude product was dissolved into TFA (10 mL). The solution was stirred at 80° C. for 1 hour. The resulting solution was concentrated under vacuum. The crude product was purified by Prep-HPLC using the following conditions: Column: XBridge Shield RP18 OBD Column 19×250 mm, 10 μm; Mobile Phase A: water (10 mmol/L $NH_4CO_3$), Mobile Phase B: ACN; Flow rate: 20 mL/min; Gradient: 0% B to 30% B in 9 min; Detector: UV 254/210 nm; Retention time: 7.8 min to afford the title compound. LCMS [M+H]$^+$: 486; $^1$H NMR (300 MHz, $CD_3OD+DCl$) δ 8.44 (d, J=8.7 Hz, 1H), 7.68 (d, J=8.8 Hz, 1H), 4.21-4.11 (m, 1H), 3.51-3.38 (m, 2H), 3.37-3.31 (m, 2H), 3.09 (d, J=12.2 Hz, 1H), 2.98 (d, J=12.1 Hz, 1H), 2.78-2.67 (m, 3H), 2.63-2.53 (m, 1H), 2.27-2.15 (m, 1H), 2.03-1.88 (m, 1H), 1.76-1.58 (m, 3H), 1.02-0.97 (m, 1H), 0.86-0.75 (m, 1H)

Step C: (R)-4-(4-(aminomethyl)piperidin-1-yl)-N1-(pyrrolidin-3-yl)-3-(2H-tetrazol-5-yl) benzene-1,2-disulfonamide dihydrochloride A solution of (R)-4-(4-(aminomethyl)piperidin-1-yl)-N1-(pyrrolidin-3-yl)-3-2H-tetrazol-5-yl)benzene-1,2-disulfonamide (4 mg, 0.008 mmol) in HCl (1 N, 0.2 mL) was lyophilized to afford the title compound. LCMS [M+H–2HCl]$^+$: 486; $^1$H NMR (300 MHz, $CD_3OD$) δ 8.44 (d, J=8.7 Hz, 1H), 7.68 (d, J=8.8 Hz, 1H), 4.21-4.11 (m, 1H), 3.46-3.35 (m, 4H), 3.09 (d, J=12.2 Hz, 1H), 2.98 (d, J=12.1 Hz, 1H), 2.88-2.73 (m, 3H), 2.68-2.52 (m, 1H), 2.27-2.15 (m, 1H), 2.03-1.88 (m, 1H), 1.76-1.58 (m, 3H), 1.10-0.90 (m, 1H), 0.86-0.75 (m, 1H).

Example 136

(R)—N1-(3-amino-2-hydroxypropyl)-4-((2-((2-hydroxyethyl)(methyl) amino)ethyl)(methyl)amino)-3-(2H-tetrazol-5-yl)benzene-1,2-disulfonamide

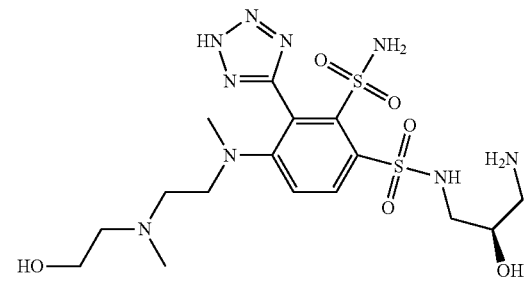 [SMILES: CN(CCO)CCN(C)c1ccc(S(=O)(=O)NC[C@H](O)CN)c(S(N)(=O)=O)c1-c1nn[nH]n1]

Step A: (R)-tert-butyl (2-((tert-butyldimethylsilyl)oxy)-3-(4-((2-((2-((tert-butyldimethylsilyl) oxy)ethyl)(methyl)amino)ethyl)methyl)amino)-2-(N,N-dibenzylsulfamoyl)-3-(2-(4-methoxybenzyl)-2H-tetrazol-5-yl)phenylsulfonamido)propyl)carbamate To a solution of (R)-tert-butyl (3-(4-bromo-2-(N,N-dibenzylsulfamoyl)-3-(2-(4-methoxybenzyl)-2H-tetrazol-5-yl)phenylsulfonamido)-2-((tert-butyldimethylsilyl)oxy)propyl)carbamate (REFERENCE EXAMPLE 51) (0.65 g, 0.67 mmol) in DME (0.80 mL) were added N1-(2-((tert-butyldimethylsilyl)oxy)ethyl)-N1,N2-dimethylethane-1,2-diamine (0.33 g, 1.34 mmol) and DIEA (0.35 mL, 2.01 mmol) at RT under argon atmosphere. The reaction mixture was stirred for 48 hours at 100° C. The resulting mixture was evaporated under vacuum. The residue was purified by a silica gel column chromatography, eluting with 65% EA in RE to afford the title compound. LCMS [M+1]$^+$: 1137.

Step B: (R)—N1-(3-amino-2-hydroxypropyl)-4-((2-((2-hydroxyethyl)(methyl)amino ethyl)methyl)amino)-3-(2H-tetrazol-5-yl)benzene-1,2-disulfonamide A solution of (R)-tert-butyl (2-((tert-butyldimethylsilyl)oxy)-3-(4-((2-((2-((tert-butyimethylsilyl)oxy)ethyl)methyl)amino)ethyl)(methyl)amino)-2-N,N-dibenzylsulfamoyl)-3-(2-(4-methoxybenzyl)-2H-tetrazol-5-yl)phenylsulfonamido)propyl)carbamate (0.14 g, 0.12 mmol) in TFA (2 mL) was stirred at RT for 0.5 hours. The resulting solution was concentrated under vacuum. The residue was co-evaporated with anisole (3×3 mL) and used in the next step without further purification. The crude product was dissolved in concentrated H$_2$SO$_4$ (2 mL) and stirred at 0° C. for 1 hour. Then water (2.0 mL) was added at 0° C. The reaction mixture was stirred at 80° C. for 3 hours. The resulting mixture was diluted with water (10 mL) and extracted with EA (3×20 mL). The pH of aqueous layer was adjusted to 7 with 28% ammonium hydroxide and concentrated under vacuum. The crude product was purified by Prep-HPLC with the following conditions: Column: X Bridge Shield RP18 OBD Column 19×250 mm, 10 µm; Mobile Phase A: water (10 mmoL/L NH$_4$HCO$_3$ with 0.1% NH$_3$·H$_2$O), Mobile Phase B: ACN Flow rate: 25 mL/min; Gradient: 5% B to 20% B in 8 min; Detector: UV 254/210 nm; Retention time: 5.07 min to afford the title compound. LCMS [M+1−2TFA]$^+$: 508; $^1$H NMR (300 MHz, D$_2$O) δ 8.15 (d, J=8.9 Hz, 1H), 7.52 (d, J=8.8 Hz, 1H), 3.89-3.82 (m, 1H), 3.65-3.62 (m, 2H), 3.18-2.91 (m, 5H), 2.84-2.70 (m, 3H), 2.48-2.40 (m, 5H), 2.35 (s, 3H).

Example 137 ammonium (R)-2-(4-(4-(N-(3-amino-2-hydroxypropyl)sulfamoyl)-3-sulfamoyl-2-(1H-tetrazol-5-yl)phenyl)piperazin-1-yl)acetate

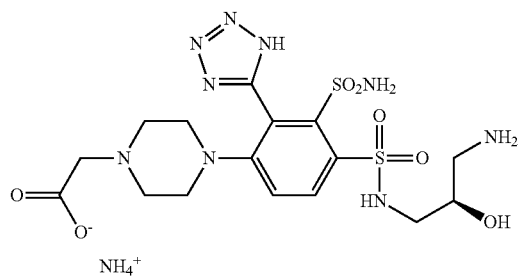 [SMILES: NC[C@@H](O)CNS(=O)(=O)c1ccc(N2CCN(CC(=O)[O-])CC2)c(-c2nnn[nH]2)c1S(N)(=O)=O ; [NH4+]]

Step A: (8)-ethyl 2-(4-(4-(N-(3-((tert-butoxycarbonyl)amino)-2-((tert-butyldimethylsilyl) oxy)propyl)sulfamoyl)-3-(N,N-dibenzylsulfamoyl)-2-(2-(4-methoxybenzyl)-2H-tetrazol-5-yl)phenyl)piperazin-1-yl)acetate The title compound was prepared as described for EXAMPLE 117 Step A using (R)-tert-butyl (3-(4-bromo-2-(N,N-dibenzylsulfamoyl)-3-(2-(4-methoxybenzyl)-2H-tetrazol-5-yl)phenylsulfonamido)-2-((tert-butyldimethylsilyl)oxy)propyl)carbamate to afford the title compound. LCMS [M+H]$^+$: 1062.

Step B: 2-(4-(4-(N—((R)-3-((tert-butoxycarbonyl)amino)-2-((tert-butyldimethylsilyl)oxy) propyl)sulfamoyl)-3-(N,N-dibenzylsulfamoyl)-2-(1-(4-methoxybenzyl)-1H-tetrazol-5-yl)phenyl)piperazin-1-yl)acetic acid To a solution of ethyl 2-(4-(4-(N—((R)-3-((tert-butoxycarbonyl)amino)-2-((tert-butyldimethylsilyl)oxy)propyl)sulfamoyl)-3-(N,N-dibenzylsulfamoyl)-2-(1-(4-methoxybenzyl)-1H-tetrazol-5-yl)phenyl)piperazin-1-yl)acetate (0.34 g, 0.32 mmol) in THF (2 mL) was added 1 M aqueous LiOH (2 mL, 2 mmol) at RT. The reaction mixture was stirred at RT for 2 hours. The pH of the resulting mixture was adjusted to 5 using 1 N aqueous HCl. The mixture was then extracted with EA (3×20 mL). The combined organic layers were washed with brine (20 mL), dried over anhydrous Na$_2$SO$_4$ and filtered. The filtrate was concentrated under reduced pressure to afford the title compound, which was used without further purification. LCMS [M+H]$^+$: 1034.

Step C: Ammonium (R)-2-(4-(4-(N-(3-amino-2-hydroxypropyl)sulfamoyl)-3-sulfamoyl-2-(1H-tetrazol-5-yl)phenyl)piperazin-1-yl)acetate The title compound was prepared as described for EXAMPLE 129 Step B using 2-(4-(4-(N—((R)-3-((tert-butoxycarbonyl)amino)-2-((tert-butyldimethylsilyl)oxy)propyl)sulfamoyl)-3-(N,N-dibenzylsulfamoyl)-2-(1-(4-methoxybenzyl)-1H-tetrazol-5-yl)phenyl)piperazin-1-yl) acetic acid to afford the crude product. The crude was purified by Prep-HPLC with the following conditions: Column: XBridge C18 OBD Prep Column 100 Å, 10 µm, 19 mm×250 mm; Mobile Phase A: water (10 mmol/L NH$_4$HCO$_3$), Mobile Phase B: ACN; Flow rate: 20 mL/min; Gradient: 1% B to 5% B in 1 min; Detector: UV 254 nm; Retention time: 3.22 min to give the title compound. LCMS (ESI) calc'd for C$_{16}$H$_{24}$N$_9$O$_7$S$_2^-$·H$_4$N$^+$ [M+H−NH$_3$]$^+$: 520, found 520; $^1$H NMR (400 MHz, CD$_3$OD+DCl) δ 8.50 (d, J=8.7 Hz, 1H), 7.83 (d, J=8.7 Hz, 1H), 4.11 (s, 2H), 4.00-3.96 (m, 1H) 3.56-3.47 (m, 2H), 3.30-3.20 (m, 4H), 3.18-3.08 (m, 3H), 2.94-2.88 (m, 3H).

EXAMPLES 138-144 were prepared in an analogous fashion as EXAMPLE 137, starting from (R)-tert-butyl(3-(4-bromo-2-(N,N-dibenzylsulfamoyl)-3-(2-(4-methoxybenzyl)-2H-tetrazol-5-yl) phenylsulfonamido)-2-((tert-butyldimethylsilyl)oxy)propyl)carbamate (REFERENCE EXAMPLE 51) and the requisite amines, which were prepared as described herein or which were available from commercial sources.

| EX. | STRUCTURE | NAME | LC/MS [M + H]+ |
|---|---|---|---|
| 138 | 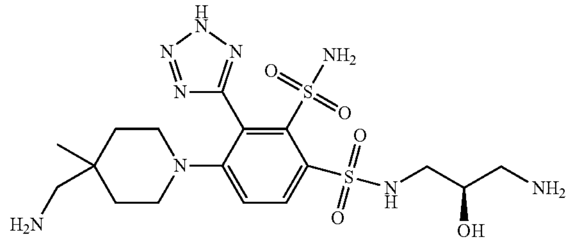 [SMILES: CC1(CN)CCN(c2ccc(S(=O)(=O)NC[C@H](O)CN)c(S(N)(=O)=O)c2-c2nn[nH]n2)CC1] | (R)-N1-(3-amino-2-hydroxypropyl)-4-(4-(aminomethyl)-4-methylpiperidin-1-yl)-3-(2H-tetrazol-5-yl)benzene-1,2-disulfonamide | 504 |
| 139 | 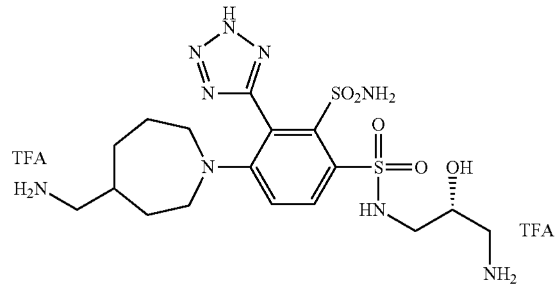 [SMILES: NCC1CCCN(c2ccc(S(=O)(=O)NC[C@H](O)CN)c(S(N)(=O)=O)c2-c2nn[nH]n2)CC1 ; "TFA"] | N1-((R)-3-amino-2-hydroxypropyl)-4-(4-(aminomethyl)azepan-1-yl)-3-(2H-tetrazol-5-yl)benzene-1,2-disulfonamide bis(2,2,2-trifluoroacetate) | 504 |
| 140 | 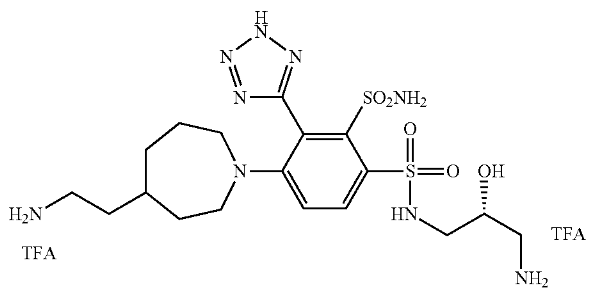 [SMILES: NCCC1CCCN(c2ccc(S(=O)(=O)NC[C@H](O)CN)c(S(N)(=O)=O)c2-c2nn[nH]n2)CC1 ; "TFA"] | N1-((R)-3-amino-2-hydroxypropyl)-4-(4-(2-aminoethyl)azepan-1-yl)-3-(2H-tetrazol-5-yl)benzene-1,2-disulfonamide bis(2,2,2-trifluoroacetate) | 518 |
| 141 | 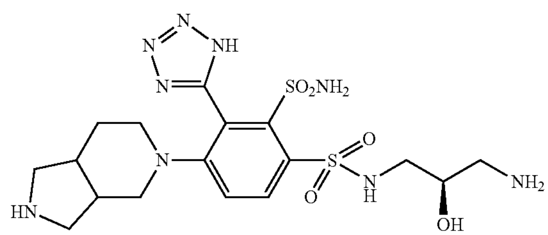 [SMILES: NC[C@@H](O)CNS(=O)(=O)c1ccc(N2CCC3CNCC3C2)c(-c2nnn[nH]2)c1S(N)(=O)=O] | N1-((R)-3-amino-2-hydroxypropyl)-4-(hexahydro-1H-pyrrolo[3,4-c]pyridin-5(6H)-yl)-3-(1H-tetrazol-5-yl)benzene-1,2-disulfonamide | 502 |
| 142 | 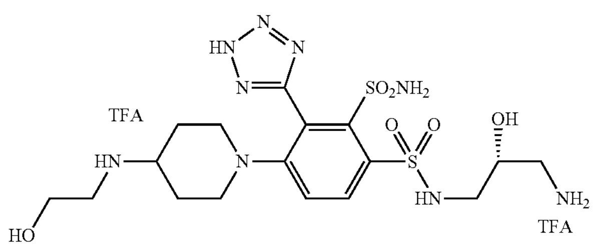 [SMILES: NC[C@@H](O)CNS(=O)(=O)c1ccc(N2CCC(NCCO)CC2)c(-c2nn[nH]n2)c1S(N)(=O)=O ; "TFA"] | (R)-N1-(3-amino-2-hydroxypropyl)-4-(4-((2-hydroxyethyl)amino)piperidin-1-yl)-3-(2H-tetrazol-5-yl)benzene-1,2-disulfonamide bis(2,2,2-trifluoroacetate) | 520 |
| 143 | 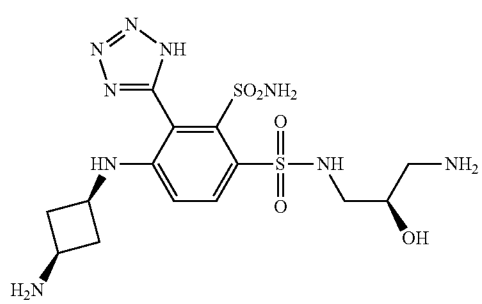 [SMILES: NC[C@@H](O)CNS(=O)(=O)c1ccc(N[C@H]2C[C@@H](N)C2)c(-c2nnn[nH]2)c1S(N)(=O)=O] | N1-((R)-3-amino-2-hydroxypropyl)-4-(((1s,3S)-3-aminocyclobutyl)amino)-3-(1H-tetrazol-5-yl)benzene-1,2-disulfonamide | 462 |

| EX. | STRUCTURE | NAME | LC/MS [M + H]⁺ |
|---|---|---|---|
| 144 | 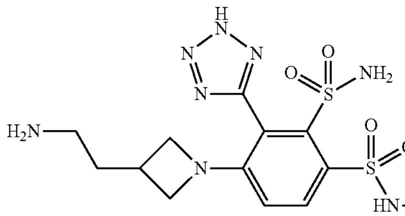 | (R)-N1-(3-amino-2-hydroxypropyl)-4-(3-(2-aminoethyl)azetidin-1-yl)-3-(2H-tetrazol-5-yl)benzene-1,2-disulfonamide | 476 |

EXAMPLE 138: $^1$H NMR (400 MHz, CD$_3$OD): δ 8.26 (d, J=8.7 Hz, 1H), 7.43 (d, J=8.8 Hz, 1H), 3.79-3.72 (m, 1H), 3.10-3.02 (m, 2H), 2.88-2.69 (m, 6H), 2.63-2.57 (m, 2H), 1.25-1.18 (m, 4H), 0.98 (s, 3H). EXAMPLE 139: $^1$H NMR (300 MHz, D$_2$O): δ 8.17 (d, J=9.0 Hz, 1H), 7.57 (d, J=9.0 Hz, 1H), 4.02-3.85 (m, 1H), 3.19-2.76 (m, 8H), 2.68 (d, J=6.8 Hz, 2H), 1.68-1.13 (m, 5H), 1.00-0.92 (m, 2H); $^{19}$F NMR (376 MHz, D$_2$O): δ −75.61 (s, 6F). EXAMPLE 140: $^1$H NMR (400 MHz, D$_2$O): δ 8.16 (d, J=9.0 Hz, 1H), 7.53 (d, J=9.0 Hz, 1H), 4.00-3.91 (m, 1H), 3.18-2.78 (m, 10H), 1.58-1.20 (m, 7H), 1.08-0.71 (m, 2H); $^{19}$F NMR (376 MHz, D$_2$O): δ −75.62 (s, 6F). EXAMPLE 141: $^1$H NMR (400 MHz, CD$_3$OD+DCl): δ 8.46 (d, J=8.8 Hz, 1H), 7.78 (d, J=8.4 Hz, 1H), 3.98-3.94 (m, 1H), 3.29-3.27 (m, 1H), 3.17-3.06 (m, 5H), 3.03-2.98 (m, 3H), 2.95-2.88 (m, 1H), 2.83-2.77 (m, 1H), 2.62-2.55 (m, 1H), 2.36-2.30 (m, 2H), 1.65-1.60 (m, 1H), 1.28-1.16 (m, 1H). EXAMPLE 142: $^1$H NMR (300 MHz, CD$_3$OD+DCl) δ 8.42 (d, J=8.7 Hz, 1H), 7.66 (d, J=9 Hz, 1H), 3.98-3.92 (m, 1H), 3.78-3.74 (m, 2H), 3.17-3.10 (m, 814), 2.99-2.88 (m, 1H), 2.82-2.77 (m, 2H), 2.03-2.00 (m, 2H), 1.31-1.16 (m, 2H). $^{19}$F NMR (376 MHz, CD$_3$OD): δ −73.09 (s, 6F). EXAMPLE 143: $^1$H NMR (300 MHz, CD$_3$OD+DCl) δ 8.25 (d, J=9.1 Hz, 1H), 6.91 (d, J=9.1 Hz, 1H), 4.33-4.29 (m, 1H), 4.08-3.73 (m, 2H), 3.15-3.10 (m, 1H), 3.09-3.02 (m, 2H), 2.97-2.85 (m, 1H), 2.65-2.56 (m, 2H), 2.48-2.29 (m, 2H). EXAMPLE 144: $^1$H NMR (300 MHz, CD$_3$OD) δ 8.18 (d, J=9.1 Hz, 1H), 6.80 (d, J=9.1 Hz, 1H), 3.58-3.50 (m, 2H), 3.19-3.01 (m, 5H), 2.91-2.73 (m, 3H), 2.65-2.50 (m, 1H), 1.85-1.77 (m, 2H), 1.28-1.25 (m, 1H).

Example 145

(R)—N1-(3-amino-2-hydroxypropyl)-4-(4-(3-aminopropanoyl)piperazin-1-yl)-3-(2H-tetrazol-5-yl)benzene-1,2-disulfonamide

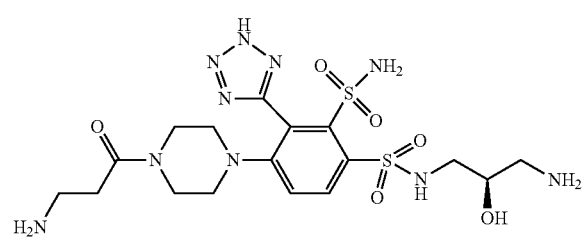 [SMILES: NCCC(=O)N1CCN(c2ccc(S(=O)(=O)NC[C@H](O)CN)c(S(N)(=O)=O)c2-c2nn[nH]n2)CC1]

Step A: tert-butyl (R)-(3-((4-(4-(3-(((benzyloxy)carbonyl)amino)propanoyl)piperazin-1-yl-2-(N,N-bis(4-methoxybenzyl)sulfamoyl)-3-(2-(4-methoxybenzyl)-2H-tetrazol-5-yl)phenyl)sulfonamido)-2-((tert-butyldimethylsilyl)oxy)propyl)carbamate To a solution of (R)-tert-butyl (3-(2-(N,N-bis(4-methoxybenzyl)sulfamoyl)-4-iodo-3-(2-(4-methoxybenzyl)-2H-tetrazol-5-yl)phenylsulfonamido)-2-((tert-butyldimethylsilyl)oxy)propyl)carbamate (REFERENCE EXAMPLE 45) (0.65 g, 0.60 mmol) in toluene (10 mL) were added benzyl (3-oxo-3-(piperazin-1-yl)propyl)carbamate (0.53 g, 1.81 mmol, prepared as described in US 2007/55065), Cs$_2$CO$_3$ (0.59 g, 1.81 mmol) and RAC-BINAP-Pd-G3 (0.12 g, 0.12 mmol) at RT. The reaction mixture was degassed with nitrogen three times and stirred at 80° C. for 40 hours under nitrogen. After cooling to RT, the resulting mixture was concentrated under vacuum. The residue was diluted with 15 mL of water, and then extracted with EA (3×10 mL). The organic layers were combined, washed with brine (2×20 mL), dried over anhydrous Na$_2$SO$_4$ and filtered. The filtrate was concentrated under vacuum. The residue was purified by silica gel column chromatography, eluting with 80% EA in PE to afford the title compound: LCMS [M+H]⁺: 1242.

Step B: (R)—N1-(3-amino-2-hydroxypropyl)-4-(4-(3-aminopropanoyl)piperazin-1-yl)-3-(2H-tetrazol-5-yl)benzene-1,2-disulfonamide The title compound was prepared as described for EXAMPLE 117 Step B using tert-butyl (R)-(3-((4-(4-(3-(((benzyloxy)carbonyl)amino)propanoyl)piperazin-1-yl)-2-(N,N-bis(4-methoxybenzyl)sulfamoyl)-3-(2-(4-methoxybenzyl)-2H-tetrazol-5-yl)phenyl)sulfonamido)-2-((tert-butyldimethylsilyl)oxy)propyl)carbamate to afford the crude product, which was purified by Prep-HPLC with the following conditions: Column: XBridge C18 OBD Prep Column 100 Å, 10 μm, 19 mm×250 mm; Mobile Phase A: water (10 mmol/L NH$_4$HCO$_3$), Mobile Phase B: ACN; Flow rate: 20 mL/min; Gradient: 1% B to 31% B in 11 min; Detector: UV 254/210 nm; Retention time: 9.42 min to give the title compound. LCMS [M+H]⁺: 533 $^1$H NMR (300 MHz, CD$_3$OD) δ 8.25 (d, J=8.8 Hz, 1H), 7.39 (d, J=8.8 Hz, 1H), 3.73-3.68 (m, 1H), 3.36-3.33 (m, 2H), 3.22-3.15 (m, 2H), 3.13-2.94 (m, 4H), 2.88-2.75 (m, 5H), 2.72-2.65 (m, 1H), 2.60-2.52 (m, 2H).

EXAMPLES 146-147 were prepared in an analogous fashion as EXAMPLE 145, starting from (R)-tert-butyl (3-(2-(N,N-bis(4-methoxybenzyl)sulfamoyl)-4-iodo-3-(2-(4-methoxybenzyl)-2H-tetrazol-5-yl)phenylsulfonamido)-2-((tert-butyldimethylsilyl)oxy)propyl)carbamate (REFER- ENCE EXAMPLE 45) and the requisite amines, which were prepared as described herein, or were available from commercial sources.

| EX. | STRUCTURE | NAME | LC/MS [M + H]+ |
|---|---|---|---|
| 146 | 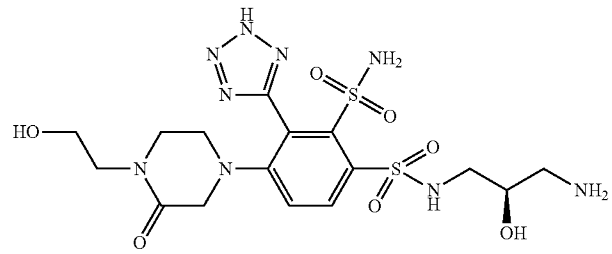 [SMILES: NC[C@@H](O)CNS(=O)(=O)c1ccc(N2CCN(CCO)C(=O)C2)c(-c2nn[nH]n2)c1S(N)(=O)=O] | (R)-N1-(3-amino-2-hydroxypropyl)-4-(4-(2-hydroxyethyl)-3-oxopiperazin-1-yl)-3-(2H-tetrazol-5-yl)benzene-1,2-disulfonamide | 520 |
| 147 | 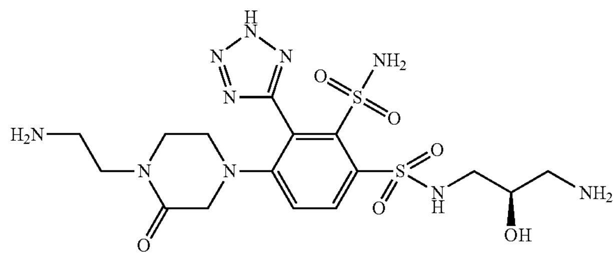 [SMILES: NCCN1CCN(c2ccc(S(=O)(=O)NC[C@H](O)CN)c(S(N)(=O)=O)c2-c2nn[nH]n2)CC1=O] | (R)-N1-(3-amino-2-hydroxypropyl)-4-(4-(2-aminoethyl)-3-oxopiperazin-1-yl)-3-(2H-tetrazol-5-yl)benzene-1,2-disulfonamide | 519 |

EXAMPLE 146: $^1$H NMR (300 MHz, D$_2$O): δ 8.22 (d, J=8.9 Hz, 1H), 7.44 (d, J=8.9 Hz, 1H), 3.94-3.90 (m, 1H), 3.65-3.60 (m, 4H), 3.42-3.35 (m, 2H), 3.24-3.01 (m, 3H), 2.95-2.79 (m, 5H). EXAMPLE 147: $^1$H NMR (400 MHz, CD$_3$OD+DCl): δ 8.47 (d, J=8.7 Hz, 1H), 7.81 (d, J=8.8 Hz, 1H), 4.01-3.91 (m, 1H), 3.65-3.55 (m, 4H), 3.26-3.02 (m, 9H), 2.94-2.89 (m, 1H).

Example 148

4-(3-hydroxy-2-oxopiperidin-1-yl)-N1-((R)-pyrrolidin-3-yl)-3-(2H-tetrazol-5-yl)benzene-1,2-disulfonamide

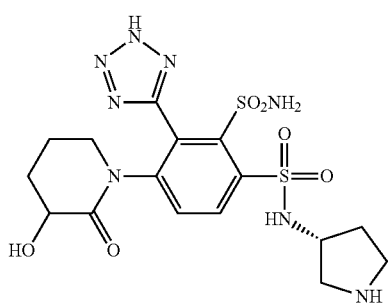 [SMILES: NS(=O)(=O)c1c(S(=O)(=O)N[C@@H]2CCNC2)ccc(N2CCCC(O)C2=O)c1-c1nn[nH]n1]

Step A: 3-(3-((Tert-butyldimethylsilyl)oxy)-2-oxopiperidin-1-yl)-N,N-bis(4-methoxybenzyl)-2-(2-(4-methoxybenzyl)-2H-tetrazol-5-yl)-6-((2-(trimethylsilyl)ethyl)sulfonyl) benzenesulfonamide To a solution of 3-iodo-N,N-bis(4-methoxybenzyl)-2-(2-(4-methoxybenzyl)-2H-tetrazol-5-yl)-6-((2-(trimethylsilyl)ethyl)sulfonyl)benzenesulfonamide (REFERENCE EXAMPLE 40) (3.50 g, 4.00 mmol) in toluene (30 mL) were added 3-((tert-butyldimethylsilyl)oxy) piperidin-2-one (1.40 g, 5.99 mmol), Pd$_2$(dba)$_3$ adduct CHCl$_3$ (0.62 g, 0.60 mmol), xantphos (0.69 g, 1.20 mmol) and Cs$_2$CO$_3$ (3.9 g, 11.99 mmol) at RT. The mixture was degassed with nitrogen three times and stirred for 16 hours at 100° C. under nitrogen. After cooling to RT, the resulting mixture was concentrated under vacuum. The residue was dissolved in EA (50 mL), washed with brine (3×50 mL), dried over anhydrous Na$_2$SO$_4$ and filtered. The filtrate was concentrated under vacuum. The residue was purified by a silica gel column chromatography, eluting with 50% EA in PE to afford the title compound. LCMS [M+H]+: 977.

Step B: 2-(N,N-bis(4-methoxybenzyl)sulfamoyl)-4-(3-hydroxy-2-oxopiperidin-1-yl)-3-(2-(4-methoxybenzyl)-2H-tetrazol-5-yl)benzenesulfinic acid To a solution of 3-(3-((tert-butyldimethylsilyl)oxy)-2-oxopiperidin-1-yl)-N,N-bis(4-methoxybenzyl)-2-(2-(4-methoxybenzyl)-2H-tetrazol-5-yl)-6-((2-(trimethylsilyl)ethyl)sulfonyl)benzenesulfonamide (0.50 g, 0.51 mmol) in THF (8 mL) was added TBAF.3H$_2$O (0.48 g, 1.53 mmol). The reaction solution was stirred for 1 hour at RT. The resulting mixture was concentrated under vacuum. The residue was diluted with EA (50 mL), washed with aqueous sat'd KHSO$_4$ (3×50 mL), brine (3×50 mL), dried over anhydrous Mg$_2$SO$_4$ and filtered. The filtrate was concentrated under vacuum to afford the title compound, which was used in the next step without further purification: LCMS [M+1]+: 763.

Step C: (3R)-tert-butyl 3-(2-(N,N-bis(4-methoxybenzyl)sulfamoyl)-4-(3-hydroxy-2-oxopiperidin-1-yl)-3-(2-(4-methoxybenzyl)-2H-tetrazol-5-yl)phenylsulfonamido) pyrrolidine-1-carboxylate To a solution of 2-(N,N-bis(4-methoxybenzyl)sulfamoyl)-4-(3-hydroxy-2-oxopiperidin-1-yl)-3-(2-(4-methoxybenzyl)-2H-tetrazol-5-yl)benzenesulfinic acid (0.40 g, 0.52 mmol) in THF (6 mL) were added (R)-tert-butyl 3-aminopyrrolidine-1-carboxylate (0.19 g, 1.05 mmol) and TEA (0.16 g, 1.57 mmol) at 0° C. and stirred for 10 minutes. Then NCS (0.11 g, 0.79 mmol) was added and the mixture was stirred at for 1.5 hours under nitrogen. The resulting mixture was concentrated under vacuum. The residue was dissolved in EA (30 mL), washed with brine (3×20 mL), dried over anhydrous $Na_2SO_4$ and filtered. The filtrate was concentrated under vacuum. The residue was purified by silica gel column chromatography, eluting with 70% EA in PE to afford the title compound. LCMS [M+1]$^+$: 947.

Step D: 4-(3-Hydroxy-2-oxopiperidin-1-yl)-N1-((R)-pyrrolidin-3-yl)-3-(2H-tetrazol-5-yl) benzene-1,2-disulfonamide The title compound was prepared as described for EXAMPLE 117 Step B using (3R)-tert-butyl3-(2-(N,N-bis(4-methoxybenzyl)sulfamoyl)-4-(3-hydroxy-2-oxopiperidin-1-yl)-3-(2-(4-methoxybenzyl)-2H-tetrazol-5-yl)phenylsulfonamido) pyrrolidine-1-carboxylate to afford the crude product. The crude product was purified by Prep-HPLC with the following conditions: Column: X Bridge Prep C18 OBD Column 10 μm, 19×250 mm; Mobile Phase A: water with 10 mmol/L $NH_4HCO_3$, Mobile Phase B: ACN; Flow rate: 25 ML/min; Gradient: 1% B to 30% B in 8 min; Detector: UV 254/220 nm. Retention time: 10.26 min to give the title compound. LCMS [M+1]$^+$: 487; $^1$H NMR (300 MHz, $CD_3OD$ DCl) δ 8.63 (d, J=8.4 Hz, 1H), 8.03-7.95 (m, 1H), 4.21-4.14 (m, 1H), 4.07-3.99 (m, 1H) 3.78-3.62 (m, 3.62-3.31 (m, 5H), 2.25-2.14 (m, 1H), 2.07-1.72 (m, 4H), 1.69-1.13 (m, 1H).

Example 149

4-(4-(aminomethyl)-2-oxopiperidin-1-yl-N1-((R)-pyrrolidin-3-yl)-3-(2H-tetrazol-5-yl)benzene-1,2-disulfonamide

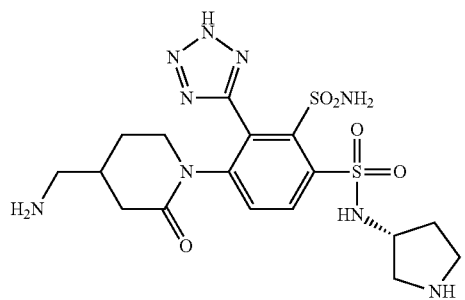 [SMILES: NCC1CCN(c2ccc(S(=O)(=O)N[C@@H]3CCNC3)c(S(N)(=O)=O)c2-c2nn[nH]n2)C(=O)C1]

Step A: 3-(4-((1,3-Dioxoisoindolin-2-yl)methyl)-2-oxopiperidin-1-yl)-N,N-bis(4-methoxy benzyl)-2-(2-(4-methoxybenzyl)-2H-tetrazol-5-yl)-6-((2-(trimethylsilyl)ethyl)sulfonyl)benzenesulfonamide The title compound was prepared as described for EXAMPLE 148 step A using ((2-oxopiperidin-4-yl)methyl) isoindoline-1,3-dione. LCMS [M+1]$^+$: 1006.

Step B: 2-(N,N-bis(4-methoxybenzyl)sulfamoyl)-4-(4-((1,3-dioxoisoindolin-2-yl)methyl)-2-oxopiperidin-1-yl)-3-(2-(4-methoxybenzyl)-2H-tetrazol-5-yl) benzenesulfinic acid The title compound was prepared as described for EXAMPLE 148 step B using 3-iodo-N,N-bis(4-methoxybenzyl)-2-(2-(4-methoxybenzyl)-2H-tetrazol-5-yl)-6-((2-(trimethylsilyl)ethyl)sulfonyl)benzenesulfonamide. LCMS [M+1]$^+$: 906.

Step C: (3R)-tert-butyl 3-(2-(N,N-bis(4-methoxybenzyl)sulfamoyl)-4-(4-((1,3-dioxoisoindolin-2-yl) methyl)-2-oxopiperidin-1-yl)-3-(2-(4-methoxybenzyl-2H-tetrazole-5-yl)phenylsulfonamido) pyrrolidine-1-carboxylate The title compound was prepared as described for EXAMPLE 148 step C using 2-(N,N-bis(4-methoxybenzyl)sulfamoyl)-4-(4-((1,3-dioxoisoindolin-2-yl)methyl)-2-oxopiperidin-1-yl)-3-(2-(4-methoxybenzyl)-2H-tetrazol-5-yl)benzenesulfinic acid. LCMS [M+1]$^+$: 1090.

Step D: (3R)-tert-butyl 3-(4-(4-(aminomethyl)-2-oxopiperidin-1-yl)-2-(N,N-bis(4-methoxybenzyl) sulfamoyl)-3-(2-(4-methoxybenzyl)-2H-tetrazol-5-yl)phenyl sulfonamido)pyrrolidine-1-carboxylate To a solution of (3R)-tert-butyl 3-(2-(N,N-bis(4-methoxybenzyl)sulfamoyl)-4-(4-((1,3-dioxoisoindolin-2-yl)methyl)-2-oxopiperidin-1-yl)-3-(2-(4-methoxybenzyl)-2H-tetrazol-5-yl)phenylsulfonamido)pyrrolidine-1-carboxylate (0.20 g, 0.18 mmol) in EtOH (10 mL) was added hydrazine hydrate (18 mg, 0.36 mmol) at RT. The reaction mixture was stirred at 70° C. for 2 hours. After cooling to RT, the resulting mixture was filtered. The filtrate was concentrated under vacuum. The residue was dissolved in DMF (2 mL) and purified by Prep-HPLC with the following conditions: Column: XBridge C18 OBD prep column, 10 μm, 19×250 mm; Mobile Phase A: water (10 mmol/L $NH_4HCO_3$), Mobile Phase B: ACN; Flow rate: 100 mL/min; Gradient: 35% B to 65% B in 11 min; Detector: UV 254/210 nm. Retention time: 9.28 min to afford the title compound. LCMS [M+1]$^+$: 960.

Step E: 4-(4-(Aminomethyl)-2-oxopiperidin-1-yl)-N1-((R)-pyrrolidin-3-yl)-3-(2H-tetrazol-5-yl)benzene-1,2-disulfonamide The title compound was prepared as described for EXAMPLE 117 Step B using (3R)-tert-butyl 3-(4-(4-(aminomethyl)-2-oxopiperidin-1-yl)-2-(N,N-bis(4-methoxy benzyl)sulfamoyl)-3-(2-(4-methoxybenzyl)-2H-tetrazol-5-yl) phenylsulfonamido) pyrrolidine-1-carboxylate to afford the crude product. The crude product was purified by Prep-HPLC with the following conditions: Column: X Bridge Prep C18 OBD Column 10 μm, 19×250 mm; Mobile Phase A: water with 10 mmol/L $NH_4HCO_3$, Mobile Phase B: ACN; Flow rate: 25 mL/min; Gradient: 1% B to 35% B in 11 min; Detector: UV 254/220 nm; Retention time: 8.95 min to give the title compound. LCMS [M+1]$^+$: 500; $^1$H NMR (300 MHz, $D_2O$) δ 8.37 (d, J=8.4 Hz, 1H), 7.70 (d, J=8.6 Hz, 1H), 4.01-3.98 (m, 1H), 3.62-2.91 (m, 5H), 2.84-2.79 (m, 1H), 2.70-2.59 (m, 1H), 2.44-2.28 (m, 1H) 2.23-2.10 (m, 2H), 1.92-1.67 (m, 3H), 1.59-1.49 (m, 1H), 0.98-0.72 (m, 1H).

Example 150

4-(3-(aminooxy-2-oxopiperidin-1-yl)-N1-((R)-pyrrolidin-3-yl)-3-(2H-tetrazol-5-yl)benzene-1,2-disulfonamide

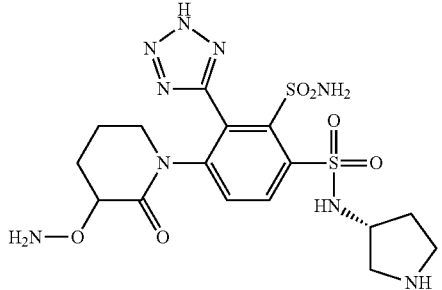 [SMILES: NOC1CCCN(c2ccc(S(=O)(=O)N[C@@H]3CCNC3)c(S(N)(=O)=O)c2-c2nn[nH]n2)C1=O]

Step A: (3R)-tert-butyl 3-(2-(N,N-bis(4-methoxybenzyl)sulfamoyl)-4-(3-((1,3-dioxoisoindolin-2-yl)oxy)-2-oxopiperidin-1-yl)-3-(2-(4-methoxybenzyl)-2H-tetrazol-5-yl)phenylsulfonamido)pyrrolidine-1-carboxylate To a solution of (3R)-tert-butyl 3-(2-(N,N-bis(4-methoxybenzyl)sulfamoyl)-4-(3-hydroxy-2-oxopiperidin-1-yl)-3-(2-(4-methoxybenzyl)-2H-tetrazol-5-yl)phenyl sulfonamido) pyrrolidine-1-carboxylate (REFERENCE EXAMPLE 40) (1.30 g, 1.37 mmol) and 2-hydroxyisoindoline-1,3-dione (0.45 g, 2.75 mmol) in toluene (15 mL) were added Ph$_3$P (0.72 g, 2.75 mmol) and DEAD (0.44 mL, 2.75 mmol) at RT. The reaction mixture was degassed with nitrogen three times and stirred at RT for 16 hours. The resulting mixture was diluted with EA (50 mL), washed with water (3×30 mL) and brine (30 mL). The separated organic phase was dried over anhydrous Na$_2$SO$_4$ and filtered. The filtrate was concentrated under vacuum. The residue was purified by a silica gel column chromatography, eluting with 60% EA in PE to afford the title compound. LCMS [M+1]$^+$: 1092.

Step B: (3R)-tert-butyl 3-(4-(3-(aminooxy)-2-oxopiperidin-1-yl)-2-(N,N-bis(4-methoxy benzyl)sulfamoyl)-3-(2-(4-m oxybenzyl)-2H-tetrazol-5-yl)phenylsulfonamido) pyrrolidine-1-carboxylate The title compound was prepared as described for EXAMPLE 149 step D using (3R)-tert-butyl 3-(2-(N,N-bis (4-methoxybenzyl)sulfamoyl)-4-(3-((1,3-dioxoisoindolin-2-yl)oxy)-2-oxopiperidin-1-yl)-3-(2-(4-methoxybenzyl)-2H-tetrazol-5-yl)phenyl sulfonamido)pyrrolidine-1-carboxylate to afford the title compound, which was used in the next step without further purification: LCMS [M+1]$^+$: 962.

Step C: 4-(3-(Aminooxy)-2-oxopiperidin-1-yl)-N1-((R)-pyrrolidin-3-yl)-3-(2H-tetrazol-5-yl) benzene-1, 2-disulfonamide The title compound was prepared as described for EXAMPLE 117 Step B using (3R)-tert-butyl 3-(4-(3-(aminooxy)-2-oxopiperidin-1-yl)-2-(N,N-bis(4-methoxybenzyl)sulfamoyl)-3-(2-(4-methoxybenzyl)-2H-tetrazol-5-yl)phenylsulfonamido)pyrrolidine-1-carboxylate to afford the crude product, which was purified by Prep-HPLC with the following conditions: Column: X Bridge Prep C18 OBD Column, 10 μm, 19×250 mm; Mobile Phase A: water (10 mmol/L NH$_4$HCO$_3$), Mobile Phase B: ACN; Flow rate: 25 mL/min; Gradient: 0% B to 30% B in 16 min; Detector: UV, 254/220 nm; Retention time: 13.13 min to give the title compound. LCMS [M+1]$^+$: 502; $^1$H NMR (300 MHz, CD$_3$OD+DCl) δ 8.69 (d, J=8.5 Hz, 1H), 8.14-8.07 (m, 1H), 4.63-4.57 (m, 0.5H), 4.26-4.22 (m, 1.5H), 3.70-3.55 (m, 1H), 3.53-3.30 (m, 4H), 2.26-2.20 (m, 2H), 2.05-1.94 (m, 3H), 1.93-1.25 (m, 2H).

Example 151

(R)-4-(2,3-di oxopiperidin-1-yl)-N1-(pyrrolidin-3-yl)-3-(2H-tetrazol-5-yl) benzene-1,2-disulfonamide

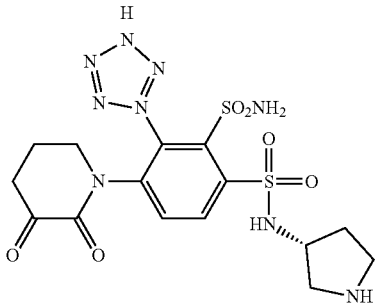

Step A: (R)-tert-butyl 3-(2-(N,N-bis(4-methoxybenzyl)sulfamoyl)-4-(2,3-dioxopiperidin-1-yl)-3-(2-(4-methoxybenzyl)-2H-tetrazol-5-yl)phenylsulfonamido)pyrrolidine-1-carboxylate To a solution of (3R)-tert-butyl 3-(2-(N,N-bis(4-methoxybenzyl)sulfamoyl)-4-(3-hydroxy-2-oxopiperidin-1-yl)-3-(2-(4-methoxybenzyl)-2H-tetrazol-5-yl)phenyl sulfonamido) pyrrolidine-1-carboxylate (0.3 g, 0.31 mmol) in DCM (6 mL) was added Dess-Martin Periodinane (0.27 g, 0.63 mmol) at RT. The reaction mixture was stirred for 16 hours at RT. The resulting mixture was filtered and the filtrate was concentrated under vacuum. The residue was dissolved in EA (30 mL). The organic layer was washed with brine (3×20 mL), dried over anhydrous Na$_2$SO$_4$ and filtered. The filtrate was concentrated under vacuum. The residue was purified by a silica gel column chromatography, eluting with 65% EA in RE to afford the title compound. LC [M+1]$^+$: 945.

Step B: (R)-4-(2,3-dioxopiperidin-1-yl)-N1-(pyrrolidin-yl)-3-(2H-tetrazol-5-yl) benzene-1,2-disulfonamide The title compound was prepared as described for EXAMPLE 117 Step B using (R)-tert-butyl 3-(2-(N,N-bis (4-methoxybenzyl)sulfamoyl)-4-(2,3-dioxopiperidin-1-yl)-3-(2-(4-methoxybenzyl)-2H-tetrazol-5-yl)phenylsulfonamido)pyrrolidine-1-carboxylate to afford the crude product. The crude product was purified by Prep-HPLC with the following conditions: Column: X Bridge Prep C18 OBD Column 10 μm, 19×250 mm; Mobile Phase A: water (10 mmol/L NH₄HCO₃), Mobile Phase B: ACN; Flow rate: 25 mL/min; Gradient: 3% B to 15% B in 9 min; Detector: UV 254/220 nm; Retention time: 7.65 min to give the title compound. LCMS [M+1]⁺: 485; ¹H NMR (300 MHz, CD₃OD+DCl) δ 8.77-8.63 (m, 1H), 8.22-7.94 (m, 1H), 4.34-4.18 (m, 1H), 3.96-3.64 (m, 1H), 3.60-3.35 (m, 5H), 2.36-2.16 (m, 2H), 2.14-1.50 (m, 4H).

Example 152

(R)-4-(3-(hydroxyimino)-2-oxopiperidin-1-yl)-N1-(pyrrolidin-3-yl)-3-(2H-tetrazol-5-yl)benzene-1,2-disulfonamide

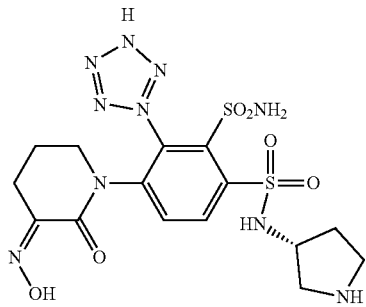

Step A: (R)-tert-butyl 3-(2-(N,N-bis(4-methoxybenzyl)sulfamoyl)-4-(3-(hydroxyimino)-2-oxopiperidin-1-yl)-3-(2-(4-methoxybenzyl)-2H-tetrazol-5-yl)phenylsulfonamido) pyrrolidine-1-carboxylate To solution of (R)-tert-butyl 3-(2-(N,N-bis(1-methoxybenzyl)sulfamoyl)-4-(2,3-dioxopiperidin-1-yl)-3-(2-(4-methoxybenzyl)-2H-tetrazol-5-yl)phenyl sulfonamido)pyrrolidine-1-carboxylate (0.20 g, 0.21 mmol) in DCM (5 mL) was added hydroxylamine hydrochloride (29 mg, 0.42 mmol) at RT. The reaction mixture was stirred at RT for 3 hours. The resulting mixture was concentrated under vacuum. The residue was diluted with water (20 mL) and extracted with EA (3×20 mL). The combined organic layers were washed with water (3×20 mL) and brine (3×20 mL), dried over anhydrous Na₂SO₄ and filtered. The filtrate was concentrated under vacuum to afford the title compound, which was used in the next step without further purification: LCMS [M+1]⁺: 960.

Step B: (R)-4-(3-(hydroxyimino)-2-oxopiperidin-1-yl)-N1-(pyrrolidin-3-yl)-3-(2H-tetrazol-5-yl)benzene-1,2-disulfonamide The title compound was prepared as described for EXAMPLE 117 Step B using (R)-tert-butyl 3-(2-(N,N-bis(1-methoxybenzyl)sulfamoyl)-4-(3-(hydroxyimino)-2-oxopiperidin-1-yl)-3-(2-(4-methoxybenzyl)-2H-tetrazol-5-yl)phenylsulfonamido) pyrrolidine-1-carboxylate to afford the crude product, which was purified by Prep-HPLC with the following conditions: Column: X-Bridge C18 OBD Column, 10 μm, 19×250 mm; Mobile Phase A: water (10 mmol/L NH₄HCO₃), Mobile Phase B: ACN; Flow rate: 20 mL/min; Gradient: 5% B to 20% B in 9 min; Detector: UV 254/210 nm; Retention time: 6.5 min to give the title compound. LCMS (ESI) [M+1]⁺: 500; ¹H NMR (300 MHz, DMSO-d₆) δ 8.21 (d, J=8.5 Hz, 1H), 8.12-7.35 (br, 3H), 7.77 (d, J=8.5 Hz, 1H), 4.12-4.01 (m, 1H), 3.24-3.16 (m, 3H), 3.11-3.01 (m, 3H), 2.86-2.67 (m, 1H), 2.09-2.00 (m, 1H), 1.89-1.74 (m, 1H), 1.67-1.49 (m, 2H), 1.45-1.29 (m, 1H).

Example 153

(R)-4-(2-oxotetrahydropyrimidin-1(2H)-yl)-N1-(pyrrolidin-3-yl)-3-(2H-tetrazol-5-yl)benzene-1,2-disulfonamide

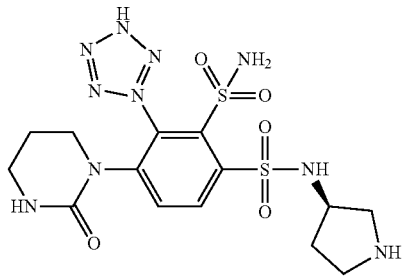

Step A: (R)-tert-butyl 3-(2-(N,N-bis(4-methoxybenzyl)sulfamoyl)-3-(2-(4-methoxybenzyl tetrazol-5-yl)-4-(2-oxotetrahydropyrimidin-1(2H)-yl)phenylsulfonamido)pyrrolidine-1-carboxylate The title compound was prepared as described for EXAMPLE 148 step A using (R)-tert-butyl 3-(2-(N,N-bis(4-methoxybenzyl)sulfamoyl)-4-iodo-3-(2-(4-methoxybenzyl)-2H-tetrazol-5-yl)phenylsulfonamido)pyrrolidine-1-carboxylate (REFERENCE EXAMPLE 40) and tetrahydropyrimidin-2(1H)-one. LCMS [M+H]⁺: 932.

Step B: (R)-4-(2-oxotetrahydropyrimidin-1(2H)-yl)-N1-(pyrrolidin-3-yl)-3-(2H-tetrazol-5-yl) benzene-1,2-disulfonamide The title compound was prepared as described for EXAMPLE 117 Step B using (R)-tert-butyl 3-(2-(N,N-bis(4-methoxybenzyl)sulfamoyl)-3-(2-(4-methoxybenzyl)-2H-tetrazol-5-yl)-4-(2-oxotetrahydropyrimidin-1(2H)-yl)phenylsulfonamido)pyrrolidine-1-carboxylate to afford the crude product. The crude product was purified by Prep-HPLC with the following conditions: Column: XBridge Prep C18 OBD Column 30×50 mm, 5 μm, 13 nm; Mobile Phase A: water (10 mmoL/L NH₄HCO₃), Mobile Phase B: ACN; Flow rate: 30 mL/min; Gradient: 10% B to 24.3% B in 6 min; Detector: UV 254/220 nm; Retention time: 7.9 min. LCMS [M+H]⁺: 472; ¹H NMR (400 MHz, CD₃OD) δ 8.58 (d, J=8.5 Hz, 1H), 7.94 (d, J=8.4 Hz, 1H), 4.25-4.03 (m, 1H), 3.72-3.49 (m, 1H), 3.48-3.30 (m, 3H), 3.29-3.13 (m, 3H), 3.12-2.98 (m, 1H), 2.23-2.18 (m, 1H), 2.06-1.79 (m, 2H), 1.49-1.40 (m, 1H).

EXAMPLES 154-159 were prepared as described for EXAMPLE 153, starting from 3-iodo-N,N-bis(4-methoxybenzyl)-2-(2-(4-methoxybenzyl)-2H-tetrazol-5-yl)-6-((2-(trimethylsilyl)ethyl)sulfonyl)benzenesulfonamide (REFERENCE EXAMPLE: 37) and the requisite amides, which were prepared as described herein or available from commercial sources.

| EX. | STRUCTURE | NAME | LC/MS [M + H]+ |
|---|---|---|---|
| 154 | 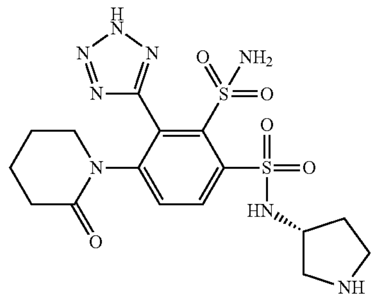 [SMILES: NS(=O)(=O)c1c(S(=O)(=O)N[C@@H]2CCNC2)ccc(N2CCCCC2=O)c1-c1nn[nH]n1] | (R)-4-(2-oxopiperidin-1-yl)-N1-(pyrrolidin-3-yl)-3-(2H-tetrazol-5-yl)benzene-1,2-disulfonamide | 471 |
| 155 | 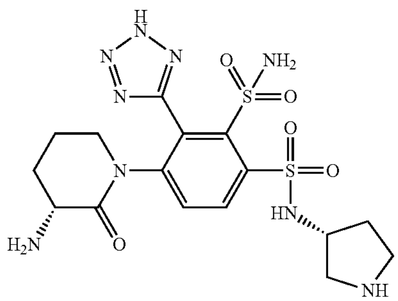 [SMILES: N[C@@H]1CCCN(c2ccc(S(=O)(=O)N[C@@H]3CCNC3)c(S(N)(=O)=O)c2-c2nn[nH]n2)C1=O] | (4-((R)-3-amino-2-oxopiperidin-1-yl)-N1-((R)-pyrrolidin-3-yl)-3-(2H-tetrazol-5-yl)benzene-1,2-disulfonamide | 486 |
| 156 | 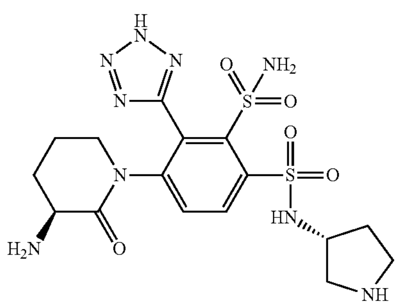 [SMILES: N[C@H]1CCCN(c2ccc(S(=O)(=O)N[C@@H]3CCNC3)c(S(N)(=O)=O)c2-c2nn[nH]n2)C1=O] | 4-((S)-3-amino-2-oxopiperidin-1-yl)-N1-((R)-pyrrolidin-3-yl)-3-(2H-tetrazol-5-yl)benzene-1,2-disulfonamide | 486 |
| 157 | 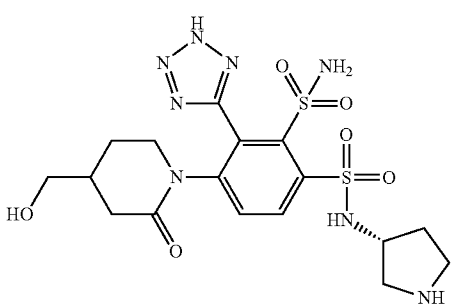 [SMILES: NS(=O)(=O)c1c(S(=O)(=O)N[C@@H]2CCNC2)ccc(N2CCC(CO)CC2=O)c1-c1nn[nH]n1] | 4-(4-(hydroxymethyl)-2-oxopiperidin-1-yl)-N1-((R)-pyrrolidin-3-yl)-3-(2H-tetrazol-5-yl)benzene-1,2-disulfonamide | 501 |
| 158 | 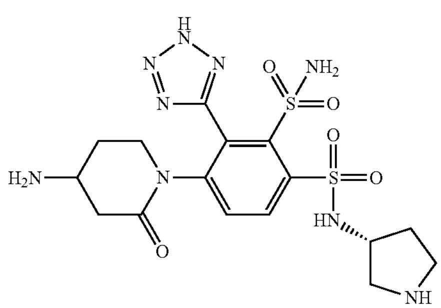 [SMILES: NC1CCN(c2ccc(S(=O)(=O)N[C@@H]3CCNC3)c(S(N)(=O)=O)c2-c2nn[nH]n2)C(=O)C1] | 4-(4-amino-2-oxopiperidin-1-yl)-N1-((R)-pyrrolidin-3-yl)-3-(2H-tetrazol-5-yl)benzene-1,2-disulfonamide | 486 |

| EX. | STRUCTURE | NAME | LC/MS [M + H]⁺ |
|---|---|---|---|
| 159 | 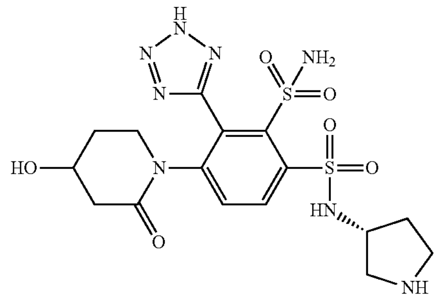 [SMILES: NS(=O)(=O)c1c(S(=O)(=O)N[C@@H]2CCNC2)ccc(N2CCC(O)CC2=O)c1-c1nn[nH]n1] | 4-(4-hydroxy-2-oxopiperidin-1-yl)-N1-((R)-pyrrolidin-3-yl)-3-(2H-tetrazol-5-yl)benzene-1,2-disulfonamide | 487 |

EXAMPLE 154: ¹H NMR (300 MHz, CD₃OD+DCl) δ 8.67 (d, J=8.5 Hz, 1H), 8.01 (d, J=8.5, 1H), 4.35-4.20 (m, 1H), 3.80-3.60 (m, 1H), 3.58-3.36 (m, 5H), 2.43-2.17 (m, 2H), 2.06-1.96 (m, 2H), 1.95-1.75 (m, 2H), 1.65-1.35 (m, 2H). EXAMPLE 155: ¹H NMR (300 MHz, CD₃OD+DCl) δ 8.64 (d, J=8.4 Hz, 1H), 8.07 (d, J=8.4 Hz, 1H), 4.23-4.18 (m, 1H), 3.86-3.73 (m, 1H), 3.50-3.32 (m, 6H), 2.25-2.20 (m, 2H), 2.08-1.94 (m, 311), 1.59-1.47 (m, 1H). EXAMPLE 156: ¹H NMR (300 MHz, DMSO-d₆+D₂O) δ 8.19 (d, J=8.7 Hz, 1H), 7.66 (d, J=8.7 Hz, 1H), 3.93-3.87 (m, 1H), 3.35-3.19 (m, 3H), 3.04-2.80 (m, 4H), 1.98-1.86 (m, 2H), 1.64-1.36 (m, 4H). EXAMPLE 157: NMR (300 MHz, CD₃OD+DCl) δ 8.62 (d, J=8.5 Hz, 1H), 7.95-7.90 (m, 1H), 4.30-4.08 (m, 1H), 3.72-3.68 (m, 1H), 3.47-3.39 (m, 3H), 3.38-3.30 (m, 4H), 2.47-1.77 (m, 5H), 1.72-1.50 (m, 1H), 1.08-0.92 (m, 1H). EXAMPLE 158: ¹H NMR (300 MHz, CD₃OD+DCl) δ 8.70-8.66 (m, 1H), 8.17-8.07 (m, 1H), 4.28-4.20 (m, 1H), 3.92-3.79 (m, 2H), 3.65-3.35 (m, 4H), 2.93-2.72 (m, 1H), 2.59-2.51 (m, 1H), 2.32-1.96 (m, 4H), 1.55-1.36 (m, 1H). EXAMPLE 159: ¹H NMR (300 MHz, CD₃OD+DCl) δ 8.74-8.61 (m, 1H), 8.00-7.96 (m, 1H), 4.31-4.16 (m, 1H), 4.15-3.96 (m, 1H), 3.92-3.82 (m, 1H), 3.73-3.36 (m, 4H), 2.72-2.55 (m, 1H), 2.44-2.15 (m, 2H), 2.15-1.82 (m, 3H), 1.75-1.28 (m, 1H).

EXAMPLES 160-161 were prepared as described for EXAMPLE 117, starting from (R)-tert-butyl (3-(2-(N,N-bis(4-methoxybenzyl)sulfamoyl)-4-iodo-3-(2-(4-methoxybenzyl)-2H-tetrazol-5-yl)phenylsulfonamido)-2-((tert-butyldimethylsilyl)oxy)propyl) carbamate (REFERENCE EXAMPLE 45) and the requisite amines, which were prepared as described herein, or which were available from commercial sources.

| EX. | STRUCTURE | NAME | LC/MS [M + 1]⁺ |
|---|---|---|---|
| 160 | 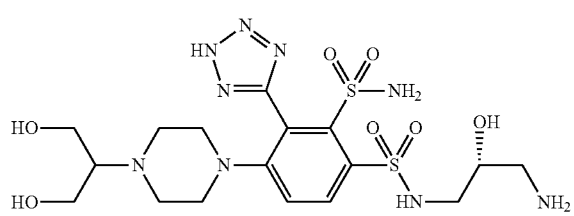 [SMILES: NC[C@@H](O)CNS(=O)(=O)c1ccc(N2CCN(C(CO)CO)CC2)c(-c2nn[nH]n2)c1S(N)(=O)=O] | (R)-N1-(3-amino-2-hydroxypropyl)-4-(4-(1,3-dihydroxypropan-2-yl)piperazin-1-yl)-3-(2H-tetrazol-5-yl)benzene-1,2-disulfonamide | 536 |
| 161 | 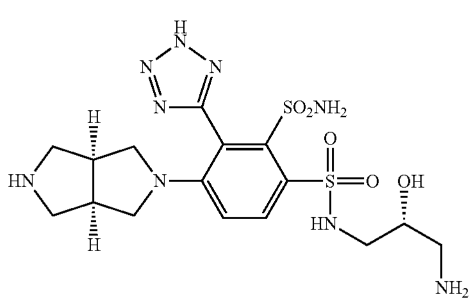 [SMILES: NC[C@@H](O)CNS(=O)(=O)c1ccc(N2C[C@H]3CNC[C@H]3C2)c(-c2nn[nH]n2)c1S(N)(=O)=O] | N1-((R)-3-amino-2-hydroxypropyl)-4-((3aR,6aS)-hexahydropyrrolo[3,4-c]pyrrol-2(1H)-yl)-3-(2H-tetrazol-5-yl)benzene-1,2-disulfonamide | 488 |

EXAMPLE 160: $^1$H NMR (300 MHz, CD$_3$OD+DCl): δ 8.50 (d, J=8.7 Hz, 1H), 7.82 (d, J=8.7 Hz, 1H), 4.05-3.82 (m, 5H), 3.59-3.56 (m, 2H), 3.42-3.00 (m, 10H), 2.93-2.95 (m, 1H). EXAMPLE 161: $^1$H NMR (300 MHz, D$_2$O) δ 8.07 (d, J=8.9 Hz, 1H), 7.22 (d, J=8.9 Hz, 1H), 3.83-3.78 (m, 1H), 3.36-2.54 (m, 12H), 2.45-2.34 (m, 2H).

Example 162

(R)-4-(4-(2-hydroxyethyl)piperazin-1-yl)-N1-(pyrrolidin-3-yl)-3-(2H-tetrazol-5-yl)benzene-1,2-disulfonamide

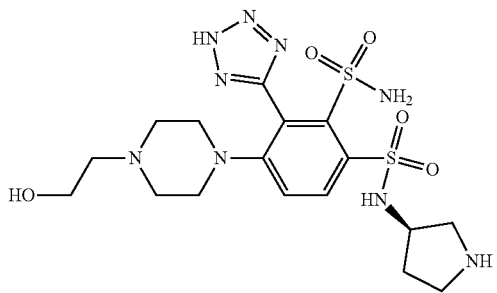 [SMILES: NS(=O)(=O)c1c(S(=O)(=O)N[C@@H]2CCNC2)ccc(N2CCN(CCO)CC2)c1-c1nn[nH]n1]

Step A: (R)-tert-butyl 3-(2-(N,N-bis(4-methoxybenzyl)sulfamoyl)-4-(4-(2-hydroxyethyl) piperazin-1-yl)-3-(2-(4-methoxybenzyl)-2H-tetrazol-5-yl phenylsulfonamido) pyrrolidine-1-carboxylate The title compound was prepared as described for EXAMPLE 117 Step A using (R)-tert-butyl 3-(2-(N,N-bis(4-methoxybenzyl)sulfamoyl)-4-iodo-3-(2-(4-methoxybenzyl)-2H-tetrazol-5-yl)phenylsulfonamido)pyrrolidine-1-carboxylate (REFERENCE EXAMPLE 40) (0.70 g, 0.729 mmol) and 2-(piperazin-1-yl)ethanol (0.285 g, 2.19 mmol). LCMS [M+1]$^+$: 962.

Step B: (R)-4-(4-(2-hydroxyethyl)piperazin-1-yl)-N1-(pyrrolidin-3-yl)-3-(2H-tetrazol-5-yl) benzene-1,2-disulfonamide The title compound was prepared as described for EXAMPLE 117 Step B using (R)-tert-butyl 3-(2-(N,N-bis(4-methoxybenzyl)sulfamoyl)-4-(4-(2-hydroxyethyl) piperazin-1-yl)-3-(2-(4-methoxybenzyl)-2H-tetrazol-5-yl)phenylsulfonamido) pyrrolidine-1-carboxylate (0.350 g, 0.364 mmol) to afford the crude product, which was purified by Prep-HPLC with the following conditions: Column: X Bridge Prep C18 OBD Column 19×250 mm 10 μm; Mobile Phase A: water (10 mmoL/L NH$_4$HCO$_3$), Mobile Phase B: ACN; Flow rate: 20 mL/min; Gradient: 3% B to 12% B in 12 min; Detector: UV 254 nm; Retention time: 8.34 min. LCMS [M+1]$^+$: 502; $^1$H NMR (300 MHz, CD$_3$OD DCl) δ 8.56 (d, J=8.7 Hz, 1H), 7.86 (d, J=8.7 Hz, 1H), 4.25-4.17 (m, 1H), 3.90-3.86 (m, 2H), 3.60-3.49 (m, 4H), 3.47-3.43 (m, 2H), 3.33-3.14 (m, 6H), 2.91-2.82 (m, 1H), 2.77-2.67 (m, 1H), 2.31-2.21 (m, 1H), 2.05-1.95 (m, 1H).

EXAMPLES 163-165 were prepared as described for EXAMPLE 162, starting from (R)-tert-butyl 3-(2-(N,N-bis(4-methoxybenzyl)sulfamoyl)-4-iodo-3-(2-(4-methoxybenzyl)-2H-tetrazol-5-yl)phenylsulfonamido)pyrrolidine-1-carboxylate (REFERENCE EXAMPLE 40) and the requisite amines, which were prepared as described herein, or which were available from commercial sources.

| EX. | STRUCTURE | NAME | LC/MS [M + 1]$^+$ |
|---|---|---|---|
| 163 | 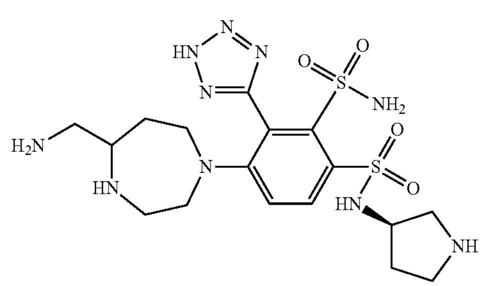 [SMILES: NCC1CCN(c2ccc(S(=O)(=O)N[C@@H]3CCNC3)c(S(N)(=O)=O)c2-c2nn[nH]n2)CCN1] | 4-(5-(Aminomethyl)-1,4-diazepan-3-yl)-N1-((R)-pyrrolidin-3-yl)-3-(2H-tetrazol-5-yl)benzene-1,2-disulfonamide | 501 |
| 164 | 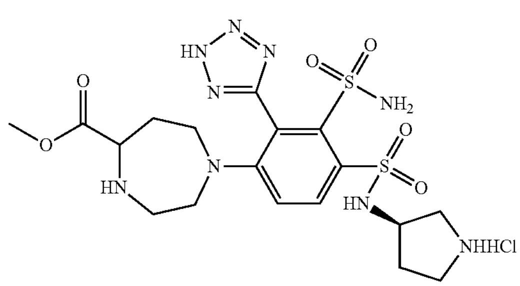 | Methyl 1-(4-(N-((R)-pyrrolidin-3-yl)sulfamoyl)-3-sulfamoyl-2-(2H-tetrazol-5-yl)phenyl)-1,4-diazepane-5-carboxylate hydrochloride | 530 |

| EX. | STRUCTURE | NAME | LC/MS [M + 1]+ |
|---|---|---|---|
| 165 | 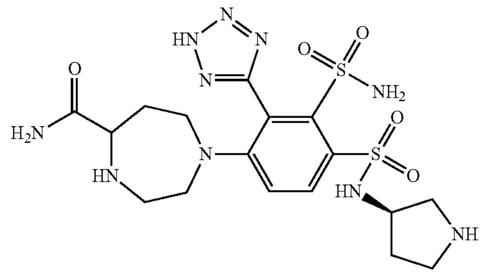 [SMILES: NC(=O)C1CCN(c2ccc(S(=O)(=O)N[C@@H]3CCNC3)c(S(N)(=O)=O)c2-c2nn[nH]n2)CCN1] | 1-(4-(N-((R)-pyrrolidin-3-yl)sulfamoyl)-3-sulfamoyl-2-(2H-tetrazol-5-yl)phenyl)-1,4-diazepane-5-carboxamide | 515 |

EXAMPLE 163: $^1$H NMR (300 MHz, CD$_3$OD+DCl) δ 8.56-8.46 (m, 1H), 7.90-7.80 (m, 1H), 4.23-4.15 (m, 1H), 3.70-3.65 (m, 1H), 3.52-3.35 (m, 4H), 3.34-3.29 (m, 4H), 3.27-3.15 (m, 2H), 3.14-2.97 (m, 2H), 2.28-2.17 (m, 1H), 2.07-1.74 (m, 3H). EXAMPLE 164: $^1$H NMR (300 MHz, CD$_3$OD+DCl) δ 8.47 (d, J=8.8 Hz, 1H), 7.76 (d, J=8.9 Hz, 1H), 4.23-4.10 (m, 1H), 4.02-3.95 (m, 1H), 3.86 (s, 3H), 3.50-3.38 (m, 4H), 3.27-3.20 (m, 3H), 2.92-2.82 (m, 2H), 2.74-2.61 (m, 1H), 2.25-2.17 (m, 2H), 2.07-1.80 (m, 2H). EXAMPLE 165: NMR (300 MHz, CD$_3$OD) δ 8.51 (d, J=8.8 Hz, 1H), 7.83 (d, J=8.8 Hz, 1H), 4.23-4.15 (m, 1H), 4.01-3.95 (m, 1H), 3.47-3.43 (m, 2H), 3.40-3.34 (m, 4H), 3.29-3.20 (m, 2H), 3.17-2.75 (m, 2H), 2.33-2.10 (m, 2H), 2.03-1.86 (m, 2H).

Example 166

(R)-4-(4-(1H-imidazol-4-yl)piperidin-1-yl)-N1-(pyrrolidin-3-yl)-3-(2H-tetrazol-5-yl)benzene-1,2-disulfonamide

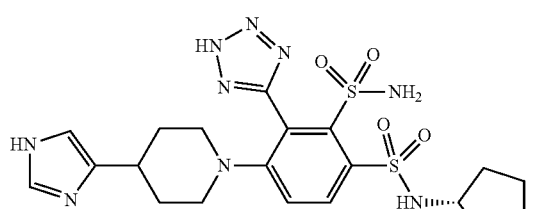

Step A: (R)-tert-butyl 3-(4-(4-(1H-imidazol-4-yl)piperidin-1-yl)-2-((4-methoxybenzyl) sulfamoyl-3-(2-(4-methoxybenzyl)-2H-tetrazol-5-yl)phenylsulfonamido)pyrrolidine-1-carboxylate The title compound was prepared as described for EXAMPLE 128 step A using (R)-tert-butyl 3-(2-(N,N-bis(4-methoxybenzyl)sulfamoyl)-4-iodo-3-(2-(4-methoxybenzyl)-2H-tetrazol-5-yl)phenylsulfonamido)pyrrolidine-1-carboxylate (0.38 g, 0.40 mmol) to afford (R)-tert-butyl 3-(4-(4-(1H-imidazol-4-yl)piperidin-1-yl)-2-(N,N-bis(4-methoxybenzyl)sulfamoyl)-3-(2-(4-methoxybenzyl)-2H-tetrazol-5-yl)phenylsulfonamido)pyrrolidine-1-carboxylate as an oil. LCMS [M+1]+: 983.

Step B: (R)-4-(4-(1H-imidazol-4-yl)piperidin-1-yl)-N1-(pyrrolidin-3-yl)-3-(2H-tetrazol-5-yl) benzene-1, 2-disulfonamide The title compound was prepared as described for EXAMPLE 117 Step B using (R)-tert-butyl 3-(4-(4-(1H-imidazol-4-yl)piperidin-1-yl)-2-(N,N-bis(4-methoxybenzyl) sulfamoyl)-3-(2-(4-methoxy benzyl)-2H-tetrazol-5-yl)phenylsulfonamido)pyrrolidine-1-carboxylate (0.10 g, 0.10 mmol) to afford crude product, which was purified by Prep-HPLC with the following conditions: Column: Xbridge C18, 19×150 mm, 10 µm; Mobile Phase A: water (10 mmol/L NH$_4$HCO$_3$), Mobile Phase B: ACN; Flow rate: 20 mid/min; Gradient: 5% B to 35% 13 in 8 min; Detector: UV 254 nm and 210 nm; Retention time: 7.50 ruin. LCMS [M+1]+: 523; $^1$H NMR (300 MHz, CD$_3$OD) δ 8.31 (d, J=8.8 Hz, 1H), 8.15 (s, 1H), 7.45 (d, J=8.8 Hz, 1H), 7.00 (s, 1H), 4.15-4.13 (m, 1H), 3.49-3.19 (m, 5H), 3.15-3.10 (m, 1H), 2.86-2.58 (m, 3H), 2.23-2.20 (m, 1H), 2.07-1.68 (m, 3H), 1.54-1.19 (m, 2H).

Example 167

(R)-4-(4-(N-(2-aminoethyl)sulfamoyl)piperidin-1-yl)-N1-(pyrrolidin-3-yl)-3-(2H-tetrazol-5-yl)benzene-1,2-disulfonamide

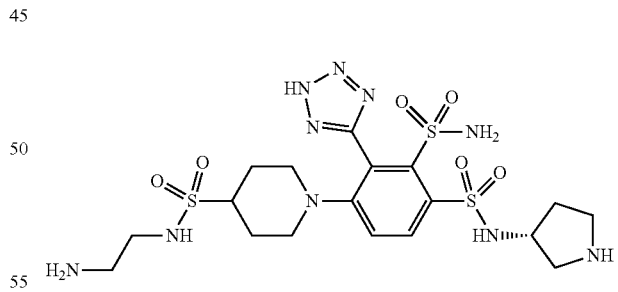

Step A: (1)-tert-butyl 3-(2-(N,N-bis(4-methoxybenzyl)sulfamoyl)-4-(4-(N-(2-((tert-butoxycarbonyl)amino)ethyl)sulfamoyl)piperidin-1-yl)-3-(2-(4-methoxybenzyl)-2H-tetrazol-5-yl) phenylsulfonamido)pyrrolidine-1-carboxylate The title compound was prepared as described for EXAMPLE 128 step A using (R)-tert-butyl 3-(2-(N,N-bis (4-methoxybenzyl)sulfamoyl)-4-iodo-3-(2-(4-methoxybenzyl)-2H-tetrazol-5-yl)phenyl sulfonamido)pyrrolidine-1- carboxylate (0.50 g, 0.52 mmol) and tert-butyl (2-(piperidine-4-sulfonamido)ethyl)carbamate (0.48 g, 1.56 mmol) in NMP (5 mL). LCMS [M+1]⁺: 1140.

Step B: (R)-4-(4-(N-(2-aminoethyl)sulfamoyl)piperidin-1-yl)-N1-(pyrrolidin-3-yl)-3-(2H-tetrazol-5-yl)benzene-1,2-disulfonamide The title compound was prepared as described for EXAMPLE 117 Step B using (R)-tert-butyl 3-(2-(N,N-bis(4-methoxybenzyl)sulfamoyl)-4-(4-(N-(2-((tert-butoxycarbonyl)amino)ethyl)sulfamoyl)piperidin-1-yl)-3-(2-(4-methoxybenzyl)-2H-tetrazol-5-yl)phenylsulfonamido)pyrrolidine-1-carboxylate (0.15 g, 0.13 mmol) to afford crude product, which was purified by Prep-HPLC with the following conditions: Column: Xbridge C18, 19×150 mm, 10 μm, Mobile Phase A: water (10 mmol/L NH₄HCO₃), Mobile Phase B: ACN; Flow rate: 20 mL/min; Gradient: 3% B to 20% B in 12 min; Detector: UV 254 nm and 210 nm; Retention time: 10.70 min to afford the title compound. LCMS [M+1]⁺: 579. ¹H NMR (400 MHz, D₂O) δ 8.20 (d, J=8.8 Hz, 1H), 7.41 (d, J=8.8 Hz, 1H), 4.05-4.02 (m, 1H), 3.36-3.09 (m, 8H), 3.03-2.90 (m, 3H), 2.69-2.49 (m, 2H), 2.18-2.04 (m, 1H), 1.93-1.72 (m, 3H), 1.20-1.17 (m, 2H).

Example 168

(S)-4-(4-(1H-imidazol-4-yl)piperidin-1-yl)-N1-(2,3-diaminopropyl)-3-(2H-tetrazol-5-yl)benzene-1,2-disulfonamide

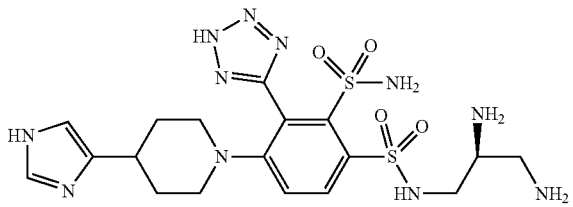

Step A: di-tert-butyl (3-((4-(4-(1H-imidazol-4-yl)piperidin-1-yl)-2-(N,N-bis(4-methoxybenzyl)sulfamoyl)-3-(2-(4-methoxybenzyl)-2H-tetrazol-5-yl)phenyl)sulfonamido)propane-1,2-diyl)(S)-dicarbamate The title compound was prepared as described for EXAMPLE 128 step A using (S)-di-tert-butyl (3-(2-(N,N-bis(4-methoxybenzyl)sulfamoyl)-4-iodo-3-(2-(4-methoxybenzyl)-2H-tetrazol-5-yl)phenylsulfonamido)propane-1,2-diyl)dicarbamate (REFERENCE EXAMPLE 63) (0.50 g, 0.47 mmol) in NMP (5 mL). LCMS [M+1]⁺: 1086.

Step B: (S)-4-(4-(1H-imidazol-4-yl)piperidin-1-yl)-N1-(2,3-diaminopropyl)-3-(2H-tetrazol-5-yl)benzene-1,2-disulfonamide The title compound was prepared as described for EXAMPLE 117 Step B using di-tert-butyl (3-((4-(4-(1H-imidazol-4-yl)piperidin-1-yl)-2-(N,N-bis(4-methoxybenzyl)sulfamoyl)-3-(2-(4-methoxybenzyl)-2H-tetrazol-5-yl)phenyl)sulfonamido)propane-1,2-diyl)(S)-dicarbamate (0.25 g, 0.23 mmol) to afford crude product, which was purified by Prep-HPLC with the following conditions: Column:)(bridge C18, 19×150 mm, 10 Mobile Phase A: water (10 mmol/L NH₄HCO₃), Mobile Phase B: ACN; Flow rate: 20 mL/min; Gradient: 3% B to 35% B in 8 min; Detector: UV 254 nm and 210 nm; Retention time: 7.50 min to afford the title compound. LCMS [M+1]⁺: 526; ¹H NMR (300 MHz, CD₃OD) δ 8.81 (s, 1H), 8.54 (d, J=8.7 Hz, 1H), 7.74 (d, J=8.8 Hz, 1H), 7.30 (s, 1H), 3.82-3.79 (m, 1H), 3.54-3.3.50 (m, 3H), 3.35-3.32 (m, 1H), 3.16-3.12 (m, 2H), 2.94-2.75 (m, 3H), 2.01-1.90 (m, 2H), 1.35-1.32 (m, 2H).

Example 169

(R)-4-(4-(1H-imidazol-4-yl)piperidin-1-yl)-N1-(3-amino-2-hydroxypropyl)-3-(1H-tetrazol-5-yl)benzene-1,2-disulfonamide

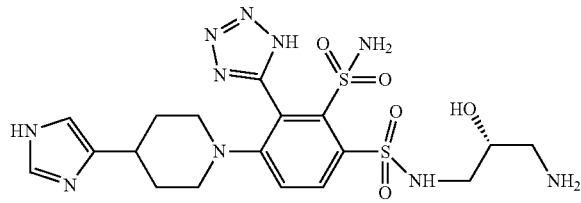 [SMILES: NC[C@@H](O)CNS(=O)(=O)c1ccc(N2CCC(c3c[nH]cn3)CC2)c(-c2nnn[nH]2)c1S(N)(=O)=O]

Step A: tert-Butyl ((2R)-3-(4-(4-(1H-imidazol-4-yl)piperidin-1-yl)-2-(N,N-dibenzyl sulfamoyl)-3-(1-(4-methoxybenzyl)-1H-tetrazol-5-yl)phenylsulfonamido)-2-((tert-butyldimethylsilyl)oxy)propyl)carbamate The title compound was prepared as described for EXAMPLE 128 step A using (R)-tert-butyl (3-(4-bromo-2-(N,N-dibenzylsulfamoyl)-3-(2-(4-methoxybenzyl)-2H-tetrazol-5-yl)phenylsulfonamido)-2-((tert-butyldimethylsilyl)oxy)propyl)carbamate (REFERENCE EXAMPLE 51) (1.94 g, 2.00 mmol) and 4-(1H-imidazol-4-yl)piperidine (0.910 g, 6.00 mmol) to afford tert-butyl ((2R)-3-(4-(4-(1H-imidazol-4-yl)piperidin-1-yl)-2-(N,N-dibenzylsulfamoyl)-3-(1-(4-methoxybenzyl)-1H-tetrazol-5-yl)phenylsulfonamido)-2-((tert-butyldimethylsilyl)oxy)propyl)carbamate as an oil. LCMS [M+1]⁺: 1041.

Step B: (R)-4-(4-(1H-imidazol-4-yl)piperidin-1-yl)-N1-(3-amino-2-hydroxypropyl)-3-(1H-tetrazol-5-yl)benzene-1,2-disulfonamide The title compound was prepared as described for EXAMPLE 129 step B using tert-butyl((2R)-3-(4-(4-(1H-imidazol-4-yl)piperidin-1-yl)-2-(N,N-dibenzyl sulfamoyl)-3-(1-(4-methoxybenzyl)-1H-tetrazol-5-yl)phenylsulfonamido)-2-((tert-butyldimethylsilyl)oxy)propyl)carbamate (0.900 g; 0.86 mmol) to afford the crude product, which was purified by Prep-HPLC with the following conditions: Column: XBridge C18 100 Å, 19 mm×150 mm, 10 μm; Phase A: water (10 mmol NH₄HCO₃), Mobile Phase B: ACN; Flow rate: 20 mL/min; Gradient: 5% B to 35% B in 8 min; Detector: U-V 254 nm; Retention time: 7.50 min to afford the title compound. LCMS [M+1]⁺: 527; ¹H NMR (300 MHz, CD₃OD): δ 8.26 (d, J=8.8 Hz, 1H), 7.57 (s, 1H), 7.43 (d, J=8.8 Hz, 1H), 6.71 (s, 1H), 4.00-3.82 (m, 1H), 3.25-3.01 (m, 5H), 2.89-2.86 (m, 1H), 2.65-2.62 (m, 3H), 1.79-1.75 (m, 2H), 1.45-1.24 (m, 2H).

Example 170

(R)—N1-(3-amino-2-hydroxypropyl)-4-(3-(aminomethyl)-2,5-dihydro-1H-pyrrol-1-yl)-3)-(2H-tetrazol-5-yl)benzene-1,2-disulfonamide bis(2,2,2-trifluoroacetate)

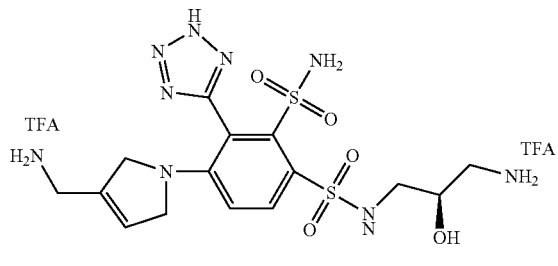

Step A: (R)-tert-butyl(2-((tert-butyldimethylsilyl)oxy)-3-(2-(N,N-dibenzylsulfamoyl)-4-(3-((1,3-dioxoisoindolin-2-yl)methyl)-2,5-dihydro-1H-pyrrol-1-yl)-3-(2-(4-methoxybenzyl)-2H-tetrazol-5-yl)phenylsulfonamido)propyl)carbamate The title compound was prepared as described for EXAMPLE 117 Step A using (R)-tert-butyl (3-(4-bromo-2-(N,N-dibenzylsulfamoyl)-3-(2-(4-methoxybenzyl)-2H-tetrazol-5-yl)phenylsulfonamido)-2-((tert-butyldimethylsilyl)oxy)propyl)carbamate (REFERENCE EXAMPLE 51) (0.40 g, 0.412 mmol). LCMS [M+1]⁺: 1118.

Step B: (R)-tert-butyl (3-(4-(3-(aminomethyl)-2,5-dihydro-1H-pyrrol-1-yl)-2-(N,N-dibenzylsulfamoyl)-3-(2-(4-methoxybenzyl)-2H-tetrazol-5-yl)phenylsulfonamido)-2-((tert-butyldimethylsilyl)oxy)propyl)carbamate The title compound was prepared as described for EXAMPLE 149 step D using (R)-tert-butyl (2-((tert-butyldimethylsilyl)oxy)-3-(2-(N,N-dibenzylsulfamoyl)-4-(3-((1,3-dioxoisoindolin-2-yl)methyl)-2,5-dihydro-1H-pyrrol-1-yl)-3-(2-(4-methoxybenzyl)-2H-tetrazol-5-yl)phenylsulfonamido)propyl)carbamate (0.100 g, 0.089 mmol). LCMS [M+1]⁺: 988.

Step C: (R)—N1-(3-amino-2-hydroxypropyl)-4-(3-(aminomethyl)-2,5-dihydro-1H-pyrrol-1-yl)-3-(2H-tetrazol-5-yl)benzene-1,2-disulfonamide bis(2,2,2-trifluoroacetate)

The title compound was prepared as described for EXAMPLE 129 step B using (R)-tert-butyl (3-(4-(3-(aminomethyl)-2,5-dihydro-1H-pyrrol-1-yl)-2-(N,N-dibenzylsulfamoyl)-3-(2-(4-methoxybenzyl)-2H-tetrazol-5-yl)phenylsulfonamido)-2-((tert-butyldimethylsilyl)oxy)propyl)carbamate (79 mg, 0.080 mmol) to afford the crude product, which was purified by Prep-HPLC with the following conditions: Column: XBridge C18 OBD Prep Column 100 Å, 10 μm, 19 mm×250 mm; Phase A: water (0.05% TFA), Mobile Phase B: ACN; Flow rate: 20 mL/min; Gradient: 3% B to 15% B in 10 min; Detector: UV 254 nm; Retention time: 5.88 min to afford the title compound. LCMS [M+1−2 TFA]⁺: 474; ¹H NMR (300 MHz, CD₃OD) δ 8.23 (d, J=9.3 Hz, 1H), 7.11 (d, J=9.4 Hz, 1H), 5.79-5.76 (m, 1H), 3.97-3.86 (m, 1H), 3.74-3.70 (m, 2H), 3.59-3.56 (m, 4H), 3.16-3.01 (m, 3H), 2.92-2.85 (m, 1H).

Example 171

(R)—N1-(3-amino-2-hydroxypropyl)-4-(2-amino-1,3,8-triazaspiro [4.5]dec-1-en-8-yl)-3-(2H-tetrazol-5-yl)benzene-1,2-disulfonamide

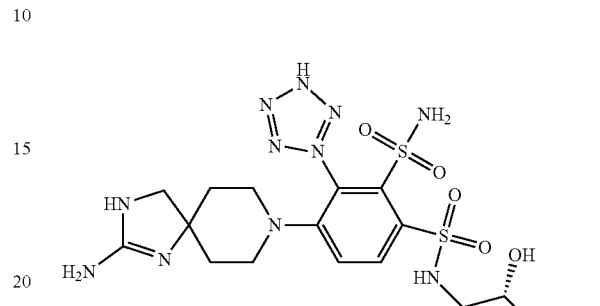

Step A: tert-butyl (R)-(3-((4-(4-amino-4-((((benzyloxy)carbonyl)amino)methyl)piperidin-1-yl)-2-(N,N-dibenzylsulfamoyl)-3-(2-(4-methoxybenzyl)-2H-tetrazol-5-yl)phenyl)sulfonamido)-2-((tert-butyldimethylsilyl)oxy)propyl)carbamate The title compound was prepared as described for EXAMPLE 117 Step A using (R)-tert-butyl (3-(4-bromo-2-(N,N-dibenzylsulfamoyl)-3-(2-(4-methoxybenzyl)-2H-tetrazol-5-yl)phenylsulfonamido)-2-((tert-butyldimethylsilyl)oxy)propyl) carbamate (REFERENCE EXAMPLE 55) (0.40 g, 0.412 mmol) and benzyl ((4-aminopiperidin-4-yl)methyl) carbamate (0.16 g, 0.618 mmol). LCMS [M+1]⁺: 1154.

Step B: (R)-tert-butyl (3-(4-(4-amino-4-(aminomethyl)piperidin-1-yl)-2-(N,N-dibenzyl sulfamoyl)-3-(2-(4-methoxybenzyl)-2H-tetrazol-5-yl)phenylsulfonamido)-2-((tert-butyldimethylsilyl)oxy)propyl) carbamate To a stirred solution of tert-butyl (R)-(3-((4-(4-amino-4-((((benzyloxy)carbonyl)amino)methyl)piperidin-1-yl)-2-(N,N-dibenzylsulfamoyl)-3-(2-(4-methoxybenzyl)-2H-tetrazol-5-yl)phenyl)sulfonamido)-2-((tert-butyldimethylsilyl)oxy)propyl)carbamate (0.20 g, 0.034 mmol) in MeOH (3 mL) was added palladium hydroxide on carbon (0.120 g, 0.173 mmol, 20% wt) at RT. The reaction mixture was degassed 3 times with hydrogen and stirred at RT for 5 hours under hydrogen atmosphere. The resulting mixture was filtered and the filtrate was concentrated under reduced pressure to afford the title compound. LCMS [M+1]⁺: 1020.

Step C: (R)-tert-butyl (3-(4-(2-amino-1,3,8-triazaspiro[4.5]dec-1-en-8-yl)-2-(N,N-dibenzyl sulfamoyl)-3-(2-(4-methoxybenzyl)-2H-tetrazol-5-yl)phenylsulfonamido)-2-((tert-butyldimethylsilyl)oxy)propyl)carbamate To a stirred solution of (R)-tert-butyl (3-(4-(4-amino-4-(aminomethyl)piperidine-1-yl)-2-(N,N-dibenzylsulfamoyl)-3-(2-(4-methoxybenzyl)-2H-tetrazol-5-yl)phenyl sulfonamido)-2-((tert-butyldimethylsilyl)oxy)propyl)carbamate (0.25 g, 0.245 mmol) in MeOH (3 mL) was added cyanic bromide (25.9 mg, 0.245 mmol) at RT. The reaction mixture was stirred at RT for 1 hour. The resulting mixture was concentrated under reduced pressure. The residue was purified by silica gel chromatography column, eluting with a gradient of 6%-9% MeOH in DCM to afford the title compound. LCMS [M+1]$^+$: 1044.

Step D: (R)—N1-(3-amino-2-hydroxypropyl)-4-(2-amino-1,3,8-triazaspiro[4.5]dec-1-en-8-yl)-3-(2H-tetrazol-5-yl)benzene-1,2-disulfonamide The title compound was prepared as described for EXAMPLE 129 step B using (R)-tert-butyl (3-(4-(2-amino-1,3,8-triazaspiro[4.5]dec-1-en-8-yl)-2-(N,N-dibenzyl sulfamoyl)-3-(2-(4-methoxybenzyl)-2H-tetrazol-5-yl)phenylsulfonamido)-2-((tert-butyldimethylsilyl)oxy)propyl)carbamate (0.17 g, 0.163 mmol) to afford crude product. The crude was purified by Prep-HPLC with the following conditions: Column: XBridge C18 OBD Prep Column 100 Å, 19 mm×250 mm, 10 μm; Mobile Phase A: water (10 mmoL/L NH$_4$HCO$_3$), Mobile Phase B: ACN; Flow rate: 20 mL/min; Gradient: 3% B to 8% B in 12 min; Detector: 254 nm and 210 nm; Retention time: 11.05 min to afford the title compound. LCMS [M+1]$^+$: 530. $^1$H NMR (400 MHz, D$_2$O) δ 8.18 (d, J=8.8 Hz, 1H), 7.42 (d, J=8.9 Hz, 1H), 3.89-3.73 (m, 1H), 3.42 (s, 2H), 3.20-3.11 (m, 1H), 3.07-2.97 (m, 1H), 2.93-2.79 (m, 3H), 2.76-2.62 (m, 3H), 1.59-1.47 (m, 2H), 1.45-1.31 (m, 2H).

EXAMPLES 172-179 were prepared as described for EXAMPLE 171, starting from (R)-tert-butyl (3-(4-bromo-2-(N,N-dibenzylsulfamoyl)-3-(2-(4-methoxybenzyl)-2H-tetrazol-5-yl) phenylsulfonamido)-2-((tert-butyldimethylsilyl)oxy)propyl)carbamate (REFERENCE EXAMPLE 51) and the requisite amines, which were prepared as described herein, or which were available from commercial sources.

| EX. | STRUCTURE | NAME | LC/MS [M + 1]$^+$ |
|---|---|---|---|
| 172 | 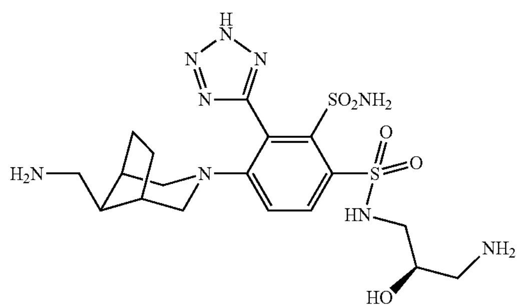 [SMILES: NCC1C2CCC1CN(c1ccc(S(=O)(=O)NC[C@H](O)CN)c(S(N)(=O)=O)c1-c1nn[nH]n1)C2] | N1-((R)-3-amino-2-hydroxypropyl)-4-((1R,5S,8R)-8-(aminomethyl)-3-azabicyclo[3.2.1]octan-3-yl)-3-(2H-tetrazol-5-yl)benzene-1,2-disulfonamide | 516 |
| 173 | 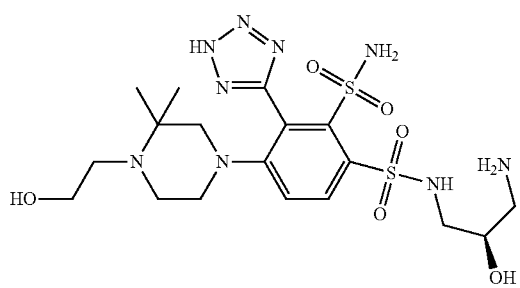 [SMILES: CC1(C)CN(c2ccc(S(=O)(=O)NC[C@H](O)CN)c(S(N)(=O)=O)c2-c2nn[nH]n2)CCN1CCO] | (R)-N1-(3-amino-2-hydroxypropyl)-4-(4-(2-hydroxyethyl)-3,3-dimethylpiperazin-1-yl)-3-(2H-tetrazol-5-yl)benzene-1,2-disulfonamide | 534 |
| 174 | 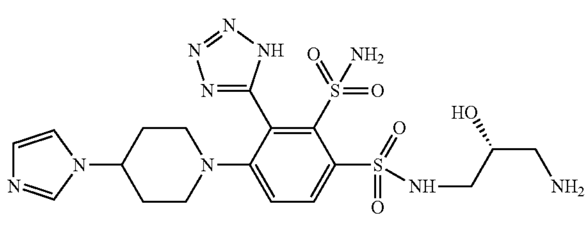 [SMILES: NC[C@@H](O)CNS(=O)(=O)c1ccc(N2CCC(n3ccnc3)CC2)c(-c2nnn[nH]2)c1S(N)(=O)=O] | (R)-4-(4-(1H-imidazol-1-yl)piperidin-1-yl)-N1-(3-amino-2-hydroxypropyl)-3-(2H-tetrazol-5-yl)benzene-1,2-disulfonamide | 527 |
| 175 | 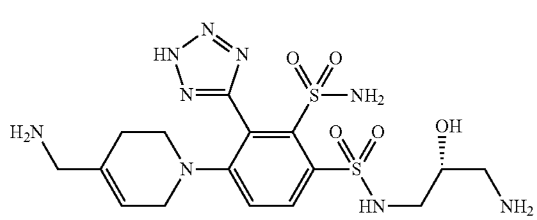 [SMILES: NCC1=CCN(c2ccc(S(=O)(=O)NC[C@H](O)CN)c(S(N)(=O)=O)c2-c2nn[nH]n2)CC1] | (R)-N1-(3-amino-2-hydroxypropyl)-4-(4-(aminomethyl)-5,6-dihydropyridin-1(2H)-yl)-3-(2H-tetrazol-5-yl)benzene-1,2-disulfonamide | 488 |

| EX. | STRUCTURE | NAME | LC/MS [M + 1]+ |
|---|---|---|---|
| 176 | 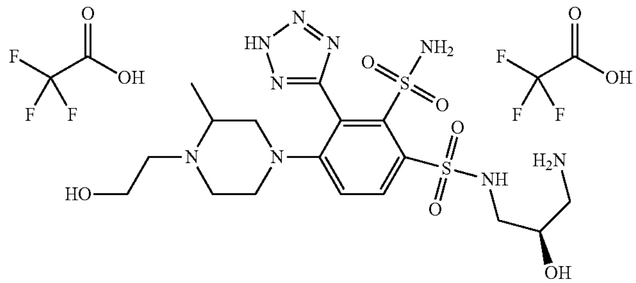 | N1-((R)-3-amino-2-hydroxypropyl)-4-(4-(2-hydroxyethyl)-3-methylpiperazin-1-yl)-3-(2H-tetrazol-5-yl)benzene-1,2-disulfonamide bis(2,2,2-trifluoroacetate) salt | 520 |
| 177 | 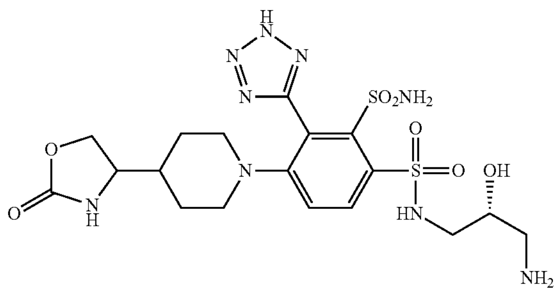 [SMILES: NC[C@@H](O)CNS(=O)(=O)c1ccc(N2CCC(C3COC(=O)N3)CC2)c(-c2nn[nH]n2)c1S(N)(=O)=O] | N1-((R)-3-amino-2-hydroxypropyl)-4-(4-(2-oxooxazolidin-4-yl)piperidin-1-yl)-3-(2H-tetrazol-5-yl)benzene-1,2-disulfonamide | 546 |
| 178 | 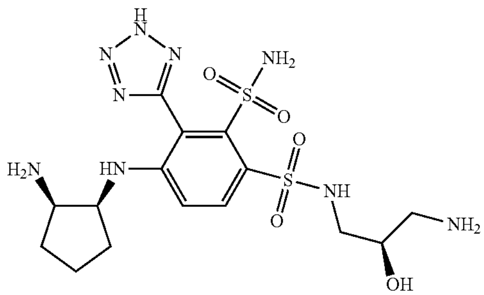 [SMILES: NC[C@@H](O)CNS(=O)(=O)c1ccc(N[C@H]2CCC[C@H]2N)c(-c2nn[nH]n2)c1S(N)(=O)=O] | N1-((R)-3-amino-2-hydroxypropyl)-4-(((1S,2R)-2-aminocyclopentyl)amino)-3-(2H-tetrazol-5-yl)benzene-1,2-disulfonamide | 476 |
| 179 | 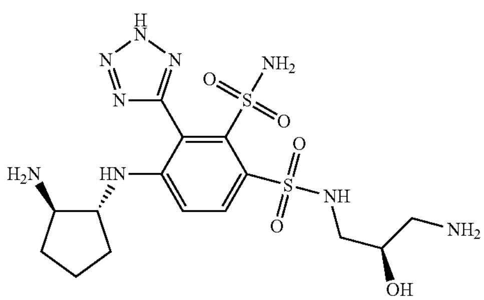 [SMILES: NC[C@@H](O)CNS(=O)(=O)c1ccc(N[C@@H]2CCC[C@H]2N)c(-c2nn[nH]n2)c1S(N)(=O)=O] | N1-((R)-3-amino-2-hydroxypropyl)-4-(((1R,2R)-2-aminocyclopentyl)amino)-3-(2H-tetrazol-5-yl)benzene-1,2-disulfonamide | 476 |

EXAMPLE 172: $^1$H NMR (300 MHz, CD$_3$OD) δ 8.42 (d, J=8.7 Hz, 1H), 7.82 (d, J=8.8 Hz, 1H), 3.98-3.88 (m, 1H), 3.15-3.04 (m, 3H), 2.92-2.78 (m, 5H), 2.72-2.69 (m, 2H), 2.07-2.05 (m, 2H), 1.93-1.90 (m, 1H), 1.51-1.46 (m, 2H), 0.89-0.86 (m, 2H). EXAMPLE 173: $^1$H NMR (400 MHz, CD$_3$OD) δ 8.30 (d, J=8.8 Hz, 1H), 7.46 (d, J=8.9 Hz, 1H), 3.79-3.78 (m, 1H), 3.50 (t, J=6.3 Hz, 2H), 3.13-3.00 (m, 2H), 2.95-2.92 (m, 3H), 2.78-2.76 (m, 1H), 2.66 (s, 2H), 2.45-2.32 (m, 4H), 0.79 (s, 6H). EXAMPLE 174: $^1$H NMR (300 MHz, CD$_3$OD) δ 8.99 (s, 1H), 8.44 (d, J=8.7 Hz, 1H), 7.75 (d, J=8.7 Hz, 1H), 7.67-7.65 (m, 1H), 7.56-7.53 (m, 1H), 4.49-4.41 (m, 1H), 3.98-3.91 (m, 1H), 3.18-3.04 (m, 5H), 2.93-2.85 (m, 3H), 2.21-2.01 (m, 2H), 1.76-1.50 (m, 2H). EXAMPLE 175: $^1$H NMR (300 MHz, CD$_3$OD) δ 8.42 (d, J=8.8 Hz, 1H), 7.71 (d, J=8.8 Hz, 1H), 5.83-5.73 (m, 1H), 4.02-3.94 (m, 1H), 3.54-3.52 (m, 2H), 3.45-3.43 (m, 2H), 3.19-3.09 (m, 3H), 3.03-2.89 (m, 3H), 1.84-1.82 (m, 2H). EXAMPLE 176: $^1$H NMR (400 MHz, D$_2$O) δ 8.29 (d, J=9.3 Hz, 1H), 7.62 (d, J=9.3 Hz, 1H), 4.06-3.86 (m, 1H), 3.85-3.61 (m, 2H), 3.49-3.46 (m, 2H), 3.18-2.59 (m, 11H), 1.15-1.10 (m, 2H), 0.83-0.80 (m, 1H); $^{19}$F NMR (376 MHz, D$_2$O) δ −75.62 (s, 6F). EXAMPLE 177: $^1$H NMR (300 MHz, D$_2$O) δ 8.10 (d, 8.8 Hz, 1H), 7.35 (d, J=8.8 Hz, 1H), 4.39-4.31 (m, 1H), 4.11-4.06 (m, 1H), 3.91-3.83 (m, 1H), 3.64-3.57 (m, 1H), 3.14-2.98 (m, 3H), 2.94-2.90 (m, 2H), 2.84-2.76 (m, 1H), 2.50-2.41 (m, 2H), 1.40-1.26 (m, 3H), 0.79-0.67 (m, 2H). EXAMPLE 178: $^1$H NMR (300 MHz, CD$_3$OD) δ 8.29 (d, J=8.6 Hz, 1H), 7.34 (d, J=8.6 Hz, 1H), 4.19-4.14 (m, 1H), 3.96-3.91 (m, 1H), 3.12-3.04 (m, 3H), 2.93-2.85 (m, 1H), 2.41-2.01 (m, 2H), 1.90-1.56 (m, 4H).

EXAMPLE 179: $^1$H NMR (300 MHz, CD$_3$OD+DCl) δ 8.30 (d, J=9.1 Hz, 1H), 7.34 (d, J=9.2 Hz, 1H), 4.21-4.14 (m, 1H), 4.01-3.94 (m, 2H), 3.14-3.07 (m, 3H), 2.96-2.89 (m, 1H), 2.28-2.02 (m, 2H), 1.81-1.55 (m, 4H).

Examples 180 and 181

4-(4-((S)-1-amino-2-hydroxyethyl)piperidin-1-yl)-N1-((R)-3-amino-2-hydroxypropyl)-3-(2H-tetrazol-5-yl)benzene-1,2-disulfonamide and 4-(4-((R)-1-amino-2-hydroxyethyl)piperidin-1-yl)-N1-((R)-3-amino-2-hydroxypropyl)-3-(2H-tetrazol-5-yl)benzene-1,2-disulfonamide

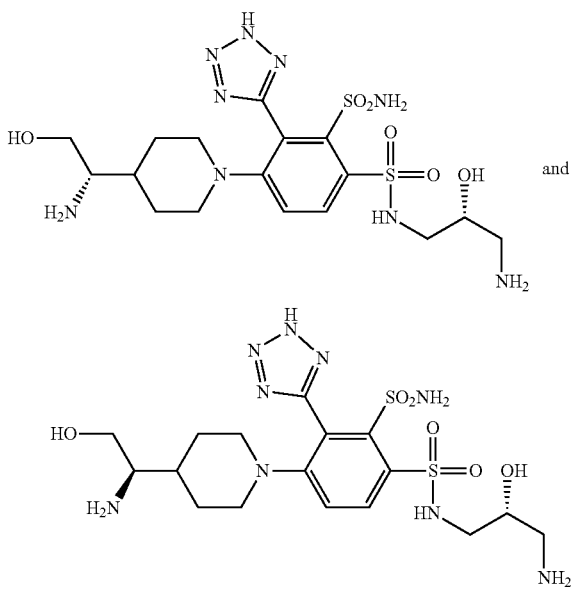

and

Example 180

Synthesis of 4-(4-(1-amino-2-hydroxyethyl)piperidin-1-yl)-N1-((R)-3-amino-2-hydroxypropyl)-3-(2H-tetrazol-5-yl)benzene-1,2-disulfonamide (Isomer A)

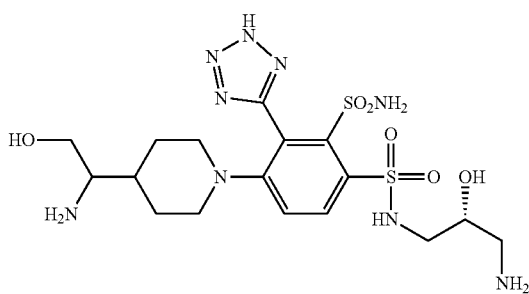 [SMILES: NC[C@@H](O)CNS(=O)(=O)c1ccc(N2CCC(C(N)CO)CC2)c(-c2nn[nH]n2)c1S(N)(=O)=O]

Step A: tert-Butyl ((R)-2-((tert-butyldimethylsilyl)oxy)-3-(2-(N,N-dibenzylsulfamoyl)-3-(2-(4-methoxybenzyl)-2H-tetrazol-5-yl)-4-(4-(2-oxooxazolidin-4-yl)piperidin-1-yl)phenylsulfonamido)propyl)carbamate The title compound was prepared as described for EXAMPLE 117 Step A using (R)-tert-butyl (3-(4-bromo-2-(N,N-dibenzylsulfamoyl)-3-(2-(4-methoxybenzyl)-2H-tetrazol-5-yl)phenylsulfonamido)-2-((tert-butyldimethylsilyl)oxy)propyl)carbamate (REFERENCE EXAMPLE 51) (0.60 g, 0.587 mmol), (S)-benzyl (2-hydroxy-1-(piperidin-4-yl)ethyl)carbamate (0.25 g, 0.704 mmol) and K$_2$CO$_3$ (0.410 g, 2.93 mmol) in DME (1 mL) to afford the title compound, which was used without further purification, LCMS [M+1]$^+$: 1060.

Step B: tert-Butyl ((R)-3-(4-(4-(1-amino-2-hydroxyethyl)piperidin-1-yl)-2-(N,N-dibenzylsulfamoyl)-3-(2-(4-methoxybenzyl)-2H-tetrazol-5-yl)phenylsulfonamido)-2-((tert-butyldimethylsilyl)oxy)propyl)carbamate To a solution of tert-butyl ((R)-2-((tert-butyldimethylsilyl)oxy)-3-(2-(N,N-dibenzylsulfamoyl)-3-(2-(4-methoxybenzyl)-2H-tetrazol-5-yl)-4-(4-(2-oxooxazolidin-4-yl)piperidin-1-yl)phenylsulfonamido)propyl)carbamate (0.43 g, 0.39 mmol) in EtOH (5 mL) were added water (5 mL), THF (1 mL) and LiOH (0.19 g, 7.70 mmol) at RT. The reaction mixture was stirred at 90° C. for 8 hours. After cooling to RT, the resulting mixture was concentrated under reduced pressure. The residue was mixed with water (50 mL), and extracted with DCM (5×50 mL). The combined organic layers was washed with brine (3×30 mL), dried over anhydrous Na$_2$SO$_4$ and concentrated under reduced pressure to afford the title compound, which was used for the next step without further purification. LCMS [M+1]$^+$: 1034.

Step C: 4-(4-(1-amino-2-hydroxyethyl)piperidin-1-yl)-N1-((R)-3-amino-2-hydroxypropyl)-3-(2H-tetrazol-5-yl)benzene-1,2-disulfonamide The title compound was prepared as described for EXAMPLE 129 step B using tert-butyl ((R)-3-(4-(4-(1-amino-2-hydroxyethyl)piperidin-1-yl)-2-(N,N-dibenzylsulfamoyl)-3-(2-(4-methoxybenzyl)-2H-tetrazol-5-yl)phenylsulfon amino)-2-((ter t-butyldimethylsilyl)oxy)propyl) carbamate (0.30 g, 0.257 mmol) to afford the crude product, which was purified by Prep-HPLC with the following conditions: Column: XBridge C18 OBD Prep Column 100 Å, 19 mm×250 mm, 10 μm; Mobile Phase A: water (10 mmol/L NH$_4$HCO$_3$), Mobile Phase B: ACN; Flow rate: 20 mL/min; Gradient: 3% B to 10% B in 12 min; Detector: UV 254 nm and 210 nm; Retention time: 11.47 min, LCMS (ESI) calc'd for C$_{17}$H$_{29}$N$_9$O$_6$S$_2$ [M+1]$^+$: 520, found 520; $^1$H NMR (300 MHz, D$_2$O) δ 8.11 (d, J=8.8 Hz, 1H), 7.35 (d, J=8.8 Hz, 1H), 3.85-3.71 (m, 1H), 3.67-3.61 (m, 1H), 3.49-3.42 (m, 1H), 3.13-3.07 (m, 1H), 3.02-2.79 (m, 5H), 2.73-2.66 (m, 1H), 2.55-2.44 (m, 2H), 1.50-1.40 (m, 3H), 0.88-0.81 (m, 2H).

EXAMPLES 181-182 were prepared in an analogous fashion to that described for EXAMPLE 137, starting from (R)-tert-butyl (3-(4-bromo-2-(N,N-dibenzylsulfamoyl)-3-(2-(4-methoxybenzyl)-2H-tetrazol-5-yl) phenylsulfonamido)-2-((tert-butyldimethylsilyl)oxy)propyl)carbamate (REFERENCE EXAMPLE 51) and the requisite amines.

| EX. | STRUCTURE | NAME | LC/MS [M + 1]+ |
|---|---|---|---|
| 181 | Isomer B (from Reference Example 32) | 4-(4-(1-amino-2-hydroxyethyl)piperidin-1-yl)-N1-((R)-3-amino-2-hydroxypropyl)-3-(2H-tetrazol-5-yl)benzene-1,2-disulfonamide | 520 |
| 182 | EXAMPLE 182 is a racemic mixture of EXAMPLES 180 and 181. | 4-(4-(1-Amino-2-hydroxyethyl)piperidin-1-yl)-N1-((R)-3-amino-2-hydroxypropyl)-3-(2H-tetrazol-5-yl)benzene-1,2-disulfonamide | 520 |

EXAMPLE 181: $^1$H NMR (300 MHz, CD$_3$OD+DCl) δ 8.42 (d, J=8.7 Hz, 1H), 7.68 (d, J=8.8 Hz, 1H), 4.06-3.91 (m, 1H), 3.78-3.73 (m, 1H), 3.63-3.57 (m, 1H), 3.23-3.03 (m, 5H), 2.97-2.89 (m, 2H), 2.79-2.62 (m, 2H), 1.80-1.67 (m, 3H), 1.05-0.94 (m, 2H), EXAMPLE 182: $^1$H NMR (300 MHz, D$_2$O) δ 8.10 (d, J=8.8 Hz, 1H), 7.34 (d, J=8.9 Hz, 1H), 3.80-3.78 (m, 1H), 3.65-3.60 (m, 1H), 3.47-3.41 (m, 1H), 3.12-3.06 (m, 1H), 3.03-2.76 (m, 5H), 2.72-2.69 (m, 1H), 2.50-2.42 (m, 2H), 1.44-1.39 (m, 3H), 0.83-0.79 (m, 2H).

Example 183

(R)-4-((piperidin-4-ylmethyl)amino)-N1-(pyrrolidin-3-yl)-3-(2H-tetrazol-5-yl)benzene-1,2-di sulfonamide

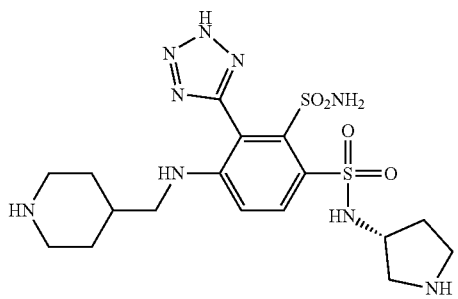 [SMILES: NS(=O)(=O)c1c(S(=O)(=O)N[C@@H]2CCNC2)ccc(NCC2CCNCC2)c1-c1nn[nH]n1]

Step A: (R)-tert-butyl 4-(((3-(N,N-bis(4-methoxybenzyl)sulfamoyl)-4-(N-(1-(tert-butoxycarbonyl)pyrrolidin-3-yl)sulfamoyl)-2-(2-(4-methoxybenzyl)-2H-tetrazol-5-yl)phenyl)amino)methyl)piperidine-1-carboxylate To a solution (R)-tert-butyl 3-(2-(N,N-bis(4-methoxybenzyl)sulfamoyl)-4-iodo-3-(2-(4-methoxybenzyl)-2H-tetrazol-5-yl)phenylsulfonamido)pyrrolidine-1-carboxylate (REFERENCE EXAMPLE 40) (0.50 g, 0.52 mmol) in toluene (5 mL) were added tert-butyl 4-(aminomethyl)piperidine-1-carboxylate (0.34 g, 1.56 mmol), Cs$_2$CO$_3$ (0.85 g, 2.60 mmol) and RAC-BINAP-Pd-G3 (51.7 mg, 0.052 mmol) at RT. The reaction mixture was degassed with nitrogen three times and stirred at 150° C. with microwave for 1 hour under nitrogen. After cooling to RT, the resulting mixture was concentrated under reduced pressure. The residue was diluted with water (25 mL) and extracted with EA (3×15 mL). The combined organic layers were washed with brine (20 mL), dried over anhydrous Na$_2$SO$_4$ and filtered. The filtrate was concentrated under reduced pressure. The residue was purified by silica gel column chromatography, eluting with a gradient of 1%-100% EA in PE to afford the title compound. LCMS [M+1]+: 1046.

Step B: (R)-4-((piperidin-4-ylmethyl)amino)-N1-(pyrrolidin-3-yl)-3-(2H-tetrazol-5-yl) benzene-1,2-disulfonamide The title compound was prepared as described for EXAMPLE 117 step B using (R)-tert-butyl 4-(((3-(N,N-bis(4-methoxybenzyl)sulfamoyl)-4-(N-(1-(tert-butoxycarbonyl)pyrrolidin-3-yl)sulfamoyl)-2-(2-(4-methoxybenzyl)-2H-tetrazol-5-yl)phenyl)amino)methyl)piperidine-1- carboxylate (0.18 g, 0.172 mmol) to afford the crude product. The crude product was purified by Prep-HPLC with the following conditions: Column: XBridge C18 OBD Prep Column 100 Å, 10 μm, 19 mm×250 mm; Mobile Phase A: water (10 mmoL/L NH$_4$HCO$_3$+0.1% NH$_3$.H$_2$O), Mobile Phase B: ACN; Flow rate: 20 mL/min; Gradient: 9% B to 10% B in 12 min; Detector: UV 254/210 nm; Retention time: 8.43 min. LCMS [M+1]$^+$: 486; $^1$H NMR (400 MHz, CD$_3$OD) δ 8.28 (d, J=9.2 Hz, 1H), 7.17 (d, J=9.3 Hz, 1H), 4.07-4.04 (m, 1H), 3.48-3.31 (m, 6H), 3.17-3.13 (m, 2H), 2.95 (t, J=12.7 Hz, 2H), 2.22-2.15 (m, 1H), 1.99-1.87 (m, 4H), 1.45-1.40 (m, 2H).

EXAMPLE 184 was prepared as described for EXAMPLE 183 starting from (R)-tert-butyl (3-(2-(N,N-bis(4-methoxybenzyl)sulfamoyl)-4-iodo-3-(2-(4-methoxybenzyl)-2H-tetrazol-5-yl)phenylsulfonamido)-2-((tert-butyldimethylsilyl)oxy)propyl)carbamate and the requisite amines, which were prepared as described herein, or which were available from commercial sources.

| EX. | STRUCTURE | NAME | MW | LC/MS [M + 1]$^+$ |
|---|---|---|---|---|
| 184 | (see structure) | N1-((R)-3-amino-2-hydroxypropyl)-4-((3-aminocyclopentyl)amino)-3-(2H-tetrazol-5-yl)benzene-1,2-disulfonamide | 475 | 476 |

EXAMPLE 184: $^1$H NMR (400 MHz, D$_2$O) δ 8.02 (d, J=9.1 Hz, 1H), 6.94 (d, J=9.1 Hz, 1H), 3.95-3.88 (m, 1H), 3.80-3.71 (m, 1H), 3.61-3.49 (m, 1H), 3.16-3.02 (m, 1H), 3.00-2.90 (m, 1H), 2.85-2.81 (m, 1H), 2.69-2.66 (m, 1H), 2.50-2.47 (m, 1H), 2.06-1.90 (m, 2H), 1.67-1.40 (m, 2H), 1.33-1.25 (m, 1H).

Example 185

(R)-4-(4-(2-aminoethyl)piperidin-1-yl)-N1-(1-aminopropan-2-yl)-3-(2H-tetrazol-5-yl)benzene-1,2-disulfonamide

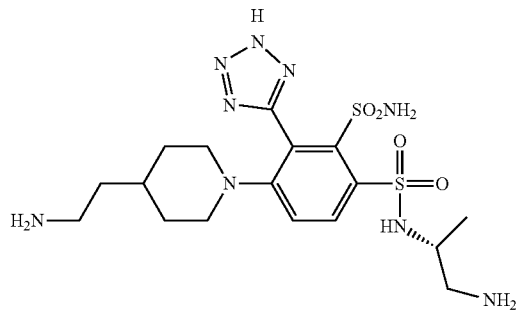

Step A: tert-Butyl (2-(1-(3-(N,N-bis(4-methoxybenzyl)sulfamoyl)-(2-(4-methoxybenzyl)-2H-tetrazol-5-yl)-4-((2-(trimethylsilyl)ethyl)sulfonyl)phenyl) piperidin-4-yl)ethyl)carbamate The title compound was prepared as described for EXAMPLE 117 Step A using 3-iodo-N,N-bis(4-methoxybenzyl)-2-(2-(4-methoxybenzyl)-2H-tetrazol-5-yl)-6-((2-(trimethylsilyl)ethyl)sulfonyl)benzenesulfonamide (REFERENCE EXAMPLE 37) (3.0 g, 3.43 mmol), LCMS [M+1]$^+$: 976.

Step B: 2-(N,N-bis(4-methoxybenzyl)sulfamoyl)-4-(4-(2-((tert-butoxycarbonyl)amino)ethyl) piperidin-1-yl)-3-(2-(4-methoxybenzyl)-2H-tetrazol-5-yl)benzenesulfinic acid The title compound was prepared as described for EXAMPLE 148 step B using tert-butyl (2-(1-(3-(N,N-bis(4-methoxybenzyl)sulfamoyl)-2-(2-(4-methoxybenzyl)-2H-tetrazol-5-yl)-4-((2-(trimethylsilyl)ethyl)sulfonyl)phenyl) piperidin-4-yl)ethyl) carbamate (2.50 g, 2.56 mmol). The crude product was used for the next step without further purification. LCMS [M+1]+: 876.

Step C: tert-butyl (R)-(2-(1-(4-(N-(1-(((benzyloxy)carbonyl)amino)propan-2-yl)sulfamoyl)-3-(N,N-bis(4-methoxybenzyl)sulfamoyl)-2-(2-(4-methoxybenzyl)-2H-tetrazol-5-yl)phenyl)piperidin-4-yl)ethyl) carbamate The title compound was prepared as described for EXAMPLE 148 step C using 2-(N,N-bis(4-methoxybenzyl)sulfamoyl)-4-(4-(2-((tert-butoxycarbonyl)amino)ethyl)piperidin-1-yl)-3-(2-(4-methoxybenzyl)-2H-tetrazol-5-yl)benzenesulfinic acid (0.50 g, 0.57 mmol). LCMS [M+1]$^+$: 1082.

Step D: (R)-4-(4-(2-aminoethyl)piperidin-1-yl)-N1-(1-aminopropan-2-yl)-3-2H-tetrazol-5-benzene-1,2-disulfonamide The title compound was prepared as described for EXAMPLE 117 Step B using tert-butyl (R)-(2-(1-(4-(N-(1-(((benzyloxy)carbonyl)amino)propan-2-yl)sulfamoyl)-3-(N,N-bis(4-methoxybenzyl)sulfamoyl)-2-(2-(4-methoxybenzyl)-2H-tetrazol-5-yl)phenyl)piperidin-4-yl)ethyl) carbamate (0.40 g, 0.370 mmol) to afford the crude product, which was purified by Prep-HPLC with the following conditions: Column: X Bridge Prep C18 OBD Column 19×250 mm, 10 μm; Mobile Phase A: water with 10 mmol/L NH₄HCO₃, Mobile Phase B: ACN; Flow rate: 20 mL/min; Gradient: 3% B to 15% B in 12 min; Detector: UV 254 nm and 220 nm; Retention time: 11.88 min to afford the title compound. LCMS [M+1]⁺: 488; ¹H NMR (300 MHz, CD₃OD) δ 8.49 (d, J=8.7 Hz, 1H), 7.69 (d, J=8.8 Hz, 1H), 3.82-3.75 (m, 1H), 3.23-3.03 (m, 2H), 3.00-2.84 (m, 5H), 2.58-2.50 (m, 1H), 1.80-1.70 (m, 1H), 1.64-1.33 (m, 4H), 1.15-1.06 (m 4H), 0.73-0.53 (m, 1H).

EXAMPLES 186-189 were prepared as described for Example 185, starting from 3-iodo-N,N-bis(4-methoxybenzyl)-2-(2-(4-methoxybenzyl)-2H-tetrazol-5-yl)-6-((2-(trimethylsilyl)ethyl)sulfonyl)benzenesulfonamide (REFERENCE EXAMPLE 37) and the requisite amines.

| EX. | STRUCTURE | NAME | LC/MS [M + 1]⁺ |
|---|---|---|---|
| 186 | 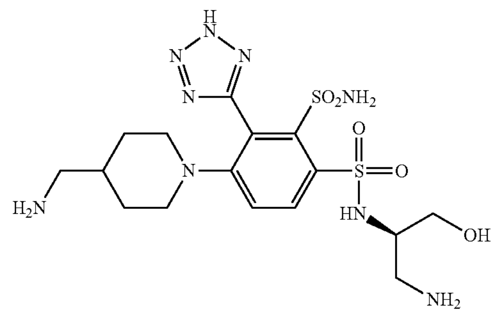 [SMILES: NCC1CCN(c2ccc(S(=O)(=O)N[C@H](CN)CO)c(S(N)(=O)=O)c2-c2nn[nH]n2)CC1] | (R)-N1-(1-amino-3-hydroxypropan-2-yl)-4-(4-(aminomethyl)piperidin-1-yl)-3-(2H-tetrazol-5-yl)benzene-1,2-disulfonamide | 490 |
| 187 | 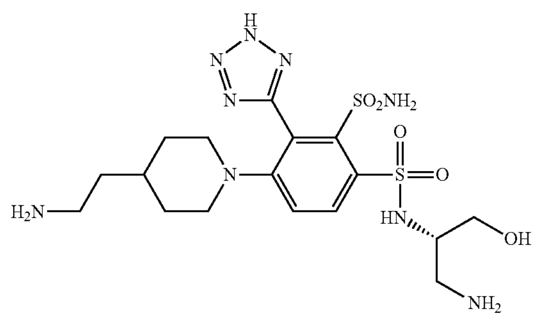 [SMILES: NCCC1CCN(c2ccc(S(=O)(=O)N[C@@H](CN)CO)c(S(N)(=O)=O)c2-c2nn[nH]n2)CC1] | (S)-N1-(1-amino-3-hydroxypropan-2-yl)-4-(4-(2-aminoethyl)piperidin-1-yl)-3-(2H-tetrazol-5-yl)benzene-1,2-disulfonamide | 504 |
| 188 | 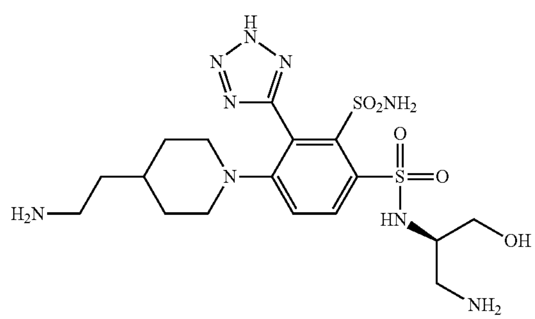 [SMILES: NCCC1CCN(c2ccc(S(=O)(=O)N[C@H](CN)CO)c(S(N)(=O)=O)c2-c2nn[nH]n2)CC1] | (R)-N1-(1-amino-3-hydroxypropan-2-yl)-4-(4-(2-aminoethyl)piperidin-1-yl)-3-(2H-tetrazol-5-yl)benzene-1,2-disulfonamide | 504 |
| 189 | 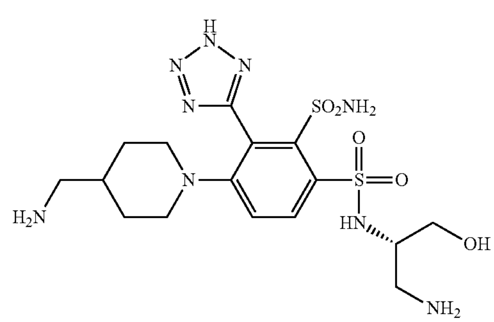 [SMILES: NCC1CCN(c2ccc(S(=O)(=O)N[C@@H](CN)CO)c(S(N)(=O)=O)c2-c2nn[nH]n2)CC1] | (S)-N1-(1-amino-3-hydroxypropan-2-yl)-4-(4-(aminomethyl)piperidin-1-yl)-3-(2H-tetrazol-5-yl)benzene-1,2-disulfonamide | 490 |

EXAMPLE 186: ¹H NMR (300 MHz, CD₃OD+DCl) δ 8.47 (d, J=8.7 Hz, 1H), 7.68 (d, J=8.8 Hz, 1H), 3.83-3.70 (m, 1H), 3.54-3.49 (m, 1H), 3.45-3.39 (m, 1H), 3.24-3.19 (m, 2H), 3.12-3.04 (m, 1H), 2.97-2.71 (m, 4H), 2.61-2.52 (m, 1H), 1.81-1.56 (m, 3H), 1.13-1.08 (m, 1H), 0.73-0.68 (m, 1H). EXAMPLE 187: NMR (300 MHz, CD₃OD+DCl) δ 8.48 (d, J=8.8 Hz, 1H), 7.67 (d, J=8.8 Hz, 1H), 3.81-3.75 (m, 1H), 3.54-3.40 (m, 2H), 3.25-3.09 (m, 3H), 3.05-2.82 (m, 4H), 2.59-2.52 (m, 1H), 1.76-1.71 (m, 1H), 1.64-1.35 (m, 4H), 1.15-0.98 (m, 1H), 0.75-0.55 (m, 1H). EXAMPLE 188: ¹H NMR (300 MHz, CD₃OD+DCl) δ 8.48 (d, J=8.7 Hz, 1H), 7.67 (d, J=8.8 Hz, 1H), 3.80-3.74 (m, 1H), 3.62-3.38 (m, 2H), 3.27-3.02 (m, 3H), 3.02-2.77 (m, 4H), 2.59-2.52 (m, 1H), 1.80-1.67 (m, 1H), 1.60-1.37 (m, 4H), 1.15-1.00 (m, 1H), 0.76-0.60 (m, 1H), EXAMPLE 189: ¹H NMR (300 MHz, D₂O) δ 8.19 (d, J=8.8 Hz, 1H), 7.35 (d, J=9.0 Hz, 1H), 3.54-3.45 (m, 1H), 3.43-3.37 (m, 2H), 3.06-2.97 (m, 1H), 2.90-2.78 (m, 2H), 2.78-2.65 (m, 3H), 2.61-2.39 (m, 2H), 1.58-1.44 (m, 2H), 1.43-1.34 (m, 1H), 0.88-0.77 (m, 1H), 0.70-0.60 (m, 1H).

Example 190

(R)—N1-(3-amino-2-hydroxypropyl)-4-(4-(N-(2-aminoethyl)sulfamoyl) piperidin-1-yl)-3-(2H-tetrazol-5-yl)benzene-1,2-disulfonamide

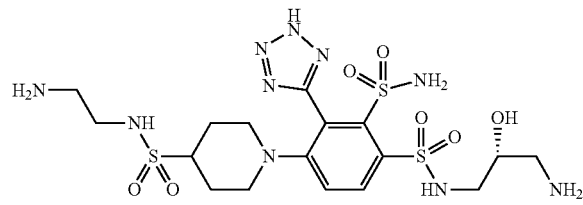

Step A: tert-Butyl (2-(1-(3-(N,N-bis(4-methoxybenzyl)sulfamoyl)-2-(2-(4-methoxybenzyl)-2H-tetrazol-5-yl)-4-((2-(trimethylsilyl)ethyl)sulfonyl)phenyl)piperidine-4-sulfonamido)ethyl)carbamate To a solution of 3-iodo-N,N-bis(4-methoxybenzyl)-2-(2-(4-methoxybenzyl)-2H-tetrazol-5-yl)-6-((2-(trimethylsilyl)ethyl)sulfonyl)benzenesulfonamide (REFERENCE EXAMPLE 37) (1.50 g, 1.71 mmol) in NMP (12 mL) were added DABCO (0.96 g, 8.56 mmol) and tert-butyl (2-(piperidine-4-sulfonamido)ethyl)carbamate (1.58 g, 5.14 mmol) at RT. The reaction mixture was stirred at 130° C. for 36 hours. After cooling to RT, the resulting mixture was diluted with water (20 mL), extracted with EA (3×10 mL). The combined organic layers were washed with aq.Na₂CO₃ (2×10 mL) and brine (2×10 mL), dried over anhydrous Na₂SO₄ and concentrated under reduced pressure. The residue was purified by a silica gel column chromatography, eluting with a gradient of 1%-60% EA in PE to afford the title compound. LCMS [M+1]⁺: 1055.

Step B: 2-(N,N-bis(4-methoxybenzyl)sulfamoyl)-4-(4-(N-(2-((tert-butoxycarbonyl) amino)ethyl)sulfamoyl)piperidin-1-yl)-3-(2-(4-methoxybenzyl)-2H-tetrazol-5-yl) benzenesulfinic acid The title compound was prepared as described for EXAMPLE 148 step B using tert-butyl (2-(1-(3-(N,N-bis (4-methoxybenzyl)sulfamoyl)-2-(2-(4-methoxybenzyl)-2H-tetrazol-5-yl)-4-((2-(trimethylsilyl)ethyl)sulfonyl)phenyl)piperidine-4-sulfonamido) ethyl)carbamate (0.63 g, 0.60 mmol). LCMS [M+1]⁺: 955.

Step C: tert-butyl (R)-(3-((2-(N,N-bis(4-methoxybenzyl)sulfamoyl)-4-(4-(N-(2-((tert-butoxycarbonyl)amino)ethyl)sulfamoyl)piperidin-1-yl)-3-(2-(4-methoxybenzyl)-2H-tetrazol-5-yl)phenyl)sulfonamido)-2-hydroxypropyl)carbamate The title compound was prepared as described for EXAMPLE 148 step C using 2-(N,N-bis(4-methoxybenzyl)sulfamoyl)-4-(4-(N-(2-((tert-butoxycarbonyl)amino)ethyl)sulfamoyl)piperidin-1-yl)-3-(2-(4-methoxybenzyl)-2H-tetrazol-5-yl)benzenesulfinic acid (0.50 g, 0.52 mmol). LCMS [M+1]⁺: 1143.

Step (R)—N1-(3-amino-2-hydroxypropyl)-4-(4-(N-(2-aminoethyl)sulfamoyl)piperidin-1-yl)-3-(2H-tetrazol-5-yl)benzene-1,2-disulfonamide The title compound was prepared as described for EXAMPLE 117 Step B using tert-butyl (R)-(3-((2-(N,N-bis (4-methoxybenzyl)sulfamoyl)-4-(4-(N-(2-((tert-butoxycarbonyl)amino)ethyl)sulfamoyl)piperidin-1-yl)-3-(2-(4-methoxybenzyl)-2H-tetrazol-5-yl)phenyl)sulfonamido)-2-hydroxypropyl)carbamate (0.30 g, 0.262 mmol) to afford the crude product, which was purified by Prep-HPLC with the following conditions: Column: X Bridge Prep C18 OBD Column 19×250 mm, 10 μm; Mobile Phase A: water (10 mmoL/L NH₄HCO₃), Mobile Phase B: ACN; Flow rate: 20 mL/min; Gradient: 2% B to 16% B in 12 min; Detector: UV 254 nm and 22.0 nm to afford the title compound. LCMS [M+1]⁺: 583; ¹H NMR (300 MHz, D₂O) δ 8.13 (d, J=8.8 Hz, 1H), 7.38 (d, J=8.9 Hz, 1H), 3.88-3.78 (m, 1H), 3.25-3.20 (m, 2H), 3.15-2.87 (m, 8H), 2.75-2.65 (m, 1H), 2.60-2.49 (m, 2H), 1.83-1.72 (m, 2H), 1.18-1.15 (m, 2H).

Example 191

(R)—N1-(pyrrolidin-3-yl)-3-(2H-tetrazol-5-yl)-4-(2-thioxoimidazolidin-1-yl)benzene-1,2-disulfonamide

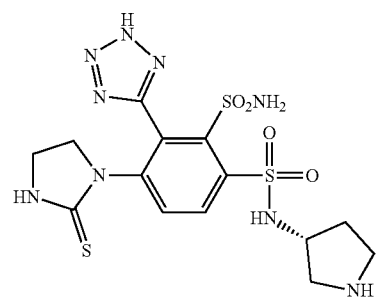 [SMILES: NS(=O)(=O)c1c(S(=O)(=O)N[C@@H]2CCNC2)ccc(N2CCNC2=S)c1-c1nn[nH]n1]

Step A: (R)-tert-butyl 3-(4-((2-(((benzyloxy)carbonyl)amino)ethyl)amino)-2-(N,N-bis(4-methoxybenzyl)sulfamoyl)-3-(2-(4-methoxybenzyl)-2H-tetrazol-5-yl) phenylsulfonamido)pyrrolidine-1-carboxylate To a stirred solution of (R)-tert-butyl 3-(2-(N,N-bis(4-methoxybenzyl)sulfamoyl)-4-iodo-3-(2-(4-methoxybenzyl)-2H-tetrazol-5-yl)phenylsulfonamido)pyrrolidine-1-carboxylate (REFERENCE EXAMPLE 40) (2.0 g, 2.08 mmol) in toluene (15 mL) were added benzyl (2-aminoethyl)carbamate (1.20 g, 6.25 mmol), rac-BINAP-PD-G3 (0.206 g, 0.208 mmol) and $Cs_2CO_3$ (3.4 g, 10.42 mmol) at RT. The mixture was degassed with nitrogen 3 times and stirred for 16 hours at 80° C. under nitrogen. After cooling to RT, the resulting mixture was concentrated under reduced pressure. The residue was dissolved with EA (50 mL), washed with brine (3×50 mL), the separated organic phase was dried over anhydrous $Na_2SO_4$ and filtered. The filtrate was concentrated under reduced pressure. The residue was purified by silica gel column chromatography, eluting with a gradient of 1%-50% EA in PE to afford the title compound. LCMS [M+1]$^+$: 1026.

Step B: (R)-tert-butyl 3-(4-((2-aminoethyl)amino)-2-(N,N-bis(4-methoxybenzyl) sulfamoyl)-3-(2-(4-methoxybenzyl)-2H-tetrazol-5-yl)phenylsulfonamido)pyrrolidine-1-carboxylate To a stirred solution of (R)-tert-butyl 3-(4-((2-(((benzyloxy)carbonyl)amino)ethyl)amino)-2-(N,N-bis(4-methoxybenzyl)sulfamoyl)-3-(2-(4-methoxybenzyl)-2H-tetrazol-5-yl)phenylsulfonamido)pyrrolidine-1-carboxylate (0.70 g, 0.682 mmol) in MeOH (15 mL) was added palladium hydroxide on carbon (0.45 g, 0.641 mmol, 20% wt) at RT. The reaction mixture was degassed with hydrogen 3 times. The mixture was stirred 30 hours at RT underhydrogen (1.5 atm). The solid was filtered out and the filtrate was concentrated under reduced pressure to afford of the title compound, which was used tin the next step without further purification. LCMS [M+1]$^+$: 892.

Step C: (R)-tert-butyl 3-(2-(N,N-bis(4-methoxybenzyl)sulfamoyl)-3-(2-(4-methoxybenzyl)-2H-tetrazol-5-yl)-4-(2-thioxoimidazolidin-1-yl)phenylsulfonamido)pyrrolidine-1-carboxylate To a solution of (R)-tert-butyl 3-(4-((2-aminoethyl)amino)-2-(N,N-bis(4-methoxy benzyl)sulfamoyl)-3-(2-(4-methoxybenzyl)-2H-tetrazol-5-yl)phenylsulfonamido) pyrrolidine-1-carboxylate (0.400 g, 0.448 mmol) in pyridine (0.75 mL) was added thiophosgene (0.310 g, 2.69 mmol) at RT. The solution was stirred at 50° C. for 16 hours. After cooling to RT, the resulting mixture was concentrated under reduced pressure. The residue was diluted with EA (20 mL), washed with brine (3×20 mL), dried over anhydrous $Na_2SO_4$ and filtered. The filtrate was concentrated under reduced pressure. The residue was purified by silica gel column chromatography, eluting with a gradient of 1% to 70% EA in PE to afford the title compound. LCMS [M+1]$^+$: 934.

Step D: (R)—N1-(pyrrolidin-3-yl)-3-(2H-tetrazol-5-yl)-4-(2-thioxoimidazolidin-1-yl)benzene-1,2-disulfonamide The title compound was prepared as described for EXAMPLE 117 Step B using (R)-tert-butyl 3-(2-(N,N-bis (4-methoxybenzyl)sulfamoyl)-3-(2-(4-methoxybenzyl)-2H-tetrazol-5-yl)-4-(2-thioxoimidazolidin-1-yl)phenylsulfonamido)pyrrolidine-1-carboxylate (50 mg, 0.054 mmol) to afford the crude product, which was purified by Prep-HPLC with the following conditions: Column: X Bridge Prep C18 OBD Column 19×250 mm, 10 µm; Mobile Phase A: water with 10 mmol/L $NH_4HCO_3$, Mobile Phase B: ACN; Flow rate: 20 mL/min; Gradient: 3% B to 12% B in 12 min; Detector: UV 254 nm and 220 nm. Retention time: 10.05 min to give the title compound. LCMS [M+1]$^+$: 474; $^1$H NMR (300 MHz, $CD_3OD$) δ 8.65 (d, J=8.5 Hz, 1H), 8.02 (d, J=8.6 Hz, 1H), 4.27-4.19 (m, 1H), 3.98-3.80 (m, 2H), 3.60-3.37 (m, 6H), 2.30-2.18 (m, 1H), 2.04-1.95 (m, 1H).

Example 192

(R)—N1-(3-amino-2-hydroxypropyl)-4-((3-aminocyclobutyl)amino)-3-(1H-tetrazol-5-yl)benzene-1,2-disulfonamide

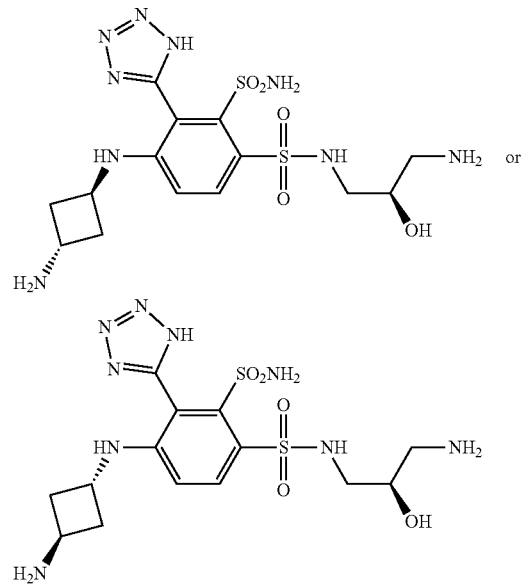

Example 192

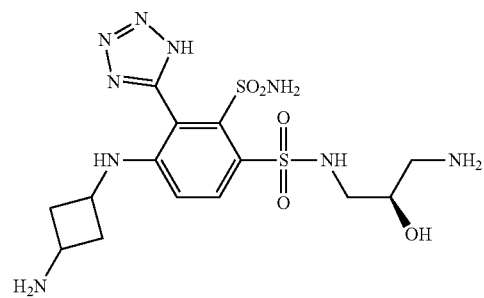 [SMILES: NC[C@@H](O)CNS(=O)(=O)c1ccc(NC2CC(N)C2)c(-c2nnn[nH]2)c1S(N)(=O)=O]

Step A: tert-butyl (R)-(3-((4-(N-(3-((tert-butoxycarbonyl)amino)-2-((tert-butyldimethylsilyl)oxy)propyl)sulfamoyl)-3-(N,N-dibenzylsulfamoyl)-2-(1-(4-methoxybenzyl)-1H-tetrazol-5-yl)phenyl)amino) cyclobutyl)carbamate To a solution of (R)-tert-butyl (3-(4-bromo-2-(N,N-dibenzylsulfamoyl)-3-(2-(4-methoxybenzyl)-2H-tetrazol-5-yl) phenylsulfonamido)-2-((tert-butyldimethylsilyl)oxy)propyl) carbamate (REFERENCE EXAMPLE 51) (0.10 g, 0.10 mmol) in toluene (1 mL) were added $Cs_2CO_3$ (60 mg, 0.31 mmol), RAC-BINAP-Pd-G3 (20.4 mg, 0.021 mmol) and tert-butyl (3-aminocyclobutyl)carbamate (19.2 mg, 0.10 mmol) at RT. The reaction mixture was degassed with nitrogen three times and stirred at 130° C. with microwave for 1 hour under nitrogen. After cooling to RT, the resulting mixture was concentrated under reduced pressure. The reaction mixture was diluted with water (10 mL) and extracted with EA (3×10 mL). The combined organic layers were washed with brine (10 mL), dried over anhydrous $Na_2SO_4$ and filtered. The filtrate was concentrated under reduced pressure, the residue was purified by a silica gel column chromatography, eluting with a gradient of 1% to 50% EA in PE to afford the title compound. LCMS [M+1]$^+$: 1076.

Step B: (R)—N1-(3-amino-2-hydroxypropyl)-4-((3-aminocyclobutyl)amino)-3-(1H-tetrazol-5-yl)benzene-1,2-disulfonamide The title compound was prepared as described for EXAMPLE 171 step B using tert-butyl(R)-(3-((4-(N-(3-((tert-butoxycarbonyl)amino)-2-((tert-butyldimethylsilyl) oxy)propyl)sulfamoyl)-3-(N,N-dibenzylsulfamoyl)-2-yl)-(4-methoxybenzyl)-1H-tetrazol-5-yl)phenyl)amino) cyclobutyl)carbamate (0.190 g, 0.177 mmol) to afford the crude product, which was purified by Prep-HPLC with the following conditions: Column: XBridge C18 OBD Prep Column 100 Å, 19 mm×250 mm, 10 μm; Mobile Phase A: water (10 mmol/L $NH_4HCO_3$), Mobile Phase B: ACN; Flow rate: 20 mL/min; Gradient: B to 12% B in 12 min; Detector: UV 254 nm and 210 nm; Retention time: 8.97 min to afford the title compound. LCMS (ESI) calc'd for $C_{14}H_{23}N_9O_5S_2$ [M+1]$^+$: 462, found 462; $^1$H NMR (300 MHz, $CD_3OD$) δ 8.2.5 (d, J=9.1 Hz, 1H), 698 (d, J=9.1 Hz, 1H), 4.03-3.80 (m, 2H), 3.65-3.53 (m, 1H), 3.19-3.00 (m, 3H), 2.91-2.86 (m, 3H), 2.06-1.96 (m, 2H).

EXAMPLES 193-195 were prepared as described for EXAMPLE 4, starting from (R)-tert-butyl(3-(2-(N,N-bis(4-methoxybenzyl)sulfamoyl)-4-iodo-3-(2-(4-methoxybenzyl)-2H-tetrazol-5-yl)phenylsulfonamido)-2-((tert-butyldimethylsilyl)oxy)propyl)carbamate (REFERENCE EXAMPLE 45) and the requisite amines.

Ex. 193: $^1$H NMR (300 MHz, $D_2O$) δ 8.10 (d, J=8.9 Hz, 1H), 7.34 (d, J=8.9 Hz, 1H), 3.90-3.75 (m, 1H), 3.18-2.67 (m, 8H), 2.49-2.42 (m, 2H), 1.58-1.43 (m, 2H), 1.43-1.32 (m, 2H), 1.15-1.08 (m, 3H), 0.74-0.63 (m, 2H). Ex. 194: $^1$H NMR (300 MHz, $CD_3OD+DCl$) δ 8.43 (d, J=8.7 Hz, 1H), 7.73 (d, J=8.7 Hz, 1H), 3.99-3.95 (m, 1H), 3.18-3.07 (m, 6H), 2.97-2.80 (m, 3H), 1.94-1.90 (m, 2H), 1.38-1.12 (m, 2H). Ex. 195: $^1$H NMR (400 MHz, $CD_3OD+DCl$) δ 8.47 (d, J=8.4, 1H), 7.78 (d, J=8.8, 1H), 4.85-4.72 (m, 1H), 4.02-3.97 (m, 1H), 3.50-3.32 (m, 2H), 3.25-3.02 (m, 5H), 2.96-2.82 (m, 2H), 1.85-1.82 (m, 1H), 1.63-1.53 (m, 1H); $^{19}$F NMR (376 MHz, $CD_3OD+DCl$) δ −206.041.

Example 196

(S)-4-(4-(N—((R)-pyrrolidin-3-yl)sulfamoyl)-3-sulfamoyl-2-(2H-tetrazol-5-yl)phenyl)piperazine-2-carboxamide

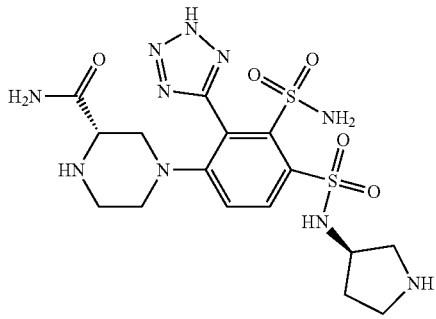

| EX. | STRUCTURE | NAME | LC/MS [M + 1]$^+$ |
|---|---|---|---|
| 193 | 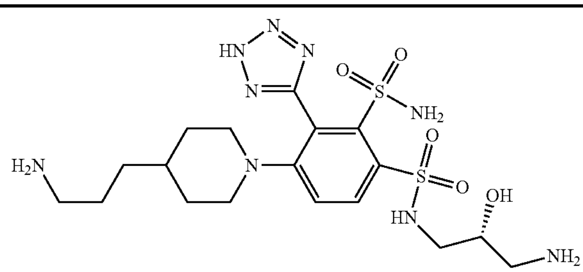 | (R)-N1-(3-amino-2-hydroxypropyl)-4-(4-(3-aminopropyl)piperidin-1-yl)-3-(2H-tetrazol-5-yl)benzene-1,2-disulfonamide | 518 |
| 194 | 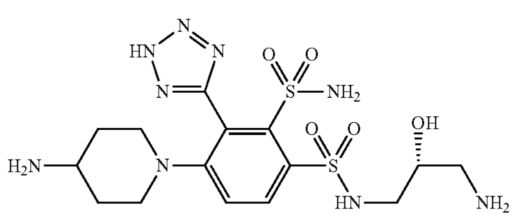 [SMILES: NC[C@@H](O)CNS(=O)(=O)c1ccc(N2CCC(N)CC2)c(-c2nn[nH]n2)c1S(N)(=O)=O] | (R)-N1-(3-amino-2-hydroxypropyl)-4-(4-aminopiperidin-1-yl)-3-(2H-tetrazol-5-yl)benzene-1,2-disulfonamide | 476 |
| 195 | 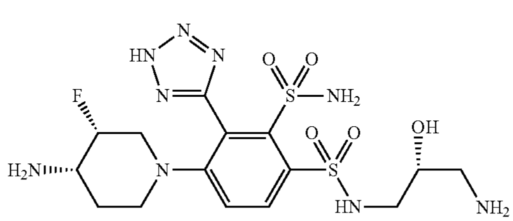 [SMILES: NC[C@@H](O)CNS(=O)(=O)c1ccc(N2CC[C@H](N)[C@H](F)C2)c(-c2nn[nH]n2)c1S(N)(=O)=O] | N1-((R)-3-amino-2-hydroxypropyl)-4-((3R,4S)-4-amino-3-fluoropiperidin-1-yl)-3-(2H-tetrazol-5-yl)benzene-1,2-disulfonamide | 494 |

Step A: (S)-tert-butyl 4-(3-(N,N-bis(4-methoxybenzyl)sulfamoyl)-4-(N—((R)-1-(tert-butoxycarbonyl)pyrrolidin-3-yl)sulfamoyl)-2-(2-(4-methoxybenzyl)-2H-tetrazol-5-yl)phenyl)-2-carbamoylpiperazine-1-carboxylate The title compound was prepared as described for EXAMPLE 117 step A using (R)-tert-butyl 3-(2-(N,N-bis(4-methoxybenzyl)sulfamoyl)-4-iodo-3-(2-(4-methoxybenzyl)-2H-tetrazol-5-yl)phenylsulfonamido)pyrrolidine-1-carboxylate (REFERENCE EXAMPLE 40) (0.900 g, 0.938 mmol) and (S)-tert-butyl 2-carbamoylpiperazine-1-carboxylate (0.645 g, 2.81 mmol). LCMS [M+1]$^+$: 1061.

Step B: (S)-4-(4-(N—((R)-pyrrolidin-3-yl)sulfamoyl)-3-sulfamoyl-(2H-tetrazol-5-yl) phenyl)piperazine-2-carboxamide The title compound was prepared as described for EXAMPLE 117 step B using (S)-tert-butyl 4-(3-(N,N-bis(4-methoxybenzyl)sulfamoyl)-4-(N—((R)-1-(tert-butoxycarbonyl)pyrrolidin-3-yl)sulfamoyl)-2-(2-(4-methoxybenzyl)-2H-tetrazol-5-yl)phenyl)-2-carbamoylpiperazine-1-carboxylate (0.250 g, 0.236 mmol) to afford the crude product. The residue was purified by Prep-HPLC with the following conditions: Column: XBridge C18 OBD Prep Column 100 Å, 19 mm×250 mm, 10 μm; Mobile Phase A: water (10 mmoL/L NH$_4$HCO$_3$), Mobile Phase B: ACN, Flow rate: 20 mL/min; Gradient: 1% B to 10% B in 12 min; Detector: 254 nm and 210 nm; Retention time: 11.05 min to afford the title compound. LCMS [M+1]$^+$: 501; $^1$H NMR (300 MHz, CD$_3$OD+DCl) δ 8.53 (d, J=8.7 Hz, 1H), 7.84 (d, J=8.7 Hz, 1H), 4.19-4.15 (m, 1H), 3.79-3.74 (m, 1H), 3.65-3.61 (m, 1H), 3.45-3.41 (m, 4H), 3.38-3.12 (m, 3H), 3.06-2.97 (m, 1H), 2.68-2.64 (m, 2.25-2.17 (m, 1H), 2.07-1.80 (m, 1H).

EXAMPLES 197-199 were prepared as described for EXAMPLE 196, starting from (R)-tert-butyl 3-(2-(N,N-bis(4-methoxybenzyl)sulfamoyl)-4-iodo-3-(2-(4-methoxybenzyl)-2H-tetrazol-5-yl)phenylsulfonamido)pyrrolidine-1-carboxylate (REFERENCE EXAMPLE 40) and the requisite amines, which were prepared as described herein, or which were available from commercial sources.

| EX. | STRUCTURE | NAME | LC/MS [M + 1]$^+$ |
|---|---|---|---|
| 197 | 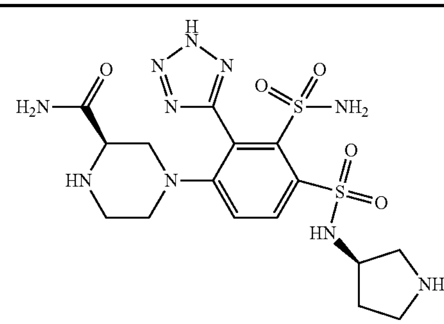 | (R)-4-(4-(N-((R)-pyrrolidin-3-yl)sulfamoyl)-3-sulfamoyl-2-(2H-tetrazol-5-yl)phenyl)piperazine-2-carboxamide | 501 |
| 198 | 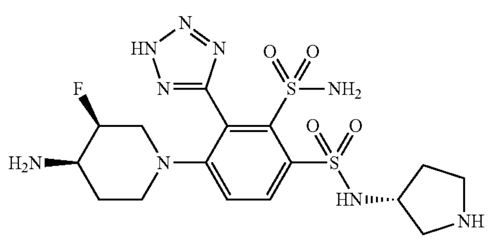 [SMILES: N[C@@H]1CCN(c2ccc(S(=O)(=O)N[C@@H]3CCNC3)c(S(N)(=O)=O)c2-c2nn[nH]n2)C[C@@H]1F] | 4-((3S,4R)-4-amino-3-fluoropiperidin-1-yl)-N1-((R)-pyrrolidin-3-yl)-3-(2H-tetrazol-5-yl)benzene-1,2-disulfonamide | 490 |
| 199 | 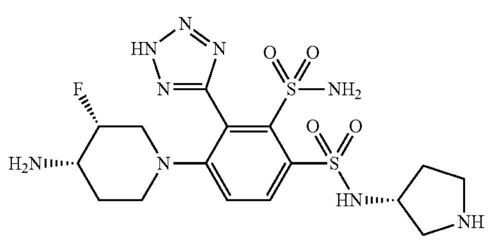 [SMILES: N[C@H]1CCN(c2ccc(S(=O)(=O)N[C@@H]3CCNC3)c(S(N)(=O)=O)c2-c2nn[nH]n2)C[C@H]1F] | 4-((3R,4S)-4-amino-3-fluoropiperidin-1-yl)-N1-((R)-pyrrolidin-3-yl)-3-(2H-tetrazol-5-yl)benzene-1,2-disulfonamide | 490 |

Ex. 197: $^1$H NMR (300 MHz, CD$_3$OD+DCl) δ 8.28 (d, J=9.0 Hz, 1H), 7.42 (d, J=8.7 Hz, 1H), 4.08-4.04 (m, 1H), 3.36-3.33 (m, 3H), 3.31-3.15 (m, 3H), 2.80-2.58 (m, 3H), 2.58-2.50 (m, 1H), 2.40-2.30 (m, 1H), 2.15-2.08 (m, 1H), 1.93-1.80 (m, 1H), Ex. 198: $^1$H NMR. (300 MHz, D$_2$O) δ 8.16 (d, J=8.7 Hz, 1H), 7.42 (d, J=9.0 Hz, 1H), 4.68-4.42 (m, 1H), 4.05-4.01 (m, 1H), 3.34-2.97 (m, 7H), 2.86-2.58 (m, 2H), 2.13-2.04 (m, 1H), 1.91-1.82 (m, 1H), 1.55-1.50 (m, 1H), 1.38-1.33 (m, 1H); $^{19}$F NMR (282 MHz, D$_2$O) δ −204.299. Ex. 199: $^1$H NMR (300 MHz, D$_2$O) δ 8.21 (d, J=8.9 Hz, 1H), 7.44 (d, J=8.9 Hz, 1H), 4.76-4.59 (m, 1H), 4.57-4.54 (m, 1H), 4.09-4.06 (m, 1H), 3.43-3.04 (m, 6H), 2.97-2.95 (m, 1H), 2.63-2.60 (m, 1H), 2.16-2.11 (m, 1H), 1.98-1.78 (m, 1H), 1.56-1.52 (m, 1H), 1.42-1.23 (m, 1H). $^{19}$F NMR (376 MHz, CD$_3$OD+DCl) δ −204.793.

Example 200

(S)-4-(4-(aminomethyl)piperidin-1-yl)-N1-(2,3-diaminopropyl)-3-(2H-tetrazol-5-yl)benzene-1,2-disulfonamide

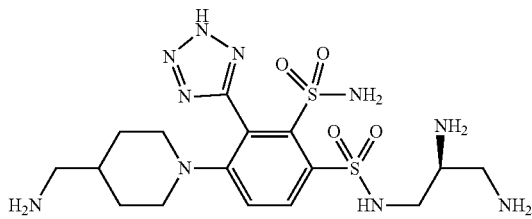 [SMILES: NCC1CCN(c2ccc(S(=O)(=O)NC[C@@H](N)CN)c(S(N)(=O)=O)c2-c2nn[nH]n2)CC1]

Step A: di-tert-butyl (3-((2-(N,N-bis(4-methoxybenzyl)sulfamoyl)-4-(4-(((tert-butoxycarbonyl)amino)methyl)piperidin-1-yl)-3-(2-(4-methoxybenzyl)-2H-tetrazol-5-yl)phenyl)sulfonamido)propane-1,2-di(S)-dicarbamate The title compound was prepared as described for EXAMPLE 117 step A using (S)-di-tert-butyl (3-(2-(N,N-bis(4-methoxybenzyl)sulfamoyl)-4-iodo-3-(2-(4-methoxybenzyl)-2H-tetrazol-5-yl)phenylsulfonamido)propane-1,2-diyl)dicarbamate (REFERENCE EXAMPLE 63) (0.400 g, 0.376 mmol) and tert-butyl (piperidin-4-ylmethyl)carbamate (0.240 g, 1.13 mmol). LCMS [M+1]$^+$: 1150.

Step B: (S)-4-(4-(aminomethyl)piperidin-1-yl)-N1-(2,3-diaminopropyl)-3-(2H-tetrazol-5-yl)benzene-1,2-disulfonamide The title compound was prepared as described for EXAMPLE 117 step B using di-tert-butyl (3-((2-(N,N-bis(4-methoxybenzyl)sulfamoyl)-4-(4-(((tert-butoxycarbonyl)amino)methyl)piperidin-1-yl)-3-(2-(4-methoxybenzyl)-2H-tetrazol-5-yl)phenyl)sulfonamido)propane-1,2-diyl)(S)-dicarbamate (0.250 g, 0.22 mmol) to afford the crude product. The residue was purified by Prep-HPLC with the following conditions: Column: XBridge C18 OBD Prep Column 100 Å, 19 mm×250 mm, 10 Mobile Phase A: water (10 mmoL/L NH$_4$HCO$_3$), Mobile Phase B: ACN; Flow rate: 20 mL/min; Gradient: 1% B to 12% B in 12 min; Detector: 254 nm and 210 nm; Retention time: 10.53 min to afford the title compound. LCMS [M+1]$^+$: 489; $^1$H NMR (400 MHz, D$_2$O) δ 8.13 (d, J=8.8 Hz, 1H), 7.38 (d, J=8.8 Hz, 1H), 3.09-2.85 (m, 6H), 2.76-2.62 (m, 3H), 2.55-2.46 (m, 2H), 1.59-1.55 (m, 1H), 1.47-1.43 (m, 2H), 0.79-0.75 (m, 2H).

Example 201

(R)-4-(4-(1H-imidazol-2-yl)piperidin-1-yl)-N1-(3-amino-2-hydroxy propyl)-3-(2H-tetrazol-5-yl)benzene-1,2-disulfonamide

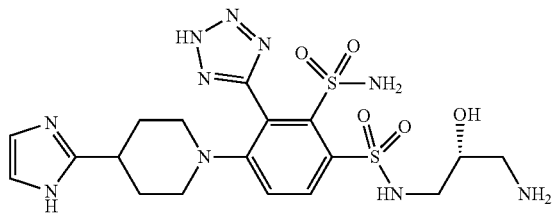 [SMILES: NC[C@@H](O)CNS(=O)(=O)c1ccc(N2CCC(c3ncc[nH]3)CC2)c(-c2nn[nH]n2)c1S(N)(=O)=O]

Step A: (R)-tert-butyl (3-(4-(4-(1H-imidazo-2-yl)piperidin-1-yl)-2-(N,N-bis(4-methoxybenzyl)sulfamoyl)-3-(2-(4-methoxybenzyl)-2H-tetrazol-5-yl)phenylsulfonamido)-2-((tert-butyldimethylsilyl)oxy)propyl)carbamate The title compound was prepared as described for EXAMPLE 128 step A using (R)-tert-butyl (3-(2-(N,N-bis(4-methoxybenzyl)sulfamoyl)-4-iodo-3-(2-(4-methoxybenzyl)-2H-tetrazol-5-yl)phenylsulfonamido)-2-((tert-butyldimethylsilyl) oxy)propyl)carbamate (REFERENCE EXAMPLE 45) (0.323 g, 0.300 mmol) and 4-(1H-imidazol-2-yl)piperidine hydrochloride (0.169 g, 0.900 mmol) in NMP (1 mL). LCMS [M+1]$^+$: 1102.

Step B: (R)-4-(4-(1H-imidazol-2-yl)piperidin-1-yl)-N1-(3-amino-2-hydroxypropy)-3-(2H-tetrazol-5-yl)benzene-1,2-disulfonamide The title compound was prepared as described for EXAMPLE 117 step B using (R)-tert-butyl (3-(4-(4-(1H-imidazol-2-yl)piperidin-1-yl)-2-(N,N-bis(4-methoxybenzyl) sulfamoyl)-3-(2-(4-methoxybenzyl)-2H-tetrazol-5-yl) phenylsulfonamido)-2-((tert-butyldimethylsilyl)oxy)propyl)carbamate (0.200 g, 0.182 mmol) to afford crude product, which was purified by Prep-HPLC with the following conditions: Column: Xbridge C18, 19×150 mm, 10 μm; Mobile Phase A: water (10 mmol/L NH$_4$HCO$_3$), Mobile Phase B: ACN; Flow rate: 20 ml/min; Gradient: 5% B to 35% B in 8 min; Detector: 254 nm and 210 nm; Retention time: 7.50 min to afford the title compound. LCMS [M+1]$^+$: 527; $^1$H NMR (300 MHz, CD$_3$OD): δ 8.27 (d, J=8.8 Hz, 1H), 7.44 (d, J=8.8 Hz, 1H), 6.92-6.90 (m, 2H), 3.90-3.87 (m, 1H), 3.27-3.00 (m, 5H), 2.94-2.63 (m, 4H), 1.77 (d, J=12.5 Hz, 2H), 1.57-1.39 (m, 2H).

Example 202

(S)-N1-(1-amino-3-hydroxypropan-2-yl)-4-(4-(N-(2-aminoethyl) sulfamoyl)piperidin-1-yl)-3-(2H-tetrazol-5-yl)benzene-1,2-disulfonamide

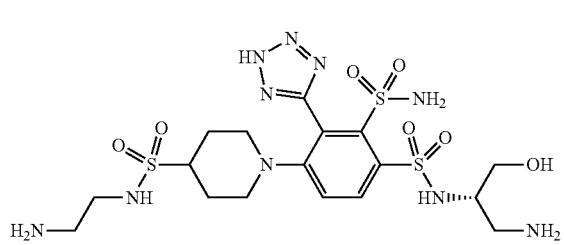 [SMILES: NCCNS(=O)(=O)C1CCN(c2ccc(S(=O)(=O)N[C@@H](CN)CO)c(S(N)(=O)=O)c2-c2nn[nH]n2)CC1]

Step A: tert-butyl(S)-(2-((1-(3-(N,N-bis(4-methoxybenzyl)sulfamoyl)-2-(2-(4-methoxybenzyl)-2H-tetrazol-5-yl)-4-(N-(9,9,10,10-tetramethyl-3-oxo-1-phenyl-2,8-dioxa-4-aza-9-silaundecan-6-yl)sulfamoyl) phenyl)piperidine)-4-sulfonamido)ethyl)carbamate The title compound was prepared as described for EXAMPLE 128 step A using benzyl (S)-(2-((2-(N,N-bis(4-methoxybenzyl)sulfamoyl)-4-iodo-3-(2-(4-methoxybenzyl)-2H-tetrazol-5-yl)phenyl)sulfonamido)-3-((tert-butyldimethylsilyl)oxy)propyl)carbamate (REFERENCE EXAMPLE 52) (0.600 g, 0.54 mmol) and tert-butyl (2-(piperidine-4-sulfonamido)ethyl)carbamate (0.829 g, 2.70 mmol) in NMP (3 mL) to afford benzyl N-[(2S)-2-(2-{bis[(4-methoxyphenyl)methyl]sulfamoyl}-4-{[(2-{[(tert-butoxy)carbonyl]amino}ethyl)sulfamoyl]piperidin-1-yl}-3-{2-[(4-methoxyphenyl) methyl]-2H-1,2,3,4-tetrazol-5-yl}benzenesulfonamido)-3-[(tert-butyldimethylsilyl) oxy]propyl]carbamate. LCMS [M+1]⁺ 1291.

Step B: (S)-N1-(1-amino-3-hydroxypropan-2-yl)-4-(4-(N-(2-aminoethyl)sulfamoyl) piperidin-1-yl)-3-(2H-tetrazol-5-yl)benzene-1,2-disulfonamide The title compound was prepared as described for EXAMPLE 117 step B using tert-butyl (S)-(2-((1-(3-(N,N-bis(4-methoxybenzyl)sulfamoyl)-2-(2-(4-methoxybenzyl)-2H-tetrazol-5-yl)-4-(N-(9,9,10,10-tetramethyl-3-oxo-1-phenyl-2,8-dioxa-4-aza-9-silaundecan-6-yl)sulfamoyl)phenyl)piperidine)-4-sulfonamido)ethyl)carbamate (0.150 g, 0,116 mmol) to afford crude product, which was purified by Prep-HPLC with the following conditions: Column: Xbridge C18, 19×150 mm, 10 μm; Mobile Phase A: water (10 mmol/L NH$_4$HCO$_3$), Mobile Phase B: ACN; Flow rate: 20 mL/min; Gradient: 4% B to 10% B in 12 min; Detector: 254 nm and 210 nm; Retention time: 10.82 min to afford the title compound. LCMS [M+1]⁺: 583; ¹H NMR (400 MHz, D$_2$O) δ 8.22 (d, J=8.8 Hz, 1H), 7.39 (d, J=8.9, 1H), 3.59-3.56 (m, 1H), 3.51-3.33 (m, 2H), 3.29-2.90 (m, 8H), 2.88-2.77 (m, 1H), 2.70-2.43 (m, 2H), 1.85-1.82 (m, 1H), 1.73-1.70 (m, 1H), 1.36-1.11 (m, 1H), 1.05-1.02 (m, 1H).

Example 203

(R)-4-((1H-imidazol-2-yl)amino)-N1-(3-amino-2-hydroxypropyl)-3-(2-tetrazol-5-yl)benzene-1,2-disulfonamide bis(2,2,2-trifluoroacetate)

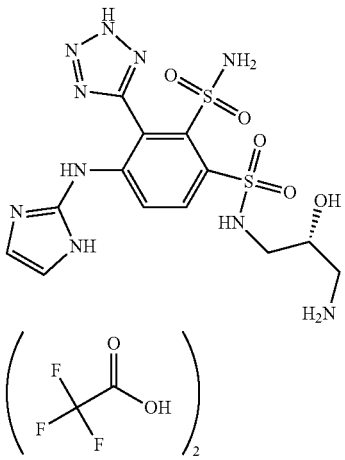

Step A: (R)-tert-butyl 3-(4-((1H-imidazol-2-yl) amino)-2-(N,N-dibenzylsulfamoyl)-3-(2-(4-methoxybenzyl)-2H-tetrazol-5-yl)phenylsulfonamido)-2-((tert-butyldimethyl silyl)oxy)propyl) carbamate To a solution of (R)-tert-butyl (3-(4-bromo-2-(N,N-dibenzylsulfamoyl)-3-(2-(4-methoxybenzyl)-2H-tetrazol-5-yl) phenylsulfonamido)-2-((tert-butyldimethylsilyl)oxy)propyl) carbamate (REFERENCE EXAMPLE 51) (2.00 g, 2.06 mmol) in DMSO (3 mL) was added 1H-imidazol-2-amine sulfate (1.12 g, 6.18 mmol) and K$_2$CO$_3$ (1.42 g, 10.3 mmol) at RT. The reaction mixture was stirred at 100° C. for 4 hours under nitrogen. After cooling to RT, the resulting mixture was diluted with water (10 mL) and extracted with EA (3×10 mL). The combined organic layers were washed with brine (10 mL). The resulting mixture was filtered. The filtrate was concentrated under reduced pressure. The residue was purified by a silica gel column chromatography, eluting using a gradient of 1% to 100% EA in PE to afford the title compound. LCMS [M+1]⁺: 973.

Step B: (R)-4-((1H-imidazol-2-yl)amino)-N1-(3-amino-2-hydroxypropyl)-3-(2H-tetrazol-5-yl)benzene-1,2-disulfonamide bis(2,2,2-trifluoroacetate)

The title compound was prepared as described for EXAMPLE 129 step B using (R)-tert-butyl (3-(4-((1H-imidazol-2-yl)amino)-2-(N,N-dibenzylsulfamoyl)-3-(2-(4-methoxybenzyl)-2H-tetrazol-5-yl)phenylsulfonamido)-2-((tert-butyldimethylsilyl)oxy)propyl)carbamate (0.200 g, 0.205 mmol) to afford the crude product, which was purified by Prep-HPLC with the following conditions: Column: Sunfire Prep C18 OBD Column, 19×250 mm, 10 μm; Mobile Phase A: water (0.05% TFA), Mobile Phase B: ACN; Flow rate: 20 mL/min; Gradient: 1% B to 8% B in 12 min; Detector: 254 nm and 210 nm; Retention time: 10.15 min to afford the title compound. LCMS [M−228+1]⁺: 459; ¹H NMR (400 MHz, DMSO) δ 12.08-12.05 (brs, 1H), 8.41 (d, J=8.4 Hz, 1H), 8.05 (d, J=8.4 Hz, 1H), 7.79-7.76 (brs, 3H), 7.67-7.65 (brs, 2H), 7.39-7.36 (brs, 3H), 5.71-5.69 (m, 2H), 3.83-3.81 (m, 1H), 3.08-2.94 (m, 3H), 2.70-2.68 (m, 1H); $^{19}$F NMR (376 MHz, D$_2$O) δ −73.80 (s, 6F).

Example 204

(R)—N1-(3-amino-2-hydroxypropyl)-4-(4-(2-aminoethylidene) piperidin-1-yl)-3-(2H-tetrazol-5-yl)benzene-1,2-disulfonamide

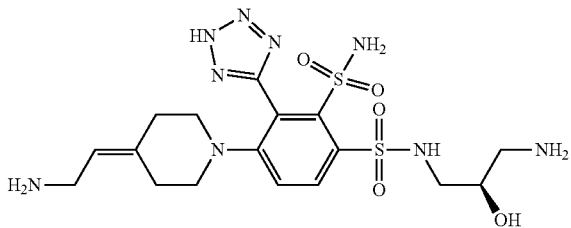 [SMILES: NCC=C1CCN(c2ccc(S(=O)(=O)NC[C@H](O)CN)c(S(N)(=O)=O)c2-c2nn[nH]n2)CC1]

Step A: (R)-tert-butyl (2-((tert-butyldimethylsilyl)oxy)-3-(2-(N,N-dibenzylsulfamoyl)-4-(4-(2-(1,3-dioxoisoindolin-2-yl)ethylidene)piperidin-1-yl)-3-(2-(4-methoxybenzyl)-2H-tetrazol-5-yl)phenylsulfonamido)propyl)carbamate To a solution of (R)-tert-butyl (3-(4-bromo-2-(N,N-dibenzylsulfamoyl)-3-(2-(4-methoxybenzyl)-2H-tetrazol-5-yl)phenylsulfonamido)-2-((tert-butyldimethylsilyl) oxy)propyl)carbamate (REFERENCE EXAMPLE 51) (0.500 g, 0.515 mmol) in NMP (0.5 mL) were added 2-(2-(piperidin-4-ylidene)ethyl)isoindoline-1,3-dione (0.396 g, 1.55 mmol, prepared as described in *Bioorg. Med. Chem. Lett.*, 2014, 24, 5502-5506) and DABCO (0.173 g, 1.55 mmol) at RT. The reaction solution was stirred at 100° C. for 48 hours under nitrogen. After cooling to RT, the resulting solution was diluted with water (20 mL) and extracted with EA (3×20 mL). The combined organic layers were washed with brine (3×10 mL), dried over anhydrous Na$_2$SO$_4$ and filtered. The filtrate was concentrated under reduced pressure, the residue was purified by a silica gel column chromatography, eluting with a gradient of 1%-60% EA in PE to afford the title compound. LCMS [M+1]$^+$: 1146.

Step B: (R)-tert-butyl (3-(4-(4-(2-aminoethylidene) piperidin-1-yl)-2-(N,N-dibenzylsulfamoyl)-3-(2-(4-methoxybenzyl)-2H-tetrazol-5-yl)phenyl sulfonamido)-2-((tert-butyldimethylsilyl)oxy)propyl) carbamate To a solution of (R)-tert-butyl (2-((tert-butyldimethylsilyl)oxy)-3-(2-(N,N-dibenzylsulfamoyl)-4-(4-(2-(1,3-dioxoisoindolin-2-yl)ethylidene)piperidin-1-yl)-3-(2-(4-methoxybenzyl)-2H-tetrazol-5-yl)phenylsulfonamido)propyl)carbamate (0.330 g, 0.288 mmol) in EtOH (15 mL) was added hydrazine hydrate (0.130 g, 2.59 mmol) at RT. The reaction solution was stirred at 70° C. for 1.5 hours. After cooling to RT, the resulting mixture was filtered. The filtrate was concentrated under reduced pressure. The residue was purified by reversed phase, eluting with a gradient of 50%-90% MeOH in water (5 mmol/L NH$_4$HCO$_3$) to afford the title compound. LCMS [M+1]$^+$: 1017.

Step C: (R)—N1-(3-amino-2-hydroxypropyl)-4-(4-(2-aminoethylidene)piperidin-1-yl)-3-(2H-tetrazol-5-yl)benzene-1,2-disulfonamide The title compound was prepared as described for EXAMPLE 129 step B using (R)-tert-butyl (3-(4-(4-(2-aminoethylidene)piperidin-1-yl)-2-(N,N-bis(4-methoxybenzyl)sulfamoyl)-3-(2-(4-methoxybenzyl)-2H-tetrazol-5-yl)phenylsulfonamido)-2-((tert-butyldimethylsilyl)oxy)propyl)carbamate (0.310 g, 0.288 mmol) to afford the crude product. The crude product was purified by Prep-HPLC with the following conditions: Column: Sunfire Prep C18 OBD Column, 19×250 mm, 10 µm; Mobile Phase A: water (10 mmol/L NH$_4$HCO$_3$), Mobile Phase B: ACN; Flow rate: 20 mL/min; Gradient: 5% B to 9% B in 12 min; Detector: 254 nm and 210 nm; Retention time: 10.92 min to afford the title compound. LCMS [M+1]$^+$: 502. $^1$H NMR. (300 MHz, CD$_3$OD+DCl) δ 8.41 (d, J=8.7 Hz, 1H), 7.64 (d, J=8.8 Hz, 1H), 5.31 (t, J=7.4 Hz, 1H), 4.02-3.94 (m, 1H), 3.54 (d, J=7.4 Hz, 2H), 3.22-3.08 (m, 3H), 3.00-2.83 (m, 5H), 2.12-2.05 (m, 4H).

Examples 205 and 206

(R,Z)-N1-(3-amino-2-hydroxypropyl)-4-(3-(2-aminoethylidene) piperidin-1-yl)-3-(2H-tetrazol-5-yl) benzene-1,2-disulfonamide and (R,E)-N1-(3-amino-2-hydroxypropyl)-4-(3-(2-aminoethylidene) piperidine-1-yl)-3-(2H-tetrazol-5-yl)benzene-1,2-disulfonamide

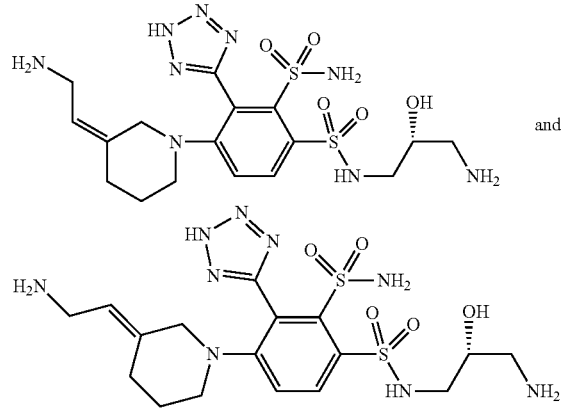

Example 205

(R)—N1-(3-amino-2-hydroxypropyl)-4-(3-(2-aminoethylidene) piperidin-1-yl)-3-(2H-tetrazol-5-yl)benzene-1,2-disulfonamide (Isomer A)

The structure of the compound of Example 205 corresponds to either (R,Z)-N1-(3-amino-2-hydroxypropyl)-4-(3-(2-aminoethylidene) piperidin-1-yl)-3-(2H-tetrazol-5-yl)benzene-1,2-disulfonamide or (R,E)-N1-(3-amino-2-hydroxypropyl)-4-(3-(2-aminoethylidene) piperidine-1-yl)-3-(2H-tetrazol-5-yl)benzene-1,2-disulfonamide, as shown above.

Step A: (R)-tert-butyl (2-((tert-butyldimethylsilyl)oxy)-3-(2-(N,N-dibenzyl sulfamoyl)-4-(3-(2-(1,3-dioxoisoindolin-2-yl)ethylidene)piperidin-1-yl)-3-(2-(4-methoxybenzyl)-2H-tetrazol-5-yl)phenylsulfonamido)propyl)carbamate (Isomer A)

The title compound was prepared as described for EXAMPLE 117 step A using (R)-tert-butyl (3-(4-bromo-2-(N,N-dibenzylsulfamoyl)-3-(2-(4-methoxybenzyl)-2H-tetrazol-5-yl)phenylsulfonamido)-2-((tert-butyldimethylsilyl)oxy)propyl)carbamate (REFERENCE EXAMPLE 51) (0.500 g, 0.515 mmol) and 2-(2-(piperidin-3-ylidene)ethyl)isoindoline-1,3-dione (Isomer A) (0.396 g, 1.55 mmol) to afford the title compound. LCMS [M+1]$^+$: 1146.

Step B: (R)-tert-butyl (3-(4-(3-(2-aminoethylidene)piperidin-1-yl)-2-(N,N-dibenzyl sulfamoyl)-3-(2-(4-methoxybenzyl)-2H-tetrazol-5-yl)phenylsulfonamido)-2-((tert-butyldimethylsilyl)oxy)propyl)carbamate (Isomer A)

The title compound was prepared as described for EXAMPLE 149 step D using (R)-tert-butyl(2-((tert-butyldimethylsilyl)oxy)-3-(2-(N,N-dibenzylsulfamoyl)-4-(3-(2-(1,3-dioxoisoindolin-2-yl)ethylidene)piperidin-1-yl)-3-(2-(4-methoxybenzyl)-2H-tetrazol-5-yl)phenylsulfonamido)propyl)carbamate (Isomer A) (0.250 g, 0.218 mmol) to afford the title compound. LCMS [M+1]$^+$: 1017.

Step C: (R)—N1-(3-amino-2-hydroxypropyl)-4-(3-(2-aminoethylidene)piperidine-1-yl)-3-(2H-tetrazol-5-yl)benzene-1,2-disulfonamide (Isomer A)

The title compound was prepared as described for EXAMPLE 129 step B using (R)-tert-butyl (3-(4-(3-(2-aminoethylidene)piperidin-1-yl)-2-(N,N-dibenzyl sulfamoyl)-3-(2-(4-methoxybenzyl)-2H-tetrazol-5-yl)phenylsulfonamido)-2-((tert-butyldimethylsilyl)oxy)propyl)carbamate (isomer A) (0.200 g, 0.197 mmol) to afford the crude product, which was purified by Prep-HPLC with the following conditions: Column: XBridge C18 OBD Prep Column 100 Å, 19 mm×250 mm, 10 μm; Mobile Phase A: water (10 mmoL/L NH$_4$HCO$_3$), Mobile Phase B: ACN; Flow rate: 25 mL/min; Gradient: 6% B to 14% B in 12 min; Detector: 254 nm and 210 nm; Retention time: 11.45 min to afford the title compound. LCMS (ESI) calc'd for C$_{17}$H$_{27}$N$_9$O$_5$S$_2$ [M+1]$^+$: 502, found 502; $^1$H NMR (300 MHz, D$_2$O) δ 8.26 (d, J=8.8 Hz, 1H), 7.68 (d, J=8.8 Hz, 1H) 5.08 (t, J=7.2 Hz, 1H), 3.94-3.90 (m, 1H), 3.35-3.29 (m, 2H), 3.22 (s, 2H), 3.17-3.00 (m, 3H), 2.90-2.78 (m, 3H), 2.08-2.00 (m, 2H), 1.35-1.22 (m, 2H).

Example 206

(R,E)-N1-(3-amino-2-hydroxypropyl)-4-(3-(2-aminoethylidene) piperidine-1-yl)-3-(2H-tetrazol-5-yl)benzene-1,2-disulfonamide (Isomer B)

The structure of the compound of Example 206 corresponds to either (R,Z)-N1-(3-amino-2-hydroxypropyl)-4-(3-(2-aminoethylidene) piperidin-1-yl)-3-(2H-tetrazol-5-yl)benzene-1,2-disulfonamide or (R,E)-N1-(3-amino-2-hydroxypropyl)-4-(3-(2-aminoethylidene) piperidine-1-yl)-3-(2H-tetrazol-5-yl)benzene-1,2-disulfonamide, as shown above.

Step A: (R)-tert-butyl (2-((tert-butyldimethylsilyl)oxy)-3-(2-(N,N-dibenzyl sulfamoyl)-4-(3-(2-(1,3-dioxoisoindolin-2-yl)ethylidene)piperidin-1-yl)-3-(2-(4-methoxybenzyl)-2H-tetrazol-5-yl)phenylsulfonamido)propyl)carbamate (Isomer B)

The title compound was prepared as described for EXAMPLE 117 step A using (R)-tert-butyl (3-(4-bromo-2-(N,N-dibenzylsulfamoyl)-3-(2-(4-methoxybenzyl)-2H-tetrazol-5-yl)phenylsulfonamido)-2-((tert-butyldimethylsilyl)oxy)propyl) carbamate (0.400 g, 0.412 mmol) and 2-(2-(piperidin-3-ylidene) ethyl)isoindoline-1,3-dione (Isomer B) (0.800 g, 3.12 mmol) to afford the title compound. LCMS [M+1]$^+$: 1147.

Step B: (R)-tert-butyl (3-(4-(3-(2-aminoethylidene)piperidin-1-yl)-2-(N,N-dibenzyl sulfamoyl)-3-(2-(4-methoxybenzyl)-2H-tetrazol-5-yl)phenylsulfonamido)-2-((tert-butyldimethylsilyl)oxy)propyl)carbamate (Isomer B)

The title compound was prepared as described for EXAMPLE 149 step D using (R)-tert-butyl (2-((tert-butyldimethylsilyl)oxy)-3-(2-(N,N-dibenzylsulfamoyl)-4-(3-(2-(1,3-dioxoisoindolin-2-yl)ethylidene)piperidin-1-yl)-3-(2-(4-methoxybenzyl)-2H-tetrazol-5-yl)phenylsulfonamido) propyl)carbamate (Isomer B) (0.380 g, 0.331 mmol) to afford the title compound. LCMS [M+1]$^+$: 1017.

Step C: (R)—N1-(3-amino-2-hydroxypropyl)-4-(3-(2-aminoethylidene)piperidine-1-yl)-3-(2H-tetrazol-5-yl)benzene-1,2-disulfonamide (Isomer B)

The title compound was prepared as described for EXAMPLE 129 step B using (R)-tert-butyl (3-(4-(3-(2-aminoethylidene)piperidin-1-yl)-2-(N,N-dibenzyl sulfamoyl)-3-(2-(4-methoxybenzyl)-2H-tetrazol-5-yl)phenylsulfonamido)-2-((tert-butyldimethylsilyl)oxy)propyl) carbamate (isomer B) (0.210 g, 0.207 mmol) to afford the crude product, which was purified by Prep-HPLC with the following conditions: Column: XBridge C18 OBD Prep Column 100 Å, 19 mm×250 mm, 10 μm; Mobile Phase A: water (10 mmoL/L NH$_4$HCO$_3$), Mobile Phase B: ACN; Flow rate: 20 ml/min; Gradient: 6% B to 16% B in 12 min; Detector: 254 and 210 nm; Retention time: 10.83 min to afford the title compound. LCMS [M+1]$^+$: 502; $^1$H NMR (300 MHz, D$_2$O) δ 8.21 (d, J=8.7 Hz, 1H), 7.57 (d, J=8.8 Hz, 1H), 4.74-4.72 (m, 1H), 3.92-3.87 (m, 1H), 3.42 (d, J=7.4 Hz, 2H), 18-2.94 (m, 5H), 2.93-2.72 (m, 3H), 2.12-2.03 (m, 2H), 1.40-1.35 (m, 2H).

EXAMPLE 207 was prepared as described in EXAMPLE 117 Step A, EXAMPLE 148 Steps B and C followed by EXAMPLE 117 Step B, starting from 3-iodo-N,N-(bis(4-methoxybenzyl)-2-(2-(4-methoxybenzyl)-2H-tetrazol-5-yl)-6-((2-(trimethylsilyl)ethyl)sulfonyl)benzenesulfonamide (REFERENCE EXAMPLE 37) and the requisite amine.

| EX. | STRUCTURE | NAME | LC/MS [M + 1]+ |
|---|---|---|---|
| 207 | 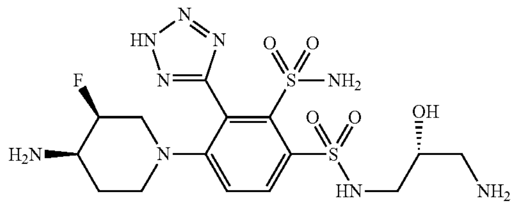 [SMILES: NC[C@@H](O)CNS(=O)(=O)c1ccc(N2CC[C@@H](N)[C@@H](F)C2)c(-c2nn[nH]n2)c1S(N)(=O)=O] | N1-((R)-3-amino-2-hydroxypropyl)-4-((3S,4R)-4-amino-3-fluoropiperidin-1-yl)-3-(2H-tetrazol-5-yl)benzene-1,2-disulfonamide | 494 |

Ex. 207: $^1$H NMR (300 MHz, D$_2$O) δ 8.13 (d, J=8.7, 1H), 7.42 d, J=9.0, 1H), 4.48-4.36 (m, 1H), 3.87-3.85 (m, 1H), 3.27-3.23 (m, 3.21-2.90 (m, 5H), 7-2.49 (m, 3H), 1.58-1.47 (m, 1H), 1.40-1.25 (m, 1H); $^{19}$F NMR (282 MHz, D$_2$O) δ −204.215.

Example 208

(R)—N1-(3-amino-2-hydroxypropyl)-4-(4-((2-aminoethoxy)methyl) piperidin-1-yl)-3-(2H-tetrazol-5-yl)benzene-1,2-disulfonamide

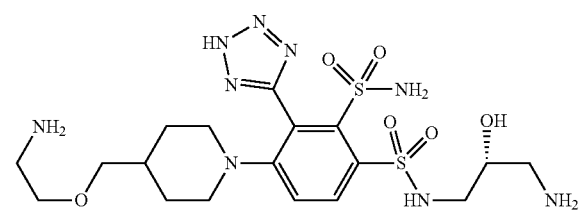 [SMILES: NCCOCC1CCN(c2ccc(S(=O)(=O)NC[C@H](O)CN)c(S(N)(=O)=O)c2-c2nn[nH]n2)CC1]

Step A: (R)-tert-butyl (2-((tert-butyldimethylsilyl)oxy)-3-(2-(N,N-dibenzylsulfamoyl)-4-(4-((2-hydroxyethoxy)methyl)piperidin-1-yl)-3-(2-(4-methoxybenzyl)-2H-tetrazol-5-yl) phenylsulfonamido)propyl)carbamate To a solution of (R)-tert-butyl (3-(4-bromo-2-(N,N-dibenzylsulfamoyl)-3-(2-(4-methoxybenzyl)-2H-tetrazol-5-yl) phenylsulfonamido)-2-((tert-butyldimethylsilyl)oxy)propyl) carbamate (1.00 g, 1.03 mmol) in DME (3 mL) were added DIEA (0.900 mL, 5.15 mmol) and 2-(piperidin-4-ylmethoxy)ethanol (0.492 g, 3.09 mmol, prepared as described in EP1746095A1). The reaction solution was stirred at 100° C., for 60 hours. After cooling to RT, the resulting solution was concentrated under reduced pressure and the residue was purified by a silica gel column chromatography, eluting using a gradient of 1%-70% EA in PE to afford the title compound. LCMS [M+1]$^+$: 1049.

Step B: (R)-2-((1-(4-(N-(3-((tert-butoxycarbonyl) amino)-2-((tert-butyldimethylsilyl) oxy)propyl)sulfamoyl)-3-(N,N-dibenzylsulfamoyl)-2-(2-(4-methoxybenzyl)-2H-tetrazol-5-yl)phenyl)piperidin-4-yl)methoxy)ethyl methanesulfonate To a solution of (R)-tert-butyl (2-((tert-butyldimethylsilyl)oxy)-3-(2-(N,N-dibenzylsulfamoyl)-4-(4-((2-hydroxyethoxy)methyl)piperidin-1-yl)-3-(2-(4-methoxy benzyl)-2H-tetrazol-5-yl)phenylsulfonamido)propyl)carbamate (0.500 g, 0.476 mmol) in DCM (3 mL) were added TEA (0.133 mL, 0.953 mmol) and MsCl (0.056 mL, 0.715 mmol). The reaction solution was stirred at RT for 1 hour. The resulting solution was quenched with sat'd NaHCO$_3$ (10 mL) and extracted with EA (3×5 mL). The combined organic layers were concentrated to afford (R)-2-((1-(4-(N-(3-((tert-butoxycarbonyl)amino)-2-((tert-butyldimethyl silyl)oxy) propyl)sulfamoyl)-3-(N,N-dibenzylsulfamoyl)-2-(2-(4-methoxybenzyl)-2H-tetrazol-5-yl)phenyl)piperidin-4-yl) methoxy)ethyl methanesulfonate as an oil which was used in the next step without further purification. LCMS [M+1]$^+$: 1127.

Step C: (R)-tert-butyl (3-(4-(4-((2-azidoethoxy) methyl)piperidin-1-yl)-2-(N,N-dibenzylsulfamoyl)-3-(2-(4-methoxybenzyl)-2H-tetrazol-5-yl)phenylsulfonamido)-2-((tert-butyldimethylsilyl)oxy) propyl)carbamate To a solution of (R)-2-((1-(4-(N-(3-((tert-butoxycarbonyl) amino)-2-((tert-butyldimethylsilyl)oxy)propyl)sulfamoyl)-3-(N,N-dibenzylsulfamoyl)-2-(2-(4-methoxybenzyl)-2H-tetrazol-5-yl)phenyl)piperidin-4-yl)methoxy)ethyl methanesulfonate (0.532 g, 0.472 mmol) in DMSO (2 mL) was added. NaN$_3$ (46.0 mg, 0.708 mmol). The reaction mixture was stirred at 100° C. for 16 hours. After cooling to RT, the resulting mixture was diluted with water (10 mL) and extracted with EA (3×5 mL). The combined organic layers were concentrated under reduced pressure. The residue was purified by a silica gel column chromatography, eluting with a gradient of 1%-40% EA in PE to afford the title compound. LCMS [M+1]$^+$: 1074.

Step D: (R)-tert-butyl (3-(4-(4-((2-aminoethoxy) methyl)piperidin-1-yl)-2-(N,N-dibenzylsulfamoyl)-3-(2-(4-methoxybenzyl)-2H-tetrazol-5-yl)phenylsulfonamido)-2-butyldimethylsilyl)oxy)propyl) carbamate To a solution of (R)-tert-butyl (3-(4-(4-((2-azidoethoxy) methyl) piperidin-1-yl)-2-(N,N-dibenzylsulfamoyl)-3-(2-(4-methoxybenzyl)-2H-tetrazol-5-yl)phenylsulfonamido)-2-((tert-butyldimethylsilyl)oxy)propyl)carbamate (0.110 g, 0.102 mmol) in MeOH (5 mL) was added palladium hydroxide on carbon (21.8 mg, 0.102 mmol, 20% wt). The mixture was degassed with hydrogen 3 times and stirred for 16 hours at RT under an atmosphere of hydrogen. The resulting mixture was filtered and the filtrate was concentrated under reduced pressure. The residue was purified by a silica gel column chromatography, eluting with a gradient of 1%-12% MeOH in DCM to afford the title compound. LCMS [M+1]$^+$: 1048.

Step E: (R)—N1-(3-amino-2-hydroxypropyl)-4-(4-((2-aminoethoxy)methyl)piperidin-1-yl)-3-(2H-tetrazol-5-yl)benzene-1,2-disulfonamide The title compound was prepared as described for EXAMPLE 129 step B using (1)-tert-butyl(3-(4-(4-((2-aminoethoxy)methyl)piperidin-1-yl)-2-(N,N-dibenzyl sulfamoyl)-3-(2-(4-methoxybenzyl)-2H-tetrazol-5-yl)phenylsulfonamido)-2-((tert-butyldimethylsilyl)oxy)propyl) carbamate (80.0 mg, 0.076 mmol) to afford the crude product, which was purified by Prep-HPLC with the following conditions: Column: XBridge C18 OBD Prep Column 100 Å, 19 mm×250 mm, 10 µm; Mobile Phase A: water (10 mmoL/L $NH_4HCO_3$), Mobile Phase B: ACN; Flow rate: 20 mL/min; Gradient: 5% B to 18% B in 10 min; Detector: 254 and 210 nm; Retention time: 9.58 min to afford the title compound. LCMS $[M+1]^+$: 534. $^1$H NMR (300 MHz, $D_2O$) δ 8.12 (d, J=8.8 Hz, 1H), 7.35 (d, J=9.0 Hz, 1H), 3.77-3.74 (m, 1H), 3.53 (t, J 5.2 Hz, 2H), 3.30-3.21 (m, 2H), 3.18-3.05 (m, 1H), 3.05-2.76 (m, 6H), 2.73-2.59 (m, 1H), 2.55-2.45 (m, 2H), 1.65-1.50 (m, 1H), 1.50-1.35 (m, 2H), 0.85-0.65 (m, 2H).

Example 209

(R)—N1-(3-amino-2-hydroxypropyl)-4-(4-(2-aminoethoxy)piperidin-1-yl)-3-(2H-tetrazol-5-yl)benzene-1,2-disulfonamide

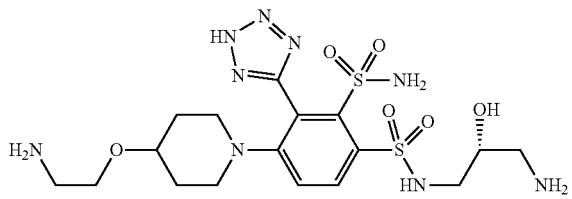 [SMILES: NCCOC1CCN(c2ccc(S(=O)(=O)NC[C@H](O)CN)c(S(N)(=O)=O)c2-c2nn[nH]n2)CC1]

Step A: (R)-tert-butyl(2-((tert-butyldimethylsilyl)oxy)-3-(2-(N,N-dibenzylsulfamoyl)-4-(4-(2-hydroxyethoxy)piperidin-1-yl)-3-(2-(4-methoxybenzyl)-2H-tetrazol-5-yl) phenylsulfonamido)propyl) carbamate To a solution of (R)-tert-butyl (3-(4-bromo-2-(N,N-dibenzylsulfamoyl)-3-(2-(4-methoxybenzyl)-2H-tetrazol-5-yl) phenylsulfonamido)-2-((tert-butyldimethyl silyl)oxy)propyl)carbamate (REFERENCE EXAMPLE 51) (0.445 g, 0.458 mmol) in DME (1.5 mL) was added DMA (0.4 mL, 2.29 mmol) and 2-(piperidin-4-yloxy)ethanol (0.200 g, 1.38 mmol). The solution was stirred at 100° C. for 60 hours. After cooling to RT, the resulting solution was concentrated under reduced pressure. The residue was purified by a silica gel column chromatography, eluting with a gradient of 1%-10% MeOH in DCM to afford the title compound. LCMS $[M+1]^+$: 1036.

Step B: (R)-2-((1-(4-(N-(3-((tert-butoxycarbonyl) amino)-2-((tert-butyldimethylsilyl) oxy)propyl)sulfamoyl)-3-(N,N-dibenzylsulfamoyl)-2-(2-(4-methoxybenzyl)-2H-tetrazol-5-yl)phenyl)piperidin-4-yl)oxy)ethyl methanesulfonate The title compound was prepared as described for EXAMPLE 208 step B using (R)-tert-butyl (2-((tert-butyldimethylsilyl)oxy)-3-(2-(N,N-dibenzylsulfamoyl)-4-(4-(2-hydroxyethoxy)piperidin-1-yl)-3-(2-(4-methoxybenzyl)-2H-tetrazol-5-yl)phenylsulfonamido)propyl)carbamate (0.311 g, 0.300 mmol) to afford (R)-2-((1-(4-(N-(3-((tert-butoxycarbonyl)amino)-2-((tert-butyldimethylsilyl)oxy)propyl) sulfamoyl)-3-(N,N-dibenzylsulfamoyl)-2-(2-(4-methoxybenzyl)-2H-tetrazol-5-yl)phenyl)piperidin-4-yl)oxy)ethyl methanesulfonate as an oil which was used in the next step without further purification. LCMS $[M+1]^+$: 1114.

Step C: (R)-tert-butyl (3-(4-(4-(2-azidoethoxy)piperidin-1-yl)-2-(N,N-dibenzyl sulfamoyl)-3-(2-(4-methoxybenzyl)-2H-tetrazol-5-yl)phenylsulfonamido)-2-((tert-butyldimethylsilyl)oxy)propyl) carbamate The title compound was prepared as described for EXAMPLE 208 step C using (R)-2-((1-(4-(N-(3-((tert-butoxycarbonyl)amino)-2-((tert-butyldimethylsilyl)oxy)propyl)sulfamoyl)-3-(N,N-dibenzylsulfamoyl)-2-(2-(4-methoxybenzyl)-2H-tetrazol-5-yl)phenyl)piperidin-4-yl) oxy)ethyl methanesulfonate (0.350 g, 0.314 mmol) to afford the title compound. LCMS $[M+1]^+$: 1060.

Step D: (R)-tert-butyl (3-(4-(4-(2-aminoethoxy) piperidin-1-yl)-2-(N,N-dibenzylsulfamoyl)-3-(2-(4-methoxybenzyl)-2H-tetrazol-5-yl)phenylsulfonamido)-2-((tert-butyldimethylsilyl)oxy)propyl) carbamate The title compound was prepared as described for EXAMPLE 208 step D using (R)-tert-butyl (3-(4-(4-(2-azidoethoxy)piperidin-1-yl)-2-(N,N-dibenzylsulfamoyl)-3-(2-(4-methoxybenzyl)-2H-tetrazol-5-yl)phenylsulfonamido)-2-((tert-butyldimethylsilyl)oxy)propyl)carbamate (0.200 g, 0.18) mmol) to afford (R)-tert-butyl (3-(4-(4-(2-aminoethoxy)piperidin-1-yl)-2-(N,N-dibenzylsulfamoyl)-3-(2-(4-methoxybenzyl)-2H-tetrazol-5-yl)phenylsulfonamido)-2-((tert-butyldimethylsilyl)oxy)propyl)carbamate, LCMS $[M+1]^+$: 1034.

Step E: (R)—N1-(3-amino-2-hydroxypropyl)-4-(4-(2-aminoethoxy)piperidin-1-yl-3-(2H-tetrazol-5-yl) benzene-1,2-disulfonamide The title compound was prepared as described for EXAMPLE 129 step B using (R)-tert-butyl(3-(4-(4-(2-aminoethoxy)piperidin-1-yl)-2-(N,N-dibenzylsulfamoyl)-3-(2-(4-methoxybenzyl)-2H-tetrazol-5-yl)phenylsulfonamido)-2-((tert-butyldimethylsilyl)oxy)propyl)carbamate (0.140 g, 0.135 mmol) to afford the crude product, which was purified by Prep-HPLC with the following conditions: Column: XBridge C18 OBD Prep Column 100 Å, 19 mm×250 mm, 10 µm; Mobile Phase A: water (10 mmol/L $NH_4HCO_3$), Mobile Phase B: ACN; Flow rate: 20 mL/min; Gradient: 5% B to 35% B in 10 min; Detector: 254 and 210 nm; Retention time: 7.50 min to afford the title compound. LCMS $[M+1]^+$: 520. $^1$H NMR (300 MHz, $CD_3OD$): δ 8.36 (d, 8.7 Hz, 1H), 7.61 (d, J=8.7 Hz, 1H), 4.01-3.80 (m, 1H), 3.63-3.60 (m, 2H), 3.43-3.40 (m, 1H), 3.18-2.97 (m, 7H), 2.92-2.85 (m, 1H), 2.69-2.66 (m, 2H), 1.72-1.66 (m, 214), 1.34-1.22 (m, 2H).

Biological Assays

Enzyme Activity: Determination of $IC_{50}$

The Class B enzyme activities were measured in the presence of the test inhibitor in a fluorescence assay against a commercially available substrate consisting of a cephalosporin core linking 7-hydroxycoumarin to fluorescein (CCF2-FA). The enzyme (NDM-1, IMP-1 or VIM-1) and the substrate were diluted in 100 mM $KH_2PO_4$ buffer (pH 7)

containing 0.005% Tween-20 and 10 µM $ZnSO_4$. In the assay, the final concentration of enzyme was 1 pM, 2 pM and 30 pM for NDM-1, IMP-1 and VIM-1, respectively, and the final concentration of CCF2-FA was 1.25 µM. The test inhibitor was dissolved in dimethylsulfoxide and diluted 1:50 in the assay, resulting in a final concentration range of 20 µM to 0.00063 µM. In a 384-well microplate, the test inhibitor was incubated with the metallo-β-lactamase enzyme and the substrate for 2 hours at 25° C. Fluorescence at 460 nm following excitation at 405 nm was measured. The $IC_{50}$ value was determined from semi-logarithmic plots of enzyme inhibition versus inhibitor concentration, with a curve generated using a 4-parameter fit.

Representative compounds of the present invention exhibit inhibition of Class B β-lactamases in this assay. For example, the compounds of Examples 1-209 were tested in this assay and were found to have the $IC_{50}$ values shown in Table 1.

Antibiotic Potentiation Activity: Determination of Synergistic Concentration

The concentrations of metallo-β-lactamase inhibitors required to restore the susceptibility of various strains of bacteria to inactive concentrations of antibiotics were determined in an assay that assessed bacterial growth by measuring the optical density at 600 nm ($OD_{600}$). The bacterial strains tested included the clinical strains *Escherichia coil* expressing NDM-1 (CLB30005, CLB30016), *Serratia marcescens* expressing IMP-1 (CL5741), and *Klebsiella pneumoniae* expressing VIM-1 (H-LMA599644). Inhibitor activity was measured in the presence and absence of imipenem in a 384-well microplate.

The clinical strains CLB30016, CL5741 and IHMA599644 were grown on trypticase soy agar containing 5% sheep's blood. The bacteria on agar plates were incubated at 35° C. with humidity overnight. The following day, individual colonies from each clinical strain were picked and resuspended in 5 ml saline to attain an $OD_{600}$ of 0.14, 0.11, 0.15 and 0.13, for CLB30016, C15741 and IHMA599644, respectively. These were further diluted 1:100 into 1.1× CAMHB and used to inoculate the test wells as described below.

Imipenem in 10 mM 3-(N-morpholino)propanesulfonic acid (MOPS, pH 7) was stored in single use aliquots at −80° C. Test inhibitors were dissolved in dimethylsulfoxide and diluted 1:50 in the assay, resulting in a final concentration range of 200 µM to 0.195 µM. On the day of the assay, 4 µl of antibiotic was added to 45 µl of bacteria followed by 1 µl of test compound and mixed by pipetting and with an orbital shaker. The concentration of antibiotic used in the assay was 1 µg/ml. Microplates were covered and incubated at 35° C. for 22 hours to 24 hours. At the end of the incubation, absorbance was determined using a spectrophotometer. The synergistic concentration of MBLI was determined by identifying the lowest concentration of test compound in the presence of a given concentration of antibiotic that was required to inhibit 95% of the growth of the bacteria. The results for Examples 1-209 are reported in Table 1, expressed as the concentration of compound that potentiated the action of antibiotic (imipenem) affecting 95% inhibition of bacterial growth (MITC95).

Representative compounds of the present invention do not have any or have minimal intrinsic antibacterial activity but display a synergistic effect when used in combination with a beta-lactam antibiotic. For example, in general, the compounds of Examples 1-209 were determined to restore susceptibility to imipenem for one or more of the test organisms at concentrations of 100 µM or less.

TABLE 1

Inhibition of metallo-β-lactamases (IMP-1, NDM-1, VIM-1, VIM-2) and antibiotic potentiation vs. MBL-expressing bacteria by Examples 1-209.

| Ex. No. | NDM 1 $IC_{50}$ (nM) | IMP1 $IC_{50}$ (nM) | VIM1 $IC_{50}$ (nM) | VIM2 $IC_{50}$ (nM) | CLB30016 E. coli MITC95 NDM (µM) | CL5741 S. marcescens MITC95 IMP (µm) | IHMA599644 K. pneumoniae MITC95 VIM (µM) |
|---|---|---|---|---|---|---|---|
| 1 | 3.76 | 5.02 | 0.31 | 3.58 | 0.10 | 0.20 | 0.39 |
| 2 | 6.51 | 3.37 | 0.17 | 4.04 | 0.20 | 0.78 | 0.78 |
| 3 | 2.43 | 3.95 | 0.61 | 3.68 | 0.78 | 1.56 | 0.78 |
| 4 | 2.17 | 9.40 | 0.18 | 2.40 | 3.13 | 1.56 | 3.13 |
| 5 | 0.96 | 1.81 | 0.13 | 2.54 | 0.10 | 0.20 | 0.78 |
| 6 | 1.12 | 3.38 | 0.17 | 4.19 | 0.20 | 0.20 | 0.78 |
| 7 | 0.68 | 3.49 | 0.24 | 4.46 | 0.20 | 0.39 | 0.78 |
| 8 | 0.19 | 1.12 | 0.07 | 2.35 | 0.20 | 0.39 | 0.78 |
| 9 | 3.46 | 15.53 | 0.26 | 6.41 | 0.39 | 0.78 | 1.56 |
| 10 | 16.40 | 28.93 | 0.43 | 27.00 | 0.39 | 0.39 | 1.56 |
| 11 | 8.96 | 35.51 | 2.03 | 24.67 | 0.78 | 1.56 | 0.78 |
| 12 | 1.51 | 4.08 | 1.48 | 17.61 | 0.78 | 1.56 | 1.56 |
| 13 | 3.01 | 3.70 | 0.14 | 4.12 | 1.56 | 0.78 | 0.78 |
| 14 | 3.94 | 1.34 | 0.73 | | 0.78 | 2.34 | 2.34 |
| 15 | 11.50 | 6.50 | 2.51 | | 1.56 | 3.13 | 3.13 |
| 16 | 0.72 | 1.85 | 0.08 | 1.61 | 1.17 | 1.56 | 1.56 |
| 17 | 16.99 | 26.88 | 15.12 | 64.57 | 0.78 | 0.78 | 1.56 |
| 18 | 0.43 | 1.48 | 0.65 | 4.80 | 0.78 | 0.78 | 1.56 |
| 19 | 0.17 | 0.37 | 0.65 | 2.27 | 3.13 | 3.13 | 12.50 |
| 20 | 0.77 | 1.53 | 0.26 | 0.49 | 1.56 | 0.78 | 3.13 |
| 21 | 0.41 | 0.56 | 1.13 | 2.70 | 12.50 | 6.25 | 12.50 |
| 22 | 0.45 | 0.70 | 0.35 | 0.79 | 3.13 | 1.56 | 6.25 |
| 23 | 19.71 | 40.51 | 1.48 | 10.03 | 0.39 | 1.56 | 0.78 |
| 24 | 5.09 | 5.79 | 0.45 | 5.60 | 1.56 | 3.13 | 6.25 |
| 25 | 0.54 | 0.39 | 0.17 | 0.74 | 3.13 | 6.25 | 6.25 |

TABLE 1-continued

Inhibition of metallo-β-lactamases (IMP-1, NDM-1, VIM-1, VIM-2) and antibiotic potentiation vs. MBL-expressing bacteria by Examples 1-209.

| Ex. No. | NDM 1 IC$_{50}$ (nM) | IMP1 IC$_{50}$ (nM) | VIM1 IC$_{50}$ (nM) | VIM2 IC$_{50}$ (nM) | CLB30016 E. coli MITC95 NDM (μM) | CL5741 S. marcescens MITC95 IMP (μm) | IHMA599644 K. pneumoniae MITC95 VIM (μM) |
|---|---|---|---|---|---|---|---|
| 26 | 0.64 | 1.02 | 0.63 | 2.74 | 12.50 | 6.25 | 12.50 |
| 27 | 0.07 | 0.05 | 0.06 | 0.18 | 3.13 | 3.13 | 6.25 |
| 28 | 61.86 | 463.40 | 37.24 | | 0.78 | 6.25 | 1.56 |
| 29 | 86.04 | 228.90 | 9.45 | | 1.56 | 6.25 | 0.78 |
| 30 | 2.62 | 5.20 | 2.01 | | 0.78 | 1.56 | 1.56 |
| 31 | 1.67 | 1.89 | 0.89 | 3.36 | 1.56 | 3.13 | 3.13 |
| 32 | 121.90 | 190.90 | 2.14 | | 6.25 | 3.13 | 1.56 |
| 33 | 109.90 | 136.80 | 4.43 | | 1.56 | 3.13 | 0.78 |
| 34 | 2.05 | 4.07 | 0.18 | 3.49 | 0.39 | 0.39 | 0.39 |
| 35 | 3.60 | 5.10 | 0.32 | 6.69 | 0.39 | 0.78 | 3.13 |
| 36 | 0.45 | 1.84 | 0.10 | 2.60 | 0.65 | 1.30 | 1.30 |
| 37 | 1.29 | 3.04 | 0.11 | 2.07 | 0.39 | 0.78 | 0.78 |
| 38 | 6.30 | 20.55 | 0.67 | 2.11 | 0.20 | 0.78 | 0.78 |
| 39 | 50.40 | 44.63 | 1.71 | 11.58 | 1.56 | 0.78 | 1.56 |
| 40 | 3.07 | 3.56 | 5.87 | 7.36 | 0.05 | 0.10 | 0.78 |
| 41 | 5.98 | 6.04 | 11.49 | 14.82 | 0.10 | 0.10 | 1.56 |
| 42 | 0.45 | 0.47 | 0.16 | 0.71 | 3.13 | 3.13 | 6.25 |
| 43 | 0.51 | 0.58 | 0.19 | 0.61 | 1.56 | 1.56 | 6.25 |
| 44 | 0.36 | 0.56 | 0.06 | 0.63 | 3.13 | 3.13 | 6.25 |
| 45 | 0.27 | 0.52 | 0.23 | 0.74 | 1.56 | 3.13 | 3.13 |
| 46 | 0.06 | 0.12 | 0.08 | 0.32 | 3.13 | 1.56 | 6.25 |
| 47 | 3.94 | 4.57 | 5.02 | 7.34 | 0.10 | 0.10 | 0.78 |
| 48 | 1.52 | 5.59 | 7.23 | 14.96 | 0.05 | 0.05 | 0.39 |
| 49 | 5.30 | 9.13 | 13.63 | 20.18 | 0.20 | 0.20 | 1.56 |
| 50 | 4.14 | 2.11 | 0.15 | 4.12 | 0.39 | 0.78 | 0.78 |
| 51 | 1.40 | 1.92 | 0.29 | 3.07 | 0.78 | 0.39 | 0.78 |
| 52 | 0.48 | 3.06 | 0.50 | 8.18 | 0.78 | 1.56 | 1.56 |
| 53 | 8.79 | 7.81 | 25.12 | 35.53 | 0.39 | 0.39 | 3.13 |
| 54 | 16.74 | 21.92 | 66.12 | 69.50 | 0.39 | 0.39 | 6.25 |
| 55 | 51.55 | 200 | 62.29 | 145.10 | 1.56 | 12.50 | 12.50 |
| 56 | 0.76 | 0.45 | 0.25 | 0.82 | 6.25 | 3.13 | 6.25 |
| 57 | 2.48 | 4.38 | 1.44 | 1.87 | 3.13 | 3.13 | 12.50 |
| 58 | 1.03 | 0.85 | 0.42 | 1.67 | 3.13 | 6.25 | 6.25 |
| 59 | 3.22 | 8.38 | 1.84 | 2.18 | 6.25 | 6.25 | 6.25 |
| 60 | 4.23 | 6.05 | 1.44 | 2.67 | 3.13 | 3.13 | 6.25 |
| 61 | 0.90 | 1.28 | 0.44 | 2.12 | 1.56 | 3.13 | 6.25 |
| 62 | 2.86 | 4.89 | 3.07 | 10.49 | 1.56 | 3.13 | 6.25 |
| 63 | 0.31 | 0.47 | 0.16 | 0.66 | 3.13 | 3.13 | 6.25 |
| 64 | 5.51 | 3.26 | 1.62 | 8.19 | 1.56 | 1.56 | 6.25 |
| 65 | 1.28 | 2.26 | 0.22 | 1.00 | 3.13 | 3.13 | 6.25 |
| 66 | 0.62 | 4.48 | 1.76 | 3.70 | 6.25 | 3.13 | 6.25 |
| 67 | 84.97 | 60.68 | 4.32 | 18.50 | 1.56 | 3.13 | 1.56 |
| 68 | 22.14 | 16.22 | 2.11 | 17.78 | 0.78 | 1.56 | 1.56 |
| 69 | 16.18 | 29.55 | 1.60 | 13.30 | 0.78 | 3.13 | 1.56 |
| 70 | 0.45 | 0.51 | 0.57 | 1.25 | 3.91 | 3.91 | 7.81 |
| 71 | 0.26 | 0.70 | 0.53 | 1.69 | 3.13 | 3.13 | 6.25 |
| 72 | 3.31 | 9.32 | 2.01 | 6.04 | 1.56 | 3.13 | 6.25 |
| 73 | 9.84 | 16.62 | 0.31 | 16.14 | 0.78 | 1.56 | 1.56 |
| 74 | 3.00 | 6.80 | 0.45 | 6.86 | 0.78 | 1.56 | 3.13 |
| 75 | 162.10 | 178.40 | 6.75 | 200 | 6.25 | 12.50 | 3.13 |
| 76 | 4.35 | 10.73 | 1.60 | 18.14 | 1.56 | 3.13 | 3.13 |
| 77 | 0.53 | 1.83 | 0.11 | 1.80 | 0.78 | 0.78 | 0.78 |
| 78 | 5.40 | 35.44 | 0.66 | 3.01 | 0.39 | 1.56 | 1.56 |
| 79 | 9.35 | 26.55 | 8.60 | 36.39 | 0.39 | 0.78 | 3.13 |
| 80 | 0.30 | 0.43 | 0.13 | 0.66 | 1.56 | 0.78 | 3.13 |
| 81 | 0.64 | 0.62 | 0.51 | 1.00 | 3.13 | 3.13 | 6.25 |
| 82 | 42.85 | 45.57 | 0.90 | 9.33 | 0.78 | 0.78 | 0.78 |
| 83 | 4.98 | 15.89 | 2.11 | 2.82 | 6.25 | 3.13 | 12.50 |
| 84 | 19.68 | 33.00 | 7.27 | 46.94 | 0.78 | 1.56 | 1.56 |
| 85 | 3.15 | 9.94 | 2.13 | 23.66 | 0.78 | 1.56 | 1.56 |
| 86 | 1.37 | 58.80 | 3.83 | 13.97 | 0.39 | 1.56 | 1.56 |
| 87 | 0.16 | 0.24 | 0.12 | 0.49 | 1.56 | 3.13 | 3.13 |
| 88 | 0.08 | 0.13 | 0.19 | 0.97 | 12.50 | 12.50 | 12.50 |
| 89 | 0.21 | 0.61 | 0.21 | 0.66 | 1.56 | 3.13 | 12.50 |
| 90 | 0.43 | 0.77 | 0.34 | 1.02 | 3.13 | 3.13 | 3.13 |

TABLE 1-continued

Inhibition of metallo-β-lactamases (IMP-1, NDM-1, VIM-1, VIM-2) and
antibiotic potentiation vs. MBL-expressing bacteria by Examples 1-209.

| Ex. No. | NDM 1 IC$_{50}$ (nM) | IMP1 IC$_{50}$ (nM) | VIM1 IC$_{50}$ (nM) | VIM2 IC$_{50}$ (nM) | CLB30016 E. coli MITC95 NDM (μM) | CL5741 S. marcescens MITC95 IMP (μm) | IHMA599644 K. pneumoniae MITC95 VIM (μM) |
|---|---|---|---|---|---|---|---|
| 91 | 0.42 | 1.26 | 0.47 | 1.65 | 3.13 | 3.13 | 6.25 |
| 92 | 0.38 | 0.31 | 0.30 | 0.74 | 0.78 | 1.56 | 3.13 |
| 93 | 1.71 | 2.52 | 3.62 | 6.73 | 0.39 | 0.20 | 1.56 |
| 94 | 0.18 | 0.50 | 0.27 | 1.18 | 3.13 | 6.25 | 6.25 |
| 95 | 4.31 | 1.55 | 1.42 | 6.09 | 6.25 | 6.25 | 12.50 |
| 96 | 1.21 | 0.98 | 0.53 | 1.02 | 3.13 | 1.56 | 6.25 |
| 97 | 6.21 | 11.64 | 2.49 | 4.43 | 3.13 | 6.25 | 12.50 |
| 98 | 0.08 | 0.13 | 0.15 | 0.59 | 12.50 | 6.25 | 12.50 |
| 99 | 0.92 | 1.33 | 2.66 | 3.22 | 1.56 | 3.13 | 6.25 |
| 100 | 17.53 | 36.99 | 12.41 | 162.10 | 12.50 | 6.25 | 12.50 |
| 101 | 0.08 | 0.16 | 0.09 | 0.39 | 0.78 | 1.56 | 3.13 |
| 102 | 1.35 | 2.07 | 3.06 | 7.94 | 0.20 | 0.20 | 3.13 |
| 103 | 0.68 | 3.46 | 0.42 | 0.59 | 3.13 | 3.13 | 6.25 |
| 104 | 0.68 | 2.06 | 0.21 | 0.65 | 3.13 | 3.13 | 3.13 |
| 105 | 0.25 | 1.16 | 0.96 | 1.79 | 6.25 | 6.25 | 12.50 |
| 106 | 0.06 | 0.12 | 0.10 | 0.46 | 6.25 | 3.13 | 6.25 |
| 107 | 0.25 | 1.10 | 0.19 | 0.42 | 3.13 | 3.13 | 6.25 |
| 108 | 0.71 | 2.39 | 0.50 | 1.77 | 6.25 | 12.50 | 12.50 |
| 109 | 0.51 | 2.21 | 0.43 | 1.90 | 3.13 | 3.13 | 6.25 |
| 110 | 0.06 | 0.10 | 0.12 | 0.47 | 3.13 | 3.13 | 6.25 |
| 111 | 4.56 | 4.16 | 1.24 | 8.65 | 0.78 | 1.56 | 3.13 |
| 112 | 8.98 | 15.02 | 2.90 | 16.63 | 0.78 | 1.56 | 3.13 |
| 113 | 13.70 | 33.09 | 0.81 | 118.50 | 0.78 | 1.56 | 1.56 |
| 114 | 11.97 | 50.47 | 1.24 | 4.27 | 1.56 | 3.13 | 3.13 |
| 115 | 6.14 | 6.06 | 2.10 | 19.23 | 0.39 | 0.78 | 3.13 |
| 116 | 29.34 | 4.62 | 6.97 | 63.94 | 1.56 | 1.56 | 3.13 |
| 117 | 0.94 | 0.55 | 2.58 | 2.28 | 3.13 | 0.78 | 6.25 |
| 118 | 1.55 | 1.25 | 1.20 | 2.44 | 1.56 | 1.56 | 3.13 |
| 119 | 3.45 | 6.56 | 0.57 | 10.14 | 0.78 | 0.78 | 1.56 |
| 120 | 0.56 | 0.76 | 0.26 | 0.79 | 1.56 | 1.56 | 3.13 |
| 121 | 58.73 | 66.80 | 4.54 | 30.43 | 1.56 | 1.56 | 0.78 |
| 122 | 14.32 | 24.36 | 3.34 | 6.86 | 0.20 | 0.39 | 0.78 |
| 123 | 10.82 | 6.18 | 0.25 | 7.51 | 0.39 | 0.39 | 1.56 |
| 124 | 16.82 | 23.06 | 3.18 | 37.20 | 0.39 | 0.78 | 0.78 |
| 125 | 88.07 | 61.44 | 10.93 | 53.85 | 0.78 | 3.13 | 1.56 |
| 126 | 200 | 124 | 7.70 | 32.54 | 1.56 | 3.13 | 0.78 |
| 127 | 18.87 | 33.67 | 1.25 | 24.57 | 0.39 | 0.78 | 0.78 |
| 128 | 8.71 | 3.65 | 0.94 | 13.32 | 0.39 | 0.78 | 0.78 |
| 129 | 2.70 | 4.72 | 3.53 | 6.44 | 6.25 | 3.13 | 12.50 |
| 130 | 31.96 | 128 | 4.21 | 5.47 | 0.78 | 3.13 | 1.56 |
| 131 | 0.79 | 0.87 | 0.11 | 1.05 | 0.39 | 0.78 | 1.56 |
| 132 | 1.34 | 2.49 | 0.19 | 4.28 | 0.39 | 0.78 | 1.56 |
| 133 | 12.70 | 24.00 | 2.07 | 57.91 | 0.78 | 1.56 | 0.78 |
| 134 | 182 | 480 | 62.92 |  | 6.25 | 12.50 | 6.25 |
| 135 | 1.13 | 3.43 | 0.16 | 3.00 | 0.59 | 0.78 | 1.17 |
| 136 | 200 | 200 | 14.17 | 27.37 | 3.13 | 12.50 | 1.56 |
| 137 | 3.50 | 4.97 | 16.07 | 15.33 | 0.78 | 1.56 | 6.25 |
| 138 | 2.47 | 6.91 | 0.71 | 10.26 | 1.56 | 1.56 | 1.56 |
| 139 | 18.21 | 18.50 | 0.39 | 4.52 | 0.78 | 0.78 | 1.56 |
| 140 | 3.75 | 6.34 | 0.10 | 1.87 | 1.56 | 0.78 | 0.78 |
| 141 | 15.84 | 11.93 | 0.43 | 15.70 | 1.56 | 1.56 | 1.56 |
| 142 | 7.59 | 5.95 | 0.42 | 9.26 | 0.39 | 0.78 | 1.56 |
| 143 | 111 | 70.42 | 100 | 200 | 1.56 | 1.56 | 12.50 |
| 144 | 111 | 89.62 | 4.23 | 200 | 3.13 | 6.25 | 3.13 |
| 145 | 1.68 | 4.70 | 0.46 | 8.32 | 0.39 | 0.78 | 1.56 |
| 146 | 2.32 | 2.25 | 0.31 | 1.77 | 1.56 | 3.13 | 6.25 |
| 147 | 26.96 | 39.65 | 0.28 | 56.22 | 0.39 | 0.78 | 1.56 |
| 148 | 0.76 | 28.09 | 0.35 | 1.50 | 0.39 | 1.56 | 3.13 |
| 149 | 4.46 | 104 | 0.96 | 48.13 | 0.20 | 1.56 | 1.56 |
| 150 | 0.62 | 17.13 | 0.38 | 1.52 | 1.56 | 6.25 | 12.50 |
| 151 | 0.53 | 6.70 | 1.15 | 5.92 | 0.39 | 1.56 | 6.25 |
| 152 | 0.08 | 6.80 | 0.16 | 0.74 | 0.39 | 1.56 | 3.13 |
| 153 | 0.21 | 7.23 | 0.20 | 1.10 | 0.78 | 1.56 | 3.13 |
| 154 | 0.35 | 8.46 | 0.26 | 0.73 | 1.56 | 1.56 | 6.25 |
| 155 | 5.12 | 81.43 | 2.14 | 6.87 | 0.39 | 3.13 | 1.56 |
| 156 | 4.64 | 67.71 | 2.14 | 7.16 | 0.39 | 1.56 | 1.56 |
| 157 | 0.24 | 6.90 | 0.25 | 1.85 | 1.56 | 3.13 | 6.25 |
| 158 | 7.19 | 88.43 | 1.22 | 22.78 | 0.10 | 1.56 | 0.78 |
| 159 | 0.61 | 15.87 | 0.38 | 2.62 | 1.56 | 0.78 | 6.25 |
| 160 | 1.16 | 1.20 | 1.34 | 5.49 | 0.78 | 0.20 | 1.56 |
| 161 | 12.21 | 45.45 | 0.89 | 14.93 | 1.56 | 3.13 | 1.56 |

TABLE 1-continued

Inhibition of metallo-β-lactamases (IMP-1, NDM-1, VIM-1, VIM-2) and antibiotic potentiation vs. MBL-expressing bacteria by Examples 1-209.

| Ex. No. | NDM 1 IC$_{50}$ (nM) | IMP1 IC$_{50}$ (nM) | VIM1 IC$_{50}$ (nM) | VIM2 IC$_{50}$ (nM) | CLB30016 E. coli MITC95 NDM (µM) | CL5741 S. marcescens MITC95 IMP (µm) | IHMA599644 K. pneumoniae MITC95 VIM (µM) |
|---|---|---|---|---|---|---|---|
| 162 | 1.20 | 2.17 | 2.45 | 6.33 | 0.29 | 0.20 | 1.95 |
| 163 | 19.24 | 48.95 | 0.74 | 52.92 | 0.39 | 1.56 | 1.56 |
| 164 | 0.63 | 0.54 | 0.12 | 0.69 | 0.39 | 1.56 | 3.13 |
| 165 | 1.21 | 2.43 | 0.38 | 2.35 | 0.20 | 0.20 | 1.56 |
| 166 | 0.12 | 0.22 | 0.09 | 0.53 | 0.78 | 0.78 | 1.56 |
| 167 | 0.25 | 0.25 | 0.05 | 0.40 | 1.17 | 1.17 | 1.56 |
| 168 | 0.17 | 0.24 | 0.07 | 0.48 | 0.39 | 0.78 | 1.56 |
| 169 | 0.23 | 0.26 | 0.10 | 0.40 | 0.39 | 1.17 | 2.34 |
| 170 | 11.36 | 15.32 | 5.64 | 42.94 | 1.56 | 1.56 | 1.56 |
| 171 | 3.38 | 7.39 | 0.92 | 27.76 | 0.39 | 0.78 | 0.78 |
| 172 | 2.15 | 3.49 | 0.66 | 3.78 | 1.17 | 2.34 | 2.34 |
| 173 | 19.83 | 10.52 | 13.69 | 114.00 | 1.56 | 3.13 | 6.25 |
| 174 | 0.69 | 0.36 | 0.07 | 0.22 | 0.78 | 0.78 | 3.13 |
| 175 | 2.55 | 3.66 | 0.24 | 4.18 | 0.39 | 0.78 | 1.56 |
| 176 | 2.51 | 5.10 | 2.76 | 11.68 | 0.39 | 0.39 | 1.56 |
| 177 | 0.57 | 0.19 | 0.15 | 0.66 | 6.25 | 3.13 | 6.25 |
| 178 | 29.04 | 101 | 80.07 | 132 | 1.56 | 6.25 | 6.25 |
| 179 | 26.19 | 69.22 | 49.91 | 83.13 | 0.78 | 6.25 | 12.50 |
| 180 | 5.73 | 6.30 | 0.44 | 5.92 | 0.39 | 0.78 | 1.56 |
| 181 | 4.62 | 5.78 | 0.22 | 5.87 | 0.39 | 0.39 | 1.56 |
| 182 | 3.77 | 4.00 | 0.27 | 3.82 | 0.39 | 0.78 | 1.56 |
| 183 | 6.26 | 12.37 | 5.89 | 69.68 | 1.17 | 1.56 | 2.34 |
| 184 | 19.36 | 39.44 | 4.61 | 44.43 | 0.78 | 1.56 | 1.56 |
| 185 | 0.33 | 0.60 | 0.04 | 0.71 | 0.78 | 1.56 | 1.56 |
| 186 | 18.72 | 40.58 | 2.85 | 68.70 | 3.13 | 1.56 | 1.56 |
| 187 | 0.13 | 0.24 | 0.03 | 0.49 | 0.78 | 0.78 | 0.78 |
| 188 | 2.86 | 3.68 | 0.13 | 4.85 | 0.78 | 0.78 | 1.56 |
| 189 | 0.30 | 0.77 | 0.06 | 2.31 | 0.39 | 0.78 | 0.78 |
| 190 | 0.67 | 0.61 | 0.09 | 0.85 | 3.13 | 0.78 | 1.56 |
| 191 | 0.94 | 25.23 | 0.21 | 1.15 | 0.78 | 1.56 | 3.13 |
| 192 | 66.35 | 97.03 | 67.49 | 200 | 1.56 | 3.13 | 6.25 |
| 193 | 0.48 | 0.67 | 0.075 | 0.75 | 1.56 | 1.56 | 1.56 |
| 194 | 26.54 | 16.04 | 0.17 | 14.92 | 0.39 | 0.20 | 0.78 |
| 195 | 1.51 | 4.27 | 0.14 | 2.86 | 0.20 | 0.20 | 0.39 |
| 196 | 0.72 | 3.26 | 0.44 | 1.70 | 0.29 | 0.20 | 1.17 |
| 197 | 1.44 | 9.95 | 0.74 | 1.89 | 0.29 | 0.39 | 1.56 |
| 198 | 1.82 | 5.62 | 0.20 | 10.97 | 0.39 | 0.20 | 0.39 |
| 199 | 1.69 | 6.11 | 0.18 | 4.27 | 0.39 | 0.10 | 0.39 |
| 200 | 3.10 | 4.57 | 0.51 | 8.28 | 0.78 | 1.56 | 3.13 |
| 201 | 1.83 | 0.77 | 0.26 | 0.64 | 0.39 | 0.78 | 1.56 |
| 202 | 0.44 | 0.58 | 0.09 | 1.60 | 0.78 | 1.56 | 1.56 |
| 203 | 10.79 | 26.37 | 8.50 | 19.60 | 0.20 | 0.78 | 0.78 |
| 204 | 0.97 | 1.55 | 0.16 | 3.44 | 0.78 | 1.56 | 1.56 |
| 205 | 7.59 | 19.73 | 0.34 | 1.07 | 0.78 | 1.56 | 1.56 |
| 206 | 9.21 | 15.15 | 0.23 | 1.52 | 0.78 | 1.56 | 1.56 |
| 207 | 15.04 | 25.21 | 0.86 | 25.58 | 0.39 | 0.20 | 0.78 |
| 208 | 1.05 | 1.84 | 0.11 | 1.19 | 1.56 | 0.78 | 3.13 |
| 209 | 0.96 | 1.69 | 0.12 | 3.32 | 0.78 | 1.56 | 1.56 |

Efflux

In order to assess the contribution of efflux to lack of whole cell inhibition of metallo-beta-lactamase inhibitors of formula I, tool strains were constructed. The strain background is *Pseudomonas aeruginosa* PAO1. A wild-type (M135919) and an isogenic strain in which multiple efflux pumps have been disrupted genetically were used. The MBL IMP-1, obtained from a clinical isolate was introduced into the strain pair by the following process:

Plasmid DNA (encoding IMP-1) was extracted from CL 5673 (IMP-1, *P. aeruginosa* clinical strain) by standard techniques. The plasmid DNA was transformed into parental MB5919 (oprD+, efflux+, inducible AmpC) and MB5890 (oprD+, efflux−, inducible AmpC) isogenic strains by electroporation. These transformed strains were plated onto cation-adjusted Muller-Hinton agar plates containing ceftazidime at 32 µg/ml (MB5919) and 16 µg/ml (MB5890) to select for those cells in which the IMP-1-expressing plasmid was introduced successfully, resulting in resistance to ceftazidime. Agarose-gel electrophoresis of PCR product for IMP-1 from the successful transformants was used to compare to control and to the original strain from which the plasmid was obtained, confirming transfer of the IMP-1 gene (data not shown).

Minimum inhibitory concentrations of sentinel antibiotics were performed to quality control the new strains. The imipenem MIC went up dramatically, as expected, due to presence of the IMP-1, also meropenem (MEM) and ceftazidime (CAZ). The efflux +/− set behaved similarly with non-BL antibiotics as they should with the efflux-strain exhibiting increased sensitivity to chloramphenicol (CAM) and ciprofloxacin (Cipro),

| | | | | MIC [μg/mL] | | | | |
|---|---|---|---|---|---|---|---|---|
| | | | CL 5673 (IMP-1) plasmid | | pFLp-Vim1 plasmid | | pFLp-Vim2 plasmid | |
| | MB5919 | MB5890 | MB9798 | MB9799 | MB9861 | MB9862 | | |
| | | | | OprD | | | | |
| | OprD+ | OprD+ | OprD+ | OprD+ Efflux | OprD+ | OprD+ | OprD+ | OprD+ |
| | efflux+ MB5919 | efflux− MB5890 | efflux+ MB5919 Trans IMP1 plasmid | efflux− MB5890 Trans IMP1 plasmid | Efflux+ MB5919 Trans pFlp-Vim1 plasmid | efflux− MB5890 trans pFlp-Vim1 | efflux+ MB5919 Trans pFlp-Vim2 plasmid | efflux− MB5890 Trans pFlp-Vim2 plasmid |
| Imipenem | 4 | 2 | 64 | 32 | >64 | 64 | >64 | 32 |
| Meropenem | 2 | 0.5 | >64 | 64 | >64 | 64 | >64 | 32 |
| Pipercillin | 2 | 1 | 4 | 4 | >256 | 128 | >256 | 128 |
| Chloramphenicol | >64 | 1 | >64 | 1 | >64 | 2 | >64 | 1 |
| Ciprofloxicin | 0.5 | 0.008 | 0.5 | 0.008 | 1 | 0.008 | 1 | 0.008 |
| CAZ | 1 | 0.5 | 256 | 256 | >256 | >256 | 128 | 64 |
| Azithromycin | 16 | 1 | 2 | 2 | 32 | 1 | 32 | 1 |

The strain set was then used as a pair to determine the effect of metallo-β-lactamase inhibitors of Formula I on the MIC of imipenem and/or ceftazidime. A fixed concentration of antibiotic is included in standard microbroth MIC tests, usually at the CLSI breakpoint concentration, A fixed amount of a class A/C beta-lactamase inhibitor is also included to inhibit the resident Pseudomonas AmpC enzyme. A serial titration of the metallo-β-lactamase inhibitor was included and the concentration of metallo-β-lactamase inhibitor which restores susceptibility of the strain to the included antibiotic was recorded. That concentration of metallo-β-lactamase inhibitor was then compared between the two strains to determine the fold difference between the efflux+(MB9798) and efflux−(MI39799) strains, which indicates the extent to which the MBLi is subject to efflux.

TABLE 2

Concentration of metallo-β-lactamase inhibitors of Formula I which restores susceptibility of efflux + (MB9798) and efflux − (MB9799) strains to imipenem at 2 μg/mL in the presence of a class A, C, D serine β-lactamase inhibitor closely related to relebactam.

| Ex. No. | MB9798 MITC95 P. aeruginosa uM Efflux WT (μM) | MB9799 MITC95 P. aeruginosa uM Efflux Mutant (μM) | Efflux ratio |
|---|---|---|---|
| 1 | 0.78 | 0.39 | 2.00 |
| 2 | 0.78 | 0.78 | 1.00 |
| 3 | 0.78 | 0.39 | 2.00 |
| 4 | 1.56 | 0.78 | 2.00 |
| 5 | 0.78 | 0.39 | 2.00 |
| 6 | 0.78 | 0.39 | 2.00 |
| 7 | 0.78 | 0.39 | 2.00 |
| 8 | 0.78 | 0.39 | 2.00 |
| 9 | 1.56 | 0.78 | 2.00 |
| 10 | 3.13 | 0.78 | 4.00 |
| 11 | 6.25 | 1.56 | 4.00 |
| 12 | 1.56 | 0.78 | 2.00 |
| 13 | 0.78 | 0.39 | 2.00 |
| 14 | 12.50 | 0.78 | 16.00 |
| 15 | 12.50 | 1.56 | 8.00 |

TABLE 2-continued

Concentration of metallo-β-lactamase inhibitors of Formula I which restores susceptibility of efflux + (MB9798) and efflux − (MB9799) strains to imipenem at 2 μg/mL in the presence of a class A, C, D serine β-lactamase inhibitor closely related to relebactam.

| Ex. No. | MB9798 MITC95 P. aeruginosa uM Efflux WT (μM) | MB9799 MITC95 P. aeruginosa uM Efflux Mutant (μM) | Efflux ratio |
|---|---|---|---|
| 16 | 0.78 | 0.78 | 1.00 |
| 17 | 1.56 | 0.78 | 2.00 |
| 18 | 0.78 | 0.78 | 1.00 |
| 19 | 3.13 | 3.13 | 1.00 |
| 20 | 3.13 | 0.78 | 4.00 |
| 21 | 3.13 | 3.13 | 1.00 |
| 22 | 1.56 | 1.56 | 1.00 |
| 23 | 3.13 | 1.56 | 2.00 |
| 24 | 1.56 | 1.56 | 1.00 |
| 25 | 3.13 | 3.13 | 1.00 |
| 26 | 6.25 | 3.13 | 2.00 |
| 27 | 25.00 | 1.56 | 15.99 |
| 28 | 50.00 | 6.25 | 8.00 |
| 29 | 25.00 | 3.13 | 8.00 |
| 30 | 1.56 | 0.78 | 2.00 |
| 31 | 6.25 | 1.56 | 4.00 |
| 32 | 12.50 | 3.13 | 4.00 |
| 33 | 25.00 | 3.13 | 8.00 |
| 34 | 0.39 | 0.20 | 2.00 |
| 35 | 0.78 | 0.78 | 1.00 |
| 36 | 0.91 | 0.65 | 1.40 |
| 37 | 0.78 | 0.78 | 1.00 |
| 38 | 3.13 | 0.78 | 4.00 |
| 39 | 3.13 | 1.56 | 2.00 |
| 40 | 1.56 | 0.78 | 2.00 |
| 41 | 1.56 | 0.39 | 4.00 |
| 42 | 1.56 | 1.56 | 1.00 |
| 43 | 1.56 | 1.56 | 1.00 |
| 44 | 3.13 | 1.56 | 2.00 |
| 45 | 1.56 | 1.56 | 1.00 |
| 46 | 1.56 | 1.56 | 1.00 |
| 47 | 1.56 | 0.78 | 2.00 |
| 48 | 1.56 | 0.39 | 4.00 |
| 49 | 1.56 | 1.56 | 1.00 |

TABLE 2-continued

Concentration of metallo-β-lactamase inhibitors of Formula I which restores susceptibility of efflux + (MB9798) and efflux − (MB9799) strains to imipenem at 2 μg/mL in the presence of a class A, C, D serine β-lactamase inhibitor closely related to relebactam.

| Ex. No. | MB9798 MITC95 P. aeruginosa uM Efflux WT (μM) | MB9799 MITC95 P. aeruginosa uM Efflux Mutant (μM) | Efflux ratio |
|---|---|---|---|
| 50 | 0.78 | 0.39 | 2.00 |
| 51 | 0.78 | 0.39 | 2.00 |
| 52 | 0.78 | 0.78 | 1.00 |
| 53 | 6.25 | 1.56 | 4.00 |
| 54 | 6.25 | 1.56 | 4.00 |
| 55 | 100.00 | 6.25 | 16.00 |
| 56 | 6.25 | 1.56 | 4.00 |
| 57 | 25.00 | 1.56 | 15.99 |
| 58 | 6.25 | 1.56 | 4.00 |
| 59 | 50.00 | 3.13 | 16.00 |
| 60 | 12.50 | 3.13 | 4.00 |
| 61 | 6.25 | 1.56 | 4.00 |
| 62 | 50.00 | 1.56 | 31.99 |
| 63 | 1.56 | 1.56 | 1.00 |
| 64 | 25.00 | 1.56 | 15.99 |
| 65 | 3.13 | 1.56 | 2.00 |
| 66 | 25.00 | 1.56 | 15.99 |
| 67 | 12.50 | 1.56 | 8.00 |
| 68 | 12.50 | 1.56 | 8.00 |
| 69 | 12.50 | 3.13 | 4.00 |
| 70 | 2.34 | 1.95 | 1.20 |
| 71 | 1.56 | 1.56 | 1.00 |
| 72 | 25.00 | 3.13 | 8.00 |
| 73 | 1.56 | 0.78 | 2.00 |
| 74 | 1.56 | 0.78 | 2.00 |
| 75 | 25.00 | 3.13 | 8.00 |
| 76 | 1.56 | 1.56 | 1.00 |
| 77 | 0.78 | 0.39 | 2.00 |
| 78 | 6.25 | 0.78 | 8.00 |
| 79 | 3.13 | 1.56 | 2.00 |
| 80 | 1.56 | 1.56 | 1.00 |
| 81 | 6.25 | 3.13 | 2.00 |
| 82 | 6.25 | 3.13 | 2.00 |
| 83 | 12.50 | 3.13 | 4.00 |
| 84 | 6.25 | 1.56 | 4.00 |
| 85 | 1.56 | 0.78 | 2.00 |
| 86 | 12.50 | 1.56 | 8.00 |
| 87 | 12.50 | 1.56 | 8.00 |
| 88 | 6.25 | 6.25 | 1.00 |
| 89 | 3.13 | 1.56 | 2.00 |
| 90 | 6.25 | 1.56 | 4.00 |
| 91 | 3.13 | 1.56 | 2.00 |
| 92 | 1.56 | 1.56 | 1.00 |
| 93 | 3.13 | 1.56 | 2.00 |
| 94 | 3.13 | 3.13 | 1.00 |
| 95 | 6.25 | 3.13 | 2.00 |
| 96 | 3.13 | 1.56 | 2.00 |
| 97 | 6.25 | 3.13 | 2.00 |
| 98 | 3.13 | 3.13 | 1.00 |
| 99 | 3.13 | 3.13 | 1.00 |
| 100 | 12.50 | 6.25 | 2.00 |
| 101 | 1.56 | 0.78 | 2.00 |
| 102 | 3.13 | 1.56 | 2.00 |
| 103 | 3.13 | 1.56 | 2.00 |
| 104 | 3.13 | 1.56 | 2.00 |
| 105 | 12.50 | 6.25 | 2.00 |
| 106 | 50.00 | 3.13 | 16.00 |
| 107 | 3.13 | 1.56 | 2.00 |
| 108 | 12.50 | 6.25 | 2.00 |
| 109 | 3.13 | 3.13 | 1.00 |
| 110 | 50.00 | 1.56 | 31.99 |
| 111 | 12.50 | 1.56 | 8.00 |
| 112 | 50.00 | 1.56 | 31.99 |
| 113 | 6.25 | 0.78 | 8.00 |
| 114 | 12.50 | 3.13 | 4.00 |
| 115 | 12.50 | 0.78 | 16.00 |
| 116 | 3.13 | 1.56 | 2.00 |
| 117 | 12.50 | 3.13 | 4.00 |
| 118 | 1.56 | 1.56 | 1.00 |
| 119 | 1.56 | 0.78 | 2.00 |
| 120 | 1.56 | 1.56 | 1.00 |
| 121 | 6.25 | 3.13 | 2.00 |
| 122 | 1.56 | 0.78 | 2.00 |
| 123 | 1.56 | 0.78 | 2.00 |
| 124 | 3.13 | 1.56 | 2.00 |
| 125 | 6.25 | 3.13 | 2.00 |
| 126 | 6.25 | 3.13 | 2.00 |
| 127 | 3.13 | 0.78 | 4.00 |
| 128 | 0.78 | 0.39 | 2.00 |
| 129 | 6.25 | 3.13 | 2.00 |
| 130 | 12.50 | 3.13 | 4.00 |
| 131 | 0.78 | 0.78 | 1.00 |
| 132 | 0.78 | 0.78 | 1.00 |
| 133 | 3.13 | 1.56 | 2.00 |
| 134 | 50.00 | 6.25 | 8.00 |
| 135 | 0.59 | 0.39 | 1.50 |
| 136 | 50.00 | 12.50 | 4.00 |
| 137 | 6.25 | 3.13 | 2.00 |
| 138 | 1.56 | 0.78 | 2.00 |
| 139 | 1.56 | 0.78 | 2.00 |
| 140 | 1.56 | 0.78 | 2.00 |
| 141 | 6.25 | 1.56 | 4.00 |
| 142 | 0.78 | 0.78 | 1.00 |
| 143 | 6.25 | 3.13 | 2.00 |
| 144 | 12.50 | 3.13 | 4.00 |
| 145 | 0.78 | 0.78 | 1.00 |
| 146 | 1.56 | 1.56 | 1.00 |
| 147 | 3.13 | 0.78 | 4.00 |
| 148 | 3.13 | 1.56 | 2.00 |
| 149 | 6.25 | 3.13 | 2.00 |
| 150 | 12.50 | 3.13 | 4.00 |
| 151 | 12.50 | 3.13 | 4.00 |
| 152 | 3.13 | 1.56 | 2.00 |
| 153 | 3.13 | 1.56 | 2.00 |
| 154 | 3.13 | 1.56 | 2.00 |
| 155 | 6.25 | 3.13 | 2.00 |
| 156 | 12.50 | 1.56 | 8.00 |
| 157 | 3.13 | 3.13 | 1.00 |
| 158 | 6.25 | 3.13 | 2.00 |
| 159 | 6.25 | 1.56 | 4.00 |
| 160 | 1.56 | 1.56 | 1.00 |
| 161 | 12.50 | 6.25 | 2.00 |
| 162 | 2.34 | 1.17 | 2.00 |
| 163 | 6.25 | 3.13 | 2.00 |
| 164 | 6.25 | 3.13 | 2.00 |
| 165 | 1.56 | 0.78 | 2.00 |
| 166 | 0.78 | 0.78 | 1.00 |
| 167 | 0.78 | 0.78 | 1.00 |
| 168 | 1.56 | 0.78 | 2.00 |
| 169 | 0.78 | 0.78 | 1.00 |
| 170 | 6.25 | 1.56 | 4.00 |
| 171 | 0.78 | 0.39 | 2.00 |
| 172 | 1.17 | 1.17 | 1.00 |
| 173 | 6.25 | 1.56 | 4.00 |
| 174 | 3.13 | 1.56 | 2.00 |
| 175 | 1.56 | 0.78 | 2.00 |
| 176 | 3.13 | 1.56 | 2.00 |
| 177 | 1.56 | 1.56 | 1.00 |
| 178 | 25.00 | 6.25 | 4.00 |
| 179 | 25.00 | 6.25 | 4.00 |
| 180 | 0.78 | 0.78 | 1.00 |
| 181 | 0.78 | 0.78 | 1.00 |
| 182 | 0.78 | 0.78 | 1.00 |
| 183 | 3.13 | 1.17 | 2.67 |

TABLE 2-continued

Concentration of metallo-β-lactamase inhibitors of Formula I which restores susceptibility of efflux + (MB9798) and efflux − (MB9799) strains to imipenem at 2 µg/mL in the presence of a class A, C, D serine β-lactamase inhibitor closely related to relebactam.

| Ex. No. | MB9798 MITC95 *P. aeruginosa* uM Efflux WT (µM) | MB9799 MITC95 *P. aeruginosa* uM Efflux Mutant (µM) | Efflux ratio |
|---|---|---|---|
| 184 | 6.25 | 3.13 | 2.00 |
| 185 | 0.78 | 0.78 | 1.00 |
| 186 | 1.56 | 0.78 | 2.00 |
| 187 | 0.39 | 0.39 | 1.00 |
| 188 | 0.78 | 0.78 | 1.00 |
| 189 | 0.78 | 0.39 | 2.00 |
| 190 | 0.78 | 0.78 | 1.00 |
| 191 | 6.25 | 1.56 | 4.00 |
| 192 | 6.25 | 3.13 | 2.00 |
| 193 | 0.78 | 0.78 | 1.00 |
| 194 | 0.78 | 0.78 | 1.00 |
| 195 | 0.78 | 0.78 | 1.00 |
| 196 | 2.34 | 0.78 | 3.00 |
| 197 | 3.13 | 1.56 | 2.00 |
| 198 | 0.78 | 0.78 | 1.00 |
| 199 | 0.78 | 0.78 | 1.00 |
| 200 | 50.00 | 50.00 | 1.00 |
| 201 | 1.56 | 0.78 | 2.00 |
| 202 | 1.56 | 1.56 | 1.00 |
| 203 | 3.13 | 1.56 | 2.00 |
| 204 | 0.78 | 0.78 | 1.00 |
| 205 | 12.50 | 1.56 | 8.00 |
| 206 | 6.25 | 1.56 | 4.00 |
| 207 | 1.56 | 1.56 | 1.00 |
| 208 | 0.78 | 0.78 | 1.00 |
| 209 | 0.78 | 0.78 | 1.00 |

What is claimed:

1. A compound having the structure:

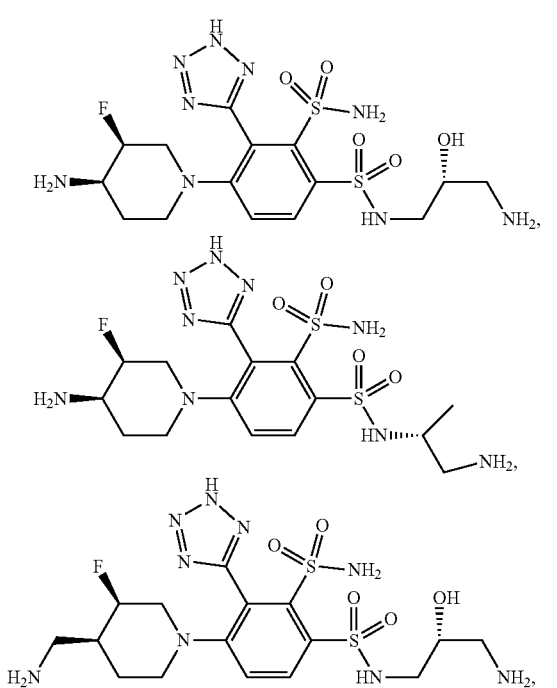

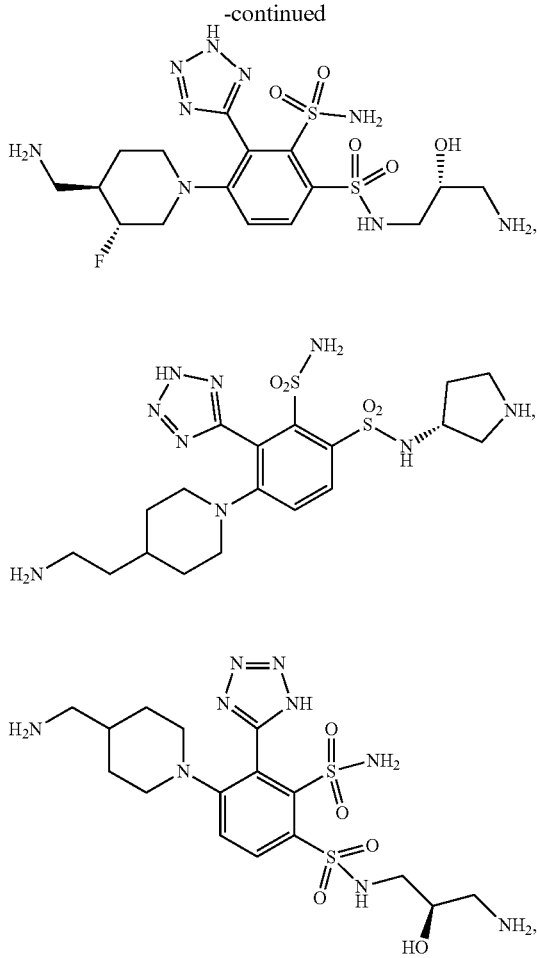

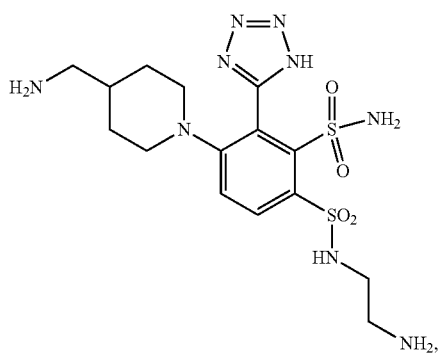

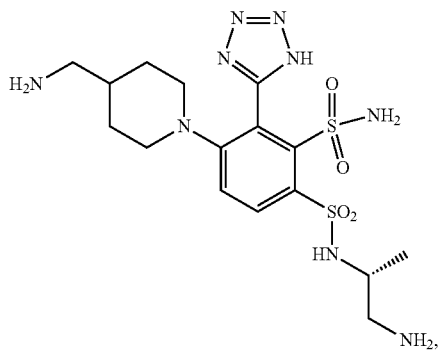

-continued
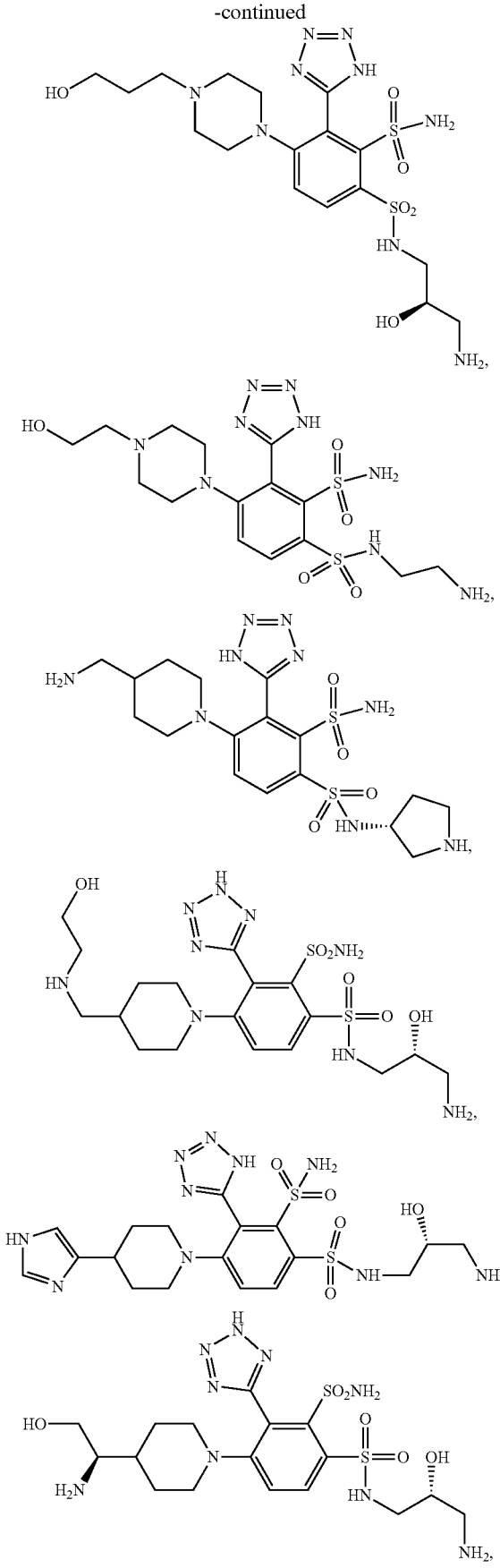
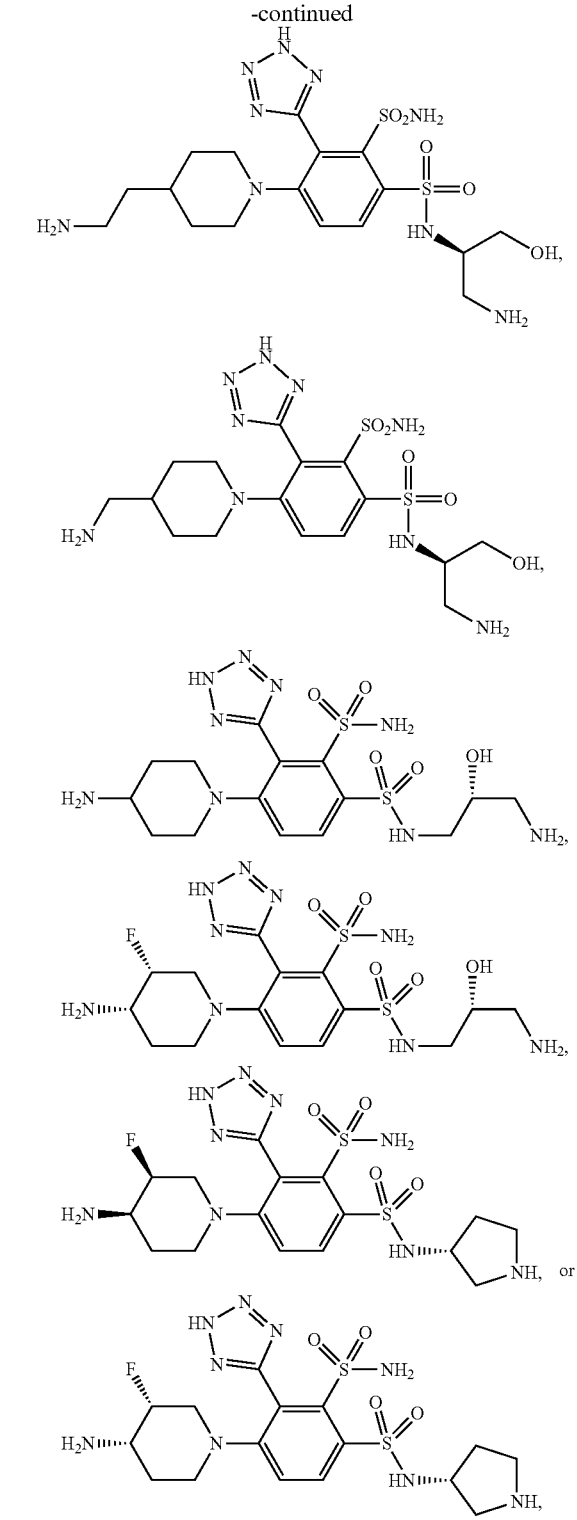
or a pharmaceutically acceptable salt thereof.
2. A pharmaceutical composition which comprises a compound according to claim 1, or a pharmaceutically acceptable salt thereof, and a pharmaceutically acceptable carrier.
3. A pharmaceutical composition according to claim 2, which further comprises an effective amount of a beta-lactam antibiotic.

4. The pharmaceutical composition according to claim 2 which further comprises an effective amount of one or more beta-lactamase inhibitor compounds.

5. The pharmaceutical composition according to claim 4, wherein the beta-lactamase inhibitor compound is selected from the group consisting of: relebactam or a pharmaceutically acceptable salt thereof, avibactam or a pharmaceutically acceptable salt thereof, vaborbactam or a pharmaceutically acceptable salt thereof, tazobactam or a pharmaceutically acceptable salt thereof, sulbactam or a pharmaceutically acceptable salt thereof, and clavulanic acid or a pharmaceutically acceptable salt thereof.

6. The pharmaceutical composition according to claim 5, wherein the beta-lactamase inhibitor compound is relebactam or a pharmaceutically acceptable salt thereof.

7. The pharmaceutical composition according to claim 3, wherein the beta-lactam antibiotic is selected from the group consisting of: (a) imipenem, (b) ertapenem, (c) meropenem, (d) doripenem, (e) biapenem, (f) panipenem, (g) ticarcillin, (h) ampicillin, (i) amoxicillin, (j) carbenicillin, (k) piperacillin, (l) azlocillin, (m) mezlocillin, (n) cefoperazone, (o) cefotaxime, (p) ceftriaxone, (q) cefipime, (r) ceftolozane, (s) ceftazidime, and (t) a pharmaceutically acceptable salt of any of (a) through (s).

8. The pharmaceutical composition according to claim 7, wherein the beta-lactam antibiotic is imipenem or a pharmaceutically acceptable salt thereof.

9. The pharmaceutical composition according to claim 8, further comprising cilastatin or a pharmaceutically acceptable salt thereof.

10. A method for inhibiting beta-lactamase in a subject which comprises administering to the subject an effective amount of a compound according to claim 1, or a pharmaceutically acceptable salt thereof, optionally in combination with a beta-lactam antibiotic.

11. A method for treating a bacterial infection which comprises administering to a subject in need of such treatment a therapeutically effective amount of a compound according to claim 1, or a pharmaceutically acceptable salt thereof, in combination with a beta-lactam antibiotic.

12. The method of claim 10, wherein the beta-lactam antibiotic is selected from the group consisting of: (a) imipenem, (b) ertapenem, (c) meropenem, (d) doripenem, (e) biapenem, (f) panipenem, (g) ticarcillin, (h) ampicillin, (i) amoxicillin, (j) carbenicillin, (k) piperacillin, (l) azlocillin, (m) mezlocillin, (n) cefoperazone, (o) cefotaxime, (p) ceftriaxone, (q) cefipime, (r) ceftolozane, (s) ceftazidime, and (t) a pharmaceutically acceptable salt of any of (a) through (s).

13. The method of claim 11, wherein the beta-lactam antibiotic is imipenem or a pharmaceutically acceptable salt thereof.

14. A method for treating a bacterial infection which comprises administering to a subject in need of such treatment a therapeutically effective amount of a compound according to claim 1, or a pharmaceutically acceptable salt thereof, and a therapeutically effective amount of imipenem or a pharmaceutically acceptable salt thereof, cilastatin or a pharmaceutically acceptable salt thereof, and relebactam or a pharmaceutically acceptable salt thereof.

* * * * *